(12) United States Patent
Xu et al.

(10) Patent No.: US 7,527,936 B2
(45) Date of Patent: May 5, 2009

(54) MODULATORS OF ANGIOGENESIS

(75) Inventors: Weiduan Xu, San Francisco, CA (US); Sacha J. Holland, San Francisco, CA (US); James Lorens, Bones (NO)

(73) Assignee: Rigel Pharmaceuticals Inc., South San Francisco, CA (US)

( * ) Notice: Subject to any disclaimer, the term of this patent is extended or adjusted under 35 U.S.C. 154(b) by 221 days.

(21) Appl. No.: 11/036,643

(22) Filed: Jan. 13, 2005

(65) Prior Publication Data

US 2005/0208472 A1   Sep. 22, 2005

Related U.S. Application Data

(60) Provisional application No. 60/536,310, filed on Jan. 13, 2004.

(51) Int. Cl.
*G01N 33/573* (2006.01)
*C12N 15/06* (2006.01)
*C12N 15/52* (2006.01)
*C12N 9/14* (2006.01)
*C12N 5/10* (2006.01)

(52) U.S. Cl. .................. 435/7.21; 435/7.1; 435/18; 435/69.2; 435/195; 435/362

(58) Field of Classification Search .............. 435/7.21, 435/18, 69.2, 195, 212, 7.92, 6, 252.3, 320
See application file for complete search history.

(56) References Cited

U.S. PATENT DOCUMENTS

2003/0232400 A1   12/2003   Radka et al.

FOREIGN PATENT DOCUMENTS

| WO | WO 2001/11086 | 2/2001 |
| WO | WO 2001/32926 | 5/2001 |
| WO | WO 02/079492 | 10/2002 |

OTHER PUBLICATIONS

Ngo et al, in The Protein Folding Problem and Tertiary Structure Prediction, 1994, Merz, et al., (ed.), Birkhauser, Boston, MA, pp. 433 and 492-495.*
Stephen et al, J Biological Chemistry 272 (16): 10895-10903, 1997.*
Griffioen et al, Pharmacological Reviews 52(2): 237-268, 2000.*
Burgers et al, Eur J Cancer 40: 2217-2229, 2004.*
Auerbach et al, Cancer and Metastasis Reviews 19: 167-172, 2000.*
Chica et al, Curr Opin Biotechnol 16(4):378-84, Aug. 2005.*
Witkowski et al, Biochemistry 38(36): 11643-50, Sep. 7, 1999.*
Seffernick et al, J Bacteriol 183 (8): 2405-10, Apr. 2001.*
Zhuang, Shu-Fei et al.; "A new model for random screening inhibitors of vascular endothelial growth factor receptor 1 kinase", 2002, *Acta Pharmacology*, vol. 23, No. 2, pp. 117-123.
Tien et al., "Comprehensive gene expression analysis of peroxisome proliferator-treated immortalized hepatocytes: identification of peroxisome proliferator-activated receptor alpha-dependent growth regulatory genes," *Cancer Research*, 63(18):5767-5780, 2003.

* cited by examiner

*Primary Examiner*—Phuong Huynh
(74) *Attorney, Agent, or Firm*—Klarquist Sparkman, LLP

(57) ABSTRACT

The present invention relates to regulation of angiogenesis. The invention further relates to methods for identifying and using agents, including small organic molecules, antibodies, peptides, cyclic peptides, nucleic acids, antisense nucleic acids, RNAi, and ribozymes, that modulate angiogenesis; as well as to the use of expression profiles and compositions in diagnosis and therapy of angiogenesis and cancer.

23 Claims, 20 Drawing Sheets

Both USP-37 and CAMKK2 show extremely high expression in *skeletal muscle*. *This will be repeated using new RNA sample*

USP-37 is Specifically Overexpressed in Colon Carcinomas

Overexpression of USP-37 mRNA in Colon carcinomas

Summary of USP-37 Validation

- USP-37 is a novel protease target for anti-angiogenic therapy

- USP-37 3' UTR hit increases surface expression of VEGFR2

- USP-37 RNAi oligos knock down USP-37 RNA expression

- USP-37 RNAi oligos reduce VEGFR2 mRNA expression

- USP-37 RNAi oligo inhibits VEGFR2 surface expression

- USP-37 exhibits a restricted mRNA expression pattern (highest in endothelial cells, mammary epithelial cells, hepatocytes, monocytes and neutrophils)

- Downregulation of specific receptor tyrosine kinases and integrins by USP-37 RNAis demonstrates some functional specificity

- USP-37 RNAi oligos inhibit tube formation in the co-culture under VEGF starvation conditions

FIG. 9

CaMKK2 Inhibitor STO-609

| Kinase | IC$_{50}$ In Vitro |
|---|---|
| CaMKK1 | 382 nM |
| CaMKK2 | 127 nM |
| CaMK I | >31.8 µM |
| CamK II | ~31.8 µM |
| CamK IV | >31.8 µM |
| MLCK | >31.8 µM |
| PKC | >31.8 µM |
| cAMP-DepPK | >31.8 µM |
| p42 MAPK | >31.8 µM |

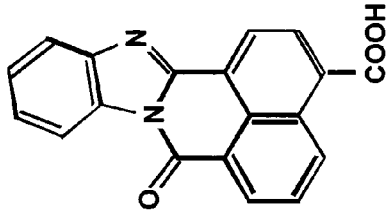

- Cell permeable, ATP competitive inhibitor of CaMKK 1 and CaMKK 2
- EC$_{50}$ for inhibition of CaMK IV activation (downstream target) in cells between 318nM - 3.18µM
- Single amino acid determines specificity for CaMKK 2 over CaMKK 1

Tokumitsu et al. JBC 277: p15813 (2002)
Kagawa University / Sumitomo Pharmaceuticals

FIG. 14

Summary of CaMKK2 Validation

- CaMKK2 is a novel druggable kinase target for anti-angiogenic therapy

- CaMKK2 RNAi Smartpool and oligo reduce CamKK2 mRNA expression

- CaMKK2 RNAi oligo decreases VEGFR2 mRNA expression

- CaMKK2 RNAi Smartpool and oligo reduce VEGFR2 surface expression

- Expression of CamKK2 is restricted (highest in endothelial cells, monocytes, reported high in brain)

- Specific CaMKK2 inhibitor STO-609 phenocopies RNAi and reduces VEGFR2 mRNA and surface levels

- Specific CaMKK2 inhibitor STO-609 inhibits tube formation in the co-culture assay

FIG. 16

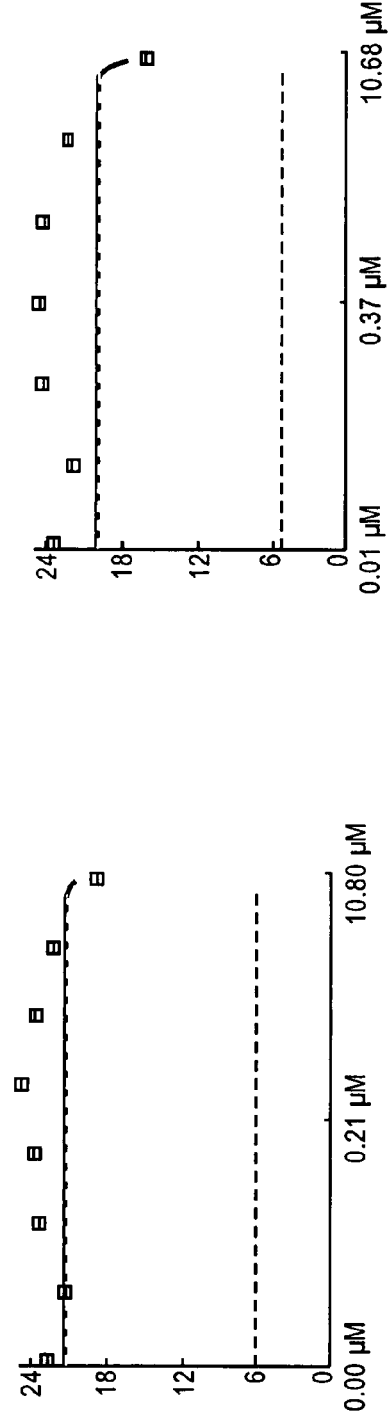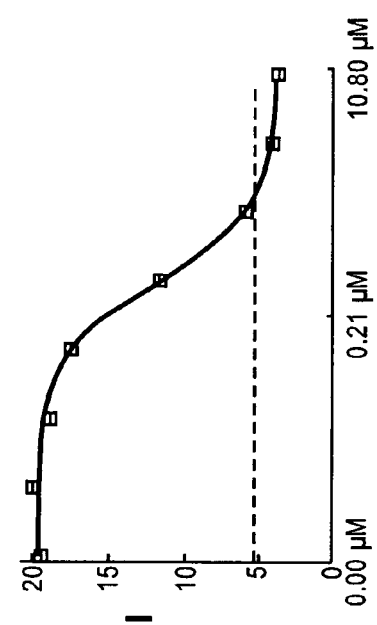
FIG. 18
Effect of CaMKK2 Inhibitor STO-609 on IL4-Induced CD23 Expression in Ramos B Cells
24 hour stimulation, compounds dosed from 10µM in 3-fold dilutions, 8 points
Duplicates were run on separate plates, hence two curves
IC50:  >10 µM      IC50:  >10 µM
Positive control
IC50=0.37µM

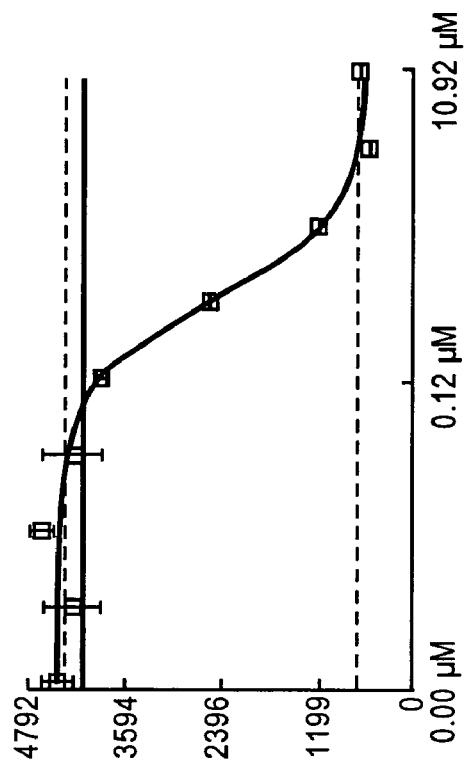
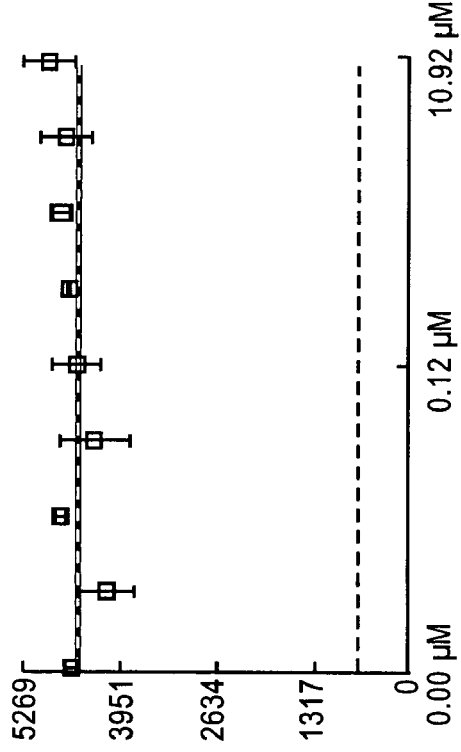
FIG. 19
Effect of CaMKK2 Inhibitor STO-609 on Anti-IgE-Induced Tryptase Release in Cultured Human Mast Cells
8 point in triplicate, 3 fold dilutions from 10μM, 30min stimulation

Summary of STO-609 Results

- Published IC50 of STO-609 in cells for activation of CaMKIV is 1-3µM

- STO-609 reduces surface VEGFR2 expression at 5-10µM (24hr treatment)

- STO-609 inhibits co-culture tube formation at ~5µM

- STO-609 inhibits proliferation of HUVECs at 1-10µM

- STO-609 inhibits proliferation of nHDFs at 1µM (CaMKK2 mRNA expressed at low level in nHDFs)

- STO-609 inhibits proliferation of Huh7 hepatocytes at about 1µM (CaMKK2 mRNA expressed at very low level in Huh7)

- STO-609 inhibits proliferation of SMCs at 10µM (CaMKK2 mRNA expressed at low level in SMCs)

- STO-609 inhibits proliferation of primary T cells with IC50 ~ 13-16µM (CaMKK2 mRNA undetectable in T cells)

- STO-609 does not affect IL-4-induced CD23 induction at doses up to 10µM (CaMKK2 mRNA expressed at low level in B cells)

- STO-609 does not affect anti-IgE-induced degranulation in CHMCs at doses up to 10µM

FIG. 20

SEQUENCE LISTING

```
<160> NUMBER OF SEQ ID NOS: 27

<210> SEQ ID NO 1
<211> LENGTH: 2828
<212> TYPE: DNA
<213> ORGANISM: Homo sapiens
<220> FEATURE:
<221> NAME/KEY: misc_feature
<222> LOCATION: (1)...(2828)
<223> OTHER INFORMATION: methionine adenosyltransferase II, alpha
      (Mat2A), S-adenosylmethionine synthetase (SAMS2) cDNA

<400> SEQUENCE: 1
ggcacgaggc gcccgcctgc tacgagtaga acgctgtccg cagcttgcgc atttcgcagc      60
cgctgccgcc tcgccgctgc tccttcgtaa ggccacttcc gcacaccgac accaacatga     120
acggacagct caacggcttc cacgaggcgt tcatcgagga gggcacattc cttttcacct     180
cagagtcggt cggggaaggc cacccagata agatttgtga ccaaatcagt gatgctgtcc     240
ttgatgccca ccttcagcag gatcctgatg ccaaagtagc ttgtgaaact gttgctaaaa     300
ctggaatgat ccttcttgct ggggaaatta catccgagc tgctgttgac taccagaaag     360
tggttcgtga agctgttaaa cacattggat atgatgattc ttccaaaggt tttgactaca     420
agacttgtaa cgtgctggta gccttggagc aacagtcacc agatattgct caaggtgttc     480
atcttgacag aaatgaagaa gacattggtg ctggagacca gggcttaatg tttggctatg     540
ccactgatga aactgaggag tgtatgcctt taaccattgt cttggcacac aagctaaatg     600
ccaaactggc agaactacgc cgtaatggca ctttgccttg gttacgccct gattctaaaa     660
ctcaagttac tgtgcagtat atgcaggatc gaggtgctgt gcttcccatc agagtccaca     720
caattgttat atctgttcag catgatgaag aggtttgtct tgatgaaatg agggatgccc     780
taaaggagaa agtcatcaaa gcagttgtgc ctgcgaaata ccttgatgag gatacaatct     840
accacctaca gccaagtggc agatttgtta ttggtgggcc tcagggtgat gctggtttga     900
ctggacgcaa aatcattgtg gacacttatg gcggttgggg tgctcatgga ggaggtgcct     960
tttcaggaaa ggattatacc aaggtcgacc gttcagctgc ttatgctgct cgttgggtgg    1020
caaaatccct tgttaaagga ggtctgtgcc ggagggttct tgttcaggtc tcttatgcta    1080
```

-continued

```
ttggagtttc tcatccatta tctatctcca ttttccatta tggtacctct cagaagagtg    1140
agagagagct attagagatt gtgaagaaga atttcgatct ccgccctggg gtcattgtca    1200
gggatctgga tctgaagaag ccaatttatc agaggactgc agcctatggc cactttggta    1260
gggacagctt cccatgggaa gtgcccaaaa agcttaaata ttgaaagtgt tagcctttt    1320 tccccagact tgttggcgta ggctacagag aagccttcaa gctctgaggg aaagggccct    1380
ccttcctaaa ttttcctgtc ctctttcagc tcctgaccag ttgcagtcac tctagtcaat    1440
gacatgaatt ttagcttttg tgggggactg taagttgggc ttgctattct gtccctaggt    1500
gttttgttca ccattataat gaatttagtg agcataggtg atccatgtaa ctgcctagaa    1560
acaacactgt agtaaataat gctttgaaat tgaacctttg tgccctatca cccaacgctc    1620
caaagtcata attgcattga ctttccccac cagatgctga aaatgtcctt gtgatgtgca    1680
cgtaaagtac ttgtagttcc acttatagcc tctgtctggc aatgccacag ccctgtcagc    1740
atgaatttgt aatgtcttga gctctattat gaatgtgaag ccttcccctt atcctccctg    1800
taacttgatc catttctaat tatgtagctc tttgtcaggg agtgttccct atccaatcaa    1860
tcttgcatgt aacgcaagtt cccagttgga gctccagcct gacatcaaaa aaggcagtta    1920
ccattaaacc atctccctgg tgcttatgct cttaattgcc acctctaaca gcaccaaatc    1980
aaaatctctc cactttcagc tgtcttttgg aggacgtacg taataaggtt ttaatttagt    2040
aaaccaatcc tatgcatggt ttcagcacta gccaaacctc accaactcct agttctagaa    2100
aaacaggcac ttggcagcct tgtgatgtca tacagagaag tcacagggca gtacctgagg    2160
gtctgtaggt tgcacacttt ggtaccagat aacttttttt tttctttata agaaagcctg    2220
agtactccac actgcacaat aactcctccc agggttttaa ctttgtttta ttttcaaaac    2280
caggtccaat gagctttctg aacagctggt gtagctacag agaaaccagc ttccttcaga    2340
gagcagtgct tttggcgggg aggaggaaat cccttcatac ttgaacgttt tctaattgct    2400
tatttattgt attctggggt atggcgtaag tacagagaag ccatcacctc agatggcagc    2460
ttttaaaaga ttttttttt ttctctcaac accatgattc ctttaacaac atgtttccag    2520
cattcccagg taggccaagg tgtcctacag aaaaaccttg ggttagacct acaggggtc    2580 tggctggtgt taacagaagg gagggcagag ctggtgcggc tggccatgga gaaagctgac    2640
ttggctggtg tggtacagag aagccagctt gtttacatgc ttattccatg actgcttgcc    2700
ctaagcagaa agtgcctttc aggatctatt tttggaggtt tattacgtat gtctggttct    2760
caattccaac agtttaatga agatctaaat aaaatgctag gttctacctt aaaaaaaaa    2820 aaaaaaaa                                                              2828
```

<210> SEQ ID NO 2
<211> LENGTH: 3090
<212> TYPE: DNA
<213> ORGANISM: Homo sapiens
<220> FEATURE:
<221> NAME/KEY: misc_feature
<222> LOCATION: (1)...(3090)
<223> OTHER INFORMATION: carnitine palmitoyltransferase II (CPT-2) mitichondrial protein cDNA

<400> SEQUENCE: 2

```
ctcatatcta gaattttggg taggtacttt gaatcattac gatctatcta cttcttaggt      60
gaggaaatag aggtttaaaa tttagtccac agtctcgcaa ggatggagcc tgatcaaat     120 tttgggttat cagattccaa tcacgttcct tagcttttct ttttttttc caactccagt     180
```

| | |
|---|---|
| ttctgtcttg ctccaaaaaa ggggaaggag cggctgcggc gctcggtttc ccgcctccta | 240 |
| gggaagggaa gggagacgag caacgcgagg gctgggggcc ccttccgggc ggggcctact | 300 |
| agtgggcggg gcctgtcagt gagcggcccc tgcccgaag gagccagtcc ggggcggagc | 360 |
| cgatggcctt acaggggccg gaagtggcct gcggcggag aagtgcctca ggagtcctga | 420 |
| cgcagtgtct tgggcgctaa cggcggcggc ggccttgtgt ttagactcca gaactcccca | 480 |
| cttgccgcgt tctcgccgcc gcaggctccc gggacgatgg tgccccgcct gctgctgcgc | 540 |
| gcctggcccc ggggcccgc ggttggtccg ggagccccca gtcggcccct cagcgccggc | 600 |
| tccgggcccg gccagtacct gcagcgcagc atcgtgccca ccatgcacta ccaggacagc | 660 |
| ctgcccaggc tgcctattcc caaacttgaa gacaccatta ggagatacct cagtgcacag | 720 |
| aagcctctct tgaatgatgg ccagttcagg aaaacagaac aatttttgcaa gagttttgaa | 780 |
| aatgggattg gaaagaact gcatgagcag ctggttgctc tggacaaaca gaataaacat | 840 |
| acaagctaca tttcgggacc ctggtttgat atgtacctat ctgctcgaga ctccgttgtt | 900 |
| ctgaacttta atccatttat ggctttcaat cctgacccaa aatctgagta taatgaccag | 960 |
| ctcacccggg caaccaacat gactgtttct gccatccggt ttctgaagac actccgggct | 1020 |
| ggccttctgg agccagaagt gttccacttg aaccctgcaa aaagtgacac tatcaccttc | 1080 |
| aagagactca tacgctttgt gccttcctct ctgtcctggt atggggccta cctggtcaat | 1140 |
| gcgtatcccc tggatatgtc ccagtatttt cggcttttca actcaactcg tttacccaaa | 1200 |
| cccagtcggg atgaactctt cactgatgac aaggccagac acctcctggt cctaaggaaa | 1260 |
| ggaaattttt atatctttga tgtcctggat caagatggga acattgtgag cccctcggaa | 1320 |
| atccaggcac atctgaagta cattctctca gacagcagcc ccgccccga gtttcccctg | 1380 |
| gcatacctga ccagtgagaa ccgagacatc tgggcagagc tcaggcagaa gctgatgagt | 1440 |
| agtggcaatg aggagagcct gaggaaagtg gactcggcag tgttctgtct ctgcctagat | 1500 |
| gacttcccca ttaaggacct tgtccacttg tcccacaata tgctgcatgg ggatggcaca | 1560 |
| aaccgctggt ttgataaatc ctttaacctc attatcgcca aggatggctc tactgccgtc | 1620 |
| cactttgagc actcttgggg tgatggtgtg gcagtgctca gatttttttaa tgaagtattt | 1680 |
| aaagacagca ctcagacccc tgccgtcact ccacagagcc agccagctac cactgactct | 1740 |
| actgtcacgg tgcagaaact caacttcgag ctgactgatg ccttaaagac tggcatcaca | 1800 |
| gctgctaagg aaaagtttga tgccaccatg aaaaccctca ctattgactg cgtccagttt | 1860 |
| cagagaggag gcaaagaatt cctgaagaag caaaagctga gccctgacgc agttgcccag | 1920 |
| ctggcattcc agatggcctt cctgcggcag tacgggcaga cagtggccac ctacgagtcc | 1980 |
| tgtagcactg ccgcattcaa gcacggccgc actgagacca tccgcccggc ctccgtctat | 2040 |
| acaaagaggt gctctgaggc ctttgtcagg gagccctcca ggcacagtgc tggtgagctt | 2100 |
| cagcagatga tggttgagtg ctccaagtac catggccagc tgaccaaaga agcagcaatg | 2160 |
| ggccagggct ttgaccgaca cttgtttgct ctgcggcatc tggcagcagc caaagggatc | 2220 |
| atcttgcctg agctctacct ggaccctgca tacgggcaga taaaccacaa tgtcctgtcc | 2280 |
| acgagcacac tgagcagccc agcagtgaac cttgggggct ttgcccctgt ggtctctgat | 2340 |
| ggctttggtg ttgggtatgc tgttcatgac aactggatag ctgcaatgt ctcttcctac | 2400 |
| ccaggccgca atgcccggga gtttctccaa tgtgtggaga aggccttaga agacatgttt | 2460 |
| gatgccttag aaggcaaatc catcaaaagt taacttctgg gcagatgaaa agctaccatc | 2520 |
| acttcctcat catgaaaact gggaggccgg gcatggtggc tcatgcctgt aatcccagca | 2580 |

-continued

| | |
|---|---|
| ttttgagagg ctgaggcggg tggatcactt gaggtcagga gtttgagacc aacctggcca | 2640 |
| acatggtgaa accttgtctc tactaaaaat acaagaatta gctgggtgtg gtggcatgtg | 2700 |
| cctatatccc agctactggg aggttgaagc agaattgctt gaacccagga ggtggaggtt | 2760 |
| gcagtgagct gagatcacac cactgcactc cggcctgggc gacagagcga gactgtctca | 2820 |
| aaaagacaaa aaagaaaaaa aactgggggcc tgtgtagcca gtgggtgcta ttctgtgaaa | 2880 |
| ctaatcataa gctgcctagg cagccagcta caggcttgag ctttaaattc atggttttaa | 2940 |
| agctaaacgt aatttccact tgggactaga tcacaactga agataacaag agatttaagt | 3000 |
| tttaagggca tttaatcagg aggaaaggtt tggaaaacta actcaggtgt atttattgtt | 3060 |
| taagcagaaa taaagtttaa tttttgcttg | 3090 |

<210> SEQ ID NO 3
<211> LENGTH: 120890
<212> TYPE: DNA
<213> ORGANISM: Homo sapiens
<220> FEATURE:
<221> NAME/KEY: misc_feature
<222> LOCATION: (1)...(120890)
<223> OTHER INFORMATION: carnitine palmitoyltransferase II (CPT-2)
    mitichondrial protein clone RP5-1024G6

<400> SEQUENCE: 3

| | |
|---|---|
| gctgtgtcgg aggaagtcag caagtggaga atagagaatc ccaccccctcc tctggagcag | 60 |
| agaactccct gggcctggtg tttggagaac acgcctggga aacccggtc tccagcatcg | 120 |
| agtctatgct cccctgcaag gcactttcac ccttttcctc acccttcag cattacctcc | 180 |
| tactccttcc gtcaccctc cagctccaat gacaccaaac cactgcaggg tcctggaacg | 240 |
| ctgcatcctg tctcaggctt ctgcaccttt gcctgtgcta tttccttggc ctagaatgtc | 300 |
| cttccttgtc atgaaagtta caggttaaat ccccctcttc ttcgaagcct tccctgatta | 360 |
| ccctagatac aataccttct ctttttctca ctctaactca ggcccttcac agtcaccagc | 420 |
| tggggattca cctagctccc ttttaagtgg ctctgacaag gaaataagaa tctatgaaaa | 480 |
| taaaatcaaa tctctgtttg ttaccatgtc atttgaaatc acctcaatgg agaatcctca | 540 |
| aagttggagg gtatattggc aggggcaggg gggtgctagg gatagcctga ggagcaaggt | 600 |
| gttgtataat gggcagcaag tggcctcaga gatgcttctg gggaggcttg agctgcacag | 660 |
| actgagatgc tatggcaaag aagagacatg gtgttggcga aaataaatgc caagtcacag | 720 |
| gtgcagctgc ctcaccctgc agaagcaggc gtgcagttga gctgttcttc accaggccct | 780 |
| ctgcttgggt tatgctgtgg ggagagcagc aggggttgac ttatttgcta atgattaatg | 840 |
| attaatgatt cgccagggct acaggcgggg ccaacccagc ctgggaaggc ggggatagga | 900 |
| aggcttccca gaggagacgt ggtttaggca gaggcctcaa taagccaggg aaggggggtgc | 960 |
| tggtcaaggg agaggggaga cgacagtctg atttaggccg gaggcgtgac agcagggcct | 1020 |
| cccagggcta gcagtgcatc ggtgggctgc agtggccatc ggggctgggg ccttacacct | 1080 |
| tccaccatgt gtcaaaatga gtttaggtct ggccgggtga gctcccatct gagtctgtcg | 1140 |
| tgacgacagc tcggggtatg ttggctgctt ccagagaca taccagaggc gccttaatct | 1200 |
| ccctgacacg tcttcccagc tcgctggaag ctgggccctt ccgggaaggt tttctgtggg | 1260 |
| caacaaatgc agctgatcca gctgggtgtg gattcctgcg agctttagtc accgaggggc | 1320 |
| tgtcctgacc tcgctgaggg ctagtccttt cccacatttg cctcagagga tgggagaaag | 1380 |
| tgactctgtg gtggcaactc agacacacgc cttccttttt cccttccagt ccccgtctca | 1440 |

```
aatctgtcac ttaatggaaa tgaggcctgg gcgcccataa gcccctgagc cgctctgtgt   1500
tgagcaccga ctgtgtacca ggctctggct gggtactctg acaccttcac ctagaagggc   1560
cctgaccagg gggagccagg gacccctcca cattcactgg gtcagtcaag cctgggggct   1620
ctaagtctgt gcagtacaat tacatagcat ccattacact acttaaattg aaattaatca   1680
aaattaaata ggaccaggcc cagaggttca tgcctgtaat cccagcactt tgggaggctg   1740
aggtgggagg atggcttgag cccgggagtt tcagaccagc ctgggcaaca tggggagacc   1800
ctgcctatac aaataatttt aaaaattcac tgggcatggt cgtgtgtgcc tgtggtctca   1860
ggtacttcgc aggctgaagt gaaaggatca tttgaagcct gggaatttga agttgcagtg   1920
agccgtgatg gaactgcact ctatgctggg caacagtgta ggatcctgtc tcaaaaaaaa   1980
atttatatag tttagaattc agtccctccg ttgcactagc cacatttcaa gggctcaata   2040
gctgtatgtg ccagtagct accatgttgg acagcacagt tagagaacgt tccatgatc   2100 acagaaagtt ctactgaact ctctacagtc accctgaacc aaattcaaag ctcagccttt   2160
ggcttggaag gtgtgcgact tgccgaagt tagcgaacct ctcagagcct cttttctgtg   2220
cctataaaag cccatgcact ttccattgca tcatacttcc tctcatttgc atataaaagt   2280
taggacaaag tataaagtta aaccctccag ccagtttaga ttaggtttcc aaattagtta   2340 ggattttttgt taataaatac taggaaacta aatcaagctg gctttggtta aaagggaatt   2400
tataagcagg gctgactgtg taatttgtga ggcccactgc aaaatgagca cgtggggctc   2460
ttctttccaa aagcaggaaa aaagtgcatc aaaggtacta aaatatatag ctttatttct   2520
tccacagttt ctctctctca acttatcatg atgtttttta tttgtgattt tgtcattctt   2580
aagtaaataa aaataacaat tttaaattag tagcattaac tttatcattc acctttttttt   2640 ttttttttt tttttgagct ggagtcttac tctgtcaccc aggctggagt tctgtggctt   2700
gatctcagct cactgcaacc tctgcctcct gggttaaaga gaatctcctg cctcagactc   2760
ctgagtagct gggattacag gcgcacacca ccacgcccgg ctaattttttg tattttttagt   2820 agagatgggg tttcaccatg ttggtcaggc tggtctcgaa ctcctgacct caagtgatcc   2880
gcccaccttg gcctcccaaa gtgctgtgat tacaagcatg agccaccgtg tccggccctt   2940
catcttcaca ctcactgtgc aatgccagtt ttaaatgcaa atataagagc atttaactca   3000
catgcagaat caccaaagtt atacagtttg tatttagtag ctcatacatg cgtgtgtatt   3060
tcattttttg ccagatggtg gaaatgctgc acaaaactaa tccaactgtt tttatttcac   3120
ttctcaatgc atatccattc catctgtcct ctctacccttt gactcactga tgagtaagga   3180
agaactggaa agaaaaggaa ctctggtggt cctctcattc ccttgctgtt gatgttatca   3240
ctttcagtgt ttaagtagtt ggctaatgca ggtgagtaac actagtaaga aaggatatga   3300
taaaattcct tggtcgtttg cattttaga atgcaatttt ttgttcttcc tatgttcgaa   3360
acaagttctg gtttgaggaa agtgaggctt ctcgtgagtc ttggtgcctc tgcttactta   3420
gctgtggaca taacacactt acctgacacc tatttgagtc ttgctgaact cccatgcgtt   3480
gccagtttac cagaactctg tgctcatggg acattacaca cgctgtatga ggatggagtg   3540
gcaactacca gtggcggcat gtatattgga cgtgttttttt ctgtttgtgt gtatactcta   3600
ttgtcccatc agactttgct tataagacac aagttcaaag ataaaattat taagaattta   3660
gtgacagtga caacagagca ttaaaccaag cacaggggcc cttctgagca tggggccctg   3720
tgctactgcg cagatcatag aaccaggaaa ccggtcccat ttataagacc aggtgagcat   3780
```

```
gggttttgca gaacccaagg acaagagcag aactgaactg caaagaccct ctgaaccagg    3840
tacttgattg ttaatggaat tatctctcac accagctctc ctttctacat gtctgatttg    3900
tccattcatt cttcattcaa catatatatg ttgagaggtg gcataaggta ttgattaaga    3960
gcacaaactc aggaaccaaa tgacttgtgt ttgaatctta gctccttcac ctactctttt    4020
tggaactgta ggcaagttac tctgtgttcc agttttagtt ttctcatatt gagtgtaggg    4080
ataataatat tctaccttat agggttgtta taaggagcaa atgaattaca tgtatgaagc    4140
ttaagacagt tgtctgatca tagtaagcac tatctatcta tctatctata tctatgttac    4200
tattattact atgtgccaga catattccgg acacttggaa tactgtaata aaccgaaata    4260
gacaacaatc cctgctttta tagagcctac atttggtgat gacatttatg ttacattatt    4320
ctttctctaa tgaacccatc tccactacta ctgtggtcca cagggaggaa gcatggccac    4380
cagcagctct gtttcactcc agtgccacag ttctcaggga aggttctgac tggcccagtt    4440
tagaccaatc tcctgcagcc agtaggggca gggagcaggg tcacattatt tacagttgct    4500
gcttctatgg taactctgta gatgtgtgta gtagcagtta gaaaagtgga tacatgaggc    4560
agacacagca aaatatctag tacattgtcc caggcactca gctcttggca tggcttgctt    4620
agtaaaacct tggttttctg ttctttcttg tgtaaaatgc ctaacatctt atatccagtg    4680
aggctgctct agaacttagg gtcagtggct cgaggttcct tgttgcttgt cttcttctct    4740
gatgtctgcc tcggcccttt atggcagcag gcacctgggg cctcacccac agagtgcaca    4800
ggattcacca atgttgttga gttgttgatt catcaatgtt gttgaaaaaa tgttaatttt    4860
cttctctgtg atatagcatt ccatgatatg aatggaatat tatatataag atactgttta    4920
tgaacgtttg tggttttttt ttccagtttt tgaccatcat tttaacaacg ctgctagaaa    4980
cattcttgaa tactaatgta catgtacaag agtttctcta ggatatatac gtagcaatag    5040
aattgctagg tcacagatta tgcagatggt caacgttagt aggtaataac tgtttccaaa    5100
ttagttttac caactaatat gttcacccac aatgtctgta agttcccatt gttccgcatg    5160
gttactgaca tttgatattg attaattttt aactcttgcc aatctggtag gtgtgaaatg    5220
gtgttccata gtggtttaaa tttgcatttc cctgattagt gagactgaat atattgtcct    5280
atgtttgtga gtcatccatg cctcctcttt ggtgaaattg ctgttcattt gcctattttt    5340
aattgggttg tttgtctttt cacatacatt ataaatattc tttatataat ctggatatta    5400
actctttatt gtttatatgt gttttcctgt ttatgactta tctgtcttta gataaacaga    5460
agttctaact tttaatgtaa ctgaatctat cattctttt tgttatgact tgtctctgtc    5520
ttattttaaa aacctcccac tccagtaaag ttattcttct gtgtaaattt ctaagagtag    5580
tttacttttc cttttctcat acaggtaatt aactaacctg gttaaagact gatgtaagag    5640
tctaatatcc cgtttttcttt aagatctact aattgtccta gtatcacata ttgaaaaatc    5700
tatccttcca cctgaaacta aaatggctgc tctgaaataa aatcaagttc tgtatatgtc    5760
tgggtctgtt tctgggttcc cattggttgg tttgtctata tctttgtcaa taccactctt    5820
gtctggatca ctataagtta atgataattt ttgatacttt gcaaggcaag tcctatcttt    5880
gtcttcttca ggaatgtatt agttttcact gggcatggtg gttcacacct gtaatcccag    5940
cactttggga ggccgaggtg ggtggattgc ctggggtcag gaattcaaga ccagcctgac    6000
aaacatggtg aaaccccgtc tctactaaaa atacaaaaat tagcagggca tggtggcgca    6060
tgcctgtaat cccagctact tggaaggctg aggctgagga atcacttgaa cctgggaggc    6120
ggaggttgca atgagccgag atggcgccac tgcactgcac tccagcctgg gcaacaagag    6180
```

```
caaaactctg cctcaaaaaa aaaaaaaaaa aaaggaatgt attagtcttc aataaaacgt    6240
tttaaaggaa aacttgtcaa gttccagaaa aaaattgaga tttttattgt aattgcatgg    6300
gaacttttaa atcaatttga gagaatgaac atctttatga tattaactct tccaatttgt    6360
gaacatatct ttcaatttat ttagatcttg tttctatagt tttattttgc tccataaaag    6420
tgttgaataa cttttaaag atcattctc atatatctta tttttatgct actgtaaata     6480
gcgttctgtt ttattgcatt ttctgttttt tgctatagac ataaaattga ttattgcacc    6540
ttgatttttt tcttttcttt tcttttttt ttttgagaca gagtcttgct cttttactca     6600
ggctgaagtg cagtggctct atcttggctc actgcaaact ccgcctcctg ggttcaaggg    6660
attcttctgc ctcagcctcc cgagtagctg gactatagg catgcgccac catgccctgc     6720 taattttgt attattagta gagatggggt ttcaccatat tggccaggct ggtcttgaac      6780
tcctgacctt gggatctgcc tgccttggcc tcccaaagtg ctgagattac aggcgtgagc    6840
aaccgcacct ggcctgcacc ttgattttgt attctgttga ctgactatat tctcttaatc    6900
tttggggttt tctatgtaga taagcatatc atcagcaaac aataaatagct ttgcttcttc   6960 catttcaatc cttacaccat attttatata tgtatattat atatgtatat atgttatgta    7020
ttttttattt gttgcttgct tgcttgtttg tttgttcacc ttacagcct ggctgagccc      7080 tctagcacaa aactgaataa aaatcatgat gtgaggcact caggtcttgg tcttgatctt    7140
aagaggaatg ctttcaacat tttaccatta gtattgccat tgctataggg ggtttttgcc     7200 catgccctt atcagattaa gaacgttctc ttttattcct agtttgttaa aaaggggttt       7260 tgcttttgg tttttgatg ttgaattta ttttatttat tttattttt tgagacaggg          7320 tctcgctctg tcacccaggc tggagtacaa tggcatgatc atagctcaca gcaatctcca    7380
cctcctgagc tcaactatcc tcccacctca ccctcccaag tagctgggac tacaggcatg    7440
cgccaccaca cctggctaat ttttgtagag acgagtttca ctatgttgcc caggctgctc    7500
tcacactcct ggcctcaagt gatccaccca cctcagcctc ctcacgtgct gggattatag    7560
gcatgagcta ccgtgcctg ccagatgtta aatttttgtc aaattatttt tctcttttaa      7620
tttattaatg tggtgaatta tattaaataa ctgtgaaaca ttgtaacaat cttgtataac    7680
agaaataaac acaacttggc catgatttct tcttcttatt gttatcatta tttttattta    7740
aacgtggttg ctttatattg cacttttaaa actcacaaaa agctttacaa tatctgcatt    7800
cctctactta atcatcaaag ctttatggta agacaatgaa aatttatttt catcaattgg    7860
gcatactaaa aaacaatgaa aaattaacaa acaaatctcc ttaatcaaga acattccgta    7920
aaatacacac tctggcatgc gtctgaattc atccctccta aaattagact ttaaaaggct    7980
ttaaaaaaaa tctcaaacag atttcaatac tgactagcct accagaacaa agctgatagc    8040
aagctataaa cagctttcaa tgttgaatgt aatttggggg aagtggagaa gaagaaatta    8100
tctgctgaac ctacatttaa gtgcatctgt tagtaagact tctctaattt aatgaatttc    8160
aacaaagtga acaagttctt tgcctttggt agtttctcgg attttatttt taaacttgtg    8220
acatcttgac taaaggaatg gaatcctggg actagaatat ttaaggaaga ggacaacatt    8280
gaggcgggaa agaggaaaaa taagattagt actttcttag atagctaaaa tgggtaacaa    8340
ataatcccag ctactcagga agctgaggca gagaattgct tgaacccaag aggcagagtt    8400
tgcagtgagc cgaaatcacg ccattgcact ccagcctggg caacatagcg agattccatc    8460
ttaaaaaaaa aaaaaaaaaa aaaagaata ccagagttga tatgtagggt ttagtttgac     8520
```

```
ttatgttttt aaaaaattag ataagtataa catctaaatg gcaaatagaa caattaaaga    8580
tggtctcatt taggaaatgt taaaaactaa ttatcctcaa ttatgtttta aatttgtgga    8640
atgacatagc agatattttg agcatcatta taggatccaa ttaaaattat gcatactgct    8700
attttcactt tttttttttcg agatgagatc ttgcttctgc tgcctaggct gaagtgcagt    8760
ggcacgatca tagctcattg caacatcaaa ttcctgggct gaagcgatcc tcccatctca    8820
gccttcagag tagctaggac tacaggcaca tgccaccatg cccagctaat ttttttttt    8880
ttttggtaga ggctgaatct cactatgttg cccaggctgg tctccaactc ctggccccaa    8940
gcaatcctca tgccttggct tcccacagtg ctgggattac aggtgtgagc cactctgcct    9000
ggcctattta cacttttttt ttttcttttt aacccaacta ctcaacgtgg catattttca    9060
cttttaatat aatttatata tacctgggga agctcttttt gatattatca gtagaggcca    9120
ctaaaaataa tgccagaatt ccagtgagaa gagagtagaa atggaaagaa aatgggagga    9180
taaagaaatt gggtagtaat aagaaacagg atttttaagg ttttctcact agttaactaa    9240
tgccacaaaa ttgcgtattt tggctcaatg tcagtgggct gctggaaggg accaggaaat    9300
gagtgcaata tcctaaccat cccaggtaga ttcttaacta acccatgatt tggatggctc    9360
acttgtgaag ggagtgcttt ggcctcctcg cttcctttct tccttttcct tttttatt    9420
ttttttttg agactgagtc tagctcttgt ttccgagcaa ttttttgagaa atctcaactt    9480
taaaatatcc ctcaagttgc cccctttcat tagtcttgta aataatattg tttaagactc    9540
acacattggt gagagtcagg aattattagg attatttta tagcagacat tgagttcatt    9600
tacttggaaa gaaaaatttt attccgaggt gactttcaga gatttaagtg ctctatttta    9660
ccattgaatg agaattttc tcaaagcaaa tattctctaa gatgctagag tattcagctt    9720
attgggatag tacccttaa cttattaaaa gttacaaagt ctaagaaaaa gcatgcaagt    9780
cttgagaatc actgctgtga attctaacag ggagggcctg aagcctggaa gcctggctga    9840
cagtcctgca gaccagagtg gggacttgtg gtgcctcttc cagtctgccc atggccgccc    9900
atagaccatt tggcatgtac ttcctcccct ctgaggtcca taaaagccct gggatcagcc    9960
agagaagggc agaggatgga gaggacagag agatgactgg cgactggatg atcagctgca   10020
gagaggagct gaaagctcct gctgaaagct gggaagccaa ccgggacctg ccttcagaga   10080
gcagccaccc tctccagggc ctcctgtctg ctgagagctg aacgctggat gagacaacct   10140
gcctacagag aggagctgcc cgctgagggt ctccctctgaa ctgtcctaac actcaacaaa   10200
gcttctcttc gtcttgctcg cccttcattg tctgagtacc ttattcttcc tggatgcagg   10260
acaagaactc gggcaaaggc accactgccc acagaagttt ctggccagaa aagtgacacc   10320
ccaaagatcc cgtaacacta tgagatgcaa agactacaaa tgtttaagtg gaatgatctc   10380
taacctgtaa attacactcc tgtaacaagc aaatgattac atactgtgga agactacaga   10440
acataagtac agaaagctgc tctccaaggc tgcattctca aagcttgaaa agttaattgg   10500
cccatcattt tggtacagta ggtagctagt caagcatgag cagggcagga gagggctccc   10560
tatacctcac cacaaatgtc aggcaaccat caggtgatgg tcaggtggtt gttaactgtc   10620
tgtttaaaat aataattggt tgcagctggt gccagggaaa ggccgtctcc cagtagatag   10680
aaacacctga aacaggtggt cagctgctta atctcaggag ttgggcaact gggctcaagc   10740
atgctcacta agaggcaaaa tggtgagttt aactgataca tgactttcca gggacattcg   10800
gctggtaagg gaagaatgcc tcaagtgagc atgcatacaa ctccagtgaa cacactgtgc   10860
acactcccct cccaagggct ggcaggtcac tgtgcacacg gacagcccaa gggaagaatc   10920
```

```
aggggagaag ggacgcaagg catgccaaca tgtacaaccc caagtcaaag gtgaaatggc   10980
acacttgatc actcaagttg cccaggtggc tctttcccaa gtgtacttta cttcctttca   11040
ttcctgccct aaagctttt  aataaacctt cactcctgct ctaaaacttg cctcagtctc   11100
tccctctgcc tcgtgcccct cggtcaaatt ctttcctctg aggacgcaag aattgaggtt   11160
gctacagacc tgtacagatt cgccgtcact aataatttta gaaagaaaaa agatgaaca    11220
tggattagga gggtctacat gtgggaaaaa aattgcaact aagatatttt agagagccca   11280
cctctagtaa caaagaaaaa aataggcccg gcacggtggc tcacacctgt aatcccagca   11340
ctttgggagg ccgaggcagg tggatcctga ggcctcccca gaagcagatg ctgccatgct   11400
ccctgtacag cctgcagaac tgtgagccaa ttaaacatct tttccttgta aattacccag   11460
tctcaggtat ttcttcatag cagtgagaga acagctaata cggtagccat ctctgggggg   11520
acatcgagga ggctctcatt ctcctagaag tctttccaat tcatattatc ctcagaccat   11580
agttcatctc ttctgtaagc cacaactctg ggccaccagg aaacccagta catgtagttg   11640
tctgcttgcc accgctcaat ttttattt   tatgcattat gtataactat gtatgtttcg   11700
taacttccca acataggctt tcctaattat ctttttgttc cttttataaa caagcttat    11760
tgaggtatga tttacatact gtataattta cccaaagtgc acacttcaat cgttttagt    11820
aggtttactg agttgtgcaa tcatcatgac agtcccattt tagaacactt ccacatcccc   11880
aagagcccct catgcccact tttagccaat ccccattccc atctccaaca ccaggcaatc   11940
actaatatgc tttccatctc catagatttg cctcttctgg acattttata aaaatgcagt   12000
catacaatct gggttctttt ttttctcatt ttactctgca tatgttctag gctcatccat   12060
gtttgcagca tggatcagta gttactccct cttaccattg aatggtaggt actacattgt   12120
atggatgtac cccatttttt tttctactca ctgattgatg acatttgta  ctcacatttt   12180
ggcttttatg aataatgctg ctatgaacct tcatgcaaaa gcttttctgt agacatgttt   12240
catttatctt gagtagctac ctatgagtcc cattgctagg ttgctggata catttatgtt   12300
tacctttta  agaaactgcc aagctgtttt ccaaagtttc cgcaccattt taccttcctg   12360
ccaccaatgt atgaggattc tgatgtctcc acagtgttgc ccacaggtat tattgtctgt   12420
gttcttcatt acagctgtcc taatggccat gaagtggtat ctcattttgg ttttaatttg   12480
catattacta atgactaata atgttgagca tcttttcatg tgcttattaa tcatttatat   12540
atcttcttca gtgaagtgtt tactcaaatc tcttccctat tttaaaaatt aggggctggg   12600
cgtggtggct catgccttgt aatcccaaca ttttgggagg ccgaggtggg tggatcacga   12660
ggtcaggaga tcgagaccat cctggctaac atggtgaaac cccattttta ataaaaatac   12720
aaaaaattag ctgggcatgg aggcacgcag ctgtagtccc agctactcag gaggctgagg   12780
caggagaatc gcttgaaccc gggaggcaga ggttgcagtg agtcgggatc gcgccactgc   12840
actccagcct gggtgataga gcgagactcc atctcaaaaa aaaaaaatt  gggttgtctt   12900
cttcttactg cgttgtaaga gttccatata ttctggatat gaaagccttt ttgttgttgt   12960
ttgttttgtg ttttgtttt  ttggagacag agtctcactc tgtcacgcag gctggaatgc   13020
cagtcatatg atcatagttc actgaggcct caaattagtt cctgggctca agcaatcctc   13080
ctgcctcagc cttccaagta actgggacta caggtgcatg ccaccatgct ggctaaaat    13140
ctttatcagt ggccaggcgc agtggttcac atctgtaatc ccacactttg gcaggccgag   13200
accagcggat cacctgaggt tagaagtttg agaccagcct ggccaacatg gtgaaacccc   13260
```

```
gtctgtactg aaaatgcaaa aattagccag gtgtggtggc aggcgcatct aatcccagct    13320
actcaggacg ctggggcagg agaatcactt gaacctggga ggcagaagct gcagtgagcg    13380
aagaccatgc cactgcactt cagcctgggc aacagagcaa gattccgtct caaaaaacta    13440
aactaaaata aaataaaaaa cctttatcag aattatgatt tgcaaatatt tactcccagc    13500
ctgtcgctta tctttctcat ttacttaata gtgactttga agtataaaa gtgtgtaatt     13560 tttattaact ccaatttatt gatttttttc atttatgagt tatgctttta atgttgtatc    13620
tgagaactct gcttaactgg agatcacgaa gagtttctcc tatgctttct tctaaaagct    13680
ttatagtttt atcacttaag tttaggtcta caatccattt tgaattaatt tttgtgtgtt    13740
gtataagtta aggatccaaa ttcacctttg tggttgggtg tgatggctca cacctataat    13800
cctagcactt gggagttga ggcaggaaga tggtttgaag tcaggagttt gagaccagcc     13860
tggccaacat agtaagaccc ccatctctac aaaaaattt tcaaattta gcctggtgtg      13920 gttgtgcatg ctggcagtcc taactactca ggaggctgaa gcaggagagt tcaagagttc    13980
aaggtcatag tgagctatga tcatgcttgc attccagcgt gggtgacaga gtgaaacctc    14040
atctcaagca atcaatcaat cagctcatct tttttatgag gataaccaat tgttccagca    14100
ccattattgg aaaaccttgt gttatggttt ggatagttgt cccctccaaa tctcatgttt     14160
gaaatgtgat cctgagtgtt agaggtgggc ctagtgggag cagtctggat catggggatg    14220
ggccgctcat gaatggcttg gtgccatcct cgcagtagag tgagttttg ctctgttagt     14280 tcactcaaga gctggttggt ttttgaaaga gtctggtgcc tcccttcttt ctcattcttt    14340
tgtgctcttt cttgccatgt gacacacctg ctccccctca ccttctgcct ggagtaacag    14400
ctgcctgagg cttcatcaga agctgggtgg atgctggagc catgctttta tagcctgcag    14460
atccatgagc caattaaacc ttttttcttt ataaattgcc tagtctaagg tattcccttta   14520 tagcagcaca aaatggacta atacaccttg ttgatttctg ataaccctat tgtggtcaga    14580
aaatgagaat atatgatagt aatcctttga atagacgtgc tttatgatac tcagttttca    14640
taaatgctcc acatgtgctt ggaaagactg tgtattttgc agatgagtcc agtgttatat    14700
gcatatccat tagattaaac ttgagaatcc attcgttcaa atctcctgta tctgtgctca    14760
tttttttttt ttttggtct acttgatcta tcaattgatt gaaacatgtt aaaatctacc     14820
attctgaggc cgggcacagt ggctcacgcc tgtaatccca gcactttggg aggccgaggt    14880
gggcggatca cctgaggtta aagtttgag accatcctgg ctaacacggt gaaaccccgt     14940
ctctactaaa aatacaaaaa caaaattagc cgagcatggt ggcaggcacc tgtaatccca    15000
gctactcggg aggctgaggc gggagaatgg cgtgaactcg ggaggtggtg cttgcagcga    15060
gccaagatcg cgccactgca ctccaacctg ggcgacagag cgagactccg tctccaaaaa    15120
aaaaaaagtg tttgattagg tcaccttctc catgattcct tcattagtaa gttgttccca    15180
ggagtaattt gtgaacactg tggggacttg gcctctgcct tctcagagct tagcgttgag    15240
cagcagatag aaaatgtacc atcaacctac ttacaaatct gcaaatgggc ctgccttcca    15300
gaatttcact tgtaaatcca tgtttagtta ttagaataat ttattctttt gggggattaa    15360
aaagttatac actcttctgt atattggatt cttggcccca ttgatggaaa aaacatttct    15420
tcctttatac ataattattt acagctactt atgatggggt tgtggctcag aaaatccatc    15480
atgaagtcaa agaatggtta agtcaagcca acctatgttg ggaaccacct gtatagtgat    15540
atatattaat atttatattg aaaaatcata ggagaaaaca tgtagctcaa aaaaaaatac    15600
tactttcttt gtgcctgaca cagagtggat actacataaa tatatgtata caaatattat    15660
```

```
agataaaact aactttcttt tggtatctgt taccttcttt aattttcaaa gttgatgcat   15720
aaggtggatt ataggaagaa aaggtggttg agggccacag gcagagaagc tggttccctc   15780
cctcaagtcc aagaggagag ctcaggccag agattggaga tgaggccaaa gaggtctgct   15840
ggaccctgaa ccagaatgag aacatctgaa tgacttctga gcagggcagg ggcccaggca   15900
tcgtggctgc cagtcacatg gggtgtggga agcctggcct gggccaaagg tccagggcca   15960
cagagtattg tcctatgaag gcaagaaggc ccctagccct aggcccctcc ctgttcccac   16020 agtgggggttg tgtacatgct cactcggatt ccacagggca ggggtcacat agctgaggcc   16080
acaaagccag tatggggaga gcctggtgct cccccagcca cctgactatt ccattccct   16140 gtggctggtc cacagggaac catggcatcc tggttgcagg tacccaccca gagaggagtg   16200
gaggggaaag gaaaaagggg tgccttttcc ttgagggaag gggcctggtc atttgcttct   16260
gataggccct gatcagccct gtaataaatt ttgaatgagt tactaaattc tgattttcaa   16320
gaactaaatt ttaggtagaa aacaatatta aaaattaaaa gtcaaaccaa aatttaaaaa   16380
actacttaag tgaccaggca cggtggctca tgcctgtaat cctggcactt tgggaggcca   16440
aggtgggtgg atcacgaggt caggagtttg agaccagcct gaccaatatg gtgaaacccc   16500
gtctctacta aaaatacaaa aattagctgg gtgtggtggc gtgctactgt aatctcagct   16560
acttgggagg ctcaggtagg agaattgctt gaacctgaga cagaggtt gcagtgagcc   16620 aagatcatgc cactgcactc cagcctgggc aacagagtga gactccgtct caaaaaacaa   16680
aacaaaaact acttaagcat aagtcaaaaa acaagagaca aactgggaaa aattatttgc   16740
agctcatatc accaaggatt aattcccta atatataaaa agcttctaga aataaagaaa   16800
tacaagatta ttaattgatg tggttttgct gtgtccccac gcaaatctca tcttgaattg   16860
tattatagtt cccataatcc ccatgtattg tgggaggtaa tttaatcatg ggggtggtca   16920
acgtcatgct attctcatga cagtgagtga gttctcatga gatctgatgg ttttataagg   16980
ggcttttccc ccttttgctc ggcacttctc cttgttacca ccttgtgaag aaggacatgt   17040
ttgcttcctc ttctgccacg attgtaagtt tcctgaggct tccccagcca tgctgaacta   17100
tgagtcaatt aaacctcttt cctttataaa ttacccagtc tcaggtatgt ctttattagc   17160
agcatgagaa tgaactaata cctcaatctc acagaaaaaa gagcagaaga cacaaaaagg   17220
tagtttacgg tcaaagaaat acagatggct ttaaacatat gcaaaggtgg gcaacttcat   17280
tcaataaata tagattaaaa ctacactagg tggctgggca aggtgtctca cacctgtaat   17340
cccagcactt tgggatgcca aagtgctagg attgctttaa cccagcagtt caagaccagc   17400
ctgggtaaca tagagagact tcatctccac aaaaaaataa aaaattaact gggcacggtg   17460
atttgtgctc gtagtcccag ctactcggga gactaaggtg aaaggatctc ttgagcctgg   17520
aaagtcgagt ctgcagtgag cagtgatcat accactgcac tccagccttg gtgacaaagc   17580
gagaccctgt ctcaaaaaca aaacaaaaca aagtacacta ggctacaact tttcacctca   17640
cagactggca aaatcccaac acattctgtt ggtaagtttg tggtgaagca aaatgctctc   17700
attcattgta gatgggaatc cttaaggagc agcaatttga caacatctat gacatttcca   17760
agtttattta ccctttgatc ctgcatctca catctaggaa ttcatcctct gatatgcaca   17820
agcacgaaat gacacatgtg caaggttagc aactgccata atagcaaata gtaacagcaa   17880
aagatggaaa taacctacga tcattcagtg ggaattggtt agtctgtgat acatccacac   17940
gatgacttca tagggatgta tagaaaataa taaactttgt acctaaatgg aaagatctct   18000
```

```
agcatacatt aagtaataaa actatggtgc agattagtaa ttgtgtaaga aaagagaaaa   18060
caagaataaa caccctgtgtt accagtattt atgaaagaga cattggaaag acacattaga   18120
aactaagagg aatgtgtgtt tattaacaga gagcagcggt tctcaaactt cagcgtggat   18180
tagcatcaca gggagggttt gttaaaatgc aaaccactgg ctcccgctcc tacagcttct   18240
gattcagtgg gtgcggagtg gagccacaaa acctgcattt ctttctttt tctccttttg     18300 cttttttttc ttttttcttt ctttctttat tttattttat tttattttt gagacaggat     18360 cttgctgtgt catcttgctg tgtcacctag gctggagtgc agtggcgcaa tcctagccca   18420
atgcaggctc atactcctgg gctcaagaaa tccttccgct ttggcctccc aaagctctgg   18480
gattgcgggc gtgaaccacc gtgccctgcc taaaaatgtg catttctaac aagttcccag   18540
gggtgctgac gctgccagtc agggaaccaa gtttgggcca gaaaatggaa tggagttaga   18600
ggctggagca ggtcttctca gggtacatct tttctatttt gattttttaa aaacttgcaa   18660
atctattacc tactcaaaaa taagcttaat tcaaaaaacg tttaaaatgt tcaataaaag   18720
aagctgctcc tcagtcactc cctactttct tagcttgttt tgttttttctt tacaacaatt   18780 aatattgtac ctaaaattat gctattttt ttttacttt ctctcccaac tagaataggg     18840
taaggacatt gtcttctatt tccctctatt tccaacacta atattgtgcc tgccacgtag   18900
taggtactca agaaatagct gtttggccag gtgtggtggc tcacgcctgt aatctttggg   18960
aggctgaggt gggtgaatca cttgaggtca tgaattcgag accagcctgg ccaacacgta   19020
tttttctcta ctaaaaatac aaaaattagc ttggcatggt ggtgtatgcc tgtagtccca   19080
gctactcagg agactgaggc agaggaatct cttgaacccg ggaggcagag gttgcagtga   19140
gccgagaacg cgccactgca ctccagtttc agtgacagag caagactcca tctccgaaga   19200
aagaaagaaa gagagaaaga gagaaagaaa gagagagaga gaaggaaaga aagaaagaaa   19260
agaaagagag aaagaaaaag aaagaaagga gggagggagg gagggaagga aggaaggaag   19320
gaagggctgt tgaatgaata aagggaatga atgaattctc ttagtcttca gtagatcagt   19380
gatcttggta agtcactgga gagcttttaa aacatacccca tatccccatc aaatccccag   19440
ttctgagtga attgtttggg ggtggggccc cgcattgagt tgagggtgat gggagcccct   19500
ggtctaaacc acagctatgt agagacttat ggtttggatt gtgcatataa agtgagtata   19560
ttagtatata gaccctgctg cattttttgta cattgctttg ggggctggtt ctgaggctct   19620
ttttgatctg gagaccctaa catccttttcc ctctcttttc tctttcagtt gcctacagat   19680
ctggaagcct tgctgaaaag acaccttaat ggcctagcag ctctttagg caaggagcaa    19740 ttcagatgtt gaatgatgga acacaaaaac ccacagcaga catggtggct gatgcttgta   19800
atcccagcac tttgcaaggt tgaggtaggg ggattgcttg agctcagaag tttaagacca   19860
gcctaggtaa cacagtgaga ccccatccct acaaaaaatc aaaaaattag ctgggcatgg   19920
tggtgcacat ctgtagtccc agcttcctgg aaggctgagg caggaggatc tcttgagccc   19980
aggaggtcaa gcctgtggtg agttgtaatt gtgccactgc actccaacct gggtgacaga   20040
gcaagacctt gtctcaaaaa aataaaataa attggtgttg cggttaatgg tcttcatgta    20100
ggtttttccc gctgtggagc agggcaggac aatgagtctg gatgctggct cccctgcatt   20160
ttagttctgc agtgaagttg tggggcctga gggctcagga cactgtgctg caatcatgct   20220
gcatagtcag agtgaaaaaa gactgggtta gggagtcaca gagtcacagc atccagcccc   20280
attggccatt cagcaattct gtgaccttcc atctctggtc agtttcctca tctgtaaaat   20340
ggggatgcta atgcctgtct cttagggcca ctgggagaat gaaatgttag ttatttttcg   20400
```

```
gcttttcagt tgagttattg catcagctac gttcgtagtt tacccccttg gtttattaag   20460
taatagttgt aaaagtttat aacaggtcac gaattggcgg cacctttgta ttgattggca   20520
ctcaaagtga cttacaaaaa cttggcttaa ttgccaacat ttaaaaacta gggatcttac   20580
ataaaaatct ggatttgtgg cttcattgga aacatctgca tgaccacaac tgctggagct   20640
gagagtcagc tgcttgttcc tgatcccaaa ccccatgact cctggacacc ttctgcctcc   20700 tacccottat ctccctggat tccctgagtg gcttgctgct ggaggctgtg agtacctagt   20760
ttataacccc agttgataaa gtgctttcac ctgcttcatc tcattagact tttacctatg   20820
agggaggtgt tagtattgtt cccttacag gagaagaaac taaagctgag atgttacagg   20880
acctactctg ggttagtaat aacagcaacc gcaataaata gtaatttgta ctggctgttt   20940
accatgtgcc aggcattatt ctaagcactt tacatgttta atttaattct ctcaatctta   21000
tcagatattg tcattattcc tattttatga ataaggaaat tgaggtagtg acaggtcaag   21060
tagatttccc aaagtcacac agccagaaag ctcaaaataa actgaagact tctgggtcct   21120
aatccacact tgttccagag tcctgcagtg caggctttcc ttcctttctc tctttctctt   21180
ctttaaaatg ggtgagtcta tggggcccag cttctggtaa gagtttgtaa gtgttgtttg   21240
gtgggagggg tgggctcgtg ttttgtagga tttgttccct gctgcctcct cagcacctgc   21300
aacaatgcct ggcatgtggc aagagcacaa gaaagagtga aagccaatgg caacagggca   21360
acatcggcag cttttcaggg ctccagtgtct ctaatgattg gcacgggc gaagacctac    21420 tacgtggcat gcagtgggtg ggctcccagc tcttgagcag ctcaagtcca ggtaagaatc   21480
actgacaaat gaaattcaaa tatggggtgt gtgtggacat gagtcgcttg ccaaaaagtt   21540 accttttcccc ttaaaaataa tcaatgaccc acttgtgata tttgcattaa aggctaaaca   21600
ttgaataagg gaagtcaagg ctgcagtgag ctgtgattgt accactgcac tctggcctgg   21660
gtgacagagc aagaccctgt ctcaaaaagg acaaaaaaag aaagaaagaa aagtccgcc    21720 aaacaaaaac cactcggatt tatgattcac ctccttttg ctttaggaaa acaaattatt    21780
ggccataatt ctcaaaatgg agttggaaac tgagctgcta gcactggatg acctctatca   21840
agaaactagc tacatctcag gaacaagata gtttctgttc agttcagcca cccgagctc    21900 ctgcctgggc tgggcgttgg gctgggcacc gaggctgcac agctgctgag ctctggccct   21960
gcctccagga gctcagtctg tgggatatgt actgcacaga gacagctcgg gactctagac   22020
atagctcgga gggtaaggga agtcttcccg ggggaggtgt cagctgggct gagtttcgat   22080
gaactaatgt tgtccaggtg aataagggag agaatggata gaaaaagcgc aaggcagtag   22140
tgagactcat gagagatctg gaaacttcac agcttctgtg gttctccatg gacttgctgt   22200
tgtctgagtg tccacatgag tgaaggtgga agaatgggtg tgggctctct gtccaggcag   22260
gtggggtccc atcagggata atcagtatct gcccagtaat gaagattgtt ttgacacatg   22320
caggtggtgc tgcactcttc cttccaacca ctgcccatta ggggacaggc cgagtcagtt   22380
tgtgcctatc ttgccctatc tccttcaatg aagaaagtga atgctgcaag taatacatgt   22440
tcattgtcaa aaactaagaa aaatgtaaat accccatagg ccaggtgcgg tggctcacac   22500
ctgtaatccc agcactgtgg aaggcaaagg caggtggact gcctgaggtc aggaatttga   22560
gaccaggctg gccaacacag caaaaccccca tttctactaa aaatacaaaa aattagctgg   22620
gcgtggtggt gcatgcctgt aatcccagct actcaggagg ctgaggcagg agaatcactt   22680
gaacccggga ggtggaggtt gtggtgagct gagattgcac cattgcactc cagcctgggc   22740
```

```
aacaagaaca aaactccatc tcagaaaaaa aaaagaaaa ttccccgtaa tccaaccctg    22800
agaaataact ttttagttta tattcccaaa tatttttcta tgtctaaatt ttttgttttg    22860
cagaaacata catattggtt tttttctttt ctgttgtggt aaaatataca ttacagaaaa    22920
ttagcaaaat catggaacca acccaagtgt ctaccagtgg ttgactggat aaagaaaata    22980
tagtacacat acaccgtgga atactatgca gcatgaaaag aatgaaatca tgtcctttgt    23040
agcaacatgg atggaactgg aggccattat cctaagtgaa ggggtggcct gcccctccac    23100
acctgtgggt atttctagtc aggtgggata agagacttag aaaagaaaga agacacagag    23160
acaaagtaca gagaaacaac agtgggccca agggaccggc gctcagcata ccaaggacct    23220
gcaccggcac cggtctctga gttccctcag tttttattga ttattatctt cattatttca    23280
gtaaaaagga atgtagtagg agggcagggt gataataagg agaaagtcag caacaaacac    23340
gtgagcaata gaatctatgt catcattaag ttcaagggaa ggtactatga ttggacgtgc    23400
acgtaggcca gatttatgtt tctctccacc caaacatctc agtggagtaa agaataacaa    23460
ggcagcattg ctgcaaacat gtctcgcctc ccaccatagg gcggttttc tctcatgtca    23520 gaattgaaca aatgtacaat cgggttttat accaagacat tcagttccca ggggcaggca    23580
ggagacagtg gccttcctct atctcaactg caagaggctt tcctctttta ttaattcatc    23640
tcagcacaga ccctttacgg gtgtcgggct ggggacagt caggtctttc tcatcccatg    23700
aggccatatt tcagactatc acatggggag aaaccttgga caataccca ctttcaaggg    23760 cagaggtccc tgcggctttc cgcagtgcac tgttccctg gtttattgag actagagaac    23820
ggcgatgact tttaccaagc atattgcttg taaacatttt gttaacaagg cacatcctgc    23880
acagccctag atcccttaaa ccttgatttc atacaacacg tgtttttgtg agctccaggt    23940
tggggcaaag tggctgggc aaagctacaa attaacatct cagcaaagca attgtttaaa    24000
atacaggtct ttttcaaaat ggagtctctt atgtctttcc tttctacata gacacagtaa    24060
cagtctgatc tctctttctt ttccctacac ctaactgaca agcagaaagt caaatattcc    24120
atgttctcag ttatacatgg gagataacaa tgggtacaca tggacataca ggtgagaaa    24180 acagacagca ggaactacaa agtgggggtg ggctgacaaa ttccctattg tgtgcaatgt    24240
tcaatatttt ggcaaagctc aatatggtgg ggattgggat tctagtgtac ccatcactaa    24300
taaaaatcaa aataaaaaat caaatcacac tacacacatg caaatatgtg acatgatgga    24360
tattttaatt aggttgattt aattattctg taatgtatac atatatcaaa aaattccatt    24420
gtaccctgta aatatataca atcattgcca atttaaaaaa ttcattgtgg gccaggcgtg    24480
gtggctcaca cctgtaatcc cagcagtttg ggggccgca gcagttgaat cacctgaggt    24540
caggagttcg aaaccagcct ggccaacatg gtgaaacccc gtctctacta aaaaatacaa    24600
aaattagtgg ggtgttgtgg tgcatgcctg taattccagc tactcaggag gctaaggcag    24660
gagaatcact tgaacccggg aggcggaggt tgcagtgagc cgagatcatg ccattcattg    24720
cactccagcc tgggcaagag agcgagactt cgtctcaaag aaaaaaaata cattgtgaaa    24780
ttaaaaaaaa atactttctc ataaaattta caatttacaa ttttatccat ttttaagcat    24840
gcagttctgt ggcactgagt gcattcaaat tgttatgcaa cgatcaccat catccatctc    24900
cagaacttta tttttatttt tttattttg tattttcttt tgagacaaag tctcactttg    24960
ttgcccaggc tggagtgcaa tggcacaatc ttggcccact gcaacctcca cctccctggt    25020
tcaagcgatt gtcctgcctc agcctcccaa gcagctggga ttacaggtgt gcaccaccac    25080
ggctggttaa ttttgtatt tttagtagag atggggtttc accatgttgg ccaggctggt    25140
```

```
ttcgaactcc tgacctcaag tgatccacct acctcagcct cccaaagtgc tgggattaca    25200
ggtgtgagcc accgtgcccg gcccagaact ttaaaaatat tctccaatgg aaactctgca    25260
tctattaaac aataactccc catttttcct cctcccagcc cctggcaacc atcattctac    25320
tttctctgaa tgccaccact ctacgtactt catataagta gaatcataaa atatttgtcc    25380
ttatgtggct gacatatttc acttagcaca atgtcctcaa cgttcgccca tgcggtagca    25440
tatatcagga tttccttcct tttaggctgc agagaattat gatcgcgcca ctgcacccca    25500
gcttgggtga cagagtgaga acctgtctct aattaaaaa aaaaaaaaaa aagagtccag     25560
gcatggtggt tcacttctgt taattctacc acttcggaag gccaaggtag gaggatccct    25620
tgagtccaag agtttgagac cagcctgggc aacatgctga acccccatct ctacaaagcc    25680
cacaaaaatt agctgggtgt ggtggcacac ttgtggtctc agctatttag gagactgagg    25740
tgggagaata acttgagcct gggaggctga ggctgcagtg agccaagatc acaccactgc    25800
actctatcct gggtgacaga ataagacctt gtctaaaaaa acaaaagaat tccttcctt    25860 tttaagtctg aataatattc cactgtatgt atagatcaca ttttgcttac ccattcacct    25920
gtcaatggac atttggattg tgtctatgtt ctagctattg tatatactgc ttttttaactt   25980 aatctattat gaacatcttt tcagatgaat aattaaattt tcccaatgcc ttttttagtg    26040
gctgctttat agtacattac ctgactgttc cacaatgtag ttgactattc cttgagggtt    26100
ggaaatttag tttgtttctg attttttgct ctaatataca cggctggaat aaatccccta    26160
cgaacaacat ctttgcatgc ctggctgatt atgactttca gacaaaagaa tgtgcacagg    26220
tttcggcctc cggcacccat tgctgggccc ttgttacaag cagcctgtgc atctgaggag    26280
gcctaagcct gagctgccgc acacatcccc atccctgaag accagagagc accatgatgc    26340
caggggtccc tgcgcctcct ggaagtgaag aatgttgctg cagctccaag ctcgtagggt    26400
aagtctgtgg gaataaatcc aggaggacct tcagggagat tccaatgaac tcctggttat    26460
tctgattctt tggaaaatga aatttttctgg ttaattgaac ttcttgactg gctgaatcca    26520
gtctaaatgc cttcaaatag accccctacct ggcacaccat catgcttccc ttttgttttg    26580
tcagtttgtt tgttttaaat aaggagtttc tctctgtcat ccatgctata gtgtagtggc    26640
atgatcctag ctcactgtgg cctccaactc ctggactcaa gtgatcatct ttcctcagcc    26700
tcccaaatag ctgggactgc aggcttgtgc caccacccc agctgattta aaaaaaaatt     26760
tgtagagatg gggtcttctt ctgttgcctg ggcttgactg gatcgcctgg cctcaagtga    26820
tcctcccacc tcagcctccc aaagcactcc cagcaccacg cctggtccat aatgcatctt    26880
aaaaatgcag atgacatgtt ataattttgc agatattgtt gtgaaatgtc ttgagtgccc    26940
agaacagggc gagccacaca aaagatgcag aagtcgaaca atgctggtgg tggggctaca    27000
tgcaacctgg gagctgctgt tgaactaagt gcccagcagg agcttgtctt cttattattt    27060
actgatcata aaattgagta cagactgctc tcatcctcct tctgtggggt tccttgattc    27120
tcttggttgt ttagactgtg gataaaaggg cttttggtag ttgctgggga aaaggtcag    27180 cagcagcagt gatgagaaag cagcatgccc acaggtggaa gcctcggaag gggttcctga    27240
gaggctgctc cgcctgtgag gtgcgggaag cacagggtcc tccagctcag ttaaccatgc    27300
atagtggcag gcactgctcc taaaacacag agtagtcaat cttcctagaa aatgcaaaat    27360
gctcttctga ctccactttt ttttttttaag tattcaaaac atccttttca agccctgttt    27420
agctcttttt atagctgtgt ttggacagac tgaacagatg aaatttactt aacacttcca    27480
```

-continued

```
gtgtgggtct ttggttgatc actacagagc ctatgttttg aataaaattt tgaatttgca    27540
catcagcaag aattctgcca tgagaattta ttttaacata aaagccaaga ctgttctcct    27600
tgcctccatc cctcggcttt tcctcccctc ctccctcttt cccttgctcc atccacaatg    27660
gaattctcac cattttccca gaacaccatg cccttttttg tctgtgtctt tgcacgctct    27720
tcccattgcc tggagtgccc tctaggtcca tctagtgacc caaataagac tttaagccta    27780
aacacaaatg tccctctctt tctgacgtcc tcatggacac accctggta taaaatcact    27840
tcctcctctg tgcaccgaat ggtgtctcac ccatccgtga cagcacttac cacaccgtgc    27900
atctgctcac ctgctcacca tctgtctccc cagaaagact gccagctcct caagggcagg    27960
gaccatgtct ccttcactca gcacctttgg ctcaagaaca ctaagatatt tggacccttg    28020
aagtctcagt ttcctcatct gtaaattagg aaaaacacaa catcactgaa ggagataggg    28080
gaggactaaa ggagctgtgc tgtgcttggt acacaggaaa tattcagtaa aaattcacca    28140
ttttcaggga ttcgttattt tagaagttta ccaaaatgct ccctctcctc tccccctgct    28200
tcctctcccc tcccctccct ctcctctccc ctctcctccc ctcccctccc tctcccctcc    28260
cctccctctc ctctcctccc ctccctctcc tcctctcccc tccctctcct cctctcccct    28320
ccctctcctc ctctcccctc cctctcctcc tctcccctcc ctctcctctc ctcctgcttc    28380
ctctcccctc cctccctgt cctctccct tccctcccct ccctccctt ccctctcct    28440
ctcctctcct cctctctcat atacacacac tcacacacac tatcactcac acacactcac    28500
acacactcta acacacactc acctacaagc acgcacgcac gcgcacgcgc gcgcgcgcac    28560
acacacacac acacacacac acacttgaga tggctgacct ggaggccacc gtttgcccca    28620
ggggtagatg ccagaaatgg gccagcttga aacagatggc aaatactcag ctctgaagga    28680
caagctgcct ggtctaggcc tacaggtata agaaagaaga tatttcaagg aggaaatgaa    28740
aaggcagaac aagttccccg tccctgtca tcatgctcgg ctctgagctg agacaggtg    28800
ggaggttttg gagaaggagt aagagctcca gatgtgagtg tgaagggacc tctaccctgc    28860
ctggctagat agcttcagga tcgccttcca cattccctct tcaccctctc cactcggctc    28920
tctgccccgg gaagttgagc tataaacaca tcaatgggcc tctctgacca gtgcctctgg    28980
ttggattcag atcatgggga acagtaacag gacaaagaag gcaggaggaa agtgagggtg    29040
ggtatttatt ccggggcttc cttctgccaa ggtcctatgg ctctggtcat ggcggctgcg    29100
ggtggtaaca gcacctacgt tactagctag ctcagggata ctgcactgga catgggtttc    29160
cccgcaccct gcccacacct tcataaataa tctctgtatt taattctctt caaaacacac    29220
catttgaaca ataccgtcgg ctccctgccc ctgcccttcc atccctggcc aaggagacac    29280
aggttaatgt tccctggaa cttgagggga cccaggagtg gagaggattt gctccctgca    29340
tactctcagg agttttcgtg agttgctgcc ttacagatgt gtctgactct gggaatgtga    29400
ggagaacgat aaatggggtg gcatggctca tgtgggcaaa acagggctgg agatggtgtg    29460
ttagtccgtt ttcacactgc tatgaagaaa tacctgagac tggtaattta taaaggaaaa    29520
aggtgggggtt ttttttttt ttttttttt ttggaggcag agtctcgctc tatccccag    29580
gctggagtgc agtggcacga tctcggctcc acctcccagg ttcaagcaat tctcctgcct    29640
aagcctcctg agtagctggg attacaggtg catgccacca tgcccggcta ttttttgtat    29700
ttttagtagt gacagggttt caccatgttg gtcaggctgg tcttgaattc ctgttctcgc    29760
gtgatcggcc tgcctcagcc tcccaaagtg ctgggattac aggcgtgagc cacagcgccc    29820
agccaggaaa aagctttaat tgactcagtt ctgcattgct gggaaggcct caggaaactt    29880
```

```
aacaatcatg gcagaaggca aaggagaagc aggcaccttc ttcacagggt ggcaggaaga   29940
agtgccaagc aaggggggaa agccccttat aaaaccatta gatctcgtga gaaatcactc   30000
actatcacaa gaacagcatg ggagtaacca cccccacatc aggaattttc cctatagtga   30060
ctctgttggg gtatagagat atcagagaga gagagagaga aagcacgctt gcagatcagc   30120
tgcagatgaa ctgactgtcc gtgtgaggga catggctgaa ttcttagagt gctgtctgtg   30180
atggttaatt ttatatgtca gcttggctgg gccatggtgc ctagatcttt ggttaaacat   30240
tctaacattt ttctggatgt ttctgtcaaa gtgtttttg gaagacatta acatttaaat   30300
gggtggattc tgagtcaacc agattgcctt ccatgacgtg ggcgagtgtc atctaataag   30360
ctgaagaaca aagactgacc tcccctaagc aagaagaatg atgccagcag gctgactgtg   30420
ggctcgatct gcagctcttc cctgggtctc cagctgctgg cctgtcctgc agactttgga   30480
cttgcacctc cacaatcaca tgagccaatt ccttaaaata gacctttctt tttctaggta   30540
taggtacaca tcctgttggc tctgttcccc tgccaagatg ggagccaatc aattccagca   30600
gaatgtgtgg ggcctcattc gaatgaatgt ttgtgccctc ttggcagaca tggcgaatta   30660
ttcaagagca ggaagccagt tcaggatgga gcaaagtgtt atccttgact tcttcctcca   30720
gcttccgtcc ccatcaatct gtgtagtggc caacccttcc cacttcccac atttactctc   30780
tctcttactg ctactcctta atccgagcca tccatggaaa tccccagcca atagcatggg   30840
acagttgacg gtctaactct cagcattcat ccctctcgtt cccagcattt gctctatgca   30900
tcaggcatgc aaacccttcc ccactacttg tagagcccat gctcctttat acctcttgta   30960
tttcattcac caaaaatctc taataagggc tgactgtgta caaccctgtg ctaagggcgg   31020
aacacgcagt cccaggtttc aaagagctca gaatctaagg gaaagagagg cttggaaacg   31080
gattaagtgc aaccacgtcc tggccacaga ggggaggaaa gaagccctgg tgaaggctct   31140
ttgcagaggg agggaacgtc tttattttat gcatgttctt cccttttgcta ccttgtgcct   31200 cttcaccagg aaacatctca tcctgcagct gaataccgtc tccctactca gtggtatcta   31260
ctgccacctc catgctctgt ccagagctag ttcattgttc ccttcccagt gctccttcat   31320
attttctatt tactactttc ttcctttatt acatcaagta atactaccaa atactgctcc   31380
tctagcattt gccctgtgct gcgcatgtgc tcgccctgca accacctttg gggcaggtac   31440
tatcgtatca tatcgtatca tcattggctc agggtataag tatcttgctt agtaactcat   31500
ggctcgtgaa attagtcatt tcataatctc aagttgctga gcacttgtct ggcgcagagt   31560
agagagcaaa tatttgtcta atggaagtgt gtttgtgaaa atgctgggct gtgtaaacta   31620
aacagaacgg aataaaatca gctagagggg tttgccaggg aagacttcaa aagcagaggg   31680
catttgtttc tctcttgcca ccactaatgt ttctcagtgt ctggggcgag agccaggaga   31740
gagaagccag gtagtcccat cgttggaaaa ggccacagcg ccttgctgcc acccactgac   31800
agcagcatgg agctctgcag ttccaggact gcctgtgcag ggggccatcc ctggtaccat   31860
gcccctctcc cttctgtgtg ccagctgggc tgtctcccctt tcctggccag ggctgtccct   31920
gctgaatgcc aaacatctgc agacagggtt tgcaaacagc tggctcaaag ttctgagctt   31980
ttgtgatctc atccaagtgc ctggctatgg ggaacaggct tattttcctg ggctaccagc   32040
actggagtgg tggaaattac attagacttg gattcagagg cctgcatttg attctgagcc   32100
ctgccacttt acagctaaat aaatgatact gaacctctgt ttccttcgct gtaaaatgga   32160
aatgatgatc attcctacct catagggttg ttaggggagt aagacaatag acatgggca   32220
```

```
tgcttgtaac tgtgttctgc tgaaacatgt gagagagtgt caataattaa aagaagcaag   32280
agttcctcaa gtcacagtca tgccaagatg tctagacaat ccctttagtt tatctcagtt   32340
cattattgag atgcgaggtc tacatagcag ggaaattaat tgttgcactg aatggaccag   32400
atttagttat tcactgaggt gggctgacac cttgggacta gcacagcatc tggaggcgga   32460
aactctggaa atgaatcccc aagtgctgtt tgtgtaatct aagcatcatt tcttcagttc   32520
taaaattggg gccataatct ccacattgta catgcccttg acccagcaa tcttgctctt    32580 ggattatatc ccagaaggcg tatacggtga tgtgtagaag gatattcgtc gtggtggtgt   32640
ttgtggtagc agacaggaga gatattggag gttttcacca ccagggaatg gataagtcaa   32700
ccacagtgga tgcgcctgtg gaattccgga cagcaggcag aagcaatgga ctagatgtac   32760
acagagcagc atggagaatt cttcaaaaca gtgttgggta ggctgggcat ggtggctcac   32820
gcctgtaatc ccagcacttt gagaggccaa ggcgggtgga tcatgaggtc aggagatcaa   32880
gaccatcctg gctaacatgg tgaaacccg tctctactaa aaaaaataca aaaaaaaaa      32940 aaaaaattag ccagacgtgg ttgcggacgc ctgtagtccc tgctacttgg gaggctgagg   33000
caggagaatg gcatgaacct gggaggcgga gcttgcagtg agccaagatc acaccactcc   33060
actccagcct gggcaacaga gcaagactcc atctcgaaag aaaaaaaaaa gtcacctaat   33120
tagaacaaag acactcctat cacccagtaa attccaagag attaggagtt ttgtgtcaga   33180
aactggggtc aaagacaaaa tattagaaca aagatgtac ctagcactct cattgcagat     33240
tacaagtgtt ttaggagctc tgtgtcagga accatggatg aggaacaaaa aaaattctta   33300
ttataaatca taatattggg ggtatagagt aaaacaagaa aagagaagag cattgcaaag   33360
atcagtgata atagtagagt gttaacctag atgtataacc aactcagttt cctgcagcag   33420
aaaatgtttt aaatgtctat cctgaggtgt tgtaagaatt agacataata ttcataaagg   33480
ttcctgacac agtgcttggc ccatgagaga tgctgcagaa atggaagctc ctttatcat    33540 tctctcattg atcaaataat gtaccaagtg cccactttgt gcaggacgct gtgcaaggat   33600
ccatgggaga gacaaagact gggtgtctct caggaacttg agcatagcag atgggacaga   33660
atggcaatgg gaggggagaa ccctcatctg aagctgcaga gaagacacta tcagacctcc   33720
tcagcttcca aattgaggct gaaagaagtg acttgctcaa ggtcacacag ccagttaggg   33780
gctgagctaa gggcaactgt ctaggtctcc agggcctttt cagagcatca cccaagccag   33840
tgtggctggt ggggtgactc agattcttga cttcaccgca caaagaatt tgagggtggg    33900 tccaaagtaa gagtaggcaa agaagtttat tgcagagtga aagtacactc tcagaggcag   33960
agtgggctgc tcagaggcag agacagcccc cagtgtccca agggaattcc ctttatgaga   34020
gctgtacaga catatgcatg aactactggt gaggtgaagt gcaaaggctg acctatggtt   34080
ggtgtatgca ctcagcatct acatgctttc acatgcattg catgttatca ctagcgtaga   34140
aaatcaccca gaggtgtgtt tattaaaatg aggaaaaatc actaagttaa accttgagcc   34200
tagctgctca tatgagaccc aggagaagtc cttagtccac ccccacaagc caggaatttg   34260
tagctaatag cttcttgggg ttttagtgct gattggctac agattgggga agctgcatca   34320
catcatgaac aatgggtttt tgttctcttt ctcaggtggt actaggtatc aggaacttgt   34380
agccatctgg cggtctgccg gtagcctgta ggactgctta caggtaggtg ctgatgcaca   34440 agggggggcct gctttgaaag gagcccatgg ggcttcacac caggggacaa gtcagtgtgg   34500
cctcctcacc ttccttatcc tgcctcacca atacatctga atccaagaga gtggaaggct   34560
ggtacctcct gtctcacctt ctgctctgac aatcctccct cacactcctc ttcggtttac   34620
```

```
ccactcaccc atgtgcatgt gtgcaatgga gaaataaatt aggagattgt tttaaaaatg    34680
caatttggta gctaaaatct ttctgaatag ggggtccatg ggaaaaaagt gaaaaggttc    34740
tgaaccctgg cagaggtgaa gctctaagga gcaaatctcc ttggggtggt taattttaca    34800
tgtcaacttg actgggtcat ggggtgtcca gatagttggc ttacttctgg gtgcatctgt    34860
gagggtgctt ctggatgatg ttggtgtttg aattggtggc tgagtaaagc agacagccct    34920
ctccagggtg ggtggcacca tccaatctgt caggggcctg aatagaacaa acaggcagag    34980
gaaggctgag tttgtcctct gcctggatgc ctgagttgca acatttgtct tctcctgctc    35040
tcagactggg accataggct cccctggtcc ttaggccttc agacttggac tgaacgacac    35100
cactgacttt cccaggtctc cagcttgcag atggcaggaa gaggttcttc ccagcctcca    35160
cagtcatgta agccaattcc ttacaataaa tgtcttcata tctacacatc ctattgctta    35220
tgtttctctg gagaagcctg actaatacat tcctgttctc ccttttccag gcctgcccag    35280
ctgctttagt gattccgggt cagagtcttg caatcagaag caactcccac cctcagccct    35340
caaaatgggc catctcaaat cttactagcc aatggcactc caaggagagg gaggagcagt    35400
gtccctgtaa gctccttcca gcctttatca tcctttgact tgtccctaaa atatcctatt    35460
ccccaaagat ggcaagagcg cctcccgaga aggaggagca agggcatctc catggagccc    35520
cgctctctga gctctgactg agggtggggg aaggagagaa ctctgggtct ggctcacggg    35580
gtgccatgtg tcaggcagca ggtccttgtg aagtctccag agatgtgagg agttggtcgt    35640
aacagcccag ggaaggagag gtagacgtgg caaacgggag agacaggtcc ccaaaggctt    35700
tgccgacttc ttgccagcct tgatccacca gagctataat ggcctttcct actatttcag    35760
aaaaacccaa aactttcccc acagagttca aatgggatt ggcaaggagc tgaataccat    35820
attggttttc tgagatgagc acagtcagca cactagctcc gagtcagaaa gggcaagaga    35880
ggagggcgag acaattctct aagtgatggg aaccttccct gtctgggagt ttggctcagc    35940
tgtgagctgg gttaatgtgg ctgcagaagg gaagcatggt tcatgtccag ccagcaggga    36000
cactgtccca gagctgcgct cagccctcat agactggctc catttacctc tcacgcagca    36060
ccccatgagc tgagggcggt tctgtggcca tgttacacat aaggaaatag gatgcagagc    36120
tgatgacttg cccaagatca cactactggg gagtggtgga attagaattt gaacccagat    36180
tgcctagccc attagcctaa ccactaatca aagcagcagc tcaactgtag ccgagtcatt    36240
aggaatctcc cagcttatgg ctgagaaagc aagaaaaatg aatctttacc atgcagggcc    36300
ggagtcaaag tgcacgtcat tcagtgcacg tttcttctga agaatatttc ttatggaaat    36360
gcattctgcg gggtcacaat ggctcatgcc tgtaatccca gcactttggg aggctgaggt    36420
gggcggatcg cttgagccca aagtttgag accagcctgg gcaaattaag gagaccttgt    36480
ctctacaaaa aattaaaaaa ttagcccagc atggtggcat gtgcctgtgg acctaggtac    36540
gcaggaggct gaggtgggag ggtcacttga gcctgggaag tcgaggctgc agtgagccgt    36600
gatcgcacca cagcactcca gcctgggtaa cagagtcaga ccccgtcccc tcccctgaca    36660
aaaaaaagag ataaatatat tctagggaaa catcaatcta taaccataat tcctatattc    36720
tcagtatcat ctcttatttt tggggggct gcctgctcat tgaacagcag agcatggcat    36780
ggggtttcat cacatccaac atacaacctc ccttccaacc taactgattt tccacagtgt    36840
ttctcagcac tgtcatagaa ctaccgctta tggaatgtat gaatgacatt attacaagat    36900
atttaaagag atttaaaagt ataaaacctg aataaaagcc accacaatca cttggtgtgt    36960
```

```
gcaaacaaca ccccggttca gacatcactg acaggacgtg tcagggattt caccttaccg   37020
gctaaagtgg cgccaccgtg tggcaagaat gtaaacgcta tttgcaatgg acttggatag   37080
gcagcttcga aattacgtga gccttagttc tttttattta attggtgaga gttgcattat   37140
tccaaagttg taggcatcaa gtcagacttt attagtatcg cgtgtcacac gatttctaat   37200
tcctatcatt taaattgggc cgataggcac ccctccatgc cgtgtggtga gtgctgggat   37260
ttgggcatgt gctgggcatc tggacatgac agggcctaga ggaggagta  aagtgtaggg   37320 aggctcccag aggaggtgac ctgtgagtca gattttgaga gttttccaaa ggaacgcacg   37380
gaagtggaca gcagagaaaa gggaggacga tattccaggc acagagagca gagtagagaa   37440
tgccataaca tcacagaagg acatgaggta ttggtgaaag gttgggtgtt tagctgttgt   37500
tttgattggt agttaggctc atggactagg gagtaagaca gtctgggttc aaattctatt   37560
ccatcacttc ccagtagtgt gatcttgggc aagtcatcag ctctgcatct tatttcctta   37620
agtcttgaga ggggagtgga ggtggagctg ggctagaga  ggagggtcag ggccgggtgg   37680
aaaatgccat acggtgccat gagaaggagc ctttctcctg caggagtgga ggtcactgaa   37740
ggacaggcag gtctgtgttt agacagatta ccagtagcag ggtggatgtt ggactagaag   37800
agagaagaaa ccacaaacag gggaactagt tagcagactg ttgaagaagt ctcccatccc   37860
ttcatgaatt ctacaaatac tgaatgccca cactgtgcca gcgactgttc tgggcattag   37920
agatctataa gacaacaaaa taaagactgt tgccctctgg gagcctacac cttactaggg   37980
ggagacaggc aacaaacaca taataatat  gatatatagt gtttcagata atatgaaaag   38040
caatgggaaa aaaataaagc agggaaggag gatagagaac gtgggcaggg ttgcaatttt   38100
agataagggg atcagcgaag gccctggtga gaaaaggatt aaaaggccta agggagtga   38160 gggaggaaag cattccaggt cccagggaaa gccttccagg cagagagaac agcaaaggca   38220
gagcctgagg tcagagcgtt cctggtgaga tcttgggaaa gcaaggaggc cagtgtggct   38280
ggagcagaat caaggcaggc agggtggggg ccaggggcaa catcagagac aggggaggag   38340
gcaaactgtg tagggtgggg ttggcaaagc ttatctgtaa agggccggac agtaaacata   38400
atatttcaga ctttgtgcac cacgtggtct ctcttgcaac tgctgaactc tgcccttgta   38460
gtgtgaaaac agccacagac caaatgtaaa agaataaaca tggctgtttc aacaaaactt   38520
tacttacaaa aatgggtgat gggtcagaat ggcctgcaca ccatagtctg tcaaccctga   38580
tgtaggacat tagagacact gaaggtctta gttttacttg aataagatgg agagctatca   38640
cagggttttg agtaaagaag gagcacaatg taactgatgt tgcatttgga tcattctggc   38700
tgctgtgtga aatagactg catggggtc  cggggtggaa gtaggagac  caactctatt   38760 atttattctc tgagtgacct tggcaagtc  acacagcctc cctggccttc agtttcctct   38820
tttgtaaact ggggtaatag tgtaatgata cctagcttat ggagcggttg tgaagggtaa   38880
atgaatcaac atatgcaaag cacaaggaa  gtgcctggca cacagtaagc actatatatg   38940
gtagccattt ttattaatgc agtcatttag acaagataca gtgatggcat gaaccaggtt   39000
atgctggtag aagtaataaa aagtgatctg attctggaca tattttgaag gtagagcaaa   39060
cagaattttc agatgatttg tacacagggt ggagagaaag agagaaatta aggaagattt   39120 taacttttt  gtctgagtaa ctgaaaaatg gagttgttct ttacctagaa gagaaaagcc   39180
gtgggaagaa tgagttttca ggggatcatg aagaattcaa tgttagacag taggatctgt   39240
aagcctcatt cagaggagag cccattgaaa gttaaggaga tgagaaagaa ccaacaaaga   39300
taatggaaat gaggcagaca gcgaggtagg cagaaaacca gaaggacttg gcatcctgga   39360
```

```
gttcaaggga ggaaggcact ggaaggaggg aggtgtgcat caaattttga taggtcaggt   39420
aagctgagga taagaatcac tgggtttagc aatgtagaag actggagcag ttttggtgga   39480
gtggtgggtg cgcaagcctg agggagcagg tttaacagag aatggaaact gagtgtttgc   39540
agacagcaag tagaaacagc tgttggggaa aattggctga aaggggaaga tggaaaatga   39600
ggccataact ggggcaagcc atgaggtcca gacagagatg acaagcgata atggagcaat   39660
agatatcaag ggccttggaa gatgggatga gacgagtcca aaggcatttc tgatgaagag   39720
gacctggaga ctgtcgaggt gtgtggagtg agggagaagt ctaggctggc tcccgggttc   39780
ctggcgtgca taactgaggg ggttgttggg agcagcattc cttctctgtg ctttggtagc   39840
atcttgggca tgctgctatt gccgcataca ttgcactgtc atataattgt ttatgagtct   39900
gcctgctatt tgaagactgt gccatgttcc atatttatct ctgtgcaact ggtgtagagt   39960
gagtgcttgg aagcgaagca gcagctccgg gaaggccgca gtttcagtgg tctggtcttg   40020
acaagacagc gatttatttc ttccatgccc catgatagag catatttctc ctgttctgtc   40080
tacatctctg tagggtccag ccctacatgg cctgtgggtt tttctcttcg tgtgcggaga   40140
tgagagatcg tagaaataaa gacacaaggc agagatagaa gaaaagacag ctgggcccag   40200
gggaccacta ccaccaaggc gcggagatcg gtagtggccc ctaatgcctg gttgtgctgt   40260
tatttattgt atacaaggca agagggcagg gtaaggagtg tgagtcgtct ccaatgatag   40320
gtaaggtcgc gcgagtcacg tggccacagg acaaataggg agcctttccc tatttggtag   40380
tcgaggaaga gagagagagg acagcttacg tcattatttc ttctatgtat ttcttggaga   40440
gatcaaagac tttaatactt tcactatttc tgctactgct atctagaagg tggagccaag   40500
tgtacagggc agaacatgaa agtggaccag gagcgtgacc gctgaagcac agcatcagaa   40560
ggagacgttt aggcctctgg atggctgtgg gtgggcctga ttaatgtcag gccttccaca   40620
agaggtggtg gagcagagtc ttctctaact cccccgggg aagggagact tcctttcccg   40680
gtctgctaag taacgggtgc cttcccaggc actggcgcta ccgctagacc aaggagccct   40740
ctagtggccc tgtctgggca taacagaggg ctcacacttg tcttctggtc acttctcacc   40800
atgtcccttc agctcctatc tctgtatggc ctggttttc ctaggttata attgtagaac    40860
aaagattatt ataatattgg aataaagagt aatgctataa actaatgatt aataatattc   40920
atatataatc atatctataa tctatttcta gtataactat tcttattgta tatattttct   40980
ttattacact ggaacagctt gtgcccttgg tctcttgcct cggcacctgg gtagcttgcc   41040
gcccacacat ctccactgcc cttccttttcc agagattcca atggattctt acctaagatg   41100
ccataactca accatagtta atagggaagt atggttggca ttccatcagg atcccagagc   41160
tgagtatgac aactagggct acaacccaac tgtttcctgt tgagtttctg gagccctgtt   41220
aggtgtggtt gtctggaatc tgagctgttg catccctatc cccatatgac tgaccctgac   41280
atcttttaga agttgattca gtggtgccct aacattggtg tggcccactg atcctccatg   41340
cccagaatct tccccatgga tgattccatc ttctgctttt taacacaagc cagcaatcca   41400
agctctagga agacaaactt tacactgatg aaatgactca atacctcttg gtgctgagga   41460
agggctattt ttatatttcc aatgctttat ggactgttgt gaggcctcag aaatccaggc   41520
tcctctgaag tacatcctct taggcaacag ccccacccac agtcccctgt cctacctgac   41580
aataaaaaac tgagatgcat gggcgaggct gagggagaag ctggtgagca acggcaacac   41640
aaggcagtga agagagggga cttgggaacg tggcagtgaa aaaagtcagc ctgtgtctca   41700
```

```
gtgatgtgtg tgtgagggac ccaaacactc aacccagatc acattctatg ggaaaggtga   41760
ggattaaatg aaatgacata gatacagcga agagcacagg gtgggcagtt agtaattttt   41820
agctgccttt tcttttacta tttgaaatgt gcattataaa ttacaaagtg acagatgcta   41880
gttgctagga tgaggcaggt accagtccaa tggactagac aagtgtttct caaactctaa   41940
tgtacctaag aaatagctgg ggatcttgtt gatctgtgga ttctgtttca gcgggtctag   42000
gatgatgtct gagatcctac aggtctaaca agctcccagg tgattccaat tcattgaact   42060
ctttgaatag caaggtcta gaacagcggt cttacccagg ctacacattc aaatgatcta   42120
gtgagattta taaagtatgg gctttctgct cttgcactcc atctactgaa tcagaatttc   42180
cagtggtgga gcttagacat ttacagtttt aataggcaag ccagatgact ctagtgttca   42240
gccaggactg aagaccactg gcctaaggcc ctgtattctt tctaattctg ttctccagct   42300
aattctgatt cattcaatca gtgatatttg ttgagcttct attctctgcc aggcagtgaa   42360
tttggcaagg agaacaaaca aaaaaaccag caatgacagt gcatatgcta aatgctgggc   42420
agaggatgcc ttgcatggga gcccaggaca gtgggtgtgg tgatttagcc atcttgattg   42480
gtcacaggca aggaaggctt ctctgtggga ggtgagggta ggactgagtt taaagaagga   42540
atagaaccaa gttagaacaa taggaaaagc cgtaaaataa cataacatgc tggaaaagac   42600
ttgagttcac tcaagggaag ggtaagtaac taggctggag aagacattag gaagaagatc   42660 atgaagggt gctaagttag gagtttgact ttcatcctga atgctaggat tttaagaaga   42720
ctgaatgttg gaaaatagca aacacaaaac aaacattcag cctcaacatt ataatttga   42780 tgttactatt attattatta ccggtttgtg tttaagagat attatactga caataggatg   42840
gagaattggc tacaggagac ctaggctaga aacaggaaa gtggtcacaa actattatag   42900
taacccagtc aaggaatgag acagatatga aggaggtaga tttggcagga cttgaaagac   42960
atggttcttg caataattta aacattccca tgtgcacata gcagtttgca aattcctttc   43020
atataacaaa cttgagaagg agttagcata agcattagtc caattttact aataaaggaa   43080
actgagactc agaaatgaac tgacttattt acggtcacat gacaagtgtg tgagcaattc   43140
tggtttatct gactcaacat caggcattcc ttttgctgtg ttgggccgcc tcctataagg   43200
tagacatcct atatgaacac tgggaagggt ggggtaaccc ctcctggttg gcatgtgggg   43260
tgtactggtg tggccttaaa gggaccctga ggccgggcgt ggtggctcat ccctataatc   43320
ccagcacttt gggagtctga agtagatgta ttgcctgagc tcaggagttt gagaccagcc   43380
tgggcaatat ggcaaaaccc cgtctctacc aaaaatacaa aaaattagct gggtgtggtg   43440
gcacgcacct gtgatccaag ctatggaggc tgaggtggga ggattgcttg agcctgggag   43500
gtggaggttg cagtgtgctg agattgggcc actgcactcc agcctgcatg acagagtgag   43560
aacccttctc aaacaaataa atacatacat ttaaaataaa taaagggacc ctgagttcaa   43620
caactctgtt accattaact cgacattccc agatatggaa atagggggcca gagtctcaac   43680 actggaattt tcagacagtt ttgagaagaa tccatcaagg gctcccagct tttcccaaca   43740
aaatcttaga gctgacaggt tatgaaagca aagtagcaat ggaagtacag atattggagc   43800
agttggcagg ggtaggggaa gttatcctga tccatctttg cctttgtctc tgtttcaaag   43860
ccatgtccct ttctccactc attccctca tttccctctt ctccatcaat taatttccac   43920
ctctctctaa tctctgcctt cccctggct gctcctctca ggcttcaagt ttgctccaaa   43980
ctcactcatc cttaaaggac cacctcatct tagtcctgcc atattctcaa gctactgccc   44040
tgcagagcta ataaacaact ccacccacgc ttcacagagg aacgggaagg tttaatctga   44100
```

```
tttttacgtc tgtcgtctga ctactgtctc tgattatctc aagttcaaag ttggccttct   44160
gattactgtg actctctttg agaactgata atggcttaca aatggattcc tttaccacac   44220
ttttgttcgt ctgatgtttc atggactgtc tctgtgtaaa cttagttatt taatgtctca   44280
tactttgggg gatagtgcat cagtgaggaa tctgtttggc tattaacttt gttttaaaca   44340
tataacatag acagagatga tacacatcaa atgatttgtc tcacaggcaa aaaggcaggg   44400
gaaggtactt gtaggctaga gcagcagccc ctttacacaa tcgtcagcgt tctaggcccc   44460
tctgtctttt cacactgtca cctttggcat gttggtttgc ggcccaaagg ctgcaagatg   44520
gcagtgcatc tccaagcatc ctccaggtag gcagaagcaa gaagggcaaa gtgggaaaa    44580 ccgggccttg ccagccaact ctgccactct ctattgagaa acaaaagct ttcctggagt    44640 ccacacccag tagaattctg tgtccatctc atttcacaca gccgcctaca gctggaaggt   44700
agctaaggag gagtgttttg gatgggctgg gtcagtcaac aagcagcatc gttcacatat   44760
cctcatatat atggggaaga ctttgcttat ggtttagctg tgtgcaaaac aagttacagt   44820
gactggtgtt tcagatgtca ggacctgtat taggtgtagc ataaattctg tcaagtgaag   44880
actaccatct cccttttaca gataaggaag ctgaagagca gagaggtgga ataacttatt   44940
gaagctcata caacctgaag aaaagtattt ttctgttaaa acaaacatac attatgacat   45000
aaaaccaaaa aatcctcacc aattttagag ataaaaatta gtgactgcac agacattcca   45060
tatggcaggg gtcaccaacc cctgggctgc agacccctgt cagtggcgtg ttaggatctg   45120
ggtcgcacag caggaggtga gccatgagcc agcattacct cctgagctcc gcctgctggt   45180
gcgagctcct tatgagaatc taactaatgc ctgatgacct gaggcaaaac agtttcatcc   45240 caaaccacc cccaccccc aaccccgtc catggaaaaa ttgtccctgg tgccaaaaag    45300
gtctgggacc actgccatat ggactatgcc cttgactctc ccaaaggaac atttccccat   45360
tcctcactcg ctgggtacc tcgctgggaa agtatgagaa gccccagcgg ccaccgtcac    45420
gtggggataa caagatatac acaaaaagt gagcttccgc cacgggaatt caggcctgat    45480
gcagtctgtg atgtgaggat gtctcaggca ctgccatgca gatgagtggg aaatgaaggg   45540
gactgatggg aagtgccctg aggtgacagg agggagcagt tcccgaggga ccacaatgg    45600 tcagggaggg cttgggggat tggcagatag aagtgggcct tgaaaggaaa ataagagttg   45660
tacaagcaag aaggagatag aaacggtatt ccaggtgatg agaaaagtat gcccaaattt   45720
tggaagccag agagtgggat actccaggga gagtgaaaag acagcctggc tagaggaaat   45780
gggtcctgaa ggagagaaat gagagatcac tctggaaagg aagtctgggg ctggttcctg   45840
aggaaagtcc cctgagatcc aacatcttct tctgttcttt ctacccacag gtcaggaatt   45900
acacagatat tgtttgctct gcagacctga gctgcctctt aagggtgctg attacacagc   45960
cttcttcatc tcagcctatg tccagatgga tcacagaatc ctcaccacaa gggagctggc   46020
cagcctgacc tggaaggtgg gggctttcct gccattggtg cctattgctt tgggcttgca   46080
tactcagtac aggttgacac ctaactctaa tgccacctgc tatgccaaca ggaccatcca   46140
gaaactcaac caaggcacca cagactgctg gggaaaggtt cttgctgttt taaataacat   46200
gtccaggccg ggcacaatgg ctcacgccag taatcccagc actttgggag ccgaggaag    46260 gcggatcacc cgagctcaag agttcaagac cagcctggcc aacatggtaa atcctgtctc   46320
tactaaaaat acaaaaaaaa aaaaaaaat tagctgggtt ggtggcacac acctgtagtc    46380
ccagctactc gggaggctga ggcatgagaa tcacttgaac ctgggtggca gaggttgcag   46440
```

```
tgagccgaga tcacaccact gcactccagc ctgggtgaca gaccaagact ccgtcttaat    46500
aaaaaataaa taaataaata acaagtccat catcagttag gccctgacca aatgggctag    46560
gggacatgag gacagatggg gacggggaaa aaaaggagca gataccttag ctcaggtcct    46620 catcccagc tgggttccct tctcctccaa ggaatccttt ccaggagtgg agaaagaggc     46680
atctcagtca gacagccagg gtccctggag gccagacttt ttcatcccct ttcacatgtg    46740
aagaggctga ataatcatct tatcccctg tattagctca ttctcacatt gctataaaga     46800
actacctgag actgggtaat ttataaagaa aagagataga gccaggcatg gtggctcatg    46860
cctgtaatca aagcactttg ggaggatgag gtgggcagat cacctgaggt caggagttcg    46920
agaccagcct ggccaacatg gtgaaaccca gtctctacta aaaatacaag aattagccag    46980
atgtggtggc ctgcgcctgc aatcccagct actcagaagg cttaggcagg agaatcactt    47040
gaacctggga ggcagaggtt gcagtgagcc aagatcccac cactgcactc cagcctgggc    47100 aagcagtga gaccatatca aaaaaaaaa aaaaaaaag aaaaaaaga aaagaaaaa         47160 gaaaagaaa aaagaaaga gaaaagaaa agaaaggaaa ggaaaaaga aagaaaaga         47220 ggtttaattg actcatggtt ccacaggctg tacaggaagc atggctgggg aggcctcagg    47280
aaacttacaa tcacggcaga agatgaaggg gaagcaggca tgtcttacat ggctggagga    47340
ggaaggagag agagtgaagg aggaggtgct acacacttta aacaaccaga tctcatgaga    47400
actcactcac tatcaagaga acagcaaggg ggaaatctgc ccccatgatc caaaccgtgt    47460
cacctgcctg tattatctct gtgtgtgtgt gtgtgtgtgt gtgtgtgtgt gtgtgtgtgt    47520
gtgtgtgtgt gtgtgtgatg gggtctcact ctgtcaccca ggctagagga gcatgatcat    47580
agctcactca ctgcagcctc aaatttgagg gatcctcctg ggctcaagct atcctcctgc    47640
cttagcctcc caagtagcta ggactgtgcc tagctaaaat accaaactct tgatttcagc    47700
tccttttgtc atcatttgtc catttcttct acaatcttaa attttttga ctggggtttc     47760 tatgttgctg aatttggtga cattttcact aacccagaac acacacacac acacacacac    47820
acacacacac acacacagcc ccattaaagt tctttccttc aatgaaattg gcaaaggggc    47880
ataaagaaaa ctggaaccta aggacccagt gaggaagcaa agttccactt tccactggaa    47940
actggtcttt tacaataatc ccattgcacc taggagctgg accaggctgt tattttagag    48000
tttaaaagtt gtcctccctt cttctacctg gctactggct tggggcttta ggtgggtgag    48060
gcctacctcc acaagaaaaa tccacagtga aaatggtgac agttggaggg tgctggagtt    48120
gagcttagcc ttcctcactt cagaagagct aaatgcatac aggagtgcaa cagaagtcag    48180
gaatctattg ccagaggggc cagagagggg caagggcctt cctgctctag ggcccttccc    48240
cagaagatgt tagctatggg tcaagtctct acctcctccc caacccccat tctccattgc    48300
atccttggaa ccaggagccc agaaacctgc cagcccagat gaccaggacc atgtttgaga    48360
tgcataaatt tggtcctctg gatccttcaa aagtacactg tatttgtcac tccccgtaga    48420
ccctcatgca ataagttctt catgctctgt acatcgattc ttttctcca gcagttctga    48480 gcaatgcttc aaaaacgaaa catcagattc cttgtaaagt taaaggaac agatttttt     48540 cccacatacc atgaatttct cattgattgg tttagttaca atatctaatg tgtccacagg    48600
tatgttttaa aagttccttt atggggcaga gagagcattt ttttaatact ctggtttcac    48660
ttttttgcat ttaaatactt tctcacatac tcaatattta taaaagggtt agagttcatt    48720
ttaacaaatc ccattaaata ggcagggctt tcaaggtctc tgcctatgaa tttcctcatt    48780
tcaagcactg tttagtccag gtaagctcca atagaacctg agaacttggg actgccaggc    48840
```

```
caactctagg tactagttcc tgacatttct ttgaatattt gggtggtcac atttgttttc    48900
tttggtcata cttacccaac tggacctctt tttgttgaa  atgtgaactc tactgctagc    48960
cagttaaagt tcattgtttt tcagaacttt gattttgaag atgaatatga ctttaacctg    49020
gccatcatgt actgcttttt catagttaat tcaaaacaga gcagaactct ggggattagt    49080
tcaatagaaa caatgtattc ttcaggatct ttctctaagt agaggaactt tcttgaccct    49140
tacacagcaa tatatggact ttttggacta ccagctcatg gttattctta atgtgatcca    49200
gaccccaggg ccatcccag  gaaaaggaag caaagcacct ccccacagta ggcctgtgct    49260
agacacagtg gacacacagt ggaaacaagg tccctgccca aagacctcaa aatttattgt    49320
gagagatgaa ttggtaatta aatagctgat tattttaaaa gccctaatac agttgtgttt    49380
catgtacata actgtaaatg aatgtaaaaa gtgctgtaaa atcacagtgg gagggattca    49440
ttcttgcagt gaggaagaag gatgaggatt gaggaagact tcaaagaggt gagttttgaa    49500
ataggGtttg aaggacaagt aagagtttac taggcagaga tgcatggaaa gaacattcca    49560
ggcagcagag acagctaaaa taataaata  aataagtcgc agagtaagga aaaggatggg    49620
aatgagaagt ggttcagtgt tactacagca tagagcaagc ttgtccaacc cacagctcag    49680
gatggctttg aatgaggcca acacaaatta gtaaacttta ttaaaatatg agatattttt    49740
acaattttgt tttgttttg  cttattagct atcattagta ttagtgtatt ttatgtgtgg    49800
cccaagacaa ttcttcttcc agtgtggctc agggaagtca aaagattgga caccctggc    49860
atagagtatt ttggggtgac atgatgggag ctggagaagt aggtagggt  cagaattcag    49920
aaggccttgg acaccagcct aaaggcttag agttgctccc attggccatg cactcaccaa    49980
aggtgttcac gtccctcttt tggctgttag attggatggg ctcaatcttt tggccctctg    50040
tctctagaat agagccgctg ctttttctact gggcccacta tttcttcctg gtcctctgat   50100
cccccttagca ctacacagat ctcgatattt gcctcgggta tcaaggctct gaaaatgatc   50160
aggatttaga ggagatggct cattttcaga aagagtttta tattctccct ctggccttat   50220
acactacagg caaatggcac cgatgttttg gagttgggcc agttgggcct tttctcccct   50280
caagagagga ggattcgata ttcagtgttt ctgaatttca tgcttagttc ttaagccatt   50340
tcccatttgc cctaagaaat aagagctggc agcaagctgc gctgtttttt tctaaacggg   50400
aaatgggtta agcatttgtg atcaccactg aatgagtgcc agagctggtt agtgatcttc   50460
ctgttcaatc cgaggtcacc taactagata acaaagagct gaaactaaaa gtccggtctc   50520
ctgactccca atccagtact ctttctggtg tgctccagct tctggctctg cttagccaat   50580
tatgaaacag acagaatgta cttggctgcc ccaaacggcc aaagggcagt tctgttccca   50640
aaatggaatt ctgttgtgcc tcaagctagg cagcataatt gtgtgtctt  tggtaactcc   50700
ctgtcttctt ctgtaaaatg ggagtagagc ctacttaatc ctgcagctac ttctaagatc   50760
agggattggg gcgtggtggg ctgttctgca gctgttttgt gatggatgag ggatgataga   50820
tctatgttca agtagcggaa tcttagagtc aggagttgga aggaatcttg gaggtggtct   50880
gtggtgacag gaagcctctt ccaatagact gaacacggaa gacttcctag agccggagga   50940
caagggtttc tttcctctta gcagtgagct tcttgttttt ggaaatgctc aagccaagaa   51000
tggatgttca ggcagagggg attccgctcg gaagggGctt tctgcactga agtggtggcc   51060
agcgggaaac tccaggtttc caactcctgc acaaatcctt tctaatatcc atccactcag   51120
gtgagctggc agggcagtag ctgtgcaggg ttcagggtca ttatatgtca atgaccttca   51180
```

```
gcacggatta ctaacaacag taacatccgt taccgtttac tgctttccta ttaagcacca   51240
tgcactgtgc ataacatgtt atctttatct catatctaga attttgggag gtactttgaa   51300
tcattacgat ctatctactt cttaggtgag gaaatagagg tttaaaattt agtccacagt   51360
ctcgcaagga tggagcctgg atcaaatttt gggttatcag attccaatca cgtttcttag   51420
cttttctttt ttttttccaa ctccagtttc tgtcttgctc caaaaagggg gaaggagcgg   51480
ctgcggcgct cggtttcccg cctcctaggg aagggaaggg agacgagcag cgcggaggct   51540
ggggccccct tccgggcggg gcctactagt gggcggggcc tgtcagtgag cggcccctgc   51600
ccggaaggag ccagtccggg gcggagccga tggccttaca ggggccggaa gtggcctgcg   51660
ggcggagaag tgcctcagga gtcctgacgc agtgtcttgg gcgctaacgg cggcggcggc   51720
cttgtgttta gactccagaa ctccccactt gccgcgttct cgccgccgca ggctcccggg   51780
acgatggtgc cccgcctgct gctgcgcgcc tggccccggg gccccgcggt tggtccggga   51840
gcccccagtc ggcccctcag cgccggctcc gggcccggcc agtacctgca gcgcagcatc   51900
gtgcccacca tgcactacca ggacagcctg cccaggtgag cctggcctcc gggtccccgc   51960
cgcccgccgc cgtcccagga tcggcccccaa cctgactgca gtcactcatg actcctctag   52020 tgaaccgtt ccgccccca agcccctacc atggaggctg ccacagcccc taatctggaa   52080
gtcttgggac ttttcacaat ctcctagcac aggaacctca gaaccctcaa attctcttcc   52140 agaaccctc gatgctatct cagattctcc atcttgaacg cttctcagat tccctctcct   52200
ttaacctaac ttccagccag ctatcctgag tcctcttctc cctgaaaaat gccagacctg   52260
catatttcca gcgccgctgt aatccctcga ctatggtgtc tcctgaagta ctttaatgac   52320
tgcctcacat tcctacccgg aatatgggta ggctgattcc taatacatca tggttaccat   52380
tccttaactt ctcccagcac cgccttcacc cctgtcactc aggaccctca gccccacctc   52440
ccatttctcc agtactctgt tctttcaccc cccatgagcc cccacaagca cagccctgaa   52500
gtgttcaccc ttgtcctcaa ctgaccctcc cccatgtttt taaatcttta atctcctaaa   52560
tccagtgttc acccggaaac cttttcactct ctccaagccc tcctcaacag gttcctcccc   52620
tcaaaatatc cttcctcacc cacagtaccc cttgtaagtg cagctcaccc tcacagaatt   52680
ctagacacca ccctcagtac cccatccaca ctccatcata ctcagatcca gggtccaccc   52740
aaatttctct tctcctcctc accactggct accctgcctt cgaaacactt cacccagaat   52800
cgacttcccc tctgaaaaga gccctagtaa atcctcttcc ccttccctcc cccagtactt   52860
tcttaaatcc agcttccagt tcttccagcc ttcgaactcc gctttcgtct gagttgccag   52920
atctccttct tcaatattag aaattttctt caccctctaa accaaaccta aactaacttc   52980
taacttactg agtgagtaac tcagttcctg gagccaagtt caaaatttgt ctcaaagacc   53040
cttctcacct tatttctcac caaactgccc tcagggattc cccacactcc aagagctaga   53100
ggccaggctt cttccccatg tgtggaacat tgtgtcacag gcctcacccg agctgctggg   53160 ttgttttttct ctgcatctgg gaccacttaa cccaacgtca tcactacata ccctcaccct   53220
ctcaggagga tcgagtgatt cttgtgaaat tacattttgt gcaaacatct aagacatgaa   53280
aatgagatta tctacacgtg gcaggaggga ggaagaaaaa ggggctttgt gcctgtggca   53340
taagcctggt acatgcttcc accctgtcaa cctgtgtgta tgagctgagc cagtatatgg   53400
gtgaaaggtg aggactgaca gaacctgtct tcacttgcca agttcagagt cagatggtca   53460
ctgactttca ggcaggcctg ggccccaccc aggtttaaga tcagagggat tttctgcact   53520
ttagaattgg aaagctggaa agaatattca agattattta ttccaacccc atccatagca   53580
```

```
cagtctgtag gaatctggag gtaccaattc aaactccagt tcaaatagta ccactagtca   53640
cctacgcata accttaagca accaacctcc cccagacctc cattacctta tttgtaaatt   53700
gggagttaga tgagagatga gattccttct gtcgctcaga ttctagactg gtaaaatgta   53760
taatctttca cactcactca ttgatgtcac acttggtgaa aagccctgac tttgaggtct   53820
ggtagaatgt agttgcagat tctggatctg caagtcttta gctataattt ggggcaattc   53880
tgttcacttc attgagccac agttttattt tggttttttt gagacagtct cgctctgttg   53940
cccaggctgg agtgcagtgg ccctatctcg gctcactgca acttctgcct cccgggttca   54000
aaggatcctc ccgcctcagc ctcccaagta gctgggatta caagcatgtg ccaccacacc   54060
cagctaattt ttgtattttt agtagagatg gagtttcacc atgttggcca ggctggtctc   54120
aatctcctga cctcaagtga tctgctcttg gcctcccatc tgggaccaca ggcatgcacc   54180
atcatgcctg gctgattttt tgtatctttt atagagacag ggtttcgcca tgttgcccag   54240
gctggtcttg aactcctgga ctcgagcaat ctgcctgcct cggcctccca agtgctggg   54300 attacaggtg tgaaccaccg tgcccagctt cactccagaa attttaagt aggactttt    54360 taaatcaaat tgccattgtc tctaatctag aattttgttt aaaaggaaga aggtaaactt   54420
tcatgaatat tcctactgta ataaaactaa atcttaaaca tatgtaggca actggaatta   54480
tgaggtagct gagatagtat ttggaatttt tctgagtaag tcagtgaatg taaggggatc   54540
tgtggtgtta aagtgttgta aatgggtact tagtgcagtc taagtccata atggcagtaa   54600
ataattgatt tattttttgtc atattatgga taaacatgca ttacaaataa actgatgaac   54660
cacagtatat cttatattag gcttttaaac tgctttatgt atcatgtttc agttttccta   54720
aatgactgat acatttcagt attttgcata tcagtgttaa ttttgagttg gtagaggcag   54780
cctaacaaac tctgattgtt ttgctattag gggatatttc cttcaataaa accaatgaat   54840
tgaaagagaa aatacacctc actttactgt ccatgtgttt tcatttcaca ataagccagt   54900
aacttcatca ccatagccat ctttgggaat cactagtaga cagaatgata agtaggcaaa   54960
ttgctgttcc tgttatttaa gcacagggac tatttggttc ttcctaatgg cgttcctggt   55020
atctgggcat ggctcactgg tcgattccta ccttttagtg actgtagccc ccatatatgg   55080
ctggcccttg gacagatctg tgtttcactc ttatataatt atttgttgta aaatgcagaa   55140
gaaaatttaa aaaatagaac cttttcattt tatcctaggg gagaaaaatg cagttgttca   55200
aactaagggt agaattaaat cagggccaat acagtgttag cacaggtgtt atcattgtga   55260
ccagaaaaca ggaattcttg gggcagcttc tgcttcccca ttttgaatct attattgtta   55320
tttaaaataa ttatatttgt attttactta aagatttagt tgttatttta cttaaagta    55380 gagttaccat tgatatactt ggcattagta aacccattga ttctgatttg tcagtcgctt   55440
ctgattattg gttttggggg aggaaattaa tgatctagta atcagttcat tagcttgtaa   55500
agctaattaa cctcttccat atactgtcag ccttacactg accctgcttt ctccccaggc   55560
tgcctattcc caaacttgaa gacaccatta ggagatacct cagtgcacag aagcctctct   55620
tgaatgatgg ccagttcagg taaacactga gaaccttggg tgagcatagt tggggtggtt   55680
caagacaggc tggcaagtag tggtggacca agcttcaggg aatgtctgtg acgtggctgg   55740
gtctccagga acccagaacc tagttgtaca tctgcaagtt caggaaatag attttcattc   55800
atgaaggact gaccaagccc cgagagttcc tctaaacagg ctcaacagga gatagtttat   55860
aagccagaat gccaaatgtg tactttccct tagcaggtgt acctgggagg ctcgctggtc   55920
```

```
ctggtcattt atagagagca tgtacccttg gaagggaggt ccattgagga gaccatacgg   55980
cagaccagaa gtctgcatcg tgagcatgtt tattgagttg gatagcatgc ctccaaaatt   56040
tatgcccttt ttcatgaaat ttagtatatg atcttatttg gaattagggt tgtggcagat   56100
gtaattagtt aagatgaggt cctactggag tattgtgggt ccttaattaa atatgactgg   56160
tgtccttgta agaagacaca gagacagcgg tgtgaggaca caggcagaga ttgtgtcctc   56220
tgcctgtgtc aacaagccaa ggcatgccag ggattgctgg caacaccaga atctaagaga   56280
aagccatgca acagattctt ccccagtctt cagagaagat atagtcctac tgacacctgg   56340
attttgtcct taaagcttcc agaactgtga gagaataaat ttctgttgtt ttcagccacc   56400
cagtttgtgg tgttttgtta tagcagtcct aggaagcaaa tacagcatgg aattggaaaa   56460
taatatcaaa tattgtcaaa aagtggattg cattaagctc ttatagccta gtgtagtact   56520 cttttttccat aatggaaatt tttctgtaca ggtaactggc attgttgttg gaatcacaga   56580
actcttcact ggacagtgat ggagaagcag atgaattatc cataatctag gcctctgttt   56640 tcaaatatt gttattagtc atttaaagtt tctcttgata tggtaatagc taccagttat   56700
tgagtattat gttttaggat attctaaatc cttagcttta taaatatttt taatcttgta   56760
aagtggtatt attatccatt ttacacatca agaaaccgag actcagatca agtaacttat   56820
ccaagatcac acagtttgaa aagcaacaga gctaggattc agacttaact tctgttgact   56880
ccagagcttg tgtccttttc tccatgccaa actgcctcct aggatatgga ttattttgtg   56940
agatgttgat tgattttcct aatcattcat tttaagaagg tagtctagat tatcaatttt   57000
agattgattc ctgttctggt tagaggtact ttctgatctc attccaggtt ttagggctat   57060
gctgttgggg acccaaaact ctattatgag ttcctcgcca tgaacctaaa aatcatgtat   57120
tccctaccat ggtttgattt tgtcttttct tgaatgtttt aggaaaacag aacaattttg   57180
caagagtttt gaaaatggga ttggaaaaga actgcatgag cagctggttg ctctggacaa   57240
acagaataaa catacaagct acatttcggg taggtaggct gggctgtggg tatgatttct   57300
cccagagccc tccataatga aaagtaaggc atattctctc ctgttttggt tcagagata   57360 ttttggtga gaccagcaaa tgaagtaacg tctcatcctc ccttcctgag gtaaattaag   57420
gctgagtgtg ttcctcctct actgaggtgt tgacttgagc ccatgctcaa gaatgatggc   57480
cagccttctc tgtagatggg attgaggcag aacctaatca atggtcctgt ctgaaaagga   57540
tgcaggatta agtcctatgt cctatatcat tctgggtcct tcactgtcag acagaactgt   57600
cctctccagc ctcttctctc accacccacc ctgcatact tcctgctaaa ctcctcattg   57660
ctccctgaac ccttagtctt tcattctttt gtgcctttat ccatgctgtt cccactacca   57720 ttttttgcc tggcaaattc ttcttttaag atccaaggag gatggtttc tgtgaaacct   57780 tctcagtcct ttttcctttc cattcagagt tggttgcttc cacctctgtt cctacagcac   57840 ttctttaat ttagtttata tatttaccaa ggttatacat gcatatagtt taaagaatca   57900
gacagttcta taaggcttgt taggaaaaac agcaacttcc tcatcatctt atttcccact   57960
tctcactttc agctcctaaa tcttttgtta tacccccg tatctctaaa ttagatactt   58020
accttactgc atcttgattt ttttgcttta gtcattagct attgacatct cactgtagaa   58080
gattagaatt cagcagtact ttacatccca ccacatatgt gggatgtgta tacacatact   58140
tcctatcccc ttattttcac agcataggga tttgtaattt tgggtaactc agtatctagt   58200
tttatgctat tatgatcata gaaacactat tgtcagctga ctcatgtagc atattgggat   58260 tgttttttcct ttccagtaca aactttttgt tttctctgaa gttaataatt gttccatctt   58320
```

```
ttctcttgtt tagttttcta tgtgcttact aatttacccc cagactcttc ccaagctgtc   58380
tgaatctcct ctcaatacat gaaagcagat tggacattct atccttttg gtcttcttga    58440 cgaaacttct tccagaactt gcgacatgct gtagtctgga tttgtgaacc tcttggccta   58500
ctgtgaagct gctctcctgt gctctttcac catcagctgg ggcatctgtc atctctctct   58560
catgttggga ctcgtgtttc ttgtctttca tattttctta tttcttggct ttttcttttt   58620 ctttttttt tttttaaat cagagcacat attccctgta ctatctggaa acagaatatg     58680
ggaagcaaaa attttaaaat ggcccttata cttcattgat aatttgtttg ctgggtttg    58740 aaattatttt cccacagaat tttggaggct ttgctccatt gtcttttagc atccagtgtt   58800
gctgttggta aatctaatgt tattctgaga cttaatcttt tgactacttc ttctctctgc   58860
ctttggaagc ttttagaat tttctctttg tccccagtgt tttgaaattt caggtaatgt    58920
gttttagtat gtgttgggcc actctgtgag tcctttgaat ctggaatctc atccttcagg   58980
tctgggatat ttccttgttt tatttctttg gctttcttcc tctccatttt ttttctctgt   59040
tttttctttg tggaactcta ttattattca ggtgtagaat ttctgggtct catcctctaa   59100
ttttcttttc tctcacattt ttcatctctt actctttttg ttacattttc ttgggagact   59160
tacttaattt taatctctca acctgttttt aaaactcctg ctttcctatt ttttacttcc   59220
acaagctctt ttttcttctt atggtgttct ttttaaaaat agtttatctc tgataatttt   59280
tttttaagat ctcttctctc ttcatagtct gttgcctcca agttgctttt cttctgtttg   59340
ctttgccctt ttcttttcttc agatgcttca taatcctgtg ttgtcttcga tatgagtgag   59400
atattaaaaa gctcttggaa gctatgtgga tgggggtgag gcttgtcagt tacaggcttt   59460
gctctaatgt gattgatatg gtttggctct atgtccccac ccaaatctca tcttgaattg   59520
taatccccac gtgttgaagg agggacctgg agggaggtga ttggatcatg ggggcagttt   59580
tccccatgct gttctcatga tagttagtgg tttctcacga gctctgatag ttaaaaagtg   59640
ttcagcagtt cccccacttg ttcgcttct ctcctgctgc cacataagat gtgccttgct    59700 tcccctt cac cttgcgctgt gattgtaagt ttcctgaggc ctcccagcc acaaggaact    59760 gtcagtcaat tagacctctt ttctttataa attacccagt ctcaggtggt tctttatagc   59820
agtgtgaaaa tggactaata tagaaaactg gtaccaggag gggggcattg ctacaaagat   59880
acctgaaaat gtggaaacaa ctttggaact ggttaatagg cagaggttgg aacagtttgg   59940 agggtcaga agaagacagg aagatgtcag acagtttgga acttcttaga gagttgaatg    60000
gttttgacca aaatgctgat agagatatgg acaatgaagt ccaggctgag gtggtctcag   60060
atggagatga ggaacttatt gggaactgga gcaaaggtca ctctactgtg ctttagcaga   60120
gagactggtg gcattttgtc cctgtcctag agatctgcag aactttgaac ttgagagggg   60180
tgatttaggg tgtctgacag aagaaacttc taagcaacaa agcattcaag atggcttttt   60240
ctgaaagcat atggtcatat gcattcacag agagatgatg tgaaagtggg acttatgttt   60300
aaaagggaag cagagcataa aagtttggac aatttgcagc ctgaccatgc agtagaaaag   60360
aaaaacccat tttctgggga gaaattcaag ccacaagctg cagaaatttg cataagtaat   60420
gagaagccaa atgttaatag ccaagacaat ggggagaatg tcttgagggc atttcagaga   60480
tctttacagt agcccctccc agcataggcc cagaggccta agagggaaaa atggtttcct   60540
gggccctgct gttctgtgca gcctcggac atggtgccct gtgtcccagg cactccagct    60600
ccagccatgg ctaaaagggg ccaaggcaca gctctggcca ttgcttcaga gggtgcaagc   60660
```

```
cccaagcatt ggaggcttcc ccatggtgtt gggcatgcag gtgtgcagaa aacaagagtt   60720
gaggtttgaa aacctcgtcc ggccgggtgc ggtggctcac gcctgtaatc ccagcacttt   60780
gggaggccaa ggcgggtgga tcacaaggtc aggagatcga gaccatcctg gctaacatgg   60840
tgaaaccctg tctgtattaa aaatacaaaa aaaattagcc gggtgtggtg gcgtgcacct   60900
gtgtcccagc tgctggggag gctgaggcag gagaatagcg tgaacccagg aggcagagct   60960
tgcagtgagc caagatagca ccactgcact ccagtctggg tgacagagca agactccatt   61020
tcaaaaaaaa aaaaaaaaaa aagagacaa cctcctccta catttcagag gctatatgga   61080
aacacctgga tgtccaggca gaagtctgct gcaggggtga agccctcatg gagatcctct   61140
actagggcaa tgcagatggg aaatatgggg ttagagcccc cacacagagt tcccaatggg   61200
gagcctagtg gaactgtgag aagagggcca ctgcccttca gaccccagaa tggtagatcc   61260
accgacagtt tgcaccatgt gcctggaaaa gccacaggca ttcaatgcca gcctgtaaaa   61320
gcaaccatgg ggctgtactc tgcagagcca caggggcagg gctaccaaag gccttgggag   61380
cccacttctt acatcagcat gccctggatg tgagacatgg agtcaaagat tattttggag   61440
ctttaagatt taatgctgc cctgctggat ttcaggcttg cgtggggcct gtagcccctc   61500
tgttttggcc aatttctccc ttttggaatg ggagcattta cccaatgctt gtaacaccag   61560
tgtatcttga aaataactaa ttggtttttg attttacaga ctcataggca gaaggaactt   61620
gcctttactc agatgagact ttggcttgta attttgagtt aatgctggaa tgagttaaga   61680
ctctggggca ctgttgggaa gacatggttg tgttttgaaa tgttagaagt acatgaaatt   61740
tgggagaggc cagggcagaa tgatgtggtt tggctctgtg tctccaacca aatctgatct   61800
tgaattgtaa taatccccaa gtgtcaaggg agggacctag tgggaggtga ttggatcatg   61860
gggtagtttc ccccatgctt tcttgtgat agtgagttct catgagatct gatggtttaa   61920
aagtgtttgg cagttcctac tccttgcttg ttctctctcc tgctgctgtg taagatgtgc   61980
cttgcttccc ctttgccttc caccatgatt gtaagttttcc taaggccttc ccagccatgc   62040
ggaactaagt cagttaagct tctcttcttt ataaattatc cagtctcagg tagttctttta   62100 tagcagtgtg aaaacagact aatacagtga tccagctaaa ctgcttccct gggttgcccc   62160
taatggtagt gtagttgggt tagcttccct agggaggctt ttccagtaaa ctgccaaaag   62220
gttgctagtg ttgtagaagg cagggtaagt aagggaagaa ggtttgagat ctcaactgtg   62280
attcaggtct cccagttta tttatttat ttatttttg agacagagtc tcattttgtc   62340
acccaggctg gagtgcagtg gtgcgatctc agctcactgc aacctcagcc tcctgggttc   62400
aagtgattct cctgcctcag ccttctgagt agctgggact acaggcacgt gccacgacac   62460
ctggctaatt ttttgtattt ttagcggaga cggtgtttca ccatgttagc caggatggtc   62520
ttgatctcct gacctcatga tacacccacc tcgccctccc aaattgctgg gattaccagc   62580
ataagccact gcaccagcc cccagttttta ttatctccag agagtaaaac ttaagtcttc   62640
tacaggagtg aggagggaat ctcaggttgt ggtagtggtg atataattga atagtccttc   62700
aaccagatgt atctaggttg ccaattactg agccctctgg gggttctgct gtgcaaatca   62760
tatgatttct tggctttctc tcctgccaat ttaggattgg cttttcttgag tctgctttag   62820 tcattaccag ttgcataagt gctttccagc ttccagtatt tgttttctcg tctcccattc   62880
tcttggcctg actggtttat gtctctttga aattcttttg ctaaagggggg gtcagaggca   62940 tgaatttatg tcttctttca tcaaatatat cttatccacc agtactttc tctcaccatt   63000 ttagtgcatt gcgttatgtt ttaattattt gcctccttca ccagagtttt tcagaatcaa   63060
```

```
agaccatgtc ctattcctct ctaaatcccc tggaccaagg cctggcacag cactgattct   63120
caagggatgg aatgagtgga tggaccaaca aatgagtaac agagaaatct gcatctatta   63180
atccttttcc cagtgctata catatgaaca ttatttgcct gaatgatagt ccttatttat   63240
agagtttatt catgtttact aatcccagca ggaactttcc ctgacatatt ttctgataaa   63300
atattgcttc tggaattttt acaggtaaaa catctatagg aactcagagg gctagtctga   63360
gtgatccatg cactgatatt tataatagct tttttagtac tttctaaaca gggagtgtac   63420
aaatgtacac tgtacataga aggacaatga agacgttccc cccttatcgg ggagcaatca   63480
agtatgattg ttgcccctga aaggagatga agcaagagaa acctaaagag atggggtggg   63540
aattaactat tctgttccag catgaatgca agtggagtgt taccatattt tattcctta    63600 aaccaagaaa ggaaacagaa gaggaagaaa aagcaattaa taaacattag gaaaatgcaa   63660
accaaatctg caatgctata ctactttaca cctaccagaa tatctccacg ccacaagaca   63720
tgtaacaagt gctgctgagg atgtggaaaa attggaaccc tcacagacag ctcgtgggaa   63780
tggtgcagcc actttggaaa acatcctggc agttcctcaa aggttaaaca gagacttacc   63840
atgtgatagt agttccactc ctagctatgt ccatacaaaa acatgtataa gaatgttcat   63900
aacaacataa ttcttaatag ctaggtgcag tggctcacac ctgtaatccc agcactttaa   63960
gaggctgagg tgagaggatt acttgaggcc aggagcttga aaccagcctg agcaacataa   64020 taagaccccca tctctaccaa aaataaaaaa attagccagg ctggtggtgt gcatctgtag   64080
tcctagctac ttgggaggct gaggtgggag gatcgcttga gcccagggtt caaggctgca   64140
gtgagccatg atcataccac tgcaatccag cctggatgat agaaatcctg tgtctcttaa   64200
aaaaaaaaaa ggcaatgtaa ttcataataa agagtggaaa cagttcaaat gtccattacc   64260
tgatgagtgg ataaacaaaa tatagtatat ccatataatg gaacattgtt cagcgctaag   64320
aagaaatgaa gaacttaaat gctacaacat ggatgaacct taaaaacatt attaggaggc   64380
cgaggcgggt ggatcacctg aggtcaggag tttgagacca gcctgcccaa catggtgaaa   64440
ccctgtctct actaaaaatc caaaaattat ctgggcatgg tggaggacgc ctgtaatccc   64500
agctactcag gaggctgagg caggagaatc gcttcaatcc gggaggcgga ggttgcagtg   64560
agccgagatt gcagcactgt tctccagcct gggcgacagg agcgagcctc cgtcccaaaa   64620
aaacaaaaca aaaacattat tgtaagtgat agaagctaaa tgcaaaacac catatattgt   64680 atgacccccat ttgtatgtct tgaattattg cagagcaaaa acattcaggg aattcttctc   64740
tctggaggtt gatgccattt cctttgtcta tgcttgaatt ttttttcttc ttcaaatttt   64800
atttttaggg acagcattaa cattttatgt tattttttc ttttattttt ttaggaccct   64860
ggtttgatat gtacctatct gctcgagact ccgttgttct gaactttaat ccatttatgg   64920
ctttcaatcc tgacccaaaa tctgagtata atgaccagct cacccgggca accaacatga   64980
ctgtttctgc catccggttt ctgaagacac tccgggctgg ccttctggag ccagaagtgt   65040
tccacttgaa ccctgcaaaa agtgacacta tcaccttcaa gagactcata cgctttgtgc   65100
cttcctctct gtcctggtat ggggcctacc tggtcaatgc gtatccctg gatatgtccc    65160 agtattttcg gcttttcaac tcaactcgtt tacccaaacc cagtcgggat gaactcttca   65220
ctgatgacaa ggccagacac ctcctggtcc taaggaaagg aaatttttat atctttgatg   65280
tcctggatca agatgggaac attgtgagcc cctcggaaat ccaggcacat ctgaagtaca   65340
ttctctcaga cagcagcccc gccccgagt ttcccctggc atacctgacc agtgagaacc     65400
```

```
gagacatctg ggcagagctc aggcagaagc tgatgagtag tggcaatgag gagagcctga  65460
ggaaagtgga ctcggcagtg ttctgtctct gcctagatga cttccccatt aaggaccttg  65520
tccacttgtc ccacaatatg ctgcatgggg atggcacaaa ccgctggttt gataaatcct  65580
ttaacctcat tatcgccaag gatggctcta ctgccgtcca ctttgagcac tcttggggtg  65640
atggtgtggc agtgctcaga ttttttaatg aagtatttaa agacagcact cagacccctg  65700
ccgtcactcc acagagccag ccagctacca ctgactctac tgtcacggtg cagaaactca  65760
acttcgagct gactgatgcc ttaaagactg catcacagc tgctaaggaa aagtttgatg  65820
ccaccatgaa aaccctcact attgactgcg tccagtttca gagaggaggc aaagaattcc  65880
tgaagaagca aaagctgagc cctgacgcag ttgcccagct ggcattccag atggccttcc  65940
tgcggcagta cgggcagaca gtggccacct acgagtcctg tagcactgcc gcattcaagc  66000
acggccgcac tgagaccatc cgcccggcct ccgtctatac aaagaggtgc tctgaggcct  66060
ttgtcaggga gccctccagg cacagtgctg gtgagcttca gcagatgatg gttgagtgct  66120
ccaagtacca tggccagctg accaaagaag cagcaatggg tgaggcaggg gtggggagca  66180
tgcccttggg tcttgtcctc agtgcttggg taagcaagcc taaatcattc tactccaaat  66240
ctgatttcta cccgttcact aggtttaatc catcgccaac tccccaaatt tttcttttct  66300
accctagcag tctgaacagc cacactagcc actagggatc agaatgttct tgcctcctaa  66360
gcaggggtgg ggaaatgcat gtgtctttgt cctcatttaa ggtcactttc agctgtgacg  66420
cattaattct tttttctttc tttttttttt ttttttttgg agacaagagt ttccctccgt  66480
ccaggctgga gtgcaatggc gtgatctcgg ctcactgcaa cctccacccc caggttcaag  66540
tgattctcct gcctctgcct cccaagtagc tgggataata ggcacccgcc actacacctg  66600
gctagttttt gcatttttag taaagaaggg gttttgccat tttggccagg ctggtcttga  66660
actcctgacc tcaggtgatc catccctctc agcctcccaa agttctagga ataccaggcgt  66720 gagccaccgc acctggcctt tttttttttg agacacggt ctcattctgt cacccaggct  66780
ggagtacagt ggtgcaatca tggctcactg caacctcaac ttccttggct caaacaatcc  66840
tcctgcctca gcctcccaaa tagctgggac tataggcatg caccaccatg cccagctgat  66900
attttaattt ttttttttt ttgagatgga ctcttgctct gttgcccagg ctggagtgca  66960
gtggcacaat ctcagctcac tgcaacctct gcctcctggg ttcaagcgat tctcctgcct  67020
cagcctcctg agtagttggg actacaggct tatgccacca tgcccagcta atttttatat  67080
tttcaataga cacggggttt cactatgttg gccaggttgg tctcaaactc ctgacctcat  67140
gatctacccg cctcaccctc ccaaagtgct gggattatag gcgtaagcca ccatgccggg  67200 cctaatttt aaaattttt gtagagatga ggtcccactg tattgcccaa ggtggtctca  67260
aactcctggg ctcaagcaat cctcctgcct tggcctccca agcactagg attataggca  67320 tgcaccactg cacccaacct ttttctatta ctgattggtt atcagactca cttttgaaaa  67380
tttaggattt ctaaacttac ggccccacta gcttcacctc agttgtaatg tgtctgctct  67440
ctgtaaacag gttatctcag aagctcttct caattgtcat ccgtcattac cttttttga   67500 taaaattcaa gacctggaaa ggacctggag ggtcatagtt gtcctttcat gttgctatga  67560
agtgctggaa gtgaaaggga cctccaagac attctaatct tctcttcctc cattttatag  67620
ggagaaaacc aagccactgg ccccgttaca cagcaagtta gtagtaagac tgagattcga  67680
accctggtca aacagacttt ccatttgtt ccactgactg aatcttctct tttcacttg    67740 aatcagactt ttagttttat tgtagttttt gagtccatag ctgtcttcct gtactgtctt  67800
```

```
gactctttga ctaaactgat ttcacatctt taaaattatg ctttccttt  aggctcattt  67860
ttagctcagc tgttgacagc tattttaaa  tgtaacatga cataatatat ttcctaaata  67920
atttaaaata atctagcttg agctgctctg aaggttagtc agttggtggt gtgcatagag  67980
gtagagcctt cccccactct caaggatgct gtgaggggta ttcctaccat gtggtgagtt  68040
gggaggtttt cctgaggtcc ttttccatcc tgagactctg gttttccatt ttgtttctca  68100
caggccaggg ctttgaccga cacttgtttg ctctgcggca tctggcagca gccaaaggga  68160
tcatcttgcc tgagctctac ctggaccctg catacgggca gataaaccac aatgtcctgt  68220
ccacgagcac actgagcagc ccagcagtga accttggggg ctttgcccct gtggtctctg  68280
atggctttgg tgttgggtat gctgttcatg acaactggat aggctgcaat gtctcttcct  68340
acccaggccg caatgcccgg gagtttctcc aatgtgtgga aaggccttaa aagacatgt  68400
ttgatgcctt agaaggcaaa tccatcaaaa gttaacttct gggcagatga aaagctacca  68460
tcacttcctc atcatgaaaa ctgggaggcc gggcatggtg gctcatgcct gtaatcccag  68520
cattttgaga ggctgaggcg ggtggatcac ttgaggtcag gagtttgaga ccaacctggc  68580
caacatggtg aaaccttgtc tctactaaaa atacaaaaat tagctgggtg tggtggcatg  68640
tgcctataat cccagctact tgggaggttg aagcagaatt gcttgaaccc aggaggtgga  68700
ggttgcagtg agctgagatc acaccactgc actccggcct gggcgacaga gcgagactgt  68760
ctcaaaaaaa caaaaaagaa aaaaaaactg gggcctgtgt agccagtggg tgctattctg  68820
tgaaactaat cataagctgc ctaggcagcc agctacaggc ttgagcttta aattcatggt  68880
tttaaagcta aacgtaattt ccacttggga ctagatcaca actgaagata caagagatt   68940
taagttttaa gggcatttaa tcaggaggaa aggtttggaa aactaactca ggtgtattta  69000
ttgtttaagc agaaataaag tttaattttt gcttgaagat ggttcttaat ttcttttaac  69060
ctaattccta atcctcacaa agatctttcc aacagcaagt tcagtaagtt caggtaacag  69120
tacgtcacca ttggcttctg gctcattgag tgatggtggg atcgcggttt catctctgta  69180
aacttgccct tgactgggga gataccatct ccttaaaaat actcttcatt ttcctaagga  69240
gtgaactgct gctgcacgaa ttcttatttg tggagggagt agctgcctcc ttacttcacc  69300
ttcatgcacc agtgcagcgt gaacaggggc tttattgatg gggcttggga agctgtaata  69360
aagtccagca tgcagattgt gaaggtttcg tatagccacc aggagacaag ggtcaaagga  69420
acgagcctct gtgggctctg ctgcttagag tactttgtcc tttctcagtt cttaagggca  69480
actgggaagg aagagggatc agcacttcac aaactggtgg gtgacctcat agattcccac  69540
agactcctgg gccttttcat catagtcagt ccagtcctgg gaaacaaaat ggcattgtta  69600
gcctcacaac gcagaatgca gccatgtgga gagcagaaaa ctgggactta aaaggcccag  69660
ctcaggctct gactcaaata atcatgaaca tgtatgaccc tgaacagagc cagatagctc  69720
aggcctgaat tctagctctt tcagttgtat gactgtgggc aaatcactta acttctctga  69780
gtcccttctc cgagtcctgt cttctatta  aaaaaacaa  aaacaaaaa  aggacaatgg  69840
agttcatatt gaatgttgaa agaatcaaat gaggtaacac atttaaaagc actcagcagc  69900
cgggcgtggt ggctcatgcc tgtaatccca gcactttggg aggccaaggc aggtggatca  69960
tttcaggtca ggggtccgag accatcctgg ccaacaaggt gaaacccggt ctctactaaa  70020
aatacaaaaa atagccagga atggtggcag gcgcctgtaa tcccagctac ttgggaggct  70080
gaggtaggag gatcacttga gcccaggagg cagaggttgc agtgagctga cattgcacca  70140
```

```
ctgcactcca gcctgggcga cagagtgaga ttgtctcaaa aaatacataa aataaaataa    70200
aagcactcag catagtgagt gcctggcaca tgtaagagct cagtagatgc tagctgctgt    70260
tattaggtgc tgagcaaatg aaatgaagtt tttgtccttc cttcaaggct tgagcacaag    70320
gcttttctat ctgcagggta gtaatatgtc cagtaataca gactatttct tgttcttcat    70380
ggtagttagg tgcagtaaag ccaccacaaa cactgaatta gggaatactg aatgaatact    70440
ccccggggaa atacagggtt aggttcctat gagcctctgg tcacattttc atcaaccaat    70500
caataatcta gctttatgtg tttctgttta aagataactt atttaatata tattgttgat    70560
tcatgaactc acagccagca gcactatagc tcatgcctga ataaagctta tctaacacgt    70620
attctctctg taagggcat catagctttc tcatacgtag aacattaga aagcacttta    70680 gcactatacc tgtggccatt tcaacagcaa aatcactaac aaaaagcaca aaatacaga    70740 gttggctttc cattgatgag ccttgtccac caaaaaaata attcccacca ggtgccctac    70800
agtacctccc aaagccccca agtctcatac cttctcctgc agattaatgt cactgaaggc    70860
tgtccctgac tccacacctt cagcagcaaa cccagcctgc agggcacaag aaggtaccag    70920
ttagtcttgg caaagaagg cattgggcta aagtaaggg ccggccaggc tgctggctct    70980
tctcacactt ctgggatgga ggacagagat gcagtatgag tacctgtctt ggaataactg    71040
ctgagcttcc aggacccggc agctgcctca gaactagagt ggtggtttct ctgaattaca    71100
gccttggacc agaaggcagc aggggcagcg taatcccttc cactagccct ggtttgctga    71160
aggctcctgg gcatgtcatt tcccaggttg gaccttagtt attgataaaa cggggatgaa    71220
gtatttgctc ttctgcctac ctcacagatt tgttgtgagg tgaaacatgc acaaataaag    71280
ggggatgagc accagctcaa gtcagataga tctgggttga aactatagct ccactgctta    71340
ctgtgtgacc ctgagcaagt tgcaaaatct cttcagttcc ttcctcatct gaagaacagg    71400
atgaataaat tcatagggtt accataagaa ttaaatgtgg taacatgtaa aaatgatggc    71460
atgggtgccc aagcatacag cagccactta agggacaatt attactaccg ctagaaagga    71520
gaatgtctag tccatggtat ctgtaggtag cacagttctg gctgtcactt catacatccc    71580
ctccccaaag acaaagattc cccagaaaga tacacacaca cctgcggctg gaaatcaact    71640
ggttcaaggc cccggcactc aaactccact attgtcttga agttctcatt gtcttcagcc    71700
tagaaaggaa gtgtgttgag gaggcaggcc caaatgagct tcaggatga ccccatggcc    71760 cctctccttc ctgccaaatg ggcacttact gcccctggag gcctagtatg agacccagga    71820
agaactcatc cccttcttag aggaagcctg ccttgggcac ctgctcccta tgaagctttc    71880
tgtagacagc agacatggag gctgcagaag agcgtggatg ctggggtcaa cctgcctgga    71940
tgtaaggtaa gctctgccta tcttcccctc tgggcccaag attcctaaac tgtcaaatag    72000
agccgaggaa acctctacaa ttttactgtc agattttgaa atgcatataa agtgcccagc    72060
acagtgctca ataaatagta aataaaatta tcaacaccaa aaatatgaac aagaatgtta    72120
agctccaaag tctctagatc atccaaacag acccagtaca cttaaccata gccttttgct    72180
gaccatctgc catgcagtaa gggcagaggg ctgtcttata gcctttgaaa tggttatgta    72240
tgtggagggg gcacctcttg ggggcaggt ggccaggaaa ttcatgccta cctgacctat    72300
gggcttaggg accacaagtg ccatgcccta cattcagtct catcctgtca ttcactgtaa    72360
agtaatttcc tgcacactga ccacatctct ggcactggta aggcacttct ctgttagggc    72420
cctagttcga ttcttgtttt ttgtattttc cactagatta ttatgtacgt gaaggcgagt    72480
cctcatttaa tttctcttta acttcaggac aaagccaaga atttggcaca actcaagata    72540
```

-continued

```
ctttaaataa ataccaaata aggaataggt gaatacatat aactggcttt ctttaaacaa    72600
acagatccaa agcacaccct ccctcacctt tgggctaact tgttaacact gatgatataa    72660
aggatgggat gcaccaaacg actacccac ccatggtttc agagaaagct tgctagtccc     72720
ctaaaatgaa gacaaggcaa gtgctctcag tgatgcaaac tgaacagcta ggttgtgtca    72780
gaggtcccct gagctctcac agcccagccc tcataagaag gcactgcaag aggcaatata    72840
ccaagcactc agtgtacagt ggataaatga ctgagtcaaa gaagaactaa gttcatgagt    72900
gaatgtccta tggcaggtca ctctgatgca ggcatgactc tagaacccag acctactaac    72960
tccagttagg atttaagccc accatccctg ccactacagc agcaaactta cattgtaagg    73020
cttgatggtg ctgcttaaaa tctctgaaat agaaaagaga acacaaagtt gacttgagtc    73080
cataccctcg ccccagccag gtgcccacat gtggccctga aaagatcac gctgtacagg     73140
tgtcggcatc ttaggcctga ctccaccctc aggtaacatg agtctacttt cagcctggtg    73200
ccaggaagct gtgggccacc ctggcagaac tcagtacgca cagcctgacc taccgatgga    73260
attttctctt gcacacagct tgcacttctg gaccatggaa gcactgccac ggcccccctt    73320
cagtgccaca ctgtcctggc aaaaagcaaa cagaactttc agtcacatat gaattagatg    73380
tacagtcctg aggagatcga gcccaccatt tattgtccac ttaaagagac caagacccag    73440
aaagggtaac ttactaggac aagactcctg ggaaggcttc ctgaggaaaa taaaaaaagg    73500
gcttccccctt gattttgaac tctgcctcat acctcaaaga tgcctattga atccagtgct   73560
gatcacactg acacctaccc tcccaaacca caaaaagcag ggagcaaaga actggagaga    73620
tgaaggccag tttccccaaa tccctgccca gaagtgtatg tgtgtttgtg agtgtttatg    73680
ttggggttg ggcggggaac agttaccatc agccggatgt actgccactt gtccgaaatc     73740
tcaccacagt tgccacattt catctttggg gaaaagaat gttagtaaag cagctggctc     73800
tgctgcacag acaccaagga aagggtaaga acagtgggag gtgggcaggc tcatgatcta    73860
ccttcttgat ggcaatctca cttcatccct aacacctgcc ccaacaagga caaaactaga    73920
actatctctg ggcaaaggat aggtaaggct gtttcctatg ccggcgtgcc caccctcctc    73980
tatgaagtgc tcagtgtggc cggggattca aggcacctgt ggtgcagaaa tggtttcagc    74040
ggaggtgagg gggggaata tggagagatt tgttagaaga tacaaaatta cagctatatg     74100
ggaggaataa gttctagtgt tctatagcac tgtaggatga ctatagctga caataatata    74160
tagtttcaaa tagctaggat attaaatgct cccaacacaa agaaatgata cacgtttgag    74220
gtgaatatgc taactaccctt gatctgatca caatacatta catttatcgg aacatcacta   74280
tatccccat aaatatgtac aattctgtgt caattaagaa aaaaaagag aaatggcctc      74340
agcaggcccc cgacccactc tgcttggtta gctttatgtt cccacaggcc ctgtatgtca    74400
ctggtataag cacttatcac tctattgtta ctctatttt ctgtctcctt cactcgattc     74460
cgcttcttca agccaaagaa cagattctcc caagtaagcc ctggtattca ggcttcaaaa    74520
tcctgggaaa caaagtagt ccggaggcag cttcccgaaa acagggctt ttgagaggta      74580
cagaaggatg ctgggatttt tgaccaggag taaaacagag cagaagctct gggatctgga    74640
agagtgaaga gcctcgaact gctggggaag gggaggcctc tgtagaccat gccactaggg    74700
taccagcttt accagtgtgg gagggctaag gaagggtgga ttacgcacaa aattaaacta    74760
tttcacaata aagaaaacca aatcaataaa cgaaaggcga actattcacc ttattaaata    74820
atcacaagcg tcccttcaag tagcatttcg tttagtgtcc atttacagac cacgaaatat    74880
```

```
ttaacacagg gaagaactac aaaatgaagc ttttccaagac tgccaattag agataaacca   74940
atacactta ataagaaagca aacgtaaaat tctaactagg aaaaccccga acacttaatg    75000
```

| | |
|---|---|
| ttaacacagg gaagaactac aaaatgaagc ttttccaagac tgccaattag agataaacca | 74940 |
| atacacttta atagaaagca aacgtaaaat tctaactagg aaaaccccga acacttaatg | 75000 |
| tgcctggtta aatattttct catactgccg gagagaaggc tccggttcag cactgagatc | 75060 |
| aggacgggcc tcctctcccc gggccccgcc ccggccgcac cttcaggtac caccggaagt | 75120 |
| cctcgcccac gggccggagg ttggtgatgt tctccagcgt ggctttgagt tgcagcgcga | 75180 |
| ttttctgagg gggagggcca gagcgactgc gtcagccgtg cctgcgcagc cccacgcctg | 75240 |
| cccgaccctc ccgcattccc agccgtgggt gccacaggga gacactcctt ctgcctcctg | 75300 |
| ctccttcagc gcgcacccac tcgcttcatc tcctcctggc gcgagctgtt gcctcccaga | 75360 |
| ccctcgccac ctcccctccg tgtcccgcg gcgggcggcc tcccctcacc cccatggtag | 75420 |
| ccctctccgc ccggtgctgg ctgcggccct tgccgttgct ttccggcgcg tcgtaaaagg | 75480 |
| cgggtgccgt ctgcgcaccc tcagtagggc ggggccgggg ccgggccgcg gggcagggac | 75540 |
| ttctgcgcgc cgctgctcgc ctggcccact gggcttttcg catctgggga tctgggcca | 75600 |
| gtggaggtca gccaggtccg cgagcaacct gtgctcaggc cagcggaagc ctgactccag | 75660 |
| gattcggtgg tgccacagac agttactgaa cgccaatttt gtgcctgctt taagcgaaca | 75720 |
| ggacagttcc tgaccctcag ttcttcccag gctcttcact actctgcctg ccctggaact | 75780 |
| tctcagatca cgtcagctcc ctctgcccag gggaaaagct acaaaaggaa gagttccaag | 75840 |
| actgccaaat aaagataaac caatacgctt taaaaagtag aatgtattgg tttatcagat | 75900 |
| ttggggatga tgcctttctt caaactgccc tttcctgttt cacccaagag acctggtttc | 75960 |
| taggcccttc tccagagttt gccctgtgtc cacatccttc tcactgtggt ccttgcgact | 76020 |
| ggacattccc cttcagctgg ctcttttttg ggagcccacc tggcttatcc ttctctcata | 76080 |
| acgtttattg aactttattt tacctggcct cctgtccagg ctacatctga gaccatgcag | 76140 |
| gagctgtgga gattaacggt aaaaggaaca gcacattcaa gactcttcta ggaggtgggg | 76200 |
| caagatagcc aaatagaacc ctccagtgat cctcctcctc ctcttccctg gcaggaacac | 76260 |
| caaactgaac aactatccac acaagaaagc accttcatga gaaccaaaac tcaggtagca | 76320 |
| atcacagtag ctggttgtaa cgtcacatca agatataagg caatggctgg gtgcggtggc | 76380 |
| tcacacctgt aatcccagtg ctttgggagg ctgaggcggg cagaccacct gaggtcagga | 76440 |
| gtttgagacc tagctggcca acatagtgaa accctgtctc tactaaaaat acaaaaatca | 76500 |
| gccgagtatg gcagtgcaca cctgtagtcc cagctactcc ggaggctaag gcaggagaat | 76560 |
| tgtttgaacc cgggaggtgg aggttgtagt gagctgagat catgccattg cactctagcc | 76620 |
| tgggtgacag agtgagactc tatctcataa aagaagaaaa aaaaaggaac aaggcaatga | 76680 |
| agagggtagg aaagacagtc ttgaattgct accaccaccc ctccctcatc ctctggcagc | 76740 |
| acctggctgc ctggcataga gagagaatct gtgtgcttat gggactttgc attggaactg | 76800 |
| agttttgccc tgtcacagtg gaaagcaact cagggcagaa ttcagctagt gcccacagag | 76860 |
| gaagcactta gagaaaccct agccagaggg gaatcatcca tcccagtggt caggttctgg | 76920 |
| cgagccccac caccactggc taaagtgctt cagggtccta aataaattcg aaaggcagtc | 76980 |
| taggccacaa agactgcaat tctgggcaa gtcctggtgc tgtgctgagc tcagagcccg | 77040 |
| tggacttggg gtgcacacag cctagtgaga taccagttgg ggagccaaag gagtgtttat | 77100 |
| gtcaccagtc ccccaacccc aggcagcaca gctcacggct ccaggagaga ctcctttccc | 77160 |
| ttagaggaaa ggagagggga aagtaaagag gactttgtct tacagcttgg ataccatccc | 77220 |
| agccacagta gaataaaaca ccacgcagag tcccgaagcc cccttgccag gctctatctc | 77280 |

```
ccagatattt ctagagctac catgggccag aagggaaccc gctgctttga aggaaaggac    77340
ccagtcctgg caggattcat cacctgctga ctaaagagct gttgggcctt gaataaacat    77400
ttgtaatagc cacagtactg ggtgaggccc agtactgtgc tgccttcagg tgtgacccag    77460
tgccttccca gtaatggttg ccacagggag agactccttc tgcttaagga aagagagga     77520 aagagttaaa aaggagttgg tcttgcaact tgggtaccag ctcagccaca gtaaaataaa    77580
gcaccaagta ggtttctaaa gcccggactc catgccctag ctcctggaca gcatttctaa    77640
acccaccctg ggccagaagg gaacctgcca ccccaaaggg taagacacaa gcctggctgg    77700
attcaccacc tgctgactaa agagcctttg gctttgaat  aaacatcagc aataaccagg    77760
caatagtcac catgggcctt gggcaagacc cactactgtg ctggcttcag gtttgacaca    77820
gcacagttcc agcagtggtg gccacagggg tgcttgtgtc actcctctcc caactccagg    77880
cagctcagca tggagagaga gactccattt atttgggaga agtaaggga  agataacaag    77940 agactctgcc tggtaatcca gggaattctc tcggatctta cccaagacca tcaaggcagt    78000
acctctgagt ctacaagagt cacagcatcg ctgggtttgg ggtgcccct  aatgcagtta    78060 cagctgcagt gaccaaatat ttacatcaca acactcattt ccctttgagt acttggaaaa    78120
gccttctgaa gaaggatgag tacaaataag cccaaactgt gaaaattatg ataaatacct    78180
aattattcaa tgctctgcat tgaccaacag tcacaaacat caataccatc caagaaaaca    78240
tgacctaatc aaatgaacta aataaggcac cagtgaccaa tcccagagtg acagagatat    78300
gtgacctttc agagaattca ctgtcactga gaaagctcag tgaaattcaa gatagcacag    78360
agaaggaact cagaatcctg ccagataaac ttaacaaaga gatggaaaaa ggaactcaga    78420
atcctgccag ataaatttga caaagagatg gaaataattt taaaaattaa atagaaattc    78480
tggagctgat aaattcaact gatacaccaa agaatgcacc agggtctcta acatgagaa     78540 ctgatcaagc agaagaaaga attagtgagc ttgaaggcag gctgtttgaa atacacaga     78600 agaattgaaa gaaaaaataa caaaaaagga tgaagtatgc ctacaatatc tagacaatgg    78660
ccacaaatgg gcaaatctaa gagttattgg ccttaaagag aaggtagaga gaaattagga    78720
tagaaagttt attcaaagga agaataacgg aactttccaa acctagagaa atatataaat    78780
attcaagtac aagaaagtta tagaatacca agcagattta acccaaataa gactacctca    78840
tgtcatttaa taatcagact cccaaagatc aaagataaag aaaggatcct aaaagcagca    78900
agaaaaaaga aacaaataac acacaaagaa gctccaatgg gtctggcagc aggcttctct    78960
gtggaaagct tacaggccag gagagtggca tgacatttaa agtactgaag aaaaaaaaca    79020
tttatcctag aatagtatat ccagcaaaaa tgtcctttaa acatgaagga aaaataaaga    79080
tttcctagac aaacaaaagc tgagggattt tgtcaacaca ccagacccttt ccttcaagaa    79140 atgctaaaga gtgttttttca gtctgaaaga aaaggatgtt aagcaatgag aaatcgtctg    79200
acggcacaaa actcattggg aatggtaact acacagacaa atgcaaaaga ttttaacact    79260
aattgtgtgt aaactactca tatattgagt agcaagacta aaagatgaac ctatcaaaaa    79320
taataacttt tcaaaacata gacagtataa gatataaata ggggccaggc acggtggctt    79380
atgcccataa tcccagcact ttgggaggcc gaggcaggtg gatcgcttga gctcaggagt    79440
tcaggggcaa catggtgaaa ccacatctct actaaaaata caaaaaatta gccaggcatg    79500
gtggcatatg cctatggtcc cagcttttcg ggagcctgag atgggaggat cgcttgagcc    79560
tgggaggcgg aggttgcaat cagccaagat cacaccacta aactccagcc tgggtgacag    79620
```

-continued

```
ggcaagaccc tgtctcaaaa aaaaaaaaaa aaaaaaatat atatatatat atagatagat    79680
agacagacag acagacagac agacagacag ataggctggg cacagtggct cacacctgta    79740
attctagcac tttgggaggc tgaggtagga cgacggcttc agcacaggag tttgagacca    79800 gccaaccct gttttttct tttgttttt ttttttttt ttgagatgga gtttcattct        79860
tgttgcccag gctggagtgc aatggcatga tctcggctca ccgcaacctc tgcctcccag    79920
attcaagtga ttctcctgtc tcagcctctc gagtagctga gattacaggc atgcaccacc    79980
atgccaggct aattttgtat ttttagtaga gatggggttt ctccatgttg gtcaggctgg    80040
tctcaaactc ctgacctcag gtgatccgcc tgcctcggcc tcccaaagtg ctgggattac    80100
aggcgtgagc caccatgccc ggtctctttt tatttttat ttttgagat ggagttttgc      80160 ttttgtcgcc caggcttgag tgcagtggcg aaatctcggc tcacggcaac ctccaactcc    80220
tgggttcgag cgattctcct gcctccgcct ctcgagtagt tgggattaca ggcgtgcgcc    80280
accacagtcg actaatttt tattttagt acagatgagg tttcaccagg ttggccagga      80340
tggtctcgaa ctcctgacct caggtgatcc acccacctca gactcccaaa gtactgggat    80400
tacagggtga gccattgcac ccggccaaga atactttact aaagtttttt ttgcctcaga    80460
aaacaaaaga ctcttttatc acctgaggtc ccgtcacttc tttaaagttt agagtgactt    80520
tttttgatgt ctactttact accaacttgc ttcattgccc caagtactct tatagggga     80580 ggtgcactgg agtcaggaac cctgacatct cagtgctgtt cttaacttgc cccatagtct    80640
ttgaaggagt agagtgtggt ggaaaaagaa tgggtccagg agtcaggaca cttgggacct    80700
tgtcccaagc tggcctgttt ttagtagggt gagtttaggc taatcacttc ccttcaaatg    80760
aggcttagta aggcctggtt cctttcagca ggtgcaatct gttcaaccag tactgtgctt    80820
aaagaagcca tgcaatttag cagaaagaaa aagttgtcta caggtctacc tgctgaacaa    80880
attcccacac tatacaactt ggtcttggtc ctgaatggct gttggtattc tgattttaaa    80940
atggattaat ggaaaacttt tctgagacca aacatttat cctgttatca tgtaagaaac     81000
caaagtattt tccctacac tgaaatacct actaaaacct aaaatatttg tatctataaa     81060
aggtgatttt aaaactcca accaccatac tatttcatac ctaaaccatc aaaccagtgt     81120
taaatttcct taatggtatt aatttactt ttttttttt tttgacatgg ggtctcgctg      81180
ttgcccaggc tgaagtgcag tggtacaaac tctgctcgct gcagcctctg ctccagggtc    81240
caagcgattt tcctgcctca gcttcctgag tagctgggat tacaggctta tgccaccacg    81300
cccagctaat ttttgtattt ctagtagaca ggttttcacc atgttagcca ggcaggtctt    81360
ggtgacccgc ctgcctcggt ctcccaaagt gttgggatta caggtgtgag ccaccacatc    81420
tggcccaatt ttacattttt ttgaatcatt atccaaatag ggtccaaaca ttgtgttatg    81480
tgtctcttaa gtctccttta taagctccca ttctatctgt ttcccttgta atttattgaa    81540
gaaaccaggt catttgcctt ggaatttcct ctcaatatgg ctgattgaag tcccactgta    81600
tttttaaaac atgtttctgt attctcttat ttcctataaa atcataggta tatctagaga    81660
gttgattaga tttgattttt gggcaatact tcacatagaa tgttagtgtt ctacaaagta    81720
attgagaaga gttcacatgt tcaggtcttt ataaataat aaaaattgga ttttatcaca     81780
tatttattaa agacaatcat ttatagttca taaaaaaata ctgccctgat atacacaaaa    81840
ttttctactc ccacccaccc cccatgtcca caccaatatt cagtctagat tggtttaatc    81900
ttgaagtgta atccaataag actgaagacc aaacacttca ggtcctggac aagataataa    81960
aatactcgta agccttctgg atccctaaaa tacaaaagga aaaagtttta ggcattaaaa    82020
```

```
ctttgaccca tcaagtgtcc ctaaaaagga aaagactata tattaaaacg gtatattatg   82080
aggtaattta aatatgctga gttttttaata tagggaaatg cttacattaa gtgaaaaaat   82140
ataattaaaa taacaattat taatctcaac tgtatttttt atgcttctta aaaagtatat   82200
attgtattaa tgcatagaat aaatgcatta aagactaaaa agaaatactg caagatagta   82260
ataatggttg tctgattgat aaacttgtgg atgattttcc cctttctact tttctacatt   82320
tcctgtattt tctacaatga gcatgtatta ctttcagagt tagaaaactt ttttttgtttt   82380 gttttgtttt gtttttttgag acagagtttt gctcttgttg cccaggctgg agtgcaatgg   82440
catgatcttg gctcactgta acctccgcct cccaggttca agagattctc ctgcctcagc   82500
ctcccgagta gctaggatta caggcatgca ccacgcctgg ctaattttt gtattttag    82560 tagagatggg gtttctccat gttggttagg ctggtcttga actcccgacc tcaggtgatc   82620
cgcctgcctc ggcctcccaa agtgctggga ttacaggtgt gagccaccac acccggcccg   82680
agttaggaaa actttttttaa aaagtagtag tactaagcag gaccaagagg ttgaagatta   82740
ctgtggcatc actggctaag aagagtgtcc aaaggaagac aattacgccc aacatttgcc   82800
aaaagtgagc cgtacctaat cctgaaccct caaaacgtaa gagccaaaga agttgccaaa   82860
ttctaaggat tctttgtagc acataggttc atgcctcaac ttgataatct gccccactga   82920
caacatgaat tttaaaatct tgatcccttt tcaccaaacc aatgcttttg taaaaaacaa   82980
taaatttaag gctgggcgcg gtggctcacg cctgtaattc cagcactttg ggaggccgag   83040
gcaggcggat catgaggtca ggagttcaag accagcctgg ccaacatggt gaaaccctgt   83100
ctctactaaa aatacaaaaa aattagccgg gtgtggtggc aggtgcctgt agtcccagct   83160
actcaggagg ctgaggcagg agaatcactt gaactcagga ggcagaggtt gcagtgagct   83220
gagattgcgc cactgcactc cagtccgggt gacagtggga gactccatct caaaataata   83280
ataataataa atttataata aaataaaact tagatcctaa aaaatgtcaa gtttcactga   83340
agtcagattt taagatgtgc cagtctcaac agtcacactg agaaagctat tcagactcgg   83400
tgactctaca gtttatcatg agcactttt tggcatattc cattttttct tctggctgct   83460
cctatgcatt aatctatatg tgtgtgtcaa caagaagctc gcagtagcaa tggctgaatg   83520
aaacaccaaa agtaatagga gcaagtcctc aaaaataatt tgggttcct ccctaacaag   83580 aaggacaaag ctgcccacct gcattttgca tttgccccag ctcttcccat aatggtccca   83640
atttggttaa ggtttcttat caatctgctc caaaacagac acaactggat ataaggatca   83700
tgcacactta cttggattga ttgacatcaa taagggaacc aattttttgat gttgtaaaag   83760 aaatgtgttc atctccaatg acgatttcaa gctcctagaa acattttaga aaatcgaagt   83820
caagtagaat tggattattc atcaagcaca cagaaggatt aatcatttgc caaatcacac   83880
aaacttgact acagatggcc acaaaaacaa gggcagttca ctctgagcac taaactgtgc   83940
tgggcactag aaacaagaga taaatacagc tcatatttag aagaagttgt acccttaagg   84000
ccctaccatt tctcagattt ggaaaaatct atgtaggttt ttttttttttt tttcctgaga   84060 cagagtctca ctctgttgcc caggctggag tgcactggca tgatctcggc tcactgcaac   84120
ctccgcctcc caggttcaag cgattctcct gcctcagctt cctgagtggc tgggactaca   84180
ggtgcccgcc accacgcccg gctaattttt ttttgtatttt tagtagagac ggggtttcac   84240
cgtgttagcc aggatggatt ttttttgtatt tttaatagag acagggtttc gccatgttgg   84300
ccaggctggt ctcgaactcc tgacctcagg tgatccgcct gcctcagcct ctcaagtgct   84360
```

```
gggattatag gtataagcca ctgcgcccag cctatgtagt attttgtatg agttttcatt    84420
gtcaacaatg tggagtaaca tgaatacacc tatgttttaa aaataccaaa caattggact    84480
gggtgtggtg actcatacct gtaatcccag cagtttggga ggccaatgca ggagaatcac    84540
ttgagcccag gagtttaaga cctgtctggg caacttggct aaacctcatc tgtacaaaaa    84600
atacgaaaac tagctgggtg tggtggtgtg catccgtggt cccagctact agagaggctg    84660
aggtgggagg attccttcac cccaggaggt caaggctgca gtgagccatg atctcatcac    84720
tgtactccag cttgggcaac agagtgagac cctgtctcca acaacaacaa acaaaaacaa    84780
aaaccaaaga atctaatcta tctaggcaac ttccagacct taggtttgat ccccactttg    84840
tcactcccta catgtatgat gttggatctc aatttccaaa cagtgacatg agtaccataa    84900
ccttcaaaaa gtatctatgt gtagcctact gggtgctggc tattgttctc agtgctttgg    84960
acagataagt aaaaccaagc aaaccaaaga tctctgccct gtggaattca tattcttgtg    85020
aggcctattt acttttcttt cttttgatt catatatcct ttttgttata attcaatcag    85080
aaaatcgaaa aaactgagat gtttccaata ctcagattta taaattattg ccatacttgt    85140
gtcagatttt ttttaaaaaa gaagtaaaat attacaaagt ttatgtccat ctcccattct    85200
gttctccctc ctgtatcccg atttgttcca ctcttgtttc agatttggta gtatgttttt    85260
acttatttct ttttagatac aggatctcac tctgtcactg aagctgaagt atagtagtag    85320
gatcatagct cactgtaacc ctgagctcct gggctcatgc tatactgcac ctttagcttc    85380
tcgaatagct aggactacag gtatgcgcca ccacgcccag ttaattttta gggttttttt    85440
ttttttcttt gtagaaaaaa aggtctcact gtgctcaggc tggtcttgag ctcctggcct    85500
caagtcatcc tcccaccttg gcctcccaat taagaacaaa agtgctggga atgcaggcat    85560
gagtcactgc acctggccta gacgtggtag tgtgctttaa aattttaca aaatggtctt    85620 attatacata cttttacat ttttcattcc acattgtttt cgagatttat caatgttgag    85680
ttacacagat ctagctcatt agtttaaat gcttgtggta ttccatttcc ctactgaaat    85740
aaacttaagt tttaaatttt tattcctata aacaatgtag caagaatatt cttctataca    85800
tctccttgta catgtgaata tgtctccata taattcctag tattttaaat gctgccagat    85860
gccacaaaat tactccctaa cgcggttata ctaattttat tctcactctt ttctcatatc    85920 atttttaaa ttcggcagat ttttttctgt ttttattcta atgggtctga aatggtatct    85980
cactgttgtc ctttcatttt acaaatgaag ccgtaaatct tttcatatta gccacttgtt    86040
tgatcttgta agttatctat tcataacctt tgcacattct gccacgggac agtcttttta    86100
ttaatttgta attctttata tattctggat ggagaactct tgccagtttt atgttttgca    86160
gataacttct tccagtctat ggcttatctt tcaactttat cttgccatct tttgtcaaac    86220
ctaagttgta aagaagtcaa atttaccaat cttaccccctt aaggagtttt aaaaactcct    86280
tctctaccca gaataatac aagtctatat tctgtttaaa atttttgatt tctatggcct    86340
aattttaaaa atattccata aatacattgt cagctgtcct ggtacaattt gttaaataat    86400
tcgttctttt cccattaatg tgaaagtcca cctctgtagc acactttttct aagtttccat    86460 atattcatag gttggtttct gggctctcta ttctgttcca ttggtttagc tgtcaattcc    86520
cgaggcaata tcatactaca aatgaccaca gctttgtaag aaatttccag tattattttg    86580
gctactcttg cctctgattt tccatgaatt taatgctcat tctatttgat tctaaaggga    86640
aaaaaatcct actgcgattt ttatttgaat taagagtgaa tttataaatt actttgttga    86700
aaactgacat cttttatgata ctgaatcttg ccatccacaa aaacgataca tattttttgtc    86760
```

```
cttctataaa gcccttttcaa gttttgtaca tcttgttaaa tgcattccca agttctttat   86820
aactcttctt gcaattatta atggaattga ttttaattac agtatccaat ggcttattgc   86880
tggtacaaag gaatatgccc ttccctcttt acagaattgt tgtgatggta aacgagtta    86940 atagaaataa aaattttata agtggtaaag caaaatacat atatatgata ttactgagct   87000
cccttgaaca taaattaaag ttaactttag taagtactga gggtggattt ttaaaaaaaa   87060
ctcttcaagg gttggtccat cattttgaga ttattaggaa tgagtttata tgggttttca   87120
tattaattta acaaatacat tattattgag cttttactat acatgggtac tattttagtc   87180
actagagata cagcagtgga aaacactgaa aagcaagtaa gacaattta gacaatagca     87240 agtgctacaa agacaacaca tattgtgata aaactgaaag caaaagaaa aaaaaacaca     87300 aaaagacaac acaacagatc ttttcttaa tgatgggaag cgacttctta gattggatgg     87360
acaggcaaga catcactgag gaagtgactt ttgaagacct caataataga gacagtcttg    87420
tataaagtta aaggaagaat attttaggcg gaatgtggca agtgcaaagg ccctgaagta    87480
agaaccacct aggtatgtct gaggaacaga aatgaagcta gtaaggtttg aacaccatga    87540
cagattggaa gcccggtaaa agataaggtg ggagtttgaa ttttaagtac agtgggaagc    87600
cattggagtt taaatcagtg gaatacataa gcaaatttac gttttttaaag atcagaccag   87660 taggatgcgg cggcttacgc ctgtaaccac agcactttgg gagggtaagg caggcggatc    87720
acctgaggtc aggagtttga gactagcctg gccaacatgg tgaaacgcca tctctactac    87780
aaatacaaaa attagctggg catggtggag gacgcctgta atcccagcta ttcgggaggc    87840
tgaggcagga gaatcgcttg aacccaggag gcagaggtta cagtgagctg agattatgcc    87900
actgcactcc agcctgggcg acagagcgag actccaactc aaaaaaaaaa taataaataa    87960
atcacactgg ctttcaggat ggaaaaatgg atggtatgga acaagaggaa aaacaaggaa    88020
atctattaga agtctggatt aggatggtag cagtcaagag tgaaaatacc ttttctgtta    88080
attcagttca atatgacagt ggcttttatt ttttagttac caaaatggtg ctcagaatga    88140
atatatacat taatgtatat aaatatacat gaatttaaat acatcactg aattatttgt      88200 atgattttcc tttcattaga ttgttgaaat aattatgttc tatttctctt tgtatctcca    88260
caatgctttg tccatagtag ttagtaagtg agataggcaa caaaagcttt aagtggagga    88320
gggagtgtgg ggggtcttat ttgtaagatt tctgcactac aggataatca ataaaacaca    88380
cctgccggcc cactcggtca ggaggaggcc acaatgcatc atcctctttg gtaatttcac    88440
tgtcgtcaat tattctcttc agttcctcca tcacgctttt atgtacataa gcctgaacgc    88500
aagttaaaaa acaaaatgta tgttgtatcc ttaagcagtg cttttgactca gatagtgatg    88560 gaagataaaa ataactgttc ctgcagactt atttctggca tctccttaag tgggaagaca    88620
ttcatgctca acctcggcat gatgcaggtg agggacacgg tcagaagtat ccagtaactg    88680
cacctcagtc ccctatctag ctgttactac ctcctggtac atcctgttca catggccctt    88740
ctgcctgccc acatacccaa ctcacaacga aacccaaaac aggtctgtga gtgcccctg     88800 ccatggtttg aatgtttttg tctcctccaa aaaaatcata ctgaaattaa tccccaaagc    88860
aacagtgtta agagataggg cctttaggag gtgatcaggc cttgagggca gaggcccag     88920 ggatagatta gtgctttagg agagagctta agggaactag ctggcccctt tcttgttctt    88980
tcaccatatg aggacacagc attcattcct tctggaggat gcaaaacaa ggcacagttg      89040 tggaagcaga gactgggccc tcactagaca ctgaacttgc cagcgccttg atcttggact    89100
```

-continued

```
ttccagcctc caaaattgtg agaaatatat ttttactgct tacaaattac ccagtctcag   89160
gcatttgtt gcagcaaaaa agagactgcg acacccacat gccctggtta ttctttttt     89220
tttttttttt tgaaacggag ccttgctctg tcgcccaggc tggagtgcag tggtgcgatc   89280
tcggctcatt gcgaactctg cctcctgggt tcatgccatt ctcctgcctc agcctcctaa   89340
gtagctggga ctacaggcac ccgccaccat gcctggctaa ttttttttgta ttttcagtac  89400
agacagggct tcaccgtatt agccaggatg gtctcgatct cctgacctcg tgatccgccc   89460
gcctcggcct cccaaagtgc tgggattaca ggtgtgagtc accgcgcccg gccagttatt   89520
cttaactagg taatacactc ctgaggagca aaatgtattt taaaagatat gcctgtgtaa   89580
aaaaatagtg aggatattga catgtgtgaa taagcataaa atcaatagct aaaataacaa   89640
tatgaaaata tatgctaaga cattttcaaa ggtggcaaag tggttaaaag gaagagtag    89700
ctttgatgaa gccttaatga tgtagtagaa atcacagaac ggagaataca aactttactg   89760
gggcaggatt gggaattcct gctgtatctc ttactagcag gggtaactca gaacaagcct   89820
cataattaat acctgggcct ttattttctt atttgtaagg gggctataat accctccccc   89880
atcacatggg cttacaatca gggttaaata agatgccacg cctgacatct aacatgcatt   89940
caatgatgtc aactgctttc ccatgctccc tttcccactc agatgtaaat taaatagctc   90000
ttcattgtgt accatgtaca cagggaatat agagcacttt aaatagaaca tatttaattt   90060
tatgacagca cttgggagtg ggaggtagct tttattattc ctgtttttac aggtgaagaa   90120
acagagattt atcaagttca gccaggaact tgcccaaggt cacatggggt agtaagcagc   90180
agactcaggg ttcaaaccaa ggtatgtcaa aggttaccag taattgattc cacaatgtaa   90240
aataaaaaaa tcccaactaa aagatgattt gggaaataat ccagaagctg tctacagaca   90300
tgtgtctctc tccctgttct ttatctttca atactactag aaacaataaa acaatgcaa    90360
gacaaaaagc tgaaatgtag caaatgaagg actctcagaa ggcagaaggc tcatacctct   90420
tttctgatca tgacatcatt cttgtaattg ctgttgttgg catatcttaa cttccctgtg   90480
ggggcaaaaa acaatttcaa cgtataataa aaacatatga ataaagcatc aataccatgc   90540
caaggcatca gcagttgccc aaaatgtatc taacttgcta aaagtgtcta acagatttat   90600
tatttactct taaggtattt caacaatact agtcttttca gttcttcact tcaggcttaa   90660
acagccaaat atacagctga aactcaacta ctgcaaaaag cagctcaggt ggggtataaa   90720
cacaggcagg ctcttttctg actttgtcaa atcacatttt tgcaggtgaa tgtcctgaaa   90780
acaggcctag taactgataa cttaccgaca cataggacct cctgaggctc aaatgagctg   90840
tgaaaacatt ttgaaaactg taggatgcag tttacatata ttatcatgtg actgtgccat   90900
actctatttc tgtgatggag aagctgctgc ttttatcact gagcacattt ggtacacaag   90960
acccttgcc catgtgtgca tctgacagat taatggtggg gatgaggaga agacagaagg   91020
aaatagaaga catgtagact agaagacata catgtgagat gagcccagtg aatttattcc   91080
aacagcctct gtgctgtctc tctgcctcaa gtttcttcac attcagttca ctgtccatac   91140
agtggacaag gtgatgtggt aacagatcta tcagattagg ttactctaat actttgataa   91200
agtcaatggc tttccactgc cttcctggta aaatccaaac tcctcaacat ggcatacagc   91260
taagctaagc ccctgcctgc ttttccagcc tcattcctgc caatattctt ctctcacaca   91320
gctgaagtca aactacttgg tttctgcctg aaacatccca agcacttttt ggttttcagc   91380
ttctttgcat gctgtctaaa atgccttctt gactcttctt cgtctcctaa ccaattcctc   91440
acatccccctc ctcccatcat tttatgtagg aagcctcctc tgaccctcag gcttggttag   91500
```

```
gtgcacccttctctgctgcgagcctcctctgtttcttttaccacaacacctaatgtgct91560
gttttatcactgcttacaaatctatctccctcacagtcgaggcctgtcagattcatcttt91620
gtgccccactagtggatgtcttctgtcatctttgattgctctttccttcaccacagtgc91680
ctctgccaacaaaatcctatcaacgatcaaagtccagttggttctgcctccaacagtttc91740
ctaaatctttctctccatttctactatctctgtagtcccaaccagtatctttttttttt91800
ttttttttgagacagagtctgctctgtcacccaggctgggtacagtggcactatctca91860
gcttgctgcaacctccgcccaggttcaagagattctcctgtctcagcctcccgagcagc91920
tgggattacaggcgtctgccaccacacccgctaattttgtatttttagtagaggcggg91980
gtttcaccatgttggccaggctggtcttgaactcctgacctcaagtgatccgcataccctc92040
ggcctcccaaagggctgagattacaggcttgagccaccgcgcccggccccaacatcttt92100
cgtgtcttgacaactgcaacagtctcctaatcaatagccctgtttccactcttgcccatt92160
ccgcacccaataaccagaatgcttttcaagaagagatcacatttcttctctgcttaaaa92220
ccttccaagcccggccgggcgcggtggctcacacctgtaatcccagcacttgggacgcc92280
gaggcgggcgtatcacctgaggtcaggagttcgagaccagcctggccaacatggtgaaac92340
tccgtctctactaaaaataacaaaattagccgggcgtggtggtgggcgcctataattccag92400
ctactcgggaggctgaggcaggagaatcacttgaacccggaggcggaggttgcaataag92460
ccgagatcgcgccattgcactccagcctgggcaaaagagcgaaagccgtctcaaaaaaa92520
aaaaaaaaaaaaggccttccaagtccaaacttttttaccgtggtctataaagacctaaga92580
ggtgccgctcctacctacctatccgacatcatctcctgctatctcccagctcaccactct92640
tcaaccacactgaccacctgagacacgcctagctcattcccgcctgcagccttgacatc92700
tggtattcccttttgtgtagaatggtcttccttatgagcttcacaaggctgagcccttctt92760
gttaattaggactcggctgcaatatacccttacagagctctctaatgccaacctat92820
ctaaaagcagcccatccagcaattattctaccatgttatttttgaccactcactgctat92880
ctggaatcatctttttgtttatgatctctccccggcagtaaaacacaagttccacgaga92940
ggggaagtttgtctaccttcgctgccgtatcccaaagagtggaacagagcctggcacac93000
agtgggcgttcagtcaacgtttgctgaatgatagaaagaccccgtggagcagacacagt93060
ggcgttccttaagatctgcactgcacaggtctcagtccctccctcctctagttccccac93120
agatttccgaccctcggcctccccactcgccggccccaggctggtcccgctcccggc93180
gggcggcaggctgcttttacgtccggtcgaaactcaaactccaggaactcgtggccgaa93240
cttgcccttgtgccccacgtagtaacgcagataaaagtcactctccatggctcccaaaag93300
acaaccgagctgaacttccaagagcaagccgcactgccgccgtctgcgccgacactga93360
cgtttgcggcggcgcgcggaagtgacgtcaggtcccgtcgtcgctgcgtggggggttcc93420
ttctcgctaacctcttcgccggaagtggcaacaagactgcaacatccccccacgcctag93480
tctgtaaagaactttgtttaacccggagccggggccagccagctccgccctccagctgg93540
acgcgggagcgaggttgaggttcatacccctgggttctctccaggcctgaggcggagagc93600
cagccgcctgcctacctctgggctttgaacccgggtctggtgacttcgcttaaagacct93660
cgggccgaagggccgccaggctcaacctcggttcacaggaccccccgacttgtgtgagtcg93720
tacaccgctctttaccgtctctggacctaggtcatctcggcagtaaaatggggtgaaatg93780
acccgacctcccggaggatgccgcgcacgatgtgtgcctcaagttggcttccactgacc93840
```

```
tgaactgtta agaaagccct cctcagtgac gccttccctg aatccacagt ggagattgcc    93900
gttttcctgg aactaattca cccacactta cccatttcat ccctttccac cttttatttc    93960
tacctttctg ccccactgat ctctagaata ggtgctggga gacgttagag tatttgatct    94020
cccactcccc agtcatccca cttaccgagc agtaattctc tgcctggctg cacattgcaa    94080
tcacttggga agcctctaaa aatactgatg ccagggctct accccaagcc agttaaaatc    94140
tccagcgctg gacctgggca ttggtacttt ttgtaaagct ttcaggtgag tcagagttga    94200
ggaccactga ccaaagaggt cctttctttt cagggtaaag ttgtcctctg tgaagccttt    94260
ctggctctgg aaaaaattta cagttgagta ggcccagggc aatcaagatc ataattatgt    94320
aataggaacc tgctttcact catctaagtt ccaggcttag aaagaatgaa tggttctaga    94380
gacagtgccg agatgacatc attcttgggt cctggcggct agaactgtat acgattctgt    94440
aagttgggac agcagtctct gattcctatt cccagtcttt tcttttggag acggagtttc    94500
gctcttgttg cccaggctgg agtgcaatgg agtgatctca gttcaccgca acctcgccta    94560
cctaattttt aaacttttttg tagaggcaaa gtctccctat gttgcccacg ctggtctcaa    94620
actcctgggt tcaagtgatt ctcctgcctt agcctcccaa gtagctggga ttacaggcat    94680
gcgccaccat gtccagctaa tttttgtaat tttctgtttt tagtagagac ggggtttcac    94740
catgttggcc aggctggtct cgaactcccg acctcaggcg atccgtctgc ctcggcctcc    94800
caaagtgctg ggattacagg catgagccac cgcgcccggc cctcagtctt aacacggagt    94860
ccttttctcc ctgcaaaagc attagcagca gagtgtagag taggtgtggt ggggggaaaaa    94920 tcactggaca caggttaaaa taatccctgt gtaacaatga ctcattgtaa ccaaaggtga    94980
accgactcaa cttttagac ttcagttcc ttctctttaa aatgagcata ataatgtaca    95040
cctagcagaa ctgttgtaag aaacaatgtc tcggaaacta aattgctgta aaaccataag    95100 acattttat tacaaaacac tggatatggg tggtaacaag ggaattgtat aaacgagaag    95160
ggggctagac acagtggctc atacctgtag tcccagcact ttgggaggct gaggcaggag    95220
gatcacttga gcccaggagt ttgagaccag cctgggcaac ataggagact gtctctacaa    95280
aaaatttaaa aaataggtag gtgtggtggt gcacacctgt agtcctagct acttgggagg    95340
ctgaggtagg aggataattt gagcctggga ggtcgaggct gtagggaacc atgatcacac    95400 cattcactc cagcctgggt gacaaagcaa gaccctgtct caaaaaaaa aaaaagaga    95460 aaaaagaaa agggaccagg tatcaagcac ctaataaatg tcagcccta gggtcaatgg    95520 gattacctgt gcttgttctt tgaatcatca caacaatctt gaggtggtaa ttagagttaa    95580
gtatgtagag ggattaagca attgctacaa ggttattttc caggagtaaa attataaaaa    95640
tcataagtga atctggggat cttcagatgt ggcaaataac aaaagtgttg agaaatttaa    95700
aggacacaca actccagtca ggctgtgaag taatccaggt ttctggatat gagacatggt    95760
gtaactgaaa gagcatggtc tgtgtgtctg cagtgcctgc attcagcatc atttatttga    95820
gcatccactg agtgtcatgt gcagagagga tacaatgttg agcaagacag ttgttcacag    95880
agcttgcaga ggaggcagtt aaggagcata caagcaatta caatgtaagg ataagattac    95940
caataaagga agcacagagg actatggaag cacatgaggt gactcctaat ccagtgcagg    96000
gtccttaggg aaatgttcct gaaggaaatg ttccagacgg aggcccagaa ctgtgtgatt    96060
agaatataga gtagtgagtg atgaagctgg agacagggca gaagccaaat catgaagggt    96120
tttataagcc atattaaaag agtttgggca aacccaagaa tattggattt ttgtgccagc    96180
aaagcagttg aagagcttta agcaggaaag tggaaagaag tggtggtgat acatctatgg    96240
```

```
tactttagaa agacactttg gctgcagtct tgtaggttag attggaaaat gaaaagacta   96300
gaagtatgac attcagataa gtagtttaag taatctatta gctgggcagg gtggcgtgca   96360
cctgtagccc cagctactcg ggaggctgag acaggagaat tgcttgagcc caggaggcgg   96420
aggttgcaat gagctatgat cctaccactg tactccagcc tgggtaacag agtacgaccc   96480
tgtctcttaa aaaaaaaaaa aaaaaaaagt aatggagata gaaaagtgga tggatttgag   96540
atggaatacc ataatttaag gggtaggcaa aggatactaa gatgtggcca gagagatagg   96600
agaaaaaaca tgaaatgtta tcatggaagc caaaataaga atatgccaag aaaagagtgg   96660
ctaacagtgt taactactgc ttccaggtca aggaagagca agactgaaaa tgtttaccag   96720
atttataatc gaggaggtcc tggatgacct tggcaaaagc aaccccaatg gcatgggaat   96780
gaatggtaag gcagaagtat tgggatgcaa gtaggcaaaa attgttatcg aagtacagag   96840
gtgagttatc taacctagtc ttagagaaaa gggaaggctt cctggaggag gcattaccta   96900
agtggagtac tcaaggacaa ataggagtta gtcatgtgga ggcagagaag gaaaatttag   96960
gcagagaatg ctacatgtac aattgctctt tgggggcact aaaaataacc ttgtgacttt   97020
gggcagttac tttgcccatt ttctcatcta taaaatggga gtggatagta ttgatagtat   97080
ttatctcacc gaattgttga caaagattgg gataatttat atagaatact ggtacacatt   97140
agggactcag taatagttca ctccccctca ttaaagtatt acaatgaaac aaaacttaaa   97200
agatttttttt taaatgaatt taatctctct ctagaaacag tgcactgatt ttacaaatgt   97260
ccacatttgg ttttcagttt accaagatga tgccagtata gctagtgaga tgcagcaccc   97320
catcctcagc cccctcgcct ctggaagaga caccagactg caaagggcac cgcgtacaga   97380
agctaacgga acttgaatga caagacaaaa agagcagaat cagttagtgt gacacaacat   97440
tctaacatgc ctgattctta catcaaatat ggtaactttg gggttggtag ggggagacaa   97500
acaaggagaa tccacttggg aacaatttga tgaagtttgc aaatcagcac tttacccccca   97560
aattaacaac agcttgtatg gaaaaaaaaa tgctctttta aaagtatatg gtttggacag   97620
gtatatttgt tttctcttgt agttttttgta aaaaagtatc aaaaccttgg ctttaaatat   97680
atatatatat atatatatac acacacacac acgtggcttt ttaaaaatta ctttttttata   97740
gcacaaagtg tttgtaaatg cagagggttt ctgctaattc ttgactgtgc acatggtgca   97800
tagcctgaat gaacagagct tcctgatttt tttttaactg aaaaattgaa gcagtaattc   97860
tttaaccttc taaattctcc atacccctaaa aatacagtgt gagaagtctg ttactctatc   97920
ttcatgcatt tcgggaaaag gaattattta ctctgaaaca tttaatgcta actcatttat   97980
attttgtgaa acgatgagtg tatggctgga gttcggggg tagggtggag aggcttgcat   98040
tcctgtgcca tttccccatt cccaccagtg cccaactgga cagtgattag tatcccctct   98100
ccagactcaa cgtcttcaac atttttcgttt ttctttctca cagttgagaa aatctaagag   98160
gctctcgaca acatggcatg catctgtgaa aatcccactg cccttatatt agtcttcatt   98220
gaccatataa aaaatctttg actcaaatat atgaaaagca gtcagcattt ccctttggcc   98280
actggaaagc ttgaggctga ataatatcag ttctgcaaag tgctggcaat gcatcctaat   98340
gaatttttcca tgatgcatgt agtgccttgt acacaatgat caagaaatgc ttcattgaat   98400
cagaaattaa tctattttat aaagtgctta cattgaatct ctttccatac agcctcattt   98460
cttgcccccc ttgagccttt tgttcctgtt agaatgaact gtgcaattcc taaagtccct   98520
gtgctctttc atacctctgt gttttagctc gatgtgtctc tgtctgaagc agcttggaat   98580
```

```
cccccttctta  attttttaaga  cttaaggtca  cttctatgat  gaccctattc  ctcatttctt   98640
aggtggaaag   acccctctct   cctttgagcc  ctaacagtgc  tctgaataga  atcaatgcct   98700
tttttgtttc   cacatatatc   atcctccact  gctactgtga  actctgtaaa  gtcagaacat   98760
gtgtgactga   cctttacatc   tgcagtgcca  ggtgtgtagt  tggtatctag  tgagtggttt   98820
tagtgaatga   atatactgca   gtcatactga  gataactgga  gggatcaata  ggacttactg   98880
ccatacattt   aaatccgatc   tcattctctt  tttgccagtt  aacaggttac  ttcaatctgt   98940
tttataaata   atctgtgtat   caagagtaaa  taagtacagt  ttcgttttct  ctgtttctag   99000
aaggcatttc   agttagtgcc   tttgtaattc  cactggagga  aaggtagacc  atagtatagg   99060
tagcaggttt   gatacaatgt   tcaggcagcc  caaatagtc   ttcctgcaga  aggaaatgga   99120
ggaaacgcac   tgggactggc   ttctgataaa  ttttctgccc  ccttggcatt  gtctctgagc   99180
ttccttccag   ctctatagtc   cagtgactct  gtgatctgtg  attggctgta  gatagctatg   99240
cacgggggca   aaaggcaaaa   gatatgtaac  tgtacctcaa  aatgaggctg  aaaagcctct   99300
atgaatgggg   gaaggtggat   ctgactcctc  aggtttcatc  ttatttactg  ccgtccaaca   99360
catgaatata   tcacaatttg   tttcttgtaa  agggttgctc  ccattgctgc  ctctttcaaa   99420
ctgcagttgt   agcatatgca   ggaaacatga  atgtctctga  gaaaagttg   tgaatttcat   99480
tgtcattttg   agatctcagg   ctgtatgtcc  agaccccatt  catcattttt  ttctgtgaat   99540
gccaggatct   tactgaaagt   ttagaaacta  tgccttagcc  actgttatca  tttaattcct   99600
tggaaaattc   agtttctttg   gaaggttaca  gaaaaagtca  cttgttttga  gtacatttcc   99660
atgtttttca   ctgtcatcat   ttttcttcag  tcaaaaataa  ttttactttc  cgttcttaaa   99720
agaatagtaa   tatgtgagta   agctccatag  gagttggcca  cctgttctta  aaattctgtt   99780
tggtattggt   cattctaggt   caactgcatt  taccctctca  atgaatgttt  caggactatc   99840
aacacatgca   tgtcatgagg   agattgctgg  attatgcaaa  acacactgcc  caagctccag   99900
aatatagtta   ttttcttaga   gtttaggagg  ccaagagtga  cacagaggaa  ggtcctaggt   99960
acaggatgct   agaactccag   aatgtctgac  tgaaaattca  aagggtatca  agctggtgag  100020
acatccaact   tcattgagtt   gggggcatct  ggcaggtagg  gatgggaagg  catttgctta  100080
agtgtgtcaa   gttccaggta   tgatgagatt  agatgcagct  cctctgctcc  tacttaagtc  100140
aaacacttcc   atgttgcacc   ttgtccctgg  ttgtctagtg  ggagtaagtg  gcagaacagc  100200
agagttaaga   aactcaaact   ctttctcttt  ggatgggaaa  gccactgggg  actgaatcct  100260
tctgggacta   taggattatg   tttccaatgg  gagaccccac  aagtagaaaa  gagcacttct  100320
cccttcctcc   cccaaggcca   agaaaagcaa  agaagatgtc  tataatgaag  aacatctata  100380
catataccccg  gagttttttcc  ttttatttac  aaagcagtaa  accaaattcc  tgtgtgaaca  100440
taaatatcca   atataatata   atattgcgta  tgccatttcc  cccctcaaat  atgacttcaa  100500
ttttggccag   ttgttctgac   ttaagccaaa  aattagtttc  atctatatga  acatatgatg  100560
gtaagtaacc   tatttattac   cttaaaatgt  ttccccacat  aaaggaaatg  gtagagagta  100620
aggggaaaag   agaaataaga   gatgtgataa  aacctattcc  accatcttta  tcttcatcca  100680
cagcatgtcc   tagacattca   gtgcctgggc  cagtctctat  agtaaacttg  gctgatctg   100740
gaaacgtctc   cacttagctc   tgtaaggatg  gcaccccttca ggggtgcttca gaggaaactt  100800
actgaattca   acccaagtgt   cctgaaagaa  attgaagaag  ttactcaaag  agctgaactt  100860
taaaacaagg   agtagctgag   ggtgaggcat  atccctatctt gagtttctga  gcactctggt  100920
accatggaat   gtctgtacac   tgaccttcgc  caaagccaag  aaagcccctgg taggagtcac 100980
```

```
agcagccatg ggtgagctga aaggcttttc ctgacttcct ggggtctcag gaatagccag   101040
aggtgaaaag atttgccttt tttactacat aattgcacaa accatggtat ctattttctg   101100
atccagattt ccaaaggctt ttctgaaaac tacaagatat accccttgtg gactgtgtga   101160
aaataaattt atctttatgt atttgaacag tagccataga tgtgcctctt ctctacagat   101220
ttttctgtca cacacataca catataaaca cacacataca cacacagagt ctgtgtggtg   101280
ggccaaacat gccaaaaata aatactctca cttctctaaa ttatttatag aactcatctg   101340
attttttaaaa tatgttaata aataatctaa atgggggagg gagttgaagt gttttttttt   101400
tttttttact tatgttgatg gatagccaca aagcataatc atcttattta caaaaaacaa   101460
atgccccaaa acctaaaaaa gccccccag caaccaaaca tcttctgtaa atatagttt    101520
taaatgatga gtaaggtact gtgccattgg cccccatttg gttatgtgca tcatgttagt   101580
cagcagtagc cattccacga attcctcatg ggtagtgcaa ccagttaaaa agtgtataaa   101640
acattataca tagaaaaact ctcacatcct ttggatgttt gcagttcatc ataactttgt   101700
ggttaccttt ccgcaacata aatttaaaaa aaaaatcaca cacacacata cactcacaca   101760
gacccatata tagaaaccca ttcatccagt catacaccat ccagagtgta gtgcatggga   101820
ctgaattcca tgaggcacga agggggtgat cccatcctca gggtagtcca tcatcttcaa   101880
ggcttaatgc cactcgctgg ggagacaaac caaagaattc atcattagat ccataagagt   101940
tactatttat ttagtattga caaatcacag acttacgtta ctttaacagg tattagctca   102000
cataatgttc aaactatcct aagagacagg atttatccta tttattttac agatgagaaa   102060
caaaactcaa tgagcttaag tagggtttgt tctggatcac atagcaagtg gctgaactaa   102120
aatttgatcc caggtctgta tgaatccaaa gctgtagatt ttttcatcat tctgttttgt   102180
atctttgtaa agaagagttg cacagatcta aattttctta atcctccctt ataggatttt   102240
aggtttggtc aatttcagtg ggttagcttt ggcaaatgtt aaatttcagg ctatggggtt   102300
acttgtctct agcatgctaa tcacatttag aaaggtaata tactgcacct tcccaacaga   102360
ttaaacacag ttgggaggca atgcaggtta attaaattcc atccctctct ccctcacccc   102420
tgctttccag tcattaggta gatgctagac tcctgtctgc caaaaatggc tgaccatggg   102480
aaggtgagcc cactaacccc tgaaccagtc tattccattg tggacaacag atttaaattc   102540
tttcctatat taatgtgaaa tttgtttgtt tatatcttct gacattccct gattccatct   102600
cagactcaga gacagttcta cataggacaa cccttgaaat ttatagatgg tgtttgaatt   102660
cccttccgtt cattctgagt gttttcttct ccagggtaca catctaactt tccccagcta   102720
gtcctgatgt aatcttgttt gcctcttttc catttcccag ataccctcct ttggaaagac   102780
cctccccagc ttcagtactt ttcctcatag ttatgtgaat ttgggccagc cactttactt   102840
ctctgagact tagtttttatc atctatcaaa tgggaatagt aacaggacct acctcacagg   102900
gttgttgagg aatcaaatga gataatgcac agagagtgtt taacatagta cctaacaaca   102960
catagggccc agaatatcct aggtcaacgt aaccaacata aaatagaatc agactagtat   103020
ctcccatctc tggacattct acatatgata aaaagtaact ctactgcctt tcaagtcatc   103080
tttgggttat ctgtagtttt tttatgaatg caatggccat cctccaccag tgtagatatt   103140
taagactatc ttattctagt ctagctaccc tcccactctc tctaagacag atctctaggc   103200
caaagatagg ccccagtagt gatggtacag ttatccgaga aatggacaga ggagagacag   103260
gttgttgaga atattgattt ccagagcttc aaggctattt acctcacgat ataaggaaa    103320
```

```
gagcatgggc ttttgtgtat atacagactg gagtttgaat tctggttctg ccacttcctg  103380
gctatgacct taggcaagtt attcaatttc tatgagtctc agtttcctca tctgcaaaat  103440
ggggcgaata atatcagctt gataaggtta ttatgaagat taaatgagaa aatatatgta  103500
aaacactggg aacagtgtct gacacacagt aggtgctcac taaatgttga tttccttatt  103560
tctctgcaac tggcagaagc ttattacttg gtccttaaca ctcatcggga gtaactcccc  103620
ctgagtcatt tctttctctg gaaataatgt cactttacat gtgcagagtg cttttgtaagt  103680 cacaaagtgc tctcacacgt gctatctcac ttgtactttta taaactcagg aggcaggtag  103740
aatgggggtt gttattctca ttttacaaat aacagtgagc agaaagaagt gactgagatc  103800
acagggcagt ggaaggatgg aactgggagt tttcttattc caagttcagt gcttcttcca  103860
ctgtgctccc tctgatcttc aaaaactggt caagcaacta tttttttgga ctggccgagg  103920
ttaaggatcc tcaaggccat ctgctaaccc tcctcatttg ctccatctca tttcccatgt  103980
ctccccttca tgaacagttt gcctcagcag caattctgtc tgccctgccc caaacttgat  104040
tgctttcttc cacatgccat tcattggtct gtgactaacc catttttctt ctttgcccca  104100
acacccagct tacaatttgc agccttccca aaccagaaag ccttctagga ttggctgcgc  104160
ctgccttggt tcatgccctc actcaccagc ccctcagact tagagtggca ctgccctacc  104220
ttggatttga cgacaggcag ctcggaaaga gggttcttcg ggagttggtg cagctgtgac  104280
cttggttccc ccggcaagac aaaaagctcc ttgagggcag gggctgggtc ttccggttct  104340
ctggtctccc caagacaggg ctctgcccac agtgggcgat caaagctgct gattgcctga  104400 caggggatg gcactgtgga tgacctctga ggtcacactc agcccctga ctgtgctgta  104460 taacagtgac acctgctgtg ccactttgtg gtcctcattc ccccaaaaag ccatgctgtg  104520
ttgtaccttc aagcctttgc acatgcctct atctggaatg ccatttccct ccttctctcc  104580
cgggaaaact gctattaatc tttcaaggac atagtccatc tgtcaccttc tctgtgaggc  104640
attccttgcc tgattcccca gacagaatta atagctccct tgttgatgtt tccatggcat  104700
ctgttcaaca atatttgtt gggagtcagc catgccgtgc taggcatcag gaaaacagat  104760
taatcagaca gttctgccct caaggatctt atgggttagt gaggagacca ctgagtaaaa  104820
gacaagtgga ctacagtgtg acaggggctg tgaggtagag aggcccagag tactgtggga  104880
gaacaaagca agccaaagat agcttttctag aagagggac tcctgagctt ccaccacggc  104940
attcagcaca caattatacc actgtatgtt agtatctcta actccctacc agcttcttgg  105000
gagcaagcat gttccttatt gacttttgaa tacttgatat ctaatgtggt gcttggcaca  105060
taactggcat acagtattga aatgaataca tttgaattaa atggccacag ttacccttcc  105120
aggctaaagg ttctgaaaat ttactgagca gaaagagaga catttggctt tttttactgc  105180
caggaagagc ctctaggtac aaggtggtcc tgatacctt ttaccttaac cacctacccc  105240
agcatttctg tgttccccag ggcctagaac agtgcctgat acatggtgcg ttttgataa  105300 atgtttgagg aaggaaagaa ggaggaaggg aaggagggag gaaaggaagg aaagaaggaa  105360 agaaaaaga cagggaggga gggaaggacg gaaggaaagg agggagggaa ggacggaagg  105420
aaggaaggga gggaagaaag gatgggaagg aagaaaggat gggaggggaa gaaaggatgg  105480
aagggaagat ggtcggaagg taggaattct cccagtgaga aatacttact gcaggataga  105540
catggccaat ctgagcagtt ctccctatat ggagctcatc ttcgtcttct tcttctgttg  105600
ttttcctgta gactgggttg tcaaaattca tgcttttggt gttcttccgc ttccagtttc  105660
tccagatcag gtatccactc atgcacagga gggctatcac cactggagga aggacacagg  105720
```

```
acactggacc tccagcaggc tccaacccac tgctcagaca tctgtacaag gcttgtcacc   105780
actccacttt tactacccct tgctcctcag gctctgtttc tgcatgttct tttactgctg   105840
tttgaaagcc catctctcat cccttctttc ctttactaac tattcatcct tcaagatcct   105900
gttcaaatgt gaagtcttcc ccaactgtgg gcagagtcag ttgctctctc atgtgtgctc   105960
ccagatcaca cacagtatct tactttatgt atctgtactc ccaactagat agctctttca   106020
aggcagggac tgtgtctttt ttttgttttt aaactctcta cgcccagttc ctagcactga   106080
ctaggtgcct agtaacatgt gctgaatgaa tgagtgaatt ttaccacacc tttgccctaa   106140
tgctgctgct tccctagatt tctctaagaa aacgattctc tcccaaaact gggggtgga    106200
gagtgggatg gggccaggca gagtgtttat ttccaaaggt gaggctccac ctgaagaaga   106260
acatctctag aaggagacac agagggcaac acaagctctg atttagaata aatgactatg   106320
ttaatgatta aaggaggaag ctctctccaa cacagctggg taaaaatgga gcaagtagct   106380
ttgtaaggtg attagcagtc actctgagca tcccagtgga ggctgaatga tcacctatct   106440
aggatgctat ggaagggggtt tctgttttag taagattaca ataattgata agcattaaag   106500
acaggaacaa ggcagttatc attgctaata tttattgtct tagagatcta gctatgcagt   106560
aaggccagaa aaaaatttaa gggtataaat atgggaaagg agcccaggtg cggtggctca   106620
cgcctgtaat cccaacactg tgggaggctg aggcaggcag attacttgag gccaggagtt   106680
cgagaccagc ctggccaaca tggcgaaaac ccatctctac aaaaaataca aagtagttgg   106740
gcatggtggc gggcacctgt agtcccagct actcagaagg ctgaggtggg aggattgctt   106800
gagcctggga ggtcaaggct gcagtgagcc acaatcatgc cactgcactc cagcctgggc   106860
aacagagtga gaccttgtct caaaaaaaaa aaaaaaaag taaataaata aatacatatg    106920
agaaaggagg aaaccaaact gttattaaca gctatttgta ttttttagaaa ctcttaagag   106980
aagctggtga aaaactatca gaaataattt tagttaatca agaatcaaca taaaagatca   107040
ttagccgtct tttttaatcag caacaaccaa ttagaaaatt taacggaggc caggcacagt   107100
ggctcacata tgtaatacca acattttggg aggctgaggc aggaggattg cttgaaccct   107160
ggagttcaag accagcccgg gcaagatggt gagccctggt ctttacaaaa aaattaattt   107220
aaaaaattag ccaggtgtgg tggtgcatgc ctgtagtccc agctactcgg gatgctgagg   107280
caggagaatc ccttgagccc aggagttcga ggatgcagtg aactgtgatc gcaccactgc   107340
actccagcct gggcaagagt gcaagatctt cttgtctctt aaaagaaaa agaaaaagaa    107400
aaagtaatgg aataaaaata cattcgtaat agcccatcaa aagctataaa atacctagga   107460
aaacctaaga agaaatacgc aagtcctgtg taatctataa aattctgctg agggacgtaa   107520
aagaagactg aaataaatag gccacatttc tggatgggaa gctttaatat aataaaaagg   107580
tatattctcc tcacataaac tcatatatct aaaacaatct tgataaaaac ttcaccaaaa   107640
tttttataga attgataaga ttattctgaa gttcacctag aagagaaact gaataaaaat   107700
agctgagaag atgttgtgag cataacatat catgaagttg tgctaatagt atgtaggaat   107760
atataaatca gtgaaggaaa ataaactgct tagacgcaaa tcaaagtacg tatgggaggt   107820
agtttataat aaagatgacg tgcaagtcag gagagaagta tggattattc aatgatggtt   107880
ttggggaaac tagacaggta tatagagaaa aaaacagtta aatctctacc tcatacgata   107940
ctctaaaatt taaattccaa atagattaat atcctaatac taaaaaaaag tttaaagtag   108000
aaaagaaaaa catcaggaga tattttaata agttagagtg aggctggcct tcttaagcaa   108060
```

```
gacacaaaac ccagaaatct taaaagattg acaaatctga tacttaaaag tttcatattt 108120
atgcatggca aaagatacca taaacaaact ttaaaaccaa atgtcagact ggaagaaaat 108180
atttgtaaca tatattttaa aggtttaata tttgtcatgt ataaatattt ctataaataa 108240 gaaaagata gccaatagaa aaataagaaa agactgtgag tgggcgattc ataacagata 108300
aaatataagt aaagggctg ataagcttac gaaaatatac tctacctcac agggaaatgt 108360
cagggaaata atactcatct ttcactcctc agattagcag aaattaaaaa tattgaatat 108420
ttcagagtga gttatgtcag caaaacagca tatatctgcc tctttctata gggcaaagga 108480
tggcaagaaa ggggtagatt tatctttctc cactccaatc aaaataatcc tggaataatc 108540
acctcaccat catctttcct ggtgaagcct ttcaaggcca attcaaatgc tgtcttctcc 108600
agaagcgcca cttttactct ggaattacct ttccttctac catcccttca caagagtatc 108660
atgccactat tacattgttc ctctgtctct atctatatcc aacatgcccc tatcatagca 108720
cataatgaca tgtattaaca tctaccttaa aggactttat ttttgcctga ttaaagactg 108780
aaagctctta aagtctttat ttttttcttc cctggatcct tggcacttgg cacagtcagt 108840
gtcttacaca ggggagaagt ttttaaaaca tttgctgact aactcggcat actgaagatt 108900
cccaggataa aaggacaaag ttcctgtcct tgaagtactc atagccaagt aagggagata 108960
aagctctgaa tggacaatca gaatgcaaag atactgctac gagatgagac tgctaagaga 109020
ggggtgtaca ggataccgtg tggtcatcag ggtggaagag aatgaatcag cccccatgat 109080
tctctgtgag gtcttaacaa agtgttatac tctggccata ctgatctcct tctagctcta 109140
aacccacccc accctgaccc ttccaggcca tttcctactc ctggctttac tcatgctgtc 109200
ttcactgctt ggactgttct tgatcctccc tcacttggct gacccagctc aaatatcact 109260
tctgttagga aacctcctct tccctcttcc ccctccccca gcccaagtta agtgtttcct 109320
cagcactgtc tctgaagtca gtgcatgcag cttaaccta ggacctacca ggtcgtaatg 109380
aacttatctg tgttatgtgg gtctctctaa caagactata aacttttgta ggacagaacc 109440
atgtcttatt catctttaac tgcctttcct ccccttatca gagtttggca catagtagct 109500
gcttaataaa tacttgttga aaaccaaaca gaaagaaaac aagacagtat gacctattaa 109560
aggaatggta agcagctcta ttcattaatt caacaaatcc ttgatatcct accatgtgct 109620
agacattgcc aggagctggg gagaatggtg agcaagagat accagccctg ttcctaggga 109680
tcatacagtc gcacttcaca tagctggagt gtagagtgtg aatcgagggg tggggagatg 109740
ggggatgtac ctggaaggtc acctggggcc aggtcctgaa gagccttgtg tgctaggcta 109800
aaaaaccaaa ttaaatcagg actgggaggt gggcaggaag gctgcaaggg cagaacaagt 109860
caatagggca ggccaagttc tctaccctgc tagcgctctt ccctaggcct aagcagggtc 109920 tctctttttct cttcagtgac tgggggccac actcacctat gggcacgatg atcccgataa 109980
cagcggcagt gactgttgag cccatcttac tgtcttcatt tgcatctgca aaacacaaac 110040
atttgcagaa tgatgctcta tcactgtgtg tccaagcccc tactggcctc aagtggtaag 110100
aactacccaa ctgctgctca tcctcattct aaaatgatga tcctggctgt tgcctaataa 110160
ttcagtcttt ccagatccta tcacaactcc tgtgaggcaa gcaggacaga ggttatctcc 110220
attttacagg caaggaaact gagtcttaac tgaggggttt cagaaaagtg gcagagctgg 110280
gacttgaacc caggactcat gtcccaagtc ccatacccatt tccatagcat catggtagta 110340
ggaagctggg ggctgtgcat ggcaaagtga gcacttaggt ctttatgttg ctgatggact 110400
aggtcatttg cctttttcca tcagtatctg ttgctttgcc agtattgttt tttgtgaact 110460
```

```
gtctgtccat ctgcattatc agattatttt tcataagtaa ttgaaatggg acatagtata 110520
gtgtagagga atcaaaagcg cagacttctg tgtcagactt ctgggttcaa gtcccagctc 110580
tactactcac tacccatgtg accttgggca aattattata tattataaat acagcacatg 110640
gtattatact tttatatctt taaaatggtg atattaccta cctcctaggg atatggtaag 110700
gattaaatga aataatttat ctaaaatgaa tataaaatgc ttggcacaac tttgcctagt 110760
tctaagaggg tggagagtgg gatggggttg ttgaataggg tctaaatttt aaaaagatat 110820
gtaaaagcac attttaaact gaaaagtgct tggaaaattt actgtctttt tgaaaaacta 110880
tgccatgcca tctttctcac tcttataacc atcttcattg taacatttgt gaagcacttt 110940
atagttcaga aagcattttt cccttagatc ctcctgacag ctccctgtgg tgtgaaaagg 111000
agctatcatc tacacttgct gcaggtgaga tgactgtccc ggcaatggcc caaggcccat 111060
cctctctcaa tgtgactgtt tatccatgtt actccaagag aatctaacag ttaaggggag 111120
aaaaagctgc actgcttgct tccagagcta actgtgtcct ccctgctgtc ctccctgctc 111180
tgggccacag cgaacactgg acagtgatat taaaacctag agcatgagga agccagtgag 111240
gagaagctgg tgagaggctc tgccctcaga tgagaggaac tggaattcac acatgctcca 111300
tctgcctctg caaacttcgg agtaagtgct ccactccaaa aagccagctt ctgctggcaa 111360
ataggaccag ttaggaagat gttgccaagc agcttggttt ctgggctgtc catgtagggg 111420
aaaaaattaa aaagatagtt tatccttttta aatgaactcc ctctggcagg taactcaatt 111480
aaaaaggtat ttgctgatta atgagataga acatttctag cagtgacaat tactgctccc 111540
aatgatttaa taagtggtga acttaattat tttcatccca gggttggaaa gaggtataag 111600
gagaccatgg ttgtagatat tactatctgg ggacctgctg tgaactgaga tcagagcttt 111660
ccaaacacaa gggacacctc ctcatataca catcagaact ttgtgaaaca tagacacaca 111720
caccctcgca gagtcagcaa cggctgtgtg cgtgagcacc tccagttata ccggttacac 111780
ctttgtctat catggcaatc ttgtgaagca ggttgtggaa gggtggttat ttccactttg 111840
taagagaagc aactgaggct cacagggtct cagcttccta caagaccctc tgtaaggtag 111900
gggcacctat gagtcctaaa tcgcaggctg gtactctacc tccctctcag atatgcagta 111960
acctcctcaa agatatgcag tattcagctc tggtaggttc tgtcttatca catccccct 112020 tcctggcttc cctaggagcc ctcccatgtc atgaaagaat gcagaactca tttccttaca 112080
gtgctgggag tggttgctgg ttgcagggct tagggtagac gggctgatgc tgggagccct 112140
ggggacacta actgagcttg ggactgcagc tgtcaggctt ggtgtctctg tgctgtggtt 112200
ctggtaggtg gatctgtgga cggtggtccc ggggctctt tggtggcag gtactgtcct 112260 cgtcatggta gaagctaacg tcgtagttga ggtagattga ggtgctggag gggaaatacc 112320
atggaggtca cttggacaga taattttgtt gcctaaggta ttgcctctga gatatactta 112380
ggaacttatc ttcatggcgt agctcaaatg ccacttctgt gaagcctttc ctaatctccc 112440
cagtgggcta tgatcttttc tttagctgaa tgctaagcac ttcactttga ttcaataaag 112500
atgagtcatt aaaacattgc tgtggaatta gttgtaagat cagcaataaa aagactgtag 112560 ggagggaaa tcagataaat ctagaaggat tttacactca tatattgtta taccaataga 112620
ttgaaattct tattccactt taaacaattg aacctgtaaa tcattaataa tgcagtagac 112680
ttaggctcaa atgaaaggcc ttggctatac atcaagatta ggacatgaat ctgtgtatgc 112740
ggttgaagta ttaactatta gtcccaatta tattgcaaaa gggctgctgt gtagtgtttg 112800
```

```
ttaagttcta ggtgagaaac aggcaaatat atagttatct gcatgtacct gaagccacgg   112860
cgattaaggg ttcttaactt gaggttttta aagcgttcca gaaactccct gaaactgaat   112920
ttaaaatgtt ttatgtatat gtgcattttt tccttgggag tgagaaaaag ctttggaagg   112980
atcctggggg catgagcatt caaggaaggt aaaaaagaga aaccccccaa aggcaacaag   113040
taaccaggga agatggaaga aaaccagcag catactgtgt cccagaagcc aagggaagat   113100
ttcagcaggg tagggtctga cactgccagg ggccatccct cctggaaggt ctgcttacct   113160
cggtagcacc tcttcatgtc tggacccagc cacattgtgt caggacaggc acatgtgtac   113220
ttgggagagt ggctggagat ctgaggagca ggaaggcaca ggtattcaca gcctccatta   113280
ggctggacac tcagctcaca ggcatctgga gctaatggca gagagggaga cagctggggc   113340
acagacagga catgccaggt cttcctgcct cctgaggatg aggcttctcc cacctggctt   113400
gctcaaaaag cttgccctat acttttttt tcacattttt tttcttttc tttcttttt   113460 tatccccaa agcttttggg atacgcgttt tttgttacat ggatgaatta tatagtggtg   113520
aattctggta ctttagcgca cctgtaaccc aagtgtagtg tacattgtac ctaatgtgta   113580
attttttttt ttttaaatct ctagcccgc tattacctc tccatttta gtctctaaag   113640 tccattatat gcccctgtgt actcatagct tagctatact ctgtatgccc ctgtgtactc   113700
atagcttagc tcctgcttat aagtgagagc atatagtttt tggttttcca ctactatcat   113760
actttactta gaataatggc ttccagctcc atccaagttg ctgcaaaata cattatttg   113820 ttcctttta tggctgagta gtattccaag gtgtatatat gccacacttt ctttattcac   113880
tcattagttg atggacactt aggttggttc cacatctctg caattgtgaa gcccttctac   113940
tttttcaatt ttttttatgt tttatgtttt gagacagggt ctcactctgt tgcctagact   114000
aagtgcagca gtgcaatcat agctcactgc agcctcaaac tcctgggctt aagaaatcct   114060
cccacctcgg cctcccgagt agctggaact ataggcgcat gccaccatac aagggtcatt   114120
tttatagttt ttgtagtgat agagtcttgc cttcttgccc aggctggtcc caaactcctg   114180
ggctcaagtg atcctcctgc gttggcctcc caaagtgctg gaattgcagg tataagccac   114240
catgcctggc ctccctacta cttttattgg gtactttcca gcaccatacc tagtgtttta   114300
tccctacact ctcatttaat ccttgcaaca attctgagag gtggggacgt tacatcccag   114360
actgacaaat aaagacacct aggctcaaag agaacaaatt cgtcaaacct atactctagg   114420 aattttttt tttttaaga ggtaggggtc ttgctctgtc gcccaggctg gagtgcagta   114480
atgcaatcat agcccactgc tgcctggagc tcctgtgctc aagggatcct cctgcctcag   114540
cctctcagtg ttgggattac aggcatgagc caccatgtct ggactagaga tagaacttaa   114600
attgaggtcg gctgggctcc aaagcccata agcccgcggt ttttattttt ccctgtgcca   114660
catactatgt ctctcattta aatttctagg tctagaatca ggcaccaatc ttagctcctt   114720 acactcccttt gctctccctc tttcaccctg gcagccaaca cttcagttac agttagaatt   114780
aatgtatcct agtgatagag gaggggacaa cctagtagta ggattcctag attctattcc   114840
caaccaataa gctgacttat tatatggccc tcggatacat tagcttatac tactgcagaa   114900
tggctacaaa tagcaagtta gatgcagtgt gtcatggtga aagcagctgt ggaaccagat   114960
agacctgggt ttaggtttca gttctgccac ctgctaacat tatttaacct ctctgagctt   115020
ccgtttcctc aactgttaga agagtaaatac ccacactttg taggattggc aaaaacagga   115080
cagttatgta ttcattata cccagcctta tttcacaaag aacttgaggt aaaatgagac   115140
aaaatatatg atgaaaaagt actctaccaa caagagggat tgttgttatt attcctgggg   115200
```

-continued

```
ttgctgagtt gtgacctgaa tgtgaacaca gcctgcctgg tgaaaggaga ggacacagtg    115260
acacagtcag gggacctggg acctaggacc agagacagct cacctcttgg ctgcttcagc    115320
tcatggaaga tgacaatgtc atgtgggttg ttgaggttct cagccaggat ggagatttcc    115380
aggccattga gccgatttgc actgaaaatg gcctcgttct ccaggtctgt ccagaacacc    115440
ttgtcctgtg gggtatagat gcagaggatg ggaggcctgg agtgtaaatc catgacctca    115500
gtctgagggg ttggccccaa accatagtca caagaacttc cctgaaatct cccctgatct    115560
gtcctgtcta tggattcacg gtgggctct cagcctctaa tctgtgatgc acgtctcctt    115620
gttcccttct atcttagagg attattcagt gattctgtgc tttgaactga cagccacaac    115680
attactcatt catgctgaac taagcctgct tgctagagcc cagcagaaac ccaaggttaa    115740
atctctatag cattatcatt actggggcct gggaccaaga ttggaaggaa tgtgtgagct    115800
atgagggtta tgccttgctg ggcttcctgt agcctctggg tatccacacg agtccacatg    115860
gttagtccat ataagcctag atgtgcatct gtcagcaaat ccacacgtac aggtacaact    115920
gtgcatcctc atacacagat ctaaacacat acccaaatgt tcatccacac acaaaaagct    115980
acatttgccc ctaaatatgc agtctatata catcttggta tatgtatgta cacacataag    116040
caccagcact tagaggaatg cacacttta ttctgatgca tttatattta cccatgcaca    116100
tacacatact ttacatgtac atgccatgta tataaacaag cacaaacact tgtgtaccaa    116160
cacacctgtc ctttaaagca ggggctggac ttagaggtgg agctttgccc acaacttcag    116220
agcagtgctg agtaactttg ctgcaagcaa atcctgccaa tgcccaccac agaccatcat    116280 cccctttgctt tccctcccct tggtggtgga gttagttttc gggaagaggt gaaggtgtga    116340
gaccttggtt ggttctggct tcttcattcc cggagaagaa aagtcattag ggtcagggca    116400
caggagggtc ttcgctcctc actttgctgg gagcttcttg agactaggat agtgtctgat    116460
tcacttctat gaccccaggg tctggcagag gtcaataaaa gtgtgcagaa ttgaacagca    116520
tctctcaggc catttcctcc agtaaatgat tctaaggata tgtatgttcc ttcttccttt    116580 cctccctta ctgggtgcct tttgtatatg ggttacagtg ctgggtgctg agggcacaga    116640
gaggaaacat acatgcctag cagctcacct gtgagaagtg ctctgggaga ggggtcttgg    116700
gaagagagcg tgggaaaggc tgccaggtgg agagtgggct gcagagcctt tgtgtgcagg    116760
cagctcacag attgtttaca aacaaatcag ttggtttccc tgttcctgtt ttcatttgaa    116820
caagtctcag ggactcatcc tatttgaaca agcattttct aggcttcagc ttcctagtgg    116880
gcccttgcct ctccttacag gactcacctc aaacacagct atcccaaaag ggtggctcag    116940
gaagtcagtg gaggagatca gcgtctttct gttgcctcca ctgaagtcaa tgctggacag    117000
ttggtgtagc ttggagtcta cccagtacaa gcgctggctc agcagatctt gggaaggaag    117060
caggatcagg tcatgaacct gggacccag tctggagctc tgttcctttg tacctctccc    117120
tgcccacatt tctaggcctc acactgaggc cagcctacgg caaccattag gaaacaaagt    117180
cactggcacc atgagaggac ccagaaacaa gactcatgga gttccagaca gtgatcagga    117240
caaggcacta gaataggccc ccaacccagg aaaggcaggg ctcacccagg gtgattccgt    117300
tgggccattc aatattgtct gacaccagtg tttgccggtc cacaccgttg agcccagatt    117360
tctcaatctt ggcctggtcc ccccagtcag accaatacat gaacctaaaa gacaaaataa    117420
cccaatttgc cttcttgctg gggacatgac cggggtggtc tgagtcacaa gagctcaata    117480
acccattgac tagttgtggt ttatgtttag tagggactga gaagacctct aaagttcttt    117540
```

```
tgaaccatca aatcttagat ttagcaggca cttttagcctt cacctcattt gagaacttga    117600
ggaaaactat tctccgagat tgcacccaga ctcagctgaa tagcctgtga ccccatctct    117660
cccacttctg gcagtgctaa ctaactagag ccctagggtg tcagtgtggg gaaggcccta    117720
gtaagccctc tcttttctgg tttcagagga gaaagtggat gagcttccta actcaggtaa    117780
ccctccctgc ttttgtctcc tcaggcctac tagggccagt agcagcccac tgttactaat    117840
ccaaggtagt aaattagacc taacccactc ctttgtaaat agtccctta ttaaaccctc    117900 ctctgattat cttgagtatg cagtgggttt cctcctggga ccctgacgat ccgcagtgga    117960
ttggggttgg gctgggtgta actctatgat gtgagggaca ggatgtggca ggtgcaacac    118020
aaggtctgca tgagaacaga cagagaacag ggatgaagtg agggtaagag gagaggctcc    118080
gtatctgtca gagtgcctag ttctgtgctg gaagcacctg acccatgctt agtgaatggc    118140
agctatcagt cacttcccaa ggcctcacat aacctcccat gtggtactcc cctcaccagc    118200
tgcccttgct cgaagaagag ggttttctta tccctgttta acaaggaaat agcagtagga    118260
agcagctgtt gattctgtta aacttaacat gatataacgc taaaaaaacc atctcaagat    118320
atccacactg agggagagag ggagtcctgt tctgttcaga atccctaact cccaaaactg    118380
aggggtggcc agagcagggc aacctaggtg gtgagggccc agagaccata ggcaacaggg    118440
gtagggatgg aggcaggcag tctgaagcag aacagaccag tgatcttggt cctcaaatct    118500
tgctggctct ctcacagggc agggaataga catgttttat gtaactccag aggccaatgg    118560
aggaagttgc agggagatag atttggcatt atgaggggaa aagacccact ttctaatgag    118620
cagagctgcc ccacggtgaa acaggcccta tgggaggtaa tgagctacct gtctttggaa    118680
gtatgtgagc agctgtcaga tgctcaccta cagcagcctg aagaaaggct tcctccccca    118740
ggagcttcta tcaggccatc tctagagccc tactctgctc tgagacactc caattctacg    118800
atataacgag tgggtgggag agtccaggga gaactttggt gaccaatgcc cagagaacct    118860
tggttgggga ttaacaagac tttcttcccc atggcctgtg tctgagtggc ccagagcttt    118920
ctagaaccct caagatagcc cttgtgacag acacaagagg actgagcacc tatggtggga    118980
gaatgggaag ttcagttggg acactcaccc tcgcagggg tcaacagcga tggcccgggg    119040
ttcactgagg ttacggctga agagagtgcg tcggcggcca ccatcaactg tggccactga    119100
gatggtctta ttgcccgagt cagtccagta gatgtgcttg tggacccagt ccactgccag    119160
gccctctgga gagtgcaact gctcgtcaat gaggacctcc tgctctttcg ggtcactggc    119220
cttgtccatg taggcgctta agagaaaaca gagatgacca tggggcagat gttccaccca    119280
tgggcccatc tggagctacc tgtgcaccct tcccctctct tccatctggg ccatggcaat    119340 agattttttag aggaacgtgg ataatttcca ctctacacat tccctggggt accagggtag    119400
gggtacagac ttacatgggc cacggtctct ggctttctaa ggtggggctg ctccacagct    119460
ctgcccatta gggtgagcca gatataatac aatgtgatta tggaaagcat tagaggctat    119520
ggcagcagag gcatggagac tgcctcatcc gagagggcgg gagaaggctt tatagttgag    119580
tcctgaagga cgagttcacc aggagcatga agtcaccagg acagaaagcc attagggaac    119640
aagaaaggct tgtgcaaatg gccagaggtg agtctgctct ggaacagtga gatacttagg    119700
ggagctgctt atgtgggtgt cagactgcaa gcaggtgtag gcaggaaccc catcttgatg    119760
ggctttgagt accacgccaa ggaattagga tttctcccca gtgataacta gacaggccag    119820
aggatatagt ccaataagca tgttagttca ctgtggcatc tatggagtgg atgggttgga    119880
aggagaggga atgaagcagg gaaactggtt aggaggacgt tacagcatct gggtgggaga    119940
```

-continued

```
ttaagagagt ctgaagaatg accgtgccag tgagaatgga aagaagggct aagaatacag    120000
tagacactca ggaggcaaca ttagcaaaat agcaaatgct gtttccccag aggttttctt    120060
cttcttgccc tctctctggg tgattagttc cttagtgtcc actgccatca ataactaagt    120120
ctccaatccc aacagctctc ttacgatcca gactgcaaag ctaactagct ccccttggat    120180
gtcccatgga caccttgaac tcaatatgtc caaaactgtt catccccatt ccttcccct     120240 cggccaacca gacggcccaa accctgagcc ctgatcctcc tctactgctt cacacatcag    120300
agaacagcac caccattcat gaaacctccc aagccaaaaa cctgaaactc caaaattca     120360 ctatgaagga gtaaatttct tccatcagcc ccatatctag tctgtcacca atcctgcct     120420 cttcagtta catctcttgg acaggcattg ttctagttat gttttggggt gtgtgtgaac    120480
ggagtgtctg tatgttgcag ggaggcagga atctagttgt cagtgagtag cacttgctat    120540
atttgcttcc atccactctt ccacccatct gtcccatcat tctttcatca gtgactcagt    120600
gtctacccag cgcctggtca tcggcattcc tgccaagtgg atctcaggac aaagaaagga    120660
catgactgcc tgaagagggc ccagacatgc agtgggcag gtgctggcat ctgagaaagt     120720
cctaggagag aacctcctcc agtgtgtgaa gagcttccca agcaccaggt ccactgactg    120780
tggcgtcaaa gacagtgaaa agctggcctt ggggtgatgc catccaggaa ggcatgccag    120840
atcagatgcc caggtgggtt cggaggcctc ctctgtactt tctcatgatc                120890
```

<210> SEQ ID NO 4
<211> LENGTH: 2325
<212> TYPE: DNA
<213> ORGANISM: Homo sapiens
<220> FEATURE:
<221> NAME/KEY: misc_feature
<222> LOCATION: (1)...(2325)
<223> OTHER INFORMATION: DEAD/H box polypeptide 5 (DDX5), RNA helicase, p68 cDNA

<400> SEQUENCE: 4

```
acctcattca tttctaccgg tctctagtag tgcagcttcg gctggtgtca tcggtgtcct      60
tcctccgctg ccgcccccgc aaggcttcgc cgtcatcgag gccatttcca gcgacttgtc     120
gcacgctttt ctatatactt cgttccccgc caaccgcaac cattgacgcc atgtcgggtt     180
attcgagtga ccgagaccgc ggccgggacc gagggtttgg tgcacctcga tttggaggaa     240
gtagggcagg gcccttatct ggaaagaagt ttggaaaccc tggggagaaa ttagttaaaa     300
agaagtggaa tcttgatgag ctgcctaaat ttgaagaaga tttttatcaa gagcaccctg     360
atttggctag gcgcacagca caagaggtgg aaacatacag aagaagcaag gaaattacag     420
ttagaggtca caactgcccg aagccagttc taaattttta tgaagccaat ttcccctgcaa    480 atgtcatgga tgttattgca agacagaatt tcactgaacc cactgctatt caagctcagg     540
gatggccagt tgctctaagt ggattggata tggttggagt ggcacagact ggatctggga     600
aaacattgtc ttatttgctt cctgccattg tccacatcaa tcatcagcca ttcctagaga     660
gaggcgatgg gcctatttgt ttggtgctgg caccaactcg ggaactggcc caacaggtgc     720
agcaagtagc tgctgaatat tgtagagcat gtcgcttgaa gtctacttgt atctacggtg     780
gtgctcctaa gggaccacaa atacgtgatt ggagagagg tgtggaaatc tgtattgcaa      840
cacctggaag actgattgac ttttttagagt gtggaaaaac caatctgaga agaacaacct    900 acctgtcct tgatgaagca gatagaatgc ttgatatggg ctttgaaccc caaataagga     960
agattgtgga tcaaataaga cctgataggc aaactctaat gtggagtgcg acttggccaa    1020
```

-continued

```
aagaagtaag acagcttgct gaagatttcc tgaaagacta tattcatata aacattggtg   1080
cacttgaact gagtgcaaac cacaacattc ttcagattgt ggatgtgtgt catgacgtag   1140
aaaaggatga aaaacttatt cgtctaatgg aagagatcat gagtgagaag gagaataaaa   1200
ccattgtttt tgtggaaacc aaaagaagat gtgatgagct taccagaaaa atgaggagag   1260
atgggtggcc tgccatgggt atccatggtg acaagagtca acaagagcgt gactgggttc   1320
taaatgaatt caaacatgga aaagctccta ttctgattgc tacagatgtg gcctccagag   1380
ggctagatgt ggaagatgtg aaatttgtca tcaattatga ctaccctaac tcctcagagg   1440
attatattca tcgaattgga agaactgctc gcagtaccaa acaggcaca gcatacactt    1500 tctttacacc taataacata aagcaagtga gcgaccttat ctctgtgctt cgtgaagcta   1560
atcaagcaat taatcccaag ttgcttcagt tggtcgaaga cagaggttca ggtcgttcca   1620
ggggtagagg aggcatgaag gatgaccgtc gggacagata ctctgcgggc aaaaggggtg   1680
gatttaatac ctttagagac agggaaaatt atgacagagg ttactctagc ctgcttaaaa   1740
gagattttgg ggcaaaaact cagaatggtg tttacagtgc tgcaaattac accaatggga   1800
gctttggaag taattttgtg tctgctggta tacagaccag ttttaggact ggtaatccaa   1860
cagggactta ccagaatggt tatgatagca ctcagcaata cggaagtaat gttccaaata   1920
tgcacaatgg tatgaaccaa caggcatatg catatcctgc tactgcagct gcacctatga   1980
ttggttatcc aatgccaaca ggatattccc aataagactt tagaagtata tgtaaatgtc   2040 tgttttcat aattgctctt tatattgtgt gttatctgac aagatagtta tttaagaaac    2100
atgggaattg cagaaatgac tgcagtgcag cagtaattat ggtgcacttt ttcgctattt   2160
aagttggata tttctctaca ttcctgaaac aattttagg ttttttttgt actagaaaat    2220
gcaggcagtg ttttcacaaa agtaaatgta cagtgatttg aaatacaata atgaaggcaa   2280
tgcatggcct tccaataaaa aatatttgaa gactgaaaaa aaaaa                   2325
```

<210> SEQ ID NO 5
<211> LENGTH: 5620
<212> TYPE: DNA
<213> ORGANISM: Homo sapiens
<220> FEATURE:
<221> NAME/KEY: misc_feature
<222> LOCATION: (1)...(5620)
<223> OTHER INFORMATION: calcium/calmodulin-dependent protein kinase
      kinase 2, beta (CAMKK2), transcript variant 1,
      serine/threonine protein kinase family, cDNA

<400> SEQUENCE: 5

```
gagcctgggg aggtcgaggg tgcagcgagc cgtgatcgtg ctactgcact ccagcctggg     60
caacacagag agaccctgtc tcaaaacaaa caaacaaaca aacaaacaaa caaacaaaaa    120
aaacaaagaa aaaaaaatgg gagtgggccg ggcgcggtga ctcacacctg taatcccagc    180
actttcggag gccaaggcgg gtggatcacg aggtcaggaa ttcaagatta gcctggacaa    240
catggtgaaa ccccatctct acgaaaaata caaaaattag ccaagtatgg tggccggcgc    300
ctgtaatccc agctactcgg gagactgagg cagagaactg cttgaacctg ggaggcagag    360
gttgcagtga tccgagatcg cgtcactgca ctccagcgtg ggcgacagag cgagactccg    420
tttcagaaaa gaaaaaaaaa aaaaaaaaaa agggagtcgg ggtggagctc tcattggctc    480
gttgcatgtg agtgtcccta cggcctagaa atacaagaga agcacatcgg aacgggctgg    540
aaatccaccc agtaactag agggctttga acctttatt aacttggagg ttgactctcc      600
```

```
tgtcaactcg attcccttt  ggctgtttgg cagggtcagt gagacatccc ctgggtcgct   660
cgaccccgta ggacggttca gggagccctc caggtcttcg tttctcctct tccccgcaca   720
gtgctgttat ccagctgggg gatccaacgc acacttaagg ctccagcaaa gtggctccgc   780
tgccggatgg gagtgcccca gtgtgctgga tgaagctggc gcatgcacca tgtcatcatg   840
tgtctctagc cagcccagca gcaaccgggc cgccccccag gatgagctgg ggggcagggg   900
cagcagcagc agcgaaagcc agaagccctg tgaggccctg cggggcctct catccttgag   960
catccacctg gcatggagt  ccttcattgt ggtcaccgag tgtgagccgg gctgtgctgt  1020
ggacctcggc ttggcgcggg accggcccct ggaggccgat ggccaagagg tcccccttga  1080
cacctccggg tcccaggccc ggccccacct ctccggtcgc aagctgtctc tgcaagagcg  1140
gtcccagggt gggctggcag ccggtggcag cctggacatg aacggacgct gcatctgccc  1200
gtccctgccc tactcacccg tcagctcccc gcagtcctcg cctcggctgc cccggcggcc  1260
gacagtggag tctcaccacg tctccatcac gggtatgcag gactgtgtgc agctgaatca  1320
gtataccctg aaggatgaaa ttggaaaggg ctcctatggt gtcgtcaagt tggcctacaa  1380
tgaaaatgac aatacctact atgcaatgaa ggtgctgtcc aaaaagaagc tgatccggca  1440
ggccggcttt ccacgtcgcc ctccacccca aggcacccgg ccagctcctg gaggctgcat  1500
ccagcccagg ggccccattg agcaggtgta ccaggaaatt gccatcctca agaagctgga  1560
ccaccccaat gtggtgaagc tggtggaggt cctggatgac cccaatgagg accatctgta  1620
catggtgttc gaactggtca accaagggcc cgtgatggaa gtgccccacc tcaaaccact  1680
ctctgaagac caggcccgtt tctacttcca ggatctgatc aaaggcatcg agtacttaca  1740
ctaccagaag atcatccacc gtgacatcaa accttccaac ctcctggtcg agaagatgg   1800
gcacatcaag atcgctgact ttggtgtgag caatgaattc aagggcagtg acgcgctcct  1860
ctccaacacc gtgggcacgc ccgccttcat ggcacccgag tcgctctctg agacccgcaa  1920
gatcttctct gggaaggcct tggatgtttg gccatgggt  gtgacactat actgctttgt  1980
ctttggccag tgcccattca tggacgagcg gatcatgtgt ttacacagta agatcaagag  2040
tcaggccctg gaatttccag accagcccga catagctgag gacttgaagg acctgatcac  2100
ccgtatgctg gacaagaacc ccgagtcgag gatcgtggtg ccggaaatca gctgcaccc   2160
ctgggtcacg aggcatgggg cggagccgtt gccgtcggag gatgagaact gcacgctggt  2220
cgaagtgact gaagaggagg tcgagaactc agtcaaacac attcccagct tggcaaccgt  2280
gatcctggtg aagaccatga tacgtaaacg ctcctttggg aacccattcg agggcagccg  2340
gcggaggaa  cgctcactgt cagcgcctgg aaacttgctc accaaaaaac caaccaggga  2400
atgtgagtcc ctgtctgagc tcaaggaagc aaggcagcga agacaacctc cagggcaccg  2460
acccgccccc cgtggggga  gaggaagtgc tcttgtgaga ggcagtccct gcgtggaaag  2520
ttgctgggcc cccgccccg  gctcccccgc acgcatgcat ccactgcggc cggaggaggc  2580
catggagccc gagtagctgc ctggatcgct cgacctcgca tgcgcgccgc gtcgcctctg  2640
gggggctgct gcaccgcgtt tccatagcag catgtcctac ggaaacccag cacgtgtgta  2700
gagcctcgat cgtcatctct ggttatttgt ttttccttt  gttgttttaa aggggacaaa  2760
aaaaaaaaaa ggacttgact ccatgacgtc gaccgtggcc gctggctggc tggacaggcg  2820
ggtgtgagga gttgcagacc caaacccacg tgcattttgg gacaattgct ttttaaaacg  2880
tttttatgcc aaaaatccct cattgtgatt ttcagaacca cgtcagatat accaagtgac  2940
tgtgtgtggg gttgacaac  tgtggaaagg cgagcagaaa actccggcgg tctgaggcca  3000
```

```
tggaggtggt tgctgcattt gagagggagt aggggggctag atgtggctcc tagtgcaaac  3060
cggaaaccat ggcaccttcc agagccgtgg tctcaaggag tcagagcagg gctggccctc  3120
agtagctgca gggagctttg atgcaactta tttgtaagaa ggattttttaa atttttttatg  3180 ggtagaattg tagtcaggaa aacagaaagg gcttgaaatt taataagtgc tgctggaagg  3240
ggattttcca agcctggaag ggtattcagc agctgtggtg gggaaacatt tctcctgaaa  3300
gactgaacgt gtttcttcat gacagctgct caaagcaggt ttctgagata gctgaccgag  3360
ctctggtaaa tctctttgtc aaattacgaa aacttcaggg tgaaatccta tgcttccatg  3420
tacattacat ggcttaagat taaacaaaaa cattttttcaa gtctctaact agagtgaact  3480
ctagagcaca gtagttcaga aactatttag agcttccagg atatatttca cagcttcagg  3540
catgtgatca gttagagccg atgaaaccta tgcccgcctg tatatatatt agcagcttag  3600
ctagttcata acctgtatat tctaaagact gctaaggttt tgttttcatt ttaaatccta  3660
gctgattgtt gtggtcaatg aaatacccag tttctggagg gccaggtggg aaatgctttc  3720
actggaccaa cacacaaatg atcatcctga ggatctgagc ttccctagac tccacacaat  3780
aaccttgggg caccctttta gagaagactg ttgaaaccca cagcactcgt tggggtatga  3840
ggaaaccagg gcttggcaca ggaagttccc cttttgtagct aaaagtccag aaagaaaggg  3900
ttcatctttt tgacttccaa ctgatattgg gaagtttggt tgaggttcaa gtgtgactcc  3960
ttccagagcc acaggtaggg gagtgtgaag ttgaggggga ggaaagctgg aaggactctg  4020
ccttgggaga ttcccagctc tgcttttcag cgcttggtgg aatctgggct ggggaaagac  4080
ggcaccggga aactctgctt ccccattgtt tccatctgat cagctgtggt gtgaggactt  4140
ctcagacaaa ggcaaggcct cgtgcccctg cccagcccat tcatgagcc ctgggccttc  4200 ttggcttcca tagatcctaa gctcttgact gtagtttagc cagacttgtt ttgctatctt  4260
ataagcagtt cagaattagg gaatgctggt tttgaagagc aaaggacagg tagtctagag  4320
agggtcgtct ggcctgcttg ctgggtcttt gtaacccagc acttcctctt gccctcctgg  4380
ctttatgttt atggggagag gactcaatag ctccacccct tctggcacca gatgggctt  4440 ggttagtttg caataagcac cttgcagagg ttaaagccag cgggtcccta gtcttaggcc  4500
cagcctgctt gtgtgggctc tggcctggcc tggtggctgg cccagggggc agcagtgctt  4560
agagcttctg cagggcttct cttgtttaca cagctgcatc agacaatgcc atttctcccc  4620
accacggaac cttccatcta agatttcttc caggaatgc cagcaatcag gcagcaccca  4680
gctgtggggg cagtggggtg ggggagaccc acattgatga cttttttttt ttcttttaat  4740
gaagaaacac caaagaaagc tgtggaaagg acctgcccca catgaaaagg ataagccaag  4800
atggctgtaa acacagagca tttgagctgc cactcttgga gcacattgat ttttcaaaag  4860
ccagctctgt caggaaagga ggtgctgtta tgagcagctc ttccagtggg caaagaggac  4920
gcccataatt tcttccattg ctagctcatc tgtgggacca atttggtgta agcaacctgt  4980
ggcctgcact tgtggcctcg aaggaagcac aaaccctcca tccacttccc atttcctctg  5040
cccttttcca cctccccctt ccatcccacc agctgccagt ggctcccaga aagccttatt  5100 gagcccttg ttgacacttg gggctgcgga ggcctctccc tactggtctg gcctttcctg  5160
agaggcaggt cttccgtcct cagagccttt ctggaacaag gagaatgcct gtgcaggtgg  5220
acacacaggc ctggcctgtc gctctcactt gtcttccagc ggggagcttc acgttgccga  5280
gtggaagaac catgaccctcc acttgcttcc aaggtgctag ggaagtttca gggtacgctg  5340
```

-continued

| | |
|---|---|
| gttcccctct ccagctggag gccgagtttc tggggactgc agattttct actctgtgat | 5400 |
| cgattcaatg cccgatgctt ctgtttcatt cccgacccct tctactatgc attttccttt | 5460 |
| tatcaggtgt ataaagttaa atactgtgta tttatcacta aaaagtacat gaacttaaga | 5520 |
| gacaactaag cctttcgtgt ttttccacag gtgtttaagc ttctctgtac agttgaaata | 5580 |
| aacagacagc aaaatggtgc aaaaaaaaa aaaaaaaaa | 5620 |

<210> SEQ ID NO 6
<211> LENGTH: 1695
<212> TYPE: DNA
<213> ORGANISM: Homo sapiens
<220> FEATURE:
<221> NAME/KEY: misc_feature
<222> LOCATION: (1)...(1695)
<223> OTHER INFORMATION: acetyl-Coenzyme A acyltransferase 1
    (peroxisomal 3-oxoacyl-Coenzyme A thiolase) (ACAA1)
    mitochondrial protein cDNA

<400> SEQUENCE: 6

| | |
|---|---|
| atgtggttct gcgcgtgtgc ggacggctgt ctgttaactc cgcggtcagt tcccggactg | 60 |
| gtggctggtc tgcaggggttg acctgcgcaa tgcagaggct gcaggtagtg ctgggccacc | 120 |
| tgaggggtcc ggccgattcc ggctggatgc cgcaggccgc gccttgcctg agcggtgccc | 180 |
| cgcaggcctc ggccgcggac gtggtggtgg tgcacgggcg gcgcacggcc atctgccggg | 240 |
| cgggccgcgg cggcttcaag gacaccaccc ccgacgagct tctctcggca gtcatgaccg | 300 |
| cggttctcaa ggacgtgaat ctgaggccgg aacagctggg ggacatctgt gtcggaaatg | 360 |
| tgctgcagcc tggggccggg gcaatcatgg cccgaatcgc ccagtttctg agtgacatcc | 420 |
| cggagactgt gcctttgtcc actgtcaata gacagtgttc gtcggggcta caggcagtgg | 480 |
| ccagcatagc aggtggcatc agaaatgggt cttatgacat tggcatggcc tgtggggtgg | 540 |
| agtccatgtc cctggctgac agagggaacc tggaaatat tacttcgcgc ttgatggaga | 600 |
| aggagaaggc cagagattgc ctgattccta tggggataac ctctgagaat gtggctgagc | 660 |
| ggtttggcat ttcacgggag aagcaggata ccttgccct ggcttccag cagaaggcag | 720 |
| caagagccca gagcaagggc tgtttccaag ctgagattgt gcctgtgacc accacggtcc | 780 |
| atgatgacaa gggcaccaag aggagcatca ctgtgcccca ggatgagggt atccgcccca | 840 |
| gcaccaccat ggagggcctg gccaaactga agcctgcctt caagaaagat ggttctacca | 900 |
| cagctggaaa ctctagccag gtgagtgatg gggcagctgc catcctgctg gcccggaggt | 960 |
| ccaaggcaga agagttgggc cttcccatcc ttggggtcct gaggtcttat gcagtggttg | 1020 |
| gggtcccacc tgacatcatg gcattggac ctgcctatgc catcccagta gctttgcaaa | 1080 |
| aagcagggct gacagtgagt gacgtggaca tcttcgagat caatgaggcc tttgcaagcc | 1140 |
| aggctgccta ctgtgtggag aagctacgac tcccccctga aaggtgaac cccctggggg | 1200 |
| gtgcagtggc cttagggcac ccactgggct gcactgggc acgacaggtc atcacgctgc | 1260 |
| tcaatgagct gaagcgccgt gggaagaggg catacggagt ggtgtccatg tgcatcggga | 1320 |
| ctggaatggg agccgctgcc gtctttgaat accctgggaa ctgagtgagg tcccaggctg | 1380 |
| gaggcgctac gcagacagtc ctgctgctct agcagcaagg cagtaacacc acaaaagcaa | 1440 |
| aaccacatgg gaaaactcag cactggtggt ggtggcagtg gacagatcaa ggcacttcaa | 1500 |
| ctcatttgga aaatgtgaac actgatgaca tggtatagga gtgggtgggg tgttgagcca | 1560 |
| cccatcagac cctctttagc tgtgcaagat aaaagcagcc tgggtcaccc aggccacaag | 1620 |
| gccatggtta attcttaagg caaggcaaat ccatggatga gaagtgcaat gggcatagta | 1680 |

-continued aaagtgcatg aattt                                                              1695

<210> SEQ ID NO 7
<211> LENGTH: 2613
<212> TYPE: DNA
<213> ORGANISM: Homo sapiens
<220> FEATURE:
<221> NAME/KEY: misc_feature
<222> LOCATION: (1)...(2613)
<223> OTHER INFORMATION: glucosamine-6-phosphate deaminase 1 (GNPDA1),
      glucosamine-6-phosphate isomerase (GNPI, GPI, HLN,
      KIAA0060, oscillin) cDNA

<400> SEQUENCE: 7

```
cggggacctt cctcgcgggc cggagcgcgg agcgctgccc cagccctacg gcactcgggg    60
tcgggacccc ggggagccgc cctcacacat tttccaggag ggatcggagg ggcgatgggg   120
tggtaatggg ggtgggggac acgctgtacc ccaccgacga ccgcgcgggc caccttcgcc   180
tctttccttc acactcccac taaccgcagt gctgggggaa caaaatgtcc tccttctgga   240
gcgattacct tttcccttt gtgctttggg ggaaactgaa gacccagagg ggttcgcaaa    300
gcaagtctgt gaagtaggta ctattgtccc aatttttaca taggaggaaa cggctcagag   360
agaacttagg tcctttgacc gaggtcctgc aggtggacaa gatgaagctc atcatcctgg   420
agcactattc tcaggcgagc gagtgggcgg ctaaatacat caggaaccgt atcatccagt   480
ttaacccagg gccagagaag tacttcaccc tgggctccc cactgggagt acccccacttg   540
gctgctacaa gaagctgatt gaatactata agaatgggga cctgtccttt aaatatgtga   600
agaccttcaa catggatgag tacgtgggcc ttcctcgaga ccacccggag agttaccact   660
ccttcatgtg gaacaacttc ttcaagcaca ttgacatcca cccagaaaac acccacattc   720
tggatgggaa tgcagtcgac ctacaggcag aatgtgatgc ctttgaagag aagatcaagg   780
ctgcaggtgg gatcgagcta tttgttggag gcatcggccc tgatggacac attgccttca   840
acgagccagg ctccagtctg tgtccagga cccgtgtgaa gacgctggcc atggatacca   900
tcctggccaa tgctaggttc ttcgatggag aactcaccaa ggtgcccacc atggccttga   960
cggtggggt gggcactgtc atggatgcta gagaggtgat gatccttatc acaggtgctc   1020
acaaggcatt tgctctgtac aaggccatcg aggagggagt gaaccacatg tggaccgtgt   1080
ctgccttcca gcagcatccc cgcaccgtgt tgtgtgtga cgaggatgcc accttggagc   1140
tgaaagtgaa gactgtcaag tatttcaaag gtttaatgct tgttcataac aagttggtgg   1200
acccccttgta cagtatcaaa gagaaagaaa ctgagaaaag ccaatcttcg aagaaaccat   1260
acagcgatta gcctgtgctg ggacctagtg tcaagtaccc atagggaaag gcaggtcttt   1320
ctggaaattg tctttagaag aaagaattgt atttctttaa tctagtatgg ttactccaga   1380
taagtgggtg aacttattgt tcttggccat gaggctggga gcctagtcac ggagtttagc   1440
tatagggaga atgtttgtaa cttaatcaga aaaaaatat ctgcaaaatg tactccatca   1500
ttctgatgtc tgccaaaccc aggttgggag ttttaaactt tttgttctgc ttcagccatg   1560
gttcacacat atgacacact cccgtcagga atttctctcc ttacacgcac tgattttcaa   1620
gtgggaggga attaggggct tatgtatatt ggataccacc tcttgagagt ccttcttgca   1680
caggcctgcc ccttggttga gaaccattgt tccaagtgaa ggcacaaact ctcaatatct   1740
aaaataagtg caaggaagca gtctctttgg tcagtaacaa gtgcaatgga agaaaacga   1800
tcccttcctt cttccacttt cacagctttt ttctgaacta ggagaacctg ggggtggatt   1860
```

```
tgggtgggtg gggccaaaga ggaggcttct attgataaat ccagagcctc aagggggccca    1920 gccacgtcaa acttctctcc ctcagggact ctccagcacc aaaaggcaga aggtggaagc    1980
cgttttcccc ccagagccct gtgttttgt gaaaggcctc actgtggctc ctctgtttta    2040
catactcatt agtaagtggg aggtccactg gggcaacaga cactgccaca atttcagtgt    2100
tgtgttcagc caaggggacg gtctggacag gcagcttaag tgtgagttta gtcacaactc    2160
ctgagtgtcc cgctctcctg cttacctagg aggtgagtgc caggaaaata caccaaatgc    2220
ttctagtatt gtttccccac ttaaaatagt cctgcttaaa ttcacatggt gtggtctgat    2280
gttctgagag catcaggaaa tacaacccct ttgcccattt accttctcc ccggatccca    2340 aggtggtctg ttgctctggc ttcctttcat tgtcttaggc cttcatggag tggatgctgc    2400
ctcctcctgg ctgttttgt gcctgtttga agctactgct gcctccattt ctgggaaaga    2460
cctttgagag cctagcccag gcctaagggc tatgtttggt accagtattt tgtctttagc    2520
ttttctatgt gattgtgccg tcattctgtt ttaagctcat ggatcaatgg atttgtttac    2580
aatgtgatat tttctattaa atccagtatt ttg    2613

<210> SEQ ID NO 8
<211> LENGTH: 4248
<212> TYPE: DNA
<213> ORGANISM: Homo sapiens
<220> FEATURE:
<221> NAME/KEY: misc_feature
<222> LOCATION: (1)...(4248)
<223> OTHER INFORMATION: 24-dehydrocholesterol reductase (DHCR24),
      KIAA0018, SELADIN1, DIMINUTO/DWARF1 homolog, cDNA

<400> SEQUENCE: 8
cccgggctgt gggctacagg cgcagagcgg gccaggcgcg gagctggcgg cagtgacagg      60
aggcgcgaac ccgcagcgct taccgcgcgg cgccgcacca tggagcccgc cgtgtcgctg     120
gccgtgtgcg cgctgctctt cctgctgtgg gtgcgcctga aggggctgga gttcgtgctc     180
atccaccagc gctgggtgtt cgtgtgcctc ttcctcctgc cgctctcgct tatcttcgat     240
atctactact acgtgcgcgc ctgggtggtg ttcaagctca gcagcgctcc cgcgcctgcac    300 gagcagcgcg tgcgggacat ccagaagcag gtgcgggaat ggaaggagca gggtagcaag     360
accttcatgt gcacggggcg ccctggctgg ctcactgtct cactacgtgt cgggaagtac     420
aagaagacac acaaaaacat catgatcaac ctgatggaca ttctggaagt ggacaccaag     480
aaacagattg tccgtgtgga gcccttggtg accatgggcc aggtgactgc cctgctgacc     540
tccattggct ggactctccc cgtgttgcct gagcttgatg acctcacagt gggggcttg      600 atcatgggca caggcatcga gtcatcatcc acaagtacg gcctgttcca acacatctgc     660
actgcttacg agctggtcct ggctgatggc agctttgtgc gatgcactcc gtccgaaaac     720
tcagacctgt tctatgccgt accctggtcc tgtgggacgc tgggtttcct ggtggccgct     780
gagatccgca tcatccctgc caagaagtac gtcaagctgc gtttcgagcc agtgcgggc     840 ctggaggcta tctgtgccaa gttcacccac gagtcccagc ggcaggagaa ccacttcgtg     900
gaagggctgc tctactccct ggatgaggct gtcattatga caggggtcat gacagatgag     960
gcagagccca gcaagctgaa tagcattggc aattactaca gccgtggtt ctttaagcat    1020 gtggagaact atctgaagac aaaccgagag ggcctggagt acattccctt gagacactac    1080
taccaccgcc acacgcgcag catcttctgt gagctccagg acatcatccc ctttggcaac    1140
aaccccatct tccgctacct ctttggctgg atggtgcctc ccaagatctc cctcctgaag     1200
```

```
ctgacccagg gtgagaccct gcgcaagctg tacgagcagc accacgtggt gcaggacatg   1260
ctggtgccca tgaagtgcct gcagcaggcc ctgcacacct ccaaaacga catccacgtc   1320 taccccatct ggctgtgtcc gttcatcctg cccagccagc caggcctagt gcaccccaaa   1380
ggaaatgagg cagagctcta catcgacatt ggagcatatg gggagccgcg tgtgaaacac   1440
tttgaagcca ggtcctgcat gaggcagctg gagaagtttg tccgcagcgt gcatggcttc   1500
cagatgctgt atgccgactg ctacatgaac cgggaggagt ctgggagat gtttgatggc   1560 tccttgtacc acaagctgcg agagaagctg ggttgccagg acgccttccc cgaggtgtac   1620
gacaagatct gcaaggccgc caggcactga gctggagccc gcctggagag acagacacgt   1680
gtgagtggtc aggcatcttc ccttcactca agcttggctg ctttcctaga tccacacttt   1740
caaagagaaa cccctccaga actcccaccc tgacagccca acaccacctt cctcctggct   1800 tccaggggc agcccagtgg aatggaaaga atgtgggatt tggagtcaga caagcctgag   1860
tccagttccc cgtttagaac tcattagctg tgtgactctg ggtgagtccc ttaacccctc   1920
tgagcccggg tctcttcatt agttgaaagg gatagtaata cctacttgca ggttgttgtc   1980
atctgagttg agcactggtc acattgaagg tgctgggtaa gtggtagctc ttgttgcttc   2040
ccgttcagcg tcacatctgc agtggagcct gaaaaggctc acattaggt cacctgtgca   2100 cagccatggc tggaatgatg aaggggatac gctggagttg ccctgccatc gcctccatca   2160
gccagacgag gtcctcacag gagaaggaca gctcttcccc accctgggat ctcaggaggg   2220
cagccacgga gtggggaggc cccagatgcg ctgtgccaaa gccaggtccg aggccaaagt   2280
tctccctgcc atccttggtg ccgtcctgcc ccttcctcct tcatgcctgg gcctgcaggc   2340
ccaccccagc caccactgag tccactcgga gtgccctgtg ttcctggaga aggcattcca   2400
gggttgaatc ttgtcccagc ctcagcctgg gacacctagg tggagagagt ggtctccgct   2460
ctgaattgga tccaggggac ctgggctcat tcttcttggc tcaccaaccc tgcaggcctc   2520
atctttccca aaacccactt tgtcttggtg ggagtgggtc cgcgctgctc tgcagcaggg   2580
gctggggagt ggacagcatc aggtgggaaa gtggagtcca ccctcatgtt tctgtaggat   2640
tctcaccgtg gggctggaag aaaagagcat cgacttgatt tctccaacca ctcatccctc   2700
tttttctttc ttccaccact ccccaccccca gctgtagtta atttcagtgc cttacaaatc   2760
ctaagctcag agaaagttcc atttccgttc cagagggaag ggaacctccc taggtccttc   2820
cctggcttgt tataacgcaa agcttggttg tttatgcaac tctatcttaa gaactgccca   2880
gcctcagctg aaaacccgaa tctgagaagg aattgcgtca tgtaagggaa gctggaatta   2940
agggagctga gccagtcatg gttgtggcgt gtgagtcagg agacctaggt ttcagcccct   3000
ctctactgtc agcgagctgt gcaacgtggg caagtcattg tcctctgagc tgcagtttcc   3060
tcatctgtca catcgctaca gacaagacct ccctggaacc cttctgattg tcttagacac   3120
tgtggttgca aaacccacgg aaagcctcat ttgtgtggaa agtcagagga aaatgatcc   3180 agtggacact tggggattat ctgtcattca agatccttcc ttcaaccca aggccagctc   3240 ccatctcatt tccagaaagg ctcatacctg gcttgcaggg aagcatctgt cttgtcattc   3300
caggtgccag aatcctctca gagtcattga agggtgttca cccatcccac ccaaggcttg   3360
gcacactgcc agtgtcttag cagggtcttg tgagggctgg gggcatccag gcactcagaa   3420
ggcaaaggaa ccaccctacc catttggcct ctggaggggg cagaagaaag aaagaaacct   3480
catcctatat tttacaaagc atgtgaattc tggcattagc tctcatagga gacccatgtg   3540
cttccttgct cagtgcaaaa ctgatgattc tacttgctgt agatgaatgg ttaacacgag   3600
```

```
ctagttaaac agtgccattg ttttgccagt gaagcctcca accctaagcc actgggacgg    3660
tggccagaga tgccagcagc ctctgtcgcc cttagtcata taaccaaaat ccagaccctta   3720 tccacaaccc ggggcttgga aaggaaggta ttttggaatc acaccctccg gttatgttgc    3780
tccagtaaaa tcttgcctgg aaagaggcag tcttcttagc atggtgagct gagttcatgg    3840
cttttttttg tagccagtcc tgtccctggc atccatgtg atggttttgg atggagttaa     3900
acttgatgcc agtgggcagt gcatgtggaa agtatcagag taagcctctc ccctccagag    3960
ccctgagttt cttggctgca tgaaggtttt ctttagaatc agaattgtag ccagtttctt    4020
tggccagaag gatgaatact tggatattac tgaaagggag gggtggagat gggtgtggca    4080
gtgtatggtg tgtgattttt attttcttct ttggtcatgg gggccaagga gaaaggcatg    4140
aatcttccct gtcaggctct tacagccaca ggcactgtgt ctactgtctg aagacatgt     4200 ccccgtggct gtggggccgc tgcttctgtt taaataaaag tggcctgg                 4248
```

<210> SEQ ID NO 9
<211> LENGTH: 3471
<212> TYPE: DNA
<213> ORGANISM: Homo sapiens
<220> FEATURE:
<221> NAME/KEY: misc_feature
<222> LOCATION: (1)...(3471)
<223> OTHER INFORMATION: selenoprotein T (SELT) (cDNA clone MGC:26803)
      cDNA

<400> SEQUENCE: 9

```
gctcctgggc tttgggctgg ctgcagtctg tctgagggcg gccgaagtgg ctggctcatt    60
taagatgagg cttctgctgc ttctcctagt ggcggcgtct gcgatggtcc ggagcgaggc    120
ctcggccaat ctgggcggcg tgcccagcaa gagattaaag atgcagtacg ccacggggcc    180
gctgctcaag ttccagattt gtgtttcctg aggttatagg cgggtgtttg aggagtacat    240
gcgggttatt agccagcggt acccagacat ccgcattgaa ggagagaatt acctccctca    300
accaatatat agacacatag catcttttcct gtcagtcttc aaactagtat taataggctt   360
aataattgtt ggcaaggatc cttttgcttt ctttggcatg caagctccta gcatctggca    420
gtggggccaa gaaaataagg tttatgcatg tatgatggtt ttcttcttga gcaacatgat    480
tgagaaccag tgtatgtcaa caggtgcatt tgagataact ttaaatgatg tacctgtgtg    540
gtctaagctg gaatctggtc accttccatc catgcaacaa cttgttcaaa ttcttgacaa    600
tgaaatgaag ctcaatgtgc atatggattc aatcccacac catcgatcat agcaccacct    660
atcagcactg aaaactcttt tgcattaagg gatcattgca agagcagcgt gactgacatt    720
atgaaggcct gtactgaaga cagcaagctg ttagtacaga ccagatgctt tcttggcagg    780
ctcgttgtac ctcttggaaa acctcaatgc aagatagtgt ttcagtgctg gcatattttg    840
gaattctgca cattcatgga gtgcaataat actgtatagc tttccccacc tcccacaaaa    900
tcacccagtt aatgtgtgtg tgtgtgtttt ttttaaggta acattacta cttgtaactt      960 tttttcttag tcatatttga aaagtagaaa aattgagtta caatttgatt ttttttccaa    1020
agatgtctgt taaatctgtt gtgcttttat atgaatattt gttttttata gtttaaaatt    1080
gatcctttgg gaatccagtt gaagttccca aatactttat aagagtttat cagacatctc    1140
taatttggcc atgtccagtt tatacagttt acaaaatata gcagatgcaa gattatgggg    1200
gaaatcctat attcagagta ctctataaat ttttgtgtat gtgtgtatgt gcgtgtgatt    1260
accagagaac tactaaaaaa accaactgct ttttaaatcc tattgtgtag ttaaagtgtc    1320
```

```
atgccttgac caatctaatg aattgattaa ttaactgggc ctttatactt aactaaataa    1380
aaaactaagc agatatgagt taaatttaaa agtttcaatt tattgctcag tgtacctgtt    1440
aacattatat ttaacaattg cttaaatttt tgttttttgat ttatggataa tttcttaaga   1500
gtacacactt tagatacaca ataatcgtt catttaccat ctttaggatc attgaaactc     1560
atctcactaa agaaagttca cttgaaccctc tttatagcat tgatactagg tgaacagaaa   1620
ttacctgact aataatttgt ctaacatcat atatcagaat tttattgtat atgatgaaca    1680
aaacttaaaa tttttttaaat ttaattttta aatactgttt cagagttcta aaaaggcagt   1740
tttttaaaaa acttaagttg ataaaaactg taagaataat ttagcagaaa tagaaccaga    1800
atgtagaaga gtagtcatgt aacagcagta ataacatact tcagcttcca tataggaata   1860
gaagtggtag agccaaaagt gatttaggag aagttataag gtacaggttg agtatcccctt  1920
ttccaaaaat gcttgggaca agaagtattt cagatttcat aatttttttc aaagtttgga   1980
atatttgcat tatacttacc agttgggcat cccaaatctg aaatctgaaa tgttccatga   2040
gcatttcctt tgagtgtcat gttggcactc aaaaaggttc aacattgagt ccacttaaca   2100
cttaggtgtt agaagaccta actttctgta acaattaacc ttatactttg tttgtcatcg   2160
aatatttgtt gaatgcatgt caggtaatgg tcttgattgt gatagcttca aggtggaaca   2220
tactgtaatc tccagatgct aggaagttag tctaataatt cactgcagaa aattgattaa   2280
gtggctgtcc ttttaattaa gagtgtggag tcataaactt aagttcttca tatagtgaca   2340
agagtcctta gagattgtta ttcaagttcc ttagaaattg ttatttaggt ataatatcat   2400
cttgtctttg actagagctt gaaaccttgt tatctgattg tgtaccactc caaattccct   2460
gccttctgca agtgaatgt cttgctgaat gtgtctaggg gttcatcttc agtaatcgac    2520
attccactag tgccatagtt aacttcatga catgtagaca ttcaaaactt gagccttgga   2580
tgttcctgtg gacctgacag ttaaaaatat aaagaaccta ggattcaatt ccaactttct   2640
ctgtttgcct tgggttgaat aacttatctt ttggagaata gctttaagtg gcttagacac   2700
tgataaaatt cagctgtgtt gttgacgctc atctcttttg tcttacgctt agccatattt   2760
aaatcttgaa tttaatagag tctagtgaaa aaaatgagtg ggaagaatga atataaaagt   2820
aataatataa ggaaaaaggg aagtaaaacta tttagaatgt agttttgtta tattcccagc   2880
atttcaatat ttattagtta cttgtaaatt actgtggctg tgtagtttat aaatgtctgt   2940
gcactatatt aattagaaga ccatagaaca tgccagcagg ttggctaatg ctatgggggt   3000
ttttaccaca gttgccattg tggaagaaat tatttggtac attaataaaa aaagttggta   3060
aaacatggtt ttatacctca gtgtataaga tgtgcaagac aaatatgctt atttcctttt   3120
ctagaatata agtgatatta tttgcttatg acactaacac tattaatgac aggagtcaat   3180
cagcctttac agctatcaaa atataatgag atcccaatga tgattctttt ttactttgaa   3240
tgttaattag tttgggactt tgattggctg gcaaacattt tatcattgtc agaatttaat   3300
ttagatttca aaaatagctt acaggatttt aaacatggtg tggtattcta aagcctttt    3360
tttaaaaaaa gagatctttt tgagagaaac aaatgaggat tgtaaagttt ggggacttac   3420
ctctgtagca ttgtgaaaat aaactttgat taagcaaaaa aaaaaaaaaa a            3471
```

<210> SEQ ID NO 10
<211> LENGTH: 1002
<212> TYPE: DNA
<213> ORGANISM: Homo sapiens
<220> FEATURE:

```
<221> NAME/KEY: misc_feature
<222> LOCATION: (1)...(1002)
<223> OTHER INFORMATION: selenoprotein T (SELT) cDNA

<400> SEQUENCE: 10
tgcagtctgt ctgagggcgg ccgaagtggc tggctcattt aagatgaggc ttctgctgct      60
tctcctagtg gcggcgtctg cgatggtccg gagcgaggcc tcggccaatc tgggcggcgt     120
gccagcaaga gattaaagat gcagtacgcc acggggccgc tgctcaagtt ccagatttgt     180
gtttcctgag gttataggcg ggtgtttgag gagtacatgc gggttattag ccagcggtac     240
ccagacatcc gcattgaagg agagaattac ctccctcaac caatatatag acacatagca     300
tctttcctgt cagtcttcaa actagtatta ataggcttaa taattgttgg caaggatcct     360
tttgctttct ttggcatgca agctcctagc atctggcagt ggggccaaga aaataaggtt     420
tatgcatgta tgatggtttt cttcttgagc aacatgattg agaaccagtg tatgtcaaca     480
ggtgcatttg agataacttt aaatgatgta cctgtgtggt ctaagctgga atctggtcac     540
cttccatcca tgcaacaact tgttcaaatt cttgacaatg aaatgaagct caatgtgcat     600
atggattcaa tcccacacca tcgatcatag caccacctat cagcactgaa aactcttttg     660
cattaaggga tcattgcaag agcagcgtga ctgacattat gaaggcctgt actgaagaca     720
gcaagctgtt agtacagacc agatgctttc ttggcaggct cgttgtacct cttgaaaaac     780
ctcaatgcaa gatagtgttt cagtgctggc atattttgga attctgcaca ttcatggagt     840
gcaataatac tgtatagctt tcccccacct cccacaaaat cacccagtta atgtgtgtgt     900
gtgtgttttt tttaaggtaa acattactac ttgtaacttt ttttctttag tcatatttgg     960
aaaaagtaga aaattggagt tacatttgga ttttttttcc aa                      1002

<210> SEQ ID NO 11
<211> LENGTH: 6331
<212> TYPE: DNA
<213> ORGANISM: Homo sapiens
<220> FEATURE:
<221> NAME/KEY: misc_feature
<222> LOCATION: (1)...(6331)
<223> OTHER INFORMATION: protein tyrosine phosphatase, receptor type, B
      (PTPRB), receptor protein tyrosine phosphatase
      beta (RPTPbeta), (PTPB, HPTPB, FLJ44133,
      MGC59935), cDNA

<400> SEQUENCE: 11
gtctcctctg gatcttaact actgagcgca atgctgagcc atggagccgg gttggccttg      60
tggatcacac tgagcctgct gcagactgga ctggcggagc cagagagatg taacttcacc     120
ctggcggagt ccaaggcctc cagccattct gtgtctatcc agtggagaat ttgggctca      180 ccctgtaact ttagcctcat ctatagcagt gacaccctgg gggccgcgtt gtgccctacc     240
tttcggatag acaacaccac atacggatgt aaccttcaag atttacaagc aggaaccatc     300
tataacttca agattatttc tctggatgaa gagagaactg tggtcttgca aacagatcct     360
ttacctcctg ctaggtttgg agtcagtaaa gagaagacga cttcaaccgg cttgcatgtt     420
tggtggactc cttcttccgg aaaagtcacc tcatatgagg tgcaattatt tgatgaaaat     480
aaccaaaaga tacaggggt tcaaattcaa gaaagtactt catggaatga atacactttt     540
ttcaatctca ctgctggtag taaatacaat attgccatca cagctgtttc tggaggaaaa     600
cgttcttttt cagtttatac caatggatca acagtgccat ctccagtgaa agatattggt     660
atttccacaa aagccaattc tctcctgatt tcctggtccc atggttctgg gaatgtggaa     720
```

```
cgataccggc tgatgctaat ggataaaggg atcctagttc atggcggtgt tgtggacaaa      780
catgctactt cctatgcttt tcacgggctg tccctggct acctctacaa cctcactgtt       840
atgactgagg ctgcagggct gcaaaactac aggtggaaac tagtcaggac agcccccatg      900
gaagtctcaa atctgaaggt gacaaatgat ggcagtttga cctctctaaa agtcaaatgg      960
caaagacctc ctggaaatgt ggattcttac aatatcaccc tgtctcacaa agggaccatc     1020
aaggaatcca gagtattagc accttggatt actgaaactc actttaaaga gttagtcccc     1080
ggtcgacttt atcaagttac tgtcagctgt gtctctggtg aactgtctgc tcagaagatg     1140
gcagtgggca gaacatttcc agacaaagtt gcaaacctgg aggcaaacaa taatggcagg     1200
atgaggtctc ttgtagtgag ctggtcgccc cctgctggag actgggagca gtatcggatc     1260
ctactcttca atgattctgt ggtgctgctc aacatcactg tgggaaagga agaaacacag     1320
tatgtcatgg atgacacggg gctcgtaccg ggaagacagt atgaggtgga agtcattgtt     1380
gagagtggaa atttgaagaa ttctgagcgt tgccaaggca ggacagtccc cctggctgtc     1440
ctccagcttc gtgtcaaaca tgccaatgaa acctcactga gtatcatgtg cagacccct    1500 gtagcagaat gggagaaata catcatttcc ctagctgaca gagacctctt actgatccac     1560
aagtcactct ccaaagatgc caaagaattc acttttactg acctggtgcc tggacgaaaa     1620
tacatggcta cagtcaccag tattagtgga gacttaaaaa attcctcttc agtaaaagga     1680
agaacagtgc ctgcccaagt gactgacttg catgtggcca accaaggaat gaccagtagt     1740
ctgtttacta actggaccca ggcacaagga gacgtagaat tttaccaagt cttactgatc     1800
catgaaaatg tggtcattaa aaatgaaagc atctccagtg agaccagcag atacagcttc     1860
cactctctca gtccggcag cctgtactcc gtggtggtaa caacagtgag tggagggatc     1920
tcttcccgac aagtggttgt ggagggaaga acagtccctt ccagtgtgag tggagtaacg     1980
gtgaacaatt ccggtcgtaa tgactacctc agcgtttcct ggctgctggc gcccggagat     2040
gtggataact atgaggtaac attgtctcat gacggcaagg tggttcagtc ccttgtcatt     2100
gccaagtctg tcagagaatg ttccttcagc tccctcaccc caggccgcct ctacaccgtg     2160
accataacta caaggagtgg caagtatgaa aatcactcct tcagccaaga gcggacagtg     2220
cctgacaaag tccagggagt cagtgttagc aactcagcca ggagtgacta tttaagggta     2280
tcctgggtgc atgccactgg agactttgat cactatgaag tcaccattaa aacaaaaac     2340 aacttcattc aaactaaaag cattcccaag tcagaaaacg aatgtgtatt tgttcagcta     2400
gtccctggac ggttgtacag tgtcactgtt actacaaaaa gtggacaata tgaagccaat     2460
gaacaaggga atgggagaac aattccagag cctgttaagg atctaacatt gcgcaacagg     2520
agcactgagg acttgcatgt gacttggtca ggagctaatg gggatgtcga ccaatatgag     2580
atccagctgc tcttcaatga catgaaagta tttcctcctt ttcaccttgt aaataccgca     2640
accgagtatc gatttacttc cctaacacca ggccgccaat acaaaattct tgtcttgacg     2700
attagcgggg atgtacagca gtcagccttc attgagggct tcacagttcc tagtgctgtc     2760
aaaaatattc acatttctcc caatggagca acagatagcc tgacggtgaa ctggactcct     2820
ggtgggggag acgttgattc ctacacggtg tcggcattca ggcacagtca aaaggttgac     2880
tctcagacta ttcccaagca cgtctttgag cacacgttcc acagactgga ggccgggag     2940 cagtaccaga tcatgattgc ctcagtcagc gggtccctga agaatcagat aaatgtggtt     3000
gggcggacta ttccagcatc tgtccaagga gtaattgcag acaatgcata cagcagttat    3060
tccttaatag taagttggca aaaagctgct ggtgtggcag aaagatatga tatcctgctt    3120
```

```
ctaactgaaa atggaatcct tctgcgcaac acatcagagc cagccaccac taagcaacac    3180
aaatttgaag atctaacacc aggcaagaaa tacaagatac agatcctaac tgtcagtgga    3240
ggcctcttta gcaaggaagc ccagactgaa ggccgaacag tcccagcagc tgtcaccgac    3300
ctgaggatca cagagaactc caccaggcac ctgtccttcc gctggaccgc ctcagagggg    3360
gagctcagct ggtacaacat cttttttgtac aacccagatg gaatctcca ggagagagct    3420 caagttgacc cactagtcca gagcttctct ttccagaact tgctacaagg cagaatgtac    3480
aagatggtga ttgtaactca cagtggggag ctgtctaatg agtctttcat atttggtaga    3540
acagtcccag cctctgtgag tcatctcagg gggtccaatc ggaacacgac agacagcctt    3600
tggttcaact ggagtccagc ctctggggac tttgactttt atgagctgat tctctataat    3660
cccaatggca caagaagga aaactggaaa gacaaggacc tgacggagtg gcggtttcaa    3720
ggccttgttc ctggaaggaa gtacgtgctg tgggtggtaa ctcacagtgg agatctcagc    3780
aataaagtca gcgcggagag cagaacagct ccaagtcctc ccagtcttat gtcatttgct    3840
gacattgcaa acacatcctt ggccatcacg tggaaagggc cccagactg acagagactac    3900 aacgactttg agctgcagtg gttgcccaga gatgcactta ctgtcttcaa ccccctacaac    3960 aacagaaaat cagaaggacg cattgtgtat ggtcttcgtc cagggagatc ctatcaattc    4020
aacgtcaaga ctgtcagtgg tgattcctgg aaaacttaca gcaaaccaat ttttggatct    4080
gtgaggacaa agcctgacaa gatacaaaac ctgcattgcc ggcctcagaa ctccacggcc    4140
attgcctgtt cttggatccc tcctgattct gactttgatg ttatagtat tgaatgccgg    4200 aaaatggaca cccaagaagt tgagttttcc agaaagctgg agaaagaaaa atctctgctc    4260
aacatcatga tgctagtgcc ccataagagg tacctggtgt ccatcaaagt gcagtcggcc    4320
ggcatgacca gcgaggtggt tgaagacagc actatcacaa tgatagaccg cccccctcct    4380 ccaccccac acattcgtgt gaatgaaaag gatgtgctaa ttagcaagtc ttccatcaac    4440
tttactgtca actgcagctg gttcagcgac accaatggag ctgtgaaata cttcacagtg    4500
gtggtgagag aggctgatgg cagtgatgag ctgaagccag aacagcagca ccctctccct    4560
tcctacctgg agtacaggca caatgcctcc attcgggtgt atcagactaa ttattttgcc    4620
agcaaatgtg ccgaaaatcc taacagcaac tccaagagtt ttaacattaa gcttggagca    4680
gagatggaga gcttaggtgg aaaacgcgat cccactcagc aaaaattctg tgatggacca    4740
ctgaagccac acactgccta cagaatcagc attcgagctt ttacacagct cttttgatgag    4800 gacctgaagg aattcacaaa gccactctat tcagacacat ttttttcttt acccatcact    4860
actgaatcag agcccttgtt tggagctatt gaaggtgtga gtgctggtct gttttaatt    4920 ggcatgctag tggctgttgt tgccttattg atctgcagac agaaagtgag ccatggtcga    4980
gaaagaccct ctgcccgtct gagcattcgt agggatcgac cattatctgt ccacttaaac    5040
ctgggccaga aggtaaccg gaaaacttct tgtccaataa aaataaatca gtttgaaggg    5100
catttcatga agctacaggc tgactccaac taccttctat ccaaggaata cgaggagtta    5160
aaagacgtgg gccgaaacca gtcatgtgac attgcactct gccggagaa tagagggaaa    5220 aatcgataca caatatatt gccctatgat gccacgcgag tgaagctctc caatgtagat    5280
gatgatcctt gctctgacta catcaatgcc agctacatcc ctggcaacaa cttcagaaga    5340
gaatacattg tcactcaggg accgcttcct ggcaccaagg atgacttctg gaaaatggtg    5400
tgggaacaaa acgttcacaa catcgtcatg gtgacccagt gtgttgagaa gggccgagta    5460
```

```
aagtgtgacc attactggcc agcggaccag gattccctct actatgggga cctcatcctg    5520
cagatgctct cagagtccgt cctgcctgag tggaccatcc gggagtttaa gatatgcggt    5580
gaggaacagc ttgatgcaca cagactcatc cgccactttc actatacggt gtggccagac    5640
catggagtcc cagaaaccac ccagtctctg atccagtttg tgagaactgt cagggactac    5700
atcaacagaa gcccgggtgc tgggcccact gtggtgcact gcagtgctgg tgtgggtagg    5760
actggaacct ttattgcatt ggaccgaatc ctccagcagt tagactccaa agactctgtg    5820
gacatttatg gagcagtgca cgacctaaga cttcacaggg ttcacatggt ccagactgag    5880
tgtcagtatg tctacctaca tcagtgtgta agagatgtcc tcagagcaag aaagctacgg    5940
agtgaacaag aaaaccccctt gtttccaatc tatgaaaatg tgaatccaga gtatcacaga    6000
gatccagtct attcaaggca tgagaatgt acctgaagag ctcctggata aaaattattc    6060
actgtgtgat ttgtttttaa aaacttgctt catgccctac agaggtgcca gctatttctg    6120
ttgatactat gtataattta ttaatctgga gaatgtttaa aattttatat aatttaaagg    6180
taacagatat tattgtacat agttgtattt tgtagtttct tctgtaaata tgtattttc     6240 ataatgttta atattaagct ttatataata ctattttcc acactaaagt gttcatgact    6300
tgttctacat aaaactaatt caacctgtaa a                                   6331

<210> SEQ ID NO 12
<211> LENGTH: 2275
<212> TYPE: DNA
<213> ORGANISM: Homo sapiens
<220> FEATURE:
<221> NAME/KEY: misc_feature
<222> LOCATION: (1)...(2275)
<223> OTHER INFORMATION: glucosidase beta, acid, beta-glucocerebrosidase
      (GBA), glucosylceramidase,
      beta-D-glycosyl-N-acylsphingosine glucohydrolase,
      cDNA
<220> FEATURE:
<221> NAME/KEY: modified_base
<222> LOCATION: (2005)...(2005)
<223> OTHER INFORMATION: n = g, a, c or t

<400> SEQUENCE: 12
gctaacctag tgcctatagc taaggcaggt acctgcatcc ttgttttgt ttagtggatc      60 ctctatcctt cagagactct ggaaccctg tggtcttctc ttcatctaat gaccctgagg     120
ggatggagtt ttcaagtcct tccagagagg aatgtcccaa gcctttgagt agggtaagca    180
tcatggctgg cagcctcaca ggtttgcttc tacttcaggc agtgtcgtgg catcaggtg     240 cccgcccctg catccctaaa agcttcggct acagctcggt ggtgtgtgtc tgcaatgcca    300
catactgtga ctcctttgac cccccgacct ttcctgccct tggtaccttc agccgctatg    360
agagtacacg cagtgggcga cggatggagc tgagtatggg gcccatccag gctaatcaca    420
cgggcacagg cctgctactg accctgcagc cagaacagaa gttccagaaa gtgaagggat    480
ttgggagggc catgacagat gctgctgctc tcaacatcct tgccctgtca cccctgccc     540 aaaatttgct acttaaatcg tacttctctg aagaaggaat cggatataac atcatccggg    600
tacccatggc cagctgtgac ttctccatcc gcacctacac ctatgcagac ccccctgatg    660
atttccagtt gcacaacttc agcctccag aggaagatac caagctcaag ataccctga    720 ttcaccgagc cctgcagttg gcccagcgtc ccgtttcact ccttgccagc ccctggacat    780
cacccacttg gctcaagacc aatgagcgg tgaatgggaa gggtcactc aagggacagc    840 ccggagacat ctaccaccag acctgggcca gatactttgt gaagttcctg gatgcctatg    900
```

-continued

```
ctgagcacaa gttacagttc tgggcagtga cagctgaaaa tgagccttct gctgggctgt    960
tgagtggata ccccttccag tgcctgggct tcacccctga acatcagcga gacttcattg   1020
cccgtgacct aggtcctacc ctcgccaaca gtactcacca caatgtccgc ctactcatgc   1080
tggatgacca acgcttgctg ctgccccact gggcaaaggt ggtactgaca gacccagaag   1140
cagctaaata tgttcatggc attgctgtac attggtacct ggactttctg gctccagcca   1200
aagccaccct aggggagaca caccgcctgt tccccaacac catgctcttt gcctcagagg   1260
cctgtgtggg ctccaagttc tgggagcaga gtgtgcggct aggctcctgg gatcgaggga   1320
tgcagtacag ccacagcatc atcacgaacc tcctgtacca tgtggtcggc tggaccgact   1380
ggaaccttgc cctgaacccc gaaggaggac ccaattgggt gcgtaacttt gtcgacagtc   1440
ccatcattgt agacatcacc aaggacacgt tttacaaaca gcccatgttc taccaccttg   1500
gccacttcag caagttcatt cctgagggct cccagagagt ggggctggtt gccagtcaga   1560
agaacgacct ggacgcagtg gcactgatgc atcccgatgg ctctgctgtt gtggtcgtgc   1620
taaaccgctc ctctaaggat gtgcctctta ccatcaagga tcctgctgtg ggcttcctgg   1680
agacaatctc acctggctac tccattcaca cctacctgtg gcatcgccag tgatggagca   1740
gatactcaag gaggcactgg gctcagcctg ggcattaaag ggacagagtc agctcacacg   1800
ctgtctgtga ctaaagaggg cacagcaggg ccagtgtgag cttacagcga cgtaagccca   1860
ggggcaatgg tttgggtgac tcactttccc ctctaggtgg tgcccagggc tggaggcccc   1920
tagaaaaaga tcagtaagcc ccagtgtccc cccagccccc atgcttatgt gaacatgcgc   1980
tgtgtgctgc ttgctttgga aactngcctg ggtccaggcc tagggtgagc tcactgtccg   2040
tacaaacaca agatcagggc tgagggtaag gaaaagaaga gactaggaaa gctgggccca   2100
aaactggaga ctgtttgtct ttcctagaga tgcagaactg ggcccgtgga gcagcagtgt   2160
cagcatcagg gcggaagcct taaagcagca gcgggtgtgc ccaggcaccc agatgattcc   2220
tatggcacca gccaggaaaa atggcagctc ttaaaggaga aaatgtttga gccca        2275
```

```

<210> SEQ ID NO 13
<211> LENGTH: 2323
<212> TYPE: DNA
<213> ORGANISM: Homo sapiens
<220> FEATURE:
<221> NAME/KEY: misc_feature
<222> LOCATION: (1)...(2323)
<223> OTHER INFORMATION: UDP-N-acetylglucosamine pyrophosphorylase 1
      (UAP1) (AgX, AGX1, SPAG2), cDNA

<400> SEQUENCE: 13
ctgtgctccc ggcgctgacg tgtctgggcg gtcggcttcc actccttcag gcgtcggcag     60
ccactagtcg tggcgagagg ggcggggtgg ccggggctgg cgctccactt ggcccccgct    120
cccggcccgc cccgccgccg cggcccccgg gatgagggta tatattcgga gcgagcgcgg    180
gacgccgatg agtggccgcg cggaaggagc tggagacggt cgtagctgcg gtcgcgccga    240
gaaaggttta caggtacata cattacaccc ctatttctac aaagcttggc tattagagca    300
ttatgaacat taatgacctc aaactcacgt tgtccaaagc tgggcaagag cacctactac    360
gtttctggaa tgagcttgaa gaagcccaac aggtagaact ttatgcagag ctccaggcca    420
tgaactttga ggagctgaac ttctttttcc aaaaggccat tgaaggtttt aaccagtctt    480
cttaccaaaa gaatgtggat gcacgaatgg aacctgtgcc tcgagaggta ttaggcagtg    540
ctacaaggga tcaagatcag ctccaggcct gggaaagtga aggacttttc cagatttctc    600
```

-continued

| | |
|---|---|
| agaataaagt agcagttctt cttctagctg gtgggcaggg gacaagactc ggcgttgcat | 660 |
| atcctaaggg gatgtatgat gttggtttgc catcccgtaa gacactttt cagattcaag | 720 |
| cagagcgtat cctgaagcta cagcaggttg ctgaaaaata ttatggcaac aaatgcatta | 780 |
| ttccatggta tataatgacc agtggcagaa caatggaatc tacaaaggag ttcttcacca | 840 |
| agcacaagta ctttggttta aaaaagaga atgtaatctt ttttcagcaa ggaatgctcc | 900 |
| ccgccatgag ttttgatggg aaaattattt tggaagagaa gaacaaagtt tctatggctc | 960 |
| cagatgggaa tggtggtctt tatcgggcac ttgcagccca gaatattgtg gaggatatgg | 1020 |
| agcaaagagg catttggagc attcatgtct attgtgttga acacatatta gtaaaagtgg | 1080 |
| cagacccacg gttcattgga ttttgcattc agaaggagc agactgtgga gcaaaggtgg | 1140 |
| tagagaaaac gaaccctaca gaaccagttg gagtggtttg ccgagtggat ggagtttacc | 1200 |
| aggtggtaga atatagtgag atttccctgg caacagctca aaaacgaagc tcagacggac | 1260 |
| gactgctgtt caatgcgggg aacattgcca accatttctt cactgtacca tttctgagag | 1320 |
| atgttgtcaa tgtttatgaa cctcagttgc agcaccatgt ggctcaaaag aagattcctt | 1380 |
| atgtggatac ccaaggacag ttaattaagc cagacaaacc caatgaata aagatggaaa | 1440 |
| aatttgtctt tgacatcttc cagtttgcaa agaagtttgt ggtatatgaa gtattgcgag | 1500 |
| aagatgagtt ttccccacta aagaatgctg atagtcagaa tgggaaagac aaccctacta | 1560 |
| ctgcaaggca tgctttgatg tcccttcatc attgctgggt cctcaatgca gggggccatt | 1620 |
| tcatagatga aaatggctct cgccttccag caattccccg cttgaaggat gccaatgatg | 1680 |
| taccaatcca atgtgaaatc tctcctctta tctcctatgc tggagaagga ttagaaagtt | 1740 |
| atgtggcaga taagaattc catgcaccctc taatcatcga tgagaatgga gttcatgagc | 1800 |
| tggtgaaaaa tggtatttga accagatacc aagttttgtt tgccacgata ggaatagctt | 1860 |
| ttatttttga tagaccaact gtgaacctac aagacgtctt ggacaactga agtttaaata | 1920 |
| tccacagggt tttatttgc ttgttgaact cttagagcta ttgcaaactt cccaagatcc | 1980 |
| agatgactga atttcagata gcattttta gattcccaac tcattgaagg tcttatttat | 2040 |
| ataatttttt ccaagccaag gagaccattg gccatccagg aaatttcgta cagctgaaat | 2100 |
| ataggcagga tgttcaacat cagtttactt gcagctggaa gcatttgttt ttgaagttgt | 2160 |
| acatagtaat aatatgtcat tgtacatgtt gaaaggtttc tatggtacta aaagtttgtt | 2220 |
| ttattttatc aaacattaag cttttttaag aaaataattg ggcagtgaaa taaatgtatc | 2280 |
| ttcttgtctc tggaaaaaaa aaaaaaaaaa aaaaaaaaa aaa | 2323 |

<210> SEQ ID NO 14
<211> LENGTH: 2408
<212> TYPE: DNA
<213> ORGANISM: Homo sapiens
<220> FEATURE:
<221> NAME/KEY: misc_feature
<222> LOCATION: (1)...(2408)
<223> OTHER INFORMATION: mitochondrial ribosomal protein L30 (MRPL30), transcript variant 1, isoform a (RPML28, MGC3314, MRP-L28, FLJ44438, MGC24095), cDNA

<400> SEQUENCE: 14

| | |
|---|---|
| gccggaacaa aaatgcctca gtttggaggt cgcgctcact gcgacggcag gctttgagtg | 60 |
| tagcacttgg tagttcttcc tctgctctgc ttcccttcgg aggaaaattt caggctgaag | 120 |
| gtttagcggg tgccgcctct aaagagagca atcactacac ttatggctgg gattttgcgc | 180 |
| ttagtagttc aatggccccc aggcagacta cagactgtga caaaaggtgt ggagtctctt | 240 |

```
atttgtacag attggattcg tcacaaattc accagatcaa gaattccaga aaaagtgttt    300
caggcctcac ctgaagatca tgaaaaatac ggtggggatc cacagaaccc tcataaactg    360
catattgtta ccagaataaa aagtacaaga agacgtccat attgggaaaa agatataata    420
aagatgcttg gattagaaaa agcacatacc cctcaagttc acaagaatat cccttcagtg    480
aatgcaaaat tgaaagtagt taagcatttg ataagaatca agcccttgaa gttgccacaa    540
ggacttccag cagaggagaa catgtctaac acgtgcctca aaagcactgg ggagttagta    600
gtgcagtggc atctgaaacc tgtggagcag aaagcacatg agtcctaatg ccccagcagc    660
ttccgattgg aaaatgcaaa ttgttttat ttaaagatgg tgagaaagtg ttttcattaa    720
aatatgtttt caaaccatt tcaggccgg cacggtggc tcacctgtaa tcccagcact    780
tgggaggcc aaggcgggca gatcacctga ggtcaagagt tcgagaccag cctgaccaac    840
atggagaaac ccccatctct actgaaaata cagaattagc caggcatggt ggcacatgcc    900
tgtaacccag ctactcggga ggctgaagca ggagaatcac ttgaacccgg gaggcagagg    960
ttgcagtgag ctgagatggt gccactgtac tccagcctgg gtgataggat gagactccat    1020
ctcaggggaa aaaaaaaaa tttttttttc actgactaaa cctgctgcag ctctcttttta   1080
ctacagactt ggagatttta gtttaatttg gtttaattct ctgtcctttc cctttcactg    1140
tttcactcca aaacatgtaa gaatggcaat gtttgaacat ctgcgtttgg gtctactgcc    1200
accttagcaa gcctcattaa ccattttata aaaattgcgt tagtattgtt gttgttgttt    1260
ttgagacagg gtcttgctct gtcacccaag ctggaataca gtggcatgat ttcagttcac    1320
tgcagcctcg acctcccagg ctcaagtgat cctcccacct cagcctccag agtagctagg    1380
actacaggca gtgtgccacc acatccagct aatttttta agttttttca tagagacagg    1440
gactcactat gttgtccaag ctggtctcaa actcctgggt tcaagccatc ctcccacctc    1500
agcctcccaa aatgctggga ttacaggcat gagccactgt acccagccaa aattgttttc    1560
tttttaagt gaattcaaca atttctgtga gtggctcttt gcatgaacac tgtgcaaggt    1620
gttggagaaa tccaaagctg accaaaacat ggtccccacc ttttggagct tacagtctgt    1680
tctggggaac agagattcag ccaaagtcaa gaaacactgg atgccagcta gattatctgt    1740
tctgtgcttt ggtgtctata agtacatatg tggatatggg ttcattttat ccctaaactt    1800
agtaccaaac cagcatttaa tatctaatta taaatctaat ttggcctaaa ctttattatt    1860
gcacactgcc tgaacaaaac ctatttgtct ctatgtaaat tttttcctca tggaacaagg    1920
gtgtgaaatg aaaatatttt aggatttatt caaaaacaga ctattctgtt ttcagcttca    1980
gaattgttct ttgaatccta aggaacctct gtcaacagtt gaggttgctg ttgaaaagaa    2040
agaagaagga ggcggaaatc tctcagggag aattatttcc tttctttct atttagata    2100
cctgaggggg tggggagaag taagaattgt aagggaggtt cagtagtggg gaattctgtg    2160
acagctgatt gaagatgatg atgaagaacc tctgcattct agttacccctt tgcttccctt    2220
cacctcttgt aaaatttggc ttggcaacaa tgacattgtc atgcttattg tcccaatatc    2280
catcctgtcg tagatcttaa tgttttgat cgttgcgtta aagtggaagt gccacccaca    2340
gtgaaaccag atcccattaa taataagct aaaggcgaa aaaaaaaaa aaaaaaaaa       2400
aaaaaaaa                                                             2408
```

<210> SEQ ID NO 15
<211> LENGTH: 649
<212> TYPE: DNA

```
<213> ORGANISM: Homo sapiens
<220> FEATURE:
<221> NAME/KEY: misc_feature
<222> LOCATION: (1)...(649)
<223> OTHER INFORMATION: mitochondrial ribosomal protein L30 (MRPL30),
      transcript variant 2, isoform b (RPML28, MGC3314,
      MRP-L28, FLJ44438, MGC24095), cDNA

<400> SEQUENCE: 15
gccggaacaa aaatgcctca gtttggaggt cgcgctcact gcgacggcag gctttgagtg      60
tagcacttgg tagttcttcc tctgctctgc ttcccttcgg aggaaaattt caggctgaag     120
gtttagcggg tgccgcctct aaagagagca atcactacac ttatggctgg gattttgcgc     180
ttagtagttc aatggccccc aggcagacta cagactgtga caaaaggtgt ggagtctctt     240
atttgtacag attggattcg tcacaaattc accagatcaa gaattccaga aaaagtgttt     300
caggcctcac ctgaagatca tgaaaaatac ggtggggatc cacagaaccc tcataaactg     360
catattgtta ccagaataaa aagtacaaga agacgtccat attgggaaaa agatataata     420
aagatgcttg gattagaaaa agcacatacc cctcaagttc acagaatat cccttcagtg      480 aatgcaaaat tgaaagtagt taagcatttg ataaggtttg ttgtttcttc tcagctcttt     540
ttaaaatgta ttgcctagtg taattctaaa tgcattttc tttttttcgtt aatgttctga     600 aaaaaacttt ttaaaaaact aaaaaaaaaa aaaaaaaaa aaaaaaaa                   649

<210> SEQ ID NO 16
<211> LENGTH: 1975
<212> TYPE: DNA
<213> ORGANISM: Homo sapiens
<220> FEATURE:
<221> NAME/KEY: misc_feature
<222> LOCATION: (1)...(1975)
<223> OTHER INFORMATION: chaperonin containing T-complex protein 1
      (TCP-1) (t-complex-1 ring complex, polypeptide 5), subunit
      3 (gamma subunit) (CCT3), HSP60, clone
      DKFZp667A196, cDNA

<400> SEQUENCE: 16
agcgttttct gggcttctgt ctggttctct ctctccagaa ggttctgccg gttcccccag      60
ctctgggtac ccggctctgc atcgcgtcgc catgatgggc catcgtccag tgctcgtgct     120
cagccagaac acaaagcgtg aatccggaag aaaagttcaa tctggaaaca tcaatgctgc     180
caagactatt gcagatatca tccgaacatg tttgggaccc aagtccatga tgaagatgct     240
tttggaccca atgggaggca ttgtgatgac caatgatggc aatgccattc ttcgagagat     300
tcaagtccag catccagcgg ccaagtccat gatcgaaatt agccggaccc aggatgaaga     360
ggttggagat gggaccacat cagtaattat tcttgcaggg aaatgctgt ctgtagctga      420 gcacttcctg gagcagcaga tgcacccaac agtggtgatc agtgcttacc gcaaggcatt     480
ggatgatatg atcagcaccc taaagaaaat aagtatccca gtcgacatca gtgacagtga     540
tatgatgctg aacatcatca cagctctat tactaccaaa gccatcagtc ggtggtcatc     600
tttggcttgc aacattgccc tggatgctgt caagatggta cagtttgagg agaatggtcg     660
gaaagagatt gacataaaaa aatatgcaag agtggaaaag ataccggag gcatcattga      720 agactcctgt gtcttgcgtg gagtcatgat taacaaggat gtgacccatc cacgtatgcg     780
gcgctatatc aagaaccctc gcattgtgct gctggattct tctctggaat acaagaaagg     840
agaaagccag actgacattg agattacacg agaggaggac ttcacccgaa ttctccagat     900
ggaggaagag tacatccagc agctctgtga ggacattatc caactgaagc ccgatgtggt     960
```

| | |
|---|---|
| catcactgaa aagggcatct cagatttagc tcagcactac cttatgcggg ccaatatcac | 1020 |
| agccatccgc agagtccgga agacagacaa taatcgcatt gctagagcct gtggggcccg | 1080 |
| gatagtcagc cgaccagagg aactgagaga agatgatgtt ggaacaggag caggcctgtt | 1140 |
| ggaaatcaag aaaattggag atgaatactt tactttcatc actgactgca aagaccccaa | 1200 |
| ggcctgcacc attctcctcc gggggctag caaagagatt ctctcggaag tagaacgcaa | 1260 |
| cctccaggat gccatgcaag tgtgtcgcaa tgttctcctg gaccctcagc tggtgccagg | 1320 |
| gggtggggcc tccgagatgg ctgtggccca tgccttgaca gaaaaatcca aggccatgac | 1380 |
| tggtgtggaa caatggccat acagggctgt tgcccaggcc ctagaggtca ttcctcgtac | 1440 |
| cctgatccag aactgtgggg ccagcaccat ccgtctactt acctcccttc gggccaagca | 1500 |
| cacccaggag aactgtgaga cctggggtgt aaatggtgag acgggtactt tggtggacat | 1560 |
| gaaggaactg ggcatatggg agccattggc tgtgaagctg cagacttata agacagcagt | 1620 |
| ggagacggca gttctgctac tgcgaattga tgacatcgtt tcaggccaca aaagaaagg | 1680 |
| cgatgaccag agccggcaag gcggggctcc tgatgctggc caggagtgag tgctaggcaa | 1740 |
| ggctacttca atgcacagaa ccagcagagt ctccccttt cctgagccag agtgccagga | 1800 |
| acactgtgga cgtctttgtt cagaagggat caggttgggg ggcagccccc agtcccttc | 1860 |
| tgtcccagct cagttttcca aaagacactg acatgtaatt cttctctatt gtaaggtttc | 1920 |
| catttagttt gcttccgatg attaaatcta agtcattcaa aaaaaaaaaa aaaaa | 1975 |

<210> SEQ ID NO 17
<211> LENGTH: 1965
<212> TYPE: DNA
<213> ORGANISM: Homo sapiens
<220> FEATURE:
<221> NAME/KEY: misc_feature
<222> LOCATION: (1)...(1965)
<223> OTHER INFORMATION: chaperonin containing T-complex protein 1
      (TCP-1) (t-complex-1 ring complex, polypeptide 5), subunit
      3 (gamma subunit) (CCT3), HSP60, cDNA

<400> SEQUENCE: 17

| | |
|---|---|
| gtctggttct ctctctccag aaggttctgc cggttccccc agctctgggt acccggctct | 60 |
| gcatcgcgtc gccatgatgg gccatcgtcc agtgctcgtg ctcagccaga acacaaagcg | 120 |
| tgaatccgga agaaaagttc aatctggaaa catcaatgct gccaagacta ttgcagatat | 180 |
| catccgaaca tgtttgggac ccaagtccat gatgaagatg cttttggacc caatgggagg | 240 |
| cattgtgatg accaatgatg gcaatgccat tcttcgagag attcaagtcc agcatccagc | 300 |
| ggccaagtcc atgatcgaaa ttagccggac ccaggatgaa gaggttggag atgggaccac | 360 |
| atcagtaatt attcttgcag gggaaatgct gtctgtagct gagcacttcc tggagcagca | 420 |
| gatgcaccca acagtggtga tcagtgctta ccgcaaggca ttggatgata tgatcagcac | 480 |
| cctaaagaaa ataagtatcc cagtcgacat cagtgacagt gatatgatgc tgaacatcat | 540 |
| caacagctct attactacca aagccatcag tcggtggtca tctttggctt gcaacattgc | 600 |
| cctggatgct gtcaagatgg tacagtttga ggagaatggt cggaaagaga ttgacataaa | 660 |
| aaaatatgca agagtggaaa agatacctgg aggcatcatt gaagactcct gtgtcttgcg | 720 |
| tggagtcatg attaacaagg atgtgaccca tccacgtatg cggcgctata tcaagaaccc | 780 |
| tcgcattgtg ctgctggatt cttctctgga atacaagaaa ggagaaagcc agactgacat | 840 |
| tgagattaca cgagaggagg acttcacccg aattctccag atggaggaag agtacatcca | 900 |
| gcagctctgt gaggacatta tccaactgaa gcccgatgtg gtcatcactg aaaagggcat | 960 |

-continued

```
ctcagattta gctcagcact accttatgcg ggccaatatc acagccatcc gcagagtccg      1020
gaagacagac aataatcgca ttgctagagc ctgtggggcc cggatagtca gccgaccaga      1080
ggaactgaga gaagatgatg ttggaacagg agcaggcctg ttggaaatca agaaaattgg      1140
agatgaatac tttactttca tcactgactg caaagacccc aaggcctgca ccattctcct      1200
ccggggggct agcaaagaga ttctctcgga agtagaacgc aacctccagg atgccatgca      1260
agtgtgtcgc aatgttctcc tggaccctca gctggtgcca gggggtgggg cctccgagat      1320
ggctgtggcc catgccttga cagaaaaatc caaggccatg actggtgtgg aacaatggcc      1380
atacagggct gttgcccagg ccctagaggt cattcctcgt accctgatcc agaactgtgg      1440
ggccagcacc atccgtctac ttacctccct tcgggccaag cacacccagg agaactgtga      1500 gacctgggt gtaaatggtg agacgggtac tttggtggac atgaaggaac tgggcatatg       1560
ggagccattg gctgtgaagc tgcagactta aagacagca gtggagacgg cagttctgct       1620
actgcgaatt gatgacatcg tttcaggcca caaaagaaa ggcgatgacc agagccggca       1680
aggcggggct cctgatgctg gccaggagtg agtgctaggc aaggctactt caatgcacag      1740
aaccagcaga gtctcccctt ttcctgagcc agagtgccag gaacactgtg gacgtctttg      1800
ttcagaaggg atcaggttgg ggggcagccc ccagtcccctt tctgtcccag ctcagttttc     1860
caaaagacac tgacatgtaa ttcttctcta ttgtaaggtt tccatttagt ttgcttccga      1920
tgattaaatc taagtcattt gaaaaaaaaa aaaaaaaaaa aaaaa                      1965
```

<210> SEQ ID NO 18
<211> LENGTH: 2276
<212> TYPE: DNA
<213> ORGANISM: Homo sapiens
<220> FEATURE:
<221> NAME/KEY: misc_feature
<222> LOCATION: (1)...(2276)
<223> OTHER INFORMATION: heat shock 70kDa protein 8, transcript variant 1, isoform 1 (HSPA8), lipopolysaccharide-associated protein 1 (LAP1), (HSC70, HSC54, HSC71, HSP71, HSP73, NIP71, HSPA10, MGC29929, bone marrow protein BM034, N-myristoyltransferase inhibitor protein 71), cDNA

<400> SEQUENCE: 18

```
ctcattgaac tcgcctgcag ctcttgggtt ttttgtggct tccttcgtta ttggagccag       60
gcctacaccc cagcaaccat gtccaaggga cctgcagttg gtattgatct tggcaccacc      120
tactcttgtg tgggtgtttt ccagcacgga aaagtcgaga taattgccaa tgatcaggga      180
aaccgaacca ctccaagcta tgtcgccttt acggacactg aacggttgat cggtgatgcc      240
gcaaagaatc aagttgcaat gaaccccacc aacacagttt ttgatgccaa acgtctgatt      300
ggacgcagat ttgatgatgc tgttgtccag tctgatatga acattggcc ctttatggtg       360 gtgaatgatg ctggcaggcc caaggtccaa gtagaataca agggagagac caaaagcttc      420
tatccagagg aggtgtcttc tatggttctg acaaagatga aggaaattgc agaagcctac      480
cttgggaaga ctgttaccaa tgctgtggtc acagtgccag cttactttaa tgactctcag      540
cgtcaggcta ccaaagatgc tggaactatt gctggtctca atgtacttag aattattaat      600
gagccaactg ctgctgctat tgcttacggc ttagacaaaa aggttggagc agaaagaaac      660
gtgctcatct ttgacctggg aggtggcact tttgatgtgt caatcctcac tattgaggat      720
ggaatctttg aggtcaagtc tacagctgga gacacccact gggtggaga agattttgac       780 aaccgaatgg tcaaccattt tattgctgag tttaagcgca agcataagaa ggacatcagt      840
```

```
gagaacaaga gagctgtaag acgcctccgt actgcttgtg aacgtgctaa gcgtaccctc    900
tcttccagca cccaggccag tattgagatc gattctctct atgaaggaat cgacttctat    960
acctccatta cccgtgcccg atttgaagaa ctgaatgctg acctgttccg tggcaccctg   1020
gacccagtag agaaagccct tcgagatgcc aaactagaca agtcacagat tcatgatatt   1080
gtcctggttg gtggttctac tcgtatcccc aagattcaga agcttctcca agacttcttc   1140
aatggaaaag aactgaataa gagcatcaac cctgatgaag ctgttgctta tggtgcagct   1200
gtccaggcag ccatcttgtc tggagacaag tctgagaatg ttcaagattt gctgctcttg   1260
gatgtcactc ctctttccct tggtattgaa actgctggtg gagtcatgac tgtcctcatc   1320
aagcgtaata ccaccattcc taccaagcag acacagacct tcactaccta ttctgacaac   1380
cagcctggtg tgcttattca ggtttatgaa ggcgagcgtg ccatgacaaa ggataacaac   1440
ctgcttggca gtttgaact cacaggcata cctcctgcac cccgaggtgt tcctcagatt   1500
gaagtcactt ttgacattga tgccaatggt atactcaatg tctctgctgt ggacaagagt   1560
acgggaaaag agaacaagat tactatcact aatgacaagg ccgtttgag caaggaagac   1620 attgaacgta tggtccagga agctgagaag tacaaagctg aagatgagaa gcagagggac   1680
aaggtgtcat ccaagaattc acttgagtcc tatgccttca acatgaaagc aactgttgaa   1740
gatgagaaac ttcaaggcaa gattaacgat gaggacaaac agaagattct ggacaagtgt   1800
aatgaaatta tcaactggct tgataagaat cagactgctg agaaggaaga atttgaacat   1860
caacagaaag agctggagaa agtttgcaac cccatcatca ccaagctgta ccagagtgca   1920
ggaggcatgc caggaggaat gcctggggga tttcctggtg gtggagctcc tccctctggt   1980
ggtgcttcct cagggcccac cattgaagag gttgattaag ccaaccaagt gtagatgtag   2040
cattgttcca cacatttaaa acatttgaag gacctaaatt cgtagcaaat tctgtggcag   2100
ttttaaaaag ttaagctgct atagtaagtt actgggcatt ctcaatactt gaatatggaa   2160
catatgcaca ggggaaggaa ataacattgc actttataaa cactgtattg taagtggaaa   2220
atgcaatgtc ttaaataaaa ctatttaaaa ttggcaccat aaaaaaaaaa aaaaaa       2276
```

<210> SEQ ID NO 19
<211> LENGTH: 3410
<212> TYPE: DNA
<213> ORGANISM: Homo sapiens
<220> FEATURE:
<221> NAME/KEY: misc_feature
<222> LOCATION: (1)...(3410)
<223> OTHER INFORMATION: solute carrier family 16, member 1 (SLC16A1), monocarboxylic acid transporter 1 (MCT1) cDNA

<400> SEQUENCE: 19

```
tgcgacgtga ctggctagct gcgtgggtac tggaacaagc aaacgaggca gcgagcgaag     60
gacgggagcc ggaccctggg ccccgtggaa ctccagcctg cgccaccacg tcacgcacac    120
gctcggcgct gcgatccgcg catataacga tatttggatt tgacctgcat tttggaattt    180
atctacactt aaaatgccac cagcagttgg aggtccagtt ggatacaccc cccagatgg    240 aggctggggc tgggcagtgg taattggagc tttcatttcc atcggcttct cttatgcatt    300
tcccaaatca attactgtct tcttcaaaga gattgaaggt atattccatg ccaccaccag    360
cgaagtgtca tggatatcct ccataatgtt ggctgtcatg tatggtggag tcctatcag    420 cagtatcctg gtgaataaat atggaagtcg tatagtcatg attgttggtg gctgcttgtc    480
aggctgtggc ttgattgcag cttctttctg taacaccgta cagcaactat acgtctgtat    540
```

```
tggagtcatt ggaggtcttg ggcttgcctt caacttgaat ccagctctga ccatgattgg      600
caagtatttc tacaagaggc gaccattggc caacggactg gccatggcag gcagccctgt      660
gttcctctgt actctggccc ccctcaatca ggttttcttc ggtatctttg gatggagagg      720
aagctttcta attcttgggg gcttgctact aaactgctgt gttgctggag ccctcatgcg      780
accaatcggg cccaagccaa ccaaggcagg gaaagataag tctaaagcat cccttgagaa      840
agctggaaaa tctggtgtga aaaagatctg catgatgca aatacagatc ttattggaag       900
acaccctaaa caagagaaac gatcagtctt ccaaacaatt aatcagttcc tggacttaac      960
cctattcacc cacagaggct ttttgctata cctctctgga aatgtgatca tgttttttgg     1020
actctttgca cctttggtgt ttcttagtag ttatgggaag agtcagcatt attctagtga     1080
gaagtctgcc ttccttcttt ccattctggc ttttgttgac atggtagccc gaccatctat     1140
gggacttgta gccaacacaa agccaataag acctcgaatt cagtatttct ttgcggcttc     1200
cgttgttgca aatggagtgt gtcatatgct agcacccttta tccactacct atgttggatt    1260
ctgtgtctat gcgggattct ttggatttgc cttcgggtgg ctcagctccg tattgtttga     1320
aacattgatg gaccttgttg acccccagag gttctccagc gctgtgggat tggtgaccat     1380
tgtggaatgc tgtcctgtcc tcctggggcc accactttta ggtcggctca atgacatgta     1440
tggagactac aaatacacat actgggcatg tggcgtcgtc ctaattattt caggtatcta     1500
tctcttcatt ggcatgggca tcaattatcg acttttggca aaagaacaga agcaaacga      1560 gcagaaaaag gaaagtaaag aggaagagac cagtatagat gttgctggga agccaaatga     1620
agttaccaaa gcagcagaat ctccggacca gaaagacaca gaaggagggc ccaaggagga     1680
ggaaagtcca gtctgaatcc atggggctga agggtaaatt gagcagttca tgacccagga     1740
tatctgaaaa tattctactg gcctgtaatc taccagtggt gctcaatgca aatagtagac     1800
atttgtgtgg aaatcatacc agttgttcat tgatgggatt tttgtttgac tccttaccaa     1860
tagcctgaat ttgaggaggg aatgattggt agcaaaggat gggggaaaga agtaggttct     1920
gttttgtttt gttttaatct tagcttttaa tagtgtcata aagattataa tatgtgcctt     1980 aagtttagt ctttagaact ctagagagcc ttaacttctt aaaccatttt tgctgaattc      2040
atctatttcg agtgttgtgt taaaaggaaa aataacaact aacttgtttg aggcaaatct     2100
aaaatttaaa attaatcttg cttcattgtt acatgtaata tatttcagac attttcactg     2160
gaagatttat gaacagaaat attggttgaa agttagagat tttacaaaat gctgacaaaa     2220
atattttcct agcatcagta gatttctggc atatgtttct gctagctata tatttaggaa     2280
attcaaagca taaaacttg gcaacatctt ggctgttcta gacacagtgt acttgtcaac      2340
ccctctcagg taccttttct tgggatgctt attagaagcc aagtaaagtg cttaaggttt     2400
gttttcatta aattagctat ttctgctccc ctgttcaaag atgcattttg agtgtttata     2460
gatcactgcc cttttgaaa tcacctggta ttattttct tactgaaaaa gttagtatta      2520
aaatctacag aactacatat ttgtgcctcc ttggtaaata caacacatct aattaaatgt     2580
agacagatat ttcaaacatc agctgaattc acttaagttt ttccaaaacc tcagttaaac     2640
tgtgaagcta ttggaatttt ttttcctgg aattttccc ctttgattca cagtggtccc       2700
atttatatct gcttctagct tagtgctatg tgtgagatat gtgtgtgttt ggtgtttttg     2760 ttttttgtt tttttttttt taaggtttgc aaattaaaaa gggccagaaa atttggcac       2820 caggcaaacg aataaagata ggattgggaa agaagttgct aagtgtgctt agttttaata    2880
agtaattcct tctcttttt cagagaaggc cttacagaaa attgttgtgc ttagaattgc      2940
```

| | | |
|---|---|---|
| tggatgcatt | tttaccctcc acacaaacct aaaaattttg tgaccccttt cacttacctg | 3000 |
| aaaagtagag | aaatggattc agtataagga taaggaggga aggtggacca gaatgaaaac | 3060 |
| tgtaaatatt | tttttaacct aatatcactt aaatcgaggc agaaagatat agacattcaa | 3120 |
| tgaattatat | tcaatgcatt taaaatacca ctgtaattga cagagtaaaa gtatagatac | 3180 |
| aaaaccttgt | gtaagaggct gacttttcca aataaacatt ttttaagaaa acatttcttc | 3240 |
| tcccaaatgt | ctattttctt gaggaaaata ttgctgtgtc ttcattttca ttaccaggtt | 3300 |
| tcattttggg | ccttgctaaa ttgattgaat taaatcctcc agcttttgaa ccttgaaaaa | 3360 |
| aaaaaaaaaa | aaaaaaaaaa aaaaaaaaa agaaaaaaaa aaaaaaaag | 3410 |

<210> SEQ ID NO 20
<211> LENGTH: 5595
<212> TYPE: DNA
<213> ORGANISM: Homo sapiens
<220> FEATURE:
<221> NAME/KEY: misc_feature
<222> LOCATION: (1)...(5595)
<223> OTHER INFORMATION: SH2 of Abl, FLJ00138 protein cDNA

<400> SEQUENCE: 20

| | | |
|---|---|---|
| ggacaagggc | aagattatta agcagcaaga gacggtcatc attttagaag actatgctga | 60 |
| cccttatgat | gccaaacgga caaagggtca aagggatgca gagagagtcg gagagaacga | 120 |
| cggttacatg | gaaccatatg atgcacagca aatgataaca gaaattagac gacggggttc | 180 |
| caaagatccc | ctggtgaagg ctctccagct gcttgacagt ccctgtgaac ccgcagacgg | 240 |
| tggcctgaaa | tcagagacct tggccaaaag acggagttcc aaggacctcc tggggaagcc | 300 |
| gccacagcta | tacgacactc cctacgagcc tgcagaaggg gggcccaggg cagaggggaa | 360 |
| ggcgcggccc | ccagacagcc ggctgcccga gaacgacgag aggcccgcgg cagagtacga | 420 |
| gcagccatgg | gagtggaaga aggagcagat cgtgcgggct ctgtcagtcc agtttgaagg | 480 |
| agctgagcga | ccttccttca gggaggagac agtgaggcag caccaccggc agaagagctg | 540 |
| gacccagaag | atcctgaagc cagccctctc ggaccacagt gagggagaga aagtggaccc | 600 |
| gggcctgccc | ctggagaagc agccctggta tcatggtgcc atcagccgtg ctgaggctga | 660 |
| gagtcgacta | cagccctgca aagaagctgg ttacctggtt cgaaatagtg agtcagggaa | 720 |
| cagcaggtac | tccattgccc taaagactag tcaaggatgt gtccacatca tagtggctca | 780 |
| gaccaaagac | aacaaataca cactgaatca gacaagcgct gtgtttgaca gcatccctga | 840 |
| agtggtacac | tattattcca atgaaaagtt gcctttcaaa ggggcagaac acatgacttt | 900 |
| actctaccca | gtgcacagca agcttcacta agattcagcc actgcaagcc ctgggcctct | 960 |
| ggcaccttca | agggcatcat cagcgcacaa ccagcatctc agaggacaag gctggactag | 1020 |
| caactgctag | aaaatgggag tcttccttga aaagtcagag agtgatttgt tttgttttgt | 1080 |
| ttgagacgaa | gtctcgctgt gttgcccagg ctggagtgca atggcgcagt cttggctcac | 1140 |
| tgcaacatct | gactcctggg ttcaagcagt tcttccccat cagcctccca agtaggtggg | 1200 |
| actataggtt | cgcaccacca ctcccagcta attttttttt tgtattttta gtagagatgg | 1260 |
| ggtttcgccg | tcttcgtcag gctggtctca aactcctgac ctcaaatgat ccacccacct | 1320 |
| cagtctcccc | gagtgcctgg attacaggca tgagccactg cacccggcca agtctttggt | 1380 |
| cttaaagtga | ttccatgaca cttgttttgt ggcctgtccc ttgttccctt gcaagtagtt | 1440 |
| ctacaataag | aaatcatgat ttagctgttg cctccagctc tggggtaggg tgttctttt | 1500 |

```
atggtgtgac cctcaggaag gttaagtcag gagttcagga gcatcagagt tctctagaaa    1560
tgtgcctact tgttacctgg aatacctggt ctctaaacaa accagcaaaa aatccacgtg    1620
gcttttccac atgatggtgc agactggaag aggatgttat attggactcg ttattgggga    1680
aatgaatgag cgggagaaaa tgtgaatgac gggcaagaag gtggtctttc tccctcagaa    1740
gtcctaattc agctctggag ttcatggaaa tccgcaactt cagagtgtgg cctaaggatt    1800
attttgttgg tcagcctttc caagaaagtg tgtgttctct caatctctgt ggattttctc    1860
attttttagc aaatcagtga gataagcata aataggaagg aagataccc aggtttaaga    1920 atcaccaata tcattaggca ttggcatcat tattagaatt ctgaattata aataaaagg    1980 tacaacaaaa atttcatttc tgaattttaa aattctggaa atttgcaaag ctccacaact    2040 gttttttac tgaattaatt acatagaact tcgatgtctt ttgtttcatc atcattgggc    2100
attttagttg ctatggaata attttaatt tttgtctcta aaattagatt tgctttgtag    2160 taaattttt aaaaatgcaa ccctaagatc tgattatatg aactgggtct ctaaagccta    2220
caaagattct ctcgttctgt accaagcaga ctgccttgta ctatacagaa gtgtttgaaa    2280
agacctagag gttttctctt aaataccatt acttaagatt catagtatta ggatctttat    2340
gatttatcat gagcttatat caccagttta tttactgtga aaaaaccat gggaatggca    2400 tactgtgaga agagtactat ggtgaatggc tccagaatta aaattcagca gatgtgtctg    2460
tattctgggg ttggtcattt gggtctcaaa actgccccat atgcaaatgt actgactgtc    2520
atcaatgaaa agttaacctt tgtagcttat aaatacacac aaaatgttga tttggttaat    2580
tttttaggaa agtataccctt tgtagttact agttacattt gactgtaaga tttagaggtt    2640
agtaaatttt tgcttcttta ttcagataag atctcagcca aaaggttgtg tgatctttga    2700
ttttaaaaat ttaagaggaa cttttcctca ctggaacaca atgatttat taataaagaa    2760 tgtaggctgg gtgcggtggc tcatgcacgt aatcccaaca atttgggagg ctgaggcagg    2820
cagatcacgt gaggtcagga gtttgggacc ggcctggcca acatggtgaa accctgtctc    2880
tagtaaaaat acaaaaatta gctgggcacg gtggcgggca cctgtagttc cagctgcttg    2940
ggaggctgag gcacgagaat cacttgagcc caggaggtgg aggttgcagt gagccaagat    3000
tgtgtcactg cactccatcc tgggtgacaa gagcgaaact ccatctcaaa aaaaaaaaa    3060 aaaaaaagc ctggcctggt ggtggatgcc tgtggttcca gctattcggg aggctgaggt    3120
aggtggatca cctctgctca ggtcaaggct gcagcgagcc atgatcgcac cattgcactc    3180
cagcctgagt gacagagtga gaccctgtct caacaagcaa gcaaacaaaa aaccaaaagg    3240
aatgtttttt tcagatactg atagaatgtt ttcagtgtgt attggttcat ttactatatc    3300
tttagtgtaa gattttaaaa ggtttttttca gcatccattc aacaaatatt tattatcttt    3360
atacaaatta ttcattgtgt taaacttatt tttagtttaa cattctagaa atgaaacgtt    3420
tttacttaac cttattctac aaagggaata cagcagttat tctaatttta ataaatgcta    3480
aaagctttat acaattttc tttgtgcact aaatgatttt tggcccatac ccagcaactg    3540
tgatgaatgt ataatgaaat aacatcttga aaacaggcca gatacattaa gtatttattg    3600
agcttctgtc atatgcccag tattatgctt cttctatact gtttctctgt gacaagtcat    3660
actatattct ttatagaatt aaaagtagag gagaggcaga gtttacatat tgtccagttg    3720
ctttacagtt gtacaggagg ttataagaag aaatatagta aattagtggg aagtcagagg    3780
tgggggcgtt agtgagctat tttcttcttg aggttgtgac acaagctgac aaaagccagg    3840
gagttcacag ctgtgtggtg gcacaaagtt ccatatgttc taaaaacaat taggcccagc    3900
```

| | |
|---|---|
| agggtgtccc taatggcttc cttgttaaac ctccatggcc agctgatctg aagctctgtg | 3960 |
| acatgttctc tgagctctga atgctctggc tttttgtcat tttgtcttga acaagtatt | 4020 |
| ttcctgtagt cctcattcct tcgagttatt ccatctccca ggatattctc tggtgagaag | 4080 |
| aatgtctttc agtgaatttg cccttgaatt tagcatccat agagctgtgt cagtgttctt | 4140 |
| cttgatcaca ccttctttaa aaaaaatact tgcttgcgat gactggacaa gttcagttgg | 4200 |
| ttagtttcag gcctataaga agagagagta aaggaccttg ctatttactt tgataccata | 4260 |
| gttgtatctc aggatggcct gcaaaccact ggccttgtgt gtatttaagc taggaataaa | 4320 |
| ataatggaga agtgttaata tgtatacaaa aaggtaaata ttgatatatc tactctctgt | 4380 |
| tgggggcaga agtgtcattt taagttattc aaagcacttt cttaagcatt ttagaaagcc | 4440 |
| tttattcttt gctgttggaa gtctccgtac tttgcagaat tggtatttgt gtactagcct | 4500 |
| ctgccgcagg atggggaggt gggcaggtag ctgatagggg cagccaggag ttttttgaggc | 4560 |
| aggtggtggg aaattgtcct aatttgttaa ttggattatg taactctgtt actagtctgt | 4620 |
| tattggctgt tgttactgga tgcatcttga tattcagaag aataactgtg aggcattctt | 4680 |
| cagttgcggg ttaagtgggg ttagtttctg ttctgtcaga tgccctttt tcagtcaaag | 4740 |
| gttagcccct tgtttctccc tccttccagg gtttagggag tgcagtgatg tcgatttcat | 4800 |
| ttcccttccc cgcaccccctt gacactcagc aggattgcac tgaaaccctt cacaatctct | 4860 |
| cgttcactag ttgtctccta tttttccata actagcacta gtttggcctt atgacctggt | 4920 |
| tagaatcact cttctgtatt ctcatttcca atttttgtgc cccactaacg tggactagag | 4980 |
| aaacttggcc tgctgtgcag tgggccttct gttcaactta ccctccaccg ctgaccctgt | 5040 |
| gtgaagagag atggtgcgtt actgccatct aatgggaaaa gagaaaactg cagttgggaa | 5100 |
| aagcagctgt gcatttaagg gtagggcttt ctgaaggatt tctgatacag tccagaaaag | 5160 |
| ggaaaatgat gacacagcag ttgccatctt gaaaaatgcc ctttcctgcg gaagggtgt | 5220 |
| tttgaagtct aatacaacta tcatcacaag gtccctggac taaggctgga tcgtgtaatt | 5280 |
| tagaatctca aattgtattt taattaatat gctggcaaca gaatcattga aacaggcatc | 5340 |
| tcattttgtc aagttcttag ccgttcagtt tgtcaggggc tttaatattt tagatatcaa | 5400 |
| ctaatacata gtttcaactt ttaaaaatgt ttgaagattg tatgtaatat aggtgcctat | 5460 |
| ctatagtgcc ttagtaattt aaatcagaaa tattttataa aacttctggt tgttttgcag | 5520 |
| tagccaatat aggcttcatg ccctcctgaa gatagtttcc tctgaaatgt aactttaaat | 5580 |
| aaacattatt ccaag | 5595 |

<210> SEQ ID NO 21
<211> LENGTH: 5595
<212> TYPE: DNA
<213> ORGANISM: Homo sapiens
<220> FEATURE:
<221> NAME/KEY: misc_feature
<222> LOCATION: (1)...(5595)
<223> OTHER INFORMATION: SH2 or Abl, hypothetical protein LOC126669,
      similar to FLJ00138 protein, Src homology 2 (SH2)
      domains

<400> SEQUENCE: 21

| | |
|---|---|
| ggacaagggc aagattatta agcagcaaga gacggtcatc attttagaag actatgctga | 60 |
| cccttatgat gccaaacgga caaagggtca aagggatgca gagagagtcg gagagaacga | 120 |
| cggttacatg gaaccatatg atgcacagca atgataaca gaaattagac gacggggttc | 180 |

-continued

```
caaagatccc ctggtgaagg ctctccagct gcttgacagt ccctgtgaac ccgcagacgg      240
tggcctgaaa tcagagacct tggccaaaag acggagttcc aaggacctcc tggggaagcc      300
gccacagcta tacgacactc cctacgagcc tgcagaaggg gggcccaggg cagaggggaa      360
ggcgcggccc ccagacagcc ggctgcccga gaacgacgag aggcccgcgg cagagtacga      420
gcagccatgg gagtggaaga aggagcagat cgtgcgggct ctgtcagtcc agtttgaagg      480
agctgagcga ccttccttca gggaggagac agtgaggcag caccaccggc agaagagctg      540
gacccagaag atcctgaagc cagccctctc ggaccacagt gagggagaga aagtggaccc      600
gggcctgccc ctggagaagc agccctggta tcatggtgcc atcagccgtg ctgaggctga      660
gagtcgacta cagccctgca agaagctgg ttacctggtt cgaaatagtg agtcagggaa       720
cagcaggtac tccattgccc taaagactag tcaaggatgt gtccacatca tagtggctca      780
gaccaaagac aacaaataca cactgaatca gacaagcgct gtgtttgaca gcatccctga      840
agtggtacac tattattcca atgaaaagtt gcctttcaaa ggggcagaac acatgacttt      900
actctaccca gtgcacagca agcttcacta agattcagcc actgcaagcc ctgggcctct      960
ggcaccttca agggcatcat cagcgcacaa ccagcatctc agaggacaag gctggactag      1020
caactgctag aaaatgggag tcttccttga aaagtcagag agtgatttgt tttgttttgt      1080
ttgagacgaa gtctcgctgt gttgcccagg ctggagtgca atggcgcaat cttggctcac      1140
tgcaacatct gactcctggg ttcaagcagt tcttccccat cagcctccca gtaggtggg       1200 actataggtt cgcaccacca ctcccagcta attttttttt ttgtattttt agtagagatg      1260
gggtttcgcc gtcttcgtca ggctggtctc aaactcctga cctcaaatga tccacccacc      1320
tcagtctccc cgagtgcctg gattacaggc atgagccact gcaccggcc aagtctttgg       1380 tcttaaagtg attccatgac actttgtttg tggcctgtcc cttgtttcct tgctaagtag      1440
ttctacaata agaaatcatg atttagctgt tgcctccagc tctggggtag ggtgttcttt      1500
ttatggtgtg accctcagga aggttaagtc aggagttcag gagcatcaga gttctctaga      1560
aatgtgccta cttgttacct ggaatacctg gtctctaaac aaaccaacaa aaaatccacg      1620
tggcttttcc acatgatggt gcagactgga agaggatgtt atattggact cgttattggg      1680
gaaatgaatg agcgggagaa aatgtgaatg acgggcaaga aggtggtctt tctccctcag      1740
aagtcctaat tcagctctgg agttcatgga aatccgcaac ttcagagtgt ggcctaagga      1800
ttattttgtt ggtcagcctt tccaagaaag tgtgtgttct ctcaatctct gtggattttc      1860
tcatttttta gcaaatcagt gagataagca taaataggaa ggaagatacc ccaggtttaa      1920
gaatcaccaa tatcattagg cattggcatc attattagaa ttctgaatta tagaataaaa      1980
ggtacaacaa aaatttcatt tctgaatttt aaaattctgg aaatttgcaa agctccacaa      2040 ctgtttttt actgaattaa ttacatagaa cttcgatgtc ttttgtttca tcatcattgg       2100
gcattttagt tgctatggaa taatttttaa ttttgtctc taaaattaga tttgctttgt       2160
agtaaatttt ttaaaaatgc aaccctaaga tctgattata tgaactgggt ctctaaagcc      2220
tacaaagatt ctctcgttct gtaccaagca gactgccttg tactatacag aagtgtttga      2280
aaagacctag aggttttctc ttaaatacca ttacttaaga ttcatagtat taggatcttt      2340
atgatttatc atgagcttat atcaccagtt tatttactgt gaaaaaaacc atgggaatgg      2400
catactgtga aagagtact atggtgaatg gctccagaat taaaattcag cagatgtgtc       2460
tgtattctgg ggttggtcat ttgggtctca aaactgcccc atatgcaaat gtactgactg      2520
tcatcaatga aaagttaacc tttgtagctt ataaatacac acaaaatgtt gatttggtta      2580
```

```
attttttagg aaagtatacc tttgtagtta ctagttacat ttgactgtaa gatttagagg    2640
ttagtaaatt tttgcttctt tattcagata agatctcagc caaaaggttg tgtgatcttt    2700 gatttttaaaa atttaagagg aactttcct cactggaaca caatgatttt attaataaag    2760
aatgtaggct gggtgcggtg gctcatgcac gtaatcccaa caatttggga ggctgaggca    2820
ggcagatcac gtgaggtcag gagtttgaga ccagcctggc caacatggtg aaaccctgtc    2880
tgtagtaaaa atacaaaaat tagctgggca cggtggcggg cacctgtagt tccagctgct    2940
tgggaggctg aggcacgaga atcacttgag cccaggagg ggaggttgca gtgagccaag    3000
attatgtcac tgcactccat cctgggtgac aagagcgaaa ctccatctca aaaaaaaaa    3060 aaaaaaaaag cctggcctgg tggtggatgc ctgtggttcc agctattcgg gaggctgagg    3120
taggtggatc acctctgctc aggtcaaggc tgcagcgagc catgatcgca ccattgcact    3180
ccagcctgag tgacagagtg agaccctgtc tcaacaagca agcaaacaaa aaaccaaaag    3240
gaatgttttt ttcagatact gatagaatgt tttcagtgtg tattggttca tttactatat    3300
ctttagtgta agattttaaa aggttttttc agcatccatt caacaaatat ttattatctt    3360
tatacaaatt attcattgtg ttaaacttat ttttagttta acattctaga aatgaaacgt    3420
ttttacttaa ccttattcta caagggaat acagcagtta ttctaatttt aataaatgct    3480
aaaagcttta tacaattttt ctttgtgcac taaatgattt ttggcccata cccagcaact    3540
gtgatgaatg tataatgaaa taacatcttg aaaacaggcc agatacatta agtatttatt    3600
gagcttctgt catatgccca gtattatgct tcttctatac tgtttctctg tgacaagtca    3660
tactatattc tttatagaat taaaagtaga ggagaggcag agtttacata ttgtccagtt    3720
gctttacagt tgtacaggag gttataagaa gaaatatagt aaattagtgg gaagtcagag    3780
gtgggggcgt tagtgagcta ttttcttctt gaggttgtga cacaagctga caaaagccag    3840
ggagttcaca gctgtgtggt ggcacaaagt tccatatgtt ctaaaaacaa ttaggcccag    3900
cagggtgtcc ctaatggctt ccttgttaaa cctccatggc cagctgatct gaagctctgt    3960
gacatgttct ctgagctctg aatgctctgg cttttttgtca ttttgtcttg agacaagtat    4020
tttcctgtag tcctcattcc ttcgagttat tccatctccc aggatattct ctggtgagaa    4080
gaatgtcttt cagtgaattt gccttgaatt tagcatccat agagctgtgt cagtgttctt    4140
cttgatcaca ccttctttaa aaaaatact tgcttgcgat gactggacaa gttcagttgg    4200
ttagtttcag gcctataaga agagagagta aaggaccttg ctatttactt tgataccata    4260
gttgtatctc aggatggcct gcaaaccact ggccttgtgt gtatttaagc taggaataaa    4320
ataatggaga agtgttaata tgtatacaaa aaggtaaata ttgatatatc tactctctgt    4380
tgggggcaga agtgtcattt taagttattc aaagcacttt cttaagcatt ttagaaagcc    4440
tttattcttt gctgttggaa gtctccgtac tttgcagaat tggtatttgt gtactagcct    4500
ctgccgcagg atggggaggt gggcaggtag ctgataggg cagccaggag ttttgaggc    4560 aggtggtggg aaattgtcct aatttgttaa ttggattatg taactctgtt actagtctgt    4620
tattggctgt tgttactgga tgcatcttga tattcagaag aataactgtg aggcattctt    4680
cagttgcggg ttaagtgggg ttagtttctg ttctgtcaga tgcccttttt cagtcaaagg    4740 ttagccccctt gtttctccct ccttccaggg tttagggagt gcagtgatgt cgatttcatt    4800
tcccttcccc gcacccccttg acactcagca ggattgcact gaaacccttc acagatctct    4860
cgttcactag ttgtctccta ttttccata actagcacta gtttggcctt atgacctggt    4920
```

```
tagaatcact cttctgtatt ctcatttcca attttttgtgc cccactaacg tggactagag    4980
aaacttggcc tgctgtgcag tgggccttct gttcaactta ccctccaccg ctgaccctgt    5040
gtgaagagag atggtgcgtt actgccatct aatgggaaaa gagaaaactg cagttgggaa    5100
aagcagctgt gcatttaagg gtagggcttt ctgaaggatt tctgatacag tccagaaaag    5160
ggaaaatgat gacacagcag ttgccatctt gaaaaatgcc ctttcctgcg gaaagggtgt    5220
tttgaagtct aatacaacta tcatcacaag gtccctggac taaggctgga tcgtgtaatt    5280
tagaatctca aattgtattt taattaatat gctggcaaca gaatcattga aacaggcgtc    5340
tcattttgtc aagttcttag ccgttcagtt tgtcaggggc tttaatattt tagatatcaa    5400
ctaatacata gtttcaactt ttaaaaatgt ttgaagattg tatgtaatat aggtgtctat    5460
ctatagtgcc ttagtaattt aaatcagaaa tattttataa aacttctggt tgttttgcag    5520
tagccaatat aggcttcatg ccctcctgaa gatagtttcc tctgaaatgt aactttaaat    5580
aaacattatt ccaag                                                      5595
```

<210> SEQ ID NO 22
<211> LENGTH: 8015
<212> TYPE: DNA
<213> ORGANISM: Homo sapiens
<220> FEATURE:
<221> NAME/KEY: misc_feature
<222> LOCATION: (1)...(8015)
<223> OTHER INFORMATION: ubiquitin specific protease 37 (USP37),
      ubiquitin hydrolase, KIAA1594 protein, cDNA

<400> SEQUENCE: 22

```
catcagccgc tctccctgac taggggtagc tagcggcctc cctcctttgg gttctgtatc      60
cctacttcca ttaccctcgg ctcctcccac tcctcggggg ctccgtgctt tccgcgggtc     120
tgtccggggg ctccggaccc tcggcgcagc tgagttgatg gcttccggag aactggcata     180
gccgcagaat atgagtagtg tcccaagaag agtgctttgc ctttggcaca aggatcagaa     240
taaaggtgaa ttgctattac atagggtttt tcggtaaaag tcactgaaaa ttatttgcca     300
tacagtaacc agagacctcc aactaggggc ccccaaactg tatcctgcct gtagccagaa     360 gcaatttta aagaaaatat gtctcctctg aagatacatg gtcctatcag aattcgaagt     420
atgcagactg ggattacaaa gtggaaagaa ggatcctttg aaattgtaga aaagagaat     480 aaagtcagcc tagtagttca ctacaatact ggaggaattc caaggatatt tcagctaagt     540
cataacatta aaaatgtggt gcttcgaccc agtggagcga acaaagccg cctaatgtta     600 actctgcaag ataacagctt cttgtctatt gacaaagtac caagtaagga tgcagaggaa     660
atgaggttgt ttctagatgc agtccatcaa aacagacttc ctgcagccat gaaaccgtct     720
caggggtctg gtagttttgg agccattctg ggcagcagga cctcacagaa ggaaaccagc     780
aggcagcttt cttactcaga caatcaggct tctgcaaaaa gaggaagttt ggaaactaaa     840
gatgatattc catttcgaaa agttcttggt aatccgggta gaggatcgat taagactgta     900
gcaggaagtg gaatagctcg gacgattcct tctttgacat ctacttcaac acctcttaga     960
tcagggttgc tagaaaatcg tactgaaaag aggaaaagaa tgatatcaac tggctcagaa    1020
ttgaatgaag attaccctaa ggaaaatgat tcatcatcga caacaaggc catgacagat    1080 ccctccagaa agtatttaac cagcagtaga gaaaagcagc tgagtttgaa acagtcagaa    1140
gagaatagga catcagggct tttacccttta cagtcatcat ccttttatgg tagcagagct    1200
ggatccaagg aacactcttc tggtggcact aacttagaca ggactaatgt ttcaagccag    1260
```

```
actccctctg ccaaaagaag tttgggattt cttcctcagc cagttcctct ttctgttaaa    1320
aaactgaggt gtaaccagga ttacactggc tggaataaac caagagtgcc cctttcctct    1380
caccaacagc agcaactgca gggcttctcc aagttgggaa atacctgcta tatgaatgct    1440
attctacaat ctctatttc actccagtca tttgcaaatg acttgcttaa acaaggtatc     1500
ccatggaaga aaattccact caatgcactt atcagacgct tgcacactt gcttgttaaa     1560 aaagatatct gtaattcaga gaccaaaaag gatttactca agaaggttaa aaatgccatt    1620
tcagctacag cagagagatt ctctggttat atgcagaatg atgctcatga attttttaagt  1680 cagtgtttgg accagctgaa agaagatatg gaaaaattaa ataaaacttg gaagactgaa    1740 cctgttctg gagaagaaaa ttccagagat atttcagcta ccagagcata cacttgccct     1800
gttattacta atttggagtt tgaggttcag cactccatca tttgtaaagc atgtggggag    1860
attatcccca aagagaaca gtttaatgac ctctctattg accttcctcg taggaaaaaa     1920
ccactccctc ctcgttcaat tcaagattct cttgatcttt tctttagggc cgaagaactg    1980
gagtattctt gtgagaagtg tggtgggaag tgtgctcttg tcaggcacaa atttaacagg    2040
cttcctaggg tcctcattct ccatttgaaa cgatatagct tcaatgtggc tctctcgctt    2100
aacaataaga ttgggcagca agtcatcatt ccaagatacc tgaccctgtc atctcattgc    2160
actgaaaata caaaaccacc ttttaccctt ggttggagtg cacatatggc aatttctaga    2220
ccattgaaag cctctcaaat ggtgaattcc tgcatcacca gcccttctac accttcaaag    2280
aaattcacct tcaaatccaa gagctccttg gctttatgcc ttgattcaga cagtgaggat    2340
gagctaaaac gttctgtggc cctcagccag agactttgtg aaatgttagg caacgaacag    2400
cagcaggaag acctggaaaa agattcaaaa ttatgcccaa tagagcctga caagtctgaa    2460
ttggaaaact caggatttga cagaatgagc gaagaagagc ttctagcagc tgtcttggag    2520
ataagtaaga gagatgcttc accatctctg agtcatgaag atgatgatga gccaactagc    2580
agcccagata ccggatttgc agaagatgat attcaagaaa tgccagaaaa tccagacact    2640
atggaaactg agaagcccaa acaatcaca gagctggatc ctgccagttt tactgagata     2700
actaaagact gtgatgagaa taaagaaaac aaaactccag aaggatctca gggagaagtt    2760
gattggctcc agcagtatga tatggagcgt gaaagggaag agcaagagct tcagcaggca    2820
ctggctcaga gccttcaaga gcaagaggct tgggaacaga agaagatga tgacctcaaa     2880 agagctaccg agttaagtct tcaagagttt aacaactcct tgtggatgc attgggttct     2940 gatgaggact ctgaaatga ggatgttttt gatatggagt acacagaagc tgaagctgag     3000
gaactgaaaa gaaatgctga gacaggaaat ctgcctcatt cgtaccggct catcagtgtt    3060
gtcagtcaca ttggtagcac ttcttcttca gatcattaca ttagtgatgt atatgacatt    3120
aagaagcaag cgtggtttac ttacaatgac ctggaggtat caaaaatcca agaggctgcc    3180
gtgcagagtg atcgagatcg gagtggctac atcttctttt atatgcacaa ggagatcttt    3240
gatgagctgc tggaaacaga aaagaactct cagtcactta gcacggaagt ggggaagact    3300
acccgtcagg cctcgtgagg aacaaactcc tgggttggca gcatgcactg catatttgtt    3360
actgctgccc acctcacctt tcctctgctg aaggagaatt tggaattcta cttgatgcgg    3420
gagcaacaaa cagctcaggg ccaaaccaaa agacaaaaat tggagtaacg tagaatgctc    3480
catgctattt tatggaaact ttggtctcac atccgtagct gattatcctc tttttctcct    3540
atgagtggca cttctttgt cttaggaata catgttgtaa atatatatct gtgtatgtgt     3600
gtatacacac acacagacac acacacacac acacgggatg aatggagcct taaagagtta   3660
```

```
ggatgagcca ccagaatatg cctgctcaaa attaatagca cagcagtttg gagaagaaat    3720
gaaggtgtca aagagtccat tcacctgaga aatgtgtgaa gacatactta tcagttggct    3780
tttagctttt atgttccttg agtagtttca ctcaagtctg taaccttttg tgttccttat    3840
tagtaaaatt cactggaaag ccagctcttc atgttacact aatgacagtt tgttctcttt    3900
gcaagagagg ggcattactg tcacctgact tgaggagctg ttttgttgtt gttgttgtct    3960
gcaaatttca tgaatttgtg atgtctttgc tgtttacatg cagtcccaag aaatggattg    4020
ttggtgcttt ggaatatgtt acagtcccac atttgatatt tcttatatac tttgttttct    4080
ctaaggagat ttcttcacac agtatgttca tcatatatca tcatcattat tatggtggta    4140
aagatagaat cttttttctt ttttgtcatt ctgccatgga gcagcattac cctaatggat    4200
tgcaaccaaa actttaaaca agtagaaaga taatatttct ccaattggga ctccccagca    4260
ggaatactta gggataagga agaatgctag catctctgtc tctcaaacat agggaggata    4320
agaagagtgt tcttctggta aagctaaaat tctggaccac tgaagctaaa agccctattg    4380
caagtatgaa attaagtact tgagctatag gacaaacctt gggcatttaa ccatttactg    4440
tctggctttg cccttaaaat agggttgcaa ttaaaatgtg attggcttag gtaatcccaa    4500
aaactaacaa ataacaaagg tgcataattt atttatctac tttttaggtg ctctgagttg    4560
aggcaaagta gagcggcaac attaagtgct atgctagtca cttagctgac gtaaccagct    4620
tggttaagca gcttatgaaa ccatataaag aattcttttg aggatggaat tctgtccaca    4680
aaataatttt gtgagcccag atatcattag gatcacacag agttaaatat agaaaaatga    4740
aaccatcatt atattctttc gtgttttttc ttttattata aacaagggga ttattcttta    4800
gttctcagag gtagggacaa aaccacatca ggttttcaga aggaaaaaac atttaaaaac    4860
ccaccatcac atgagagaat cacttgaacc caggaggcag aggttgcagt gagctgagat    4920
cgcatcattg cactgcagtc tgagtgacag agtgagactc catctcatta aaaaaaacga    4980
aaacaaaaac aaaaaaaaca caaaccatca tcacagaaga tgcaacatct tttctgaaag    5040
attgccttaa gagagctcca gtcctactct tggaacttgg atgtattcta atgtagtaaa    5100
ctattctaag ttttcattct ttgaattata aatggcctca gcagttttgc tcaactactg    5160
ataaatgctt tgcctcctac catctaccta tataccttat tgtaatgaat gttccaaaat    5220
ggtagagtgg tagaaaacgc cagagtagtt tagagcagag gaaatatttt gttttaaaac    5280
tagctttaaa gttttgtttc atttctacca ggagcctctt tggtttggtt tgattttgct    5340
tggaaataat tggttttctt ataaatgagt gaagcggtga taaaattctt tggctagtta    5400
ttaattcttt tacgtgtctt tgcatttgag aggcactgtt aaaaattatt gggaaagatt    5460
taaagtgcag gctgcaatta aaacatggag aaaagtagaa ataatgccat aagtctagat    5520
tgcctcatga agcagcctca tttgaattgc tttcatagct ttcatgtgtg tatggtttag    5580
aagtacactt acctcagaaa cctgatttga tcttcatgtc ttgggcagga gttgttgaaa    5640
ataggttatt ggaatatata agttatctca ctgctcatgt acttgcatgt ttgggactca    5700 aatttttactt gatgtctgtc cattcttgtg gccctatcag ccttctcctt cctttactcc    5760
tttaatctac ttcttgact accagtggag atttcagctg gactatgttg atggggtttg    5820
ttgttgtttt tgagctggct gtatatattt taaaattata aatagataat atattatttt    5880
ttgcacattg tgatcagttt gcccagaatt ggggatgggg cagttagcat gttggggcca    5940
ggaagggaca agttagataa ggactgagtg cttccgttgc aggcagtttg cacaatacct    6000
```

```
aattaacctt cctattgaaa ataccaaatg tgtggttaca ttactttaaa tgacattgaa    6060
ttggaacttg atggcaatta gttctagata caacctttg atctttgttg gaattttaag    6120
ggaaaaatga actaaacttc atatttgttg attttaatca cctaatagta ctgaaggttg    6180
gaaagttgca tgtggctgga tgctgttaat ttctttaata gccatgacta aatttaagc    6240 ctatgagaag atagactgtt tcgtagggat atatttacat gtgtgtgcac actcatgagt    6300
tttgtctcag caggatagaa taagcaaatc catgaactgg tcttctatta atactttgat    6360
tctaaaaatt atttgtttac ttgctatggt ctgttcattc tgggcctaac cctaaaggct    6420
caataacaaa tacaacaaat gtaaatatgt ttacatttta agacatatgc agtggttctt    6480
acagatcagt taattaactc cagaaagcaa atgttagact acacatttat ttttctcctt    6540
gatcaagtgt aaaattctga aacagaggct ttaaaattta aaacctcagc aaaataatcc    6600
atgaatttac tgattcttct gtatcgtgtg tagttaccat tatgtaacta tacacacata    6660
cagctatgga tatagttgta taatgaaaat tatctgcaaa cacctaaatt aaagagaaaa    6720
aaaagtagtt tgtaaactca tttgtgatct actgaaaaga ggttatatta aagcaaatta    6780
aaatattttc cttctctgtc ctctgaaatg actgcagtag atactcttag ttatcccatt    6840
tagggtggtt ggagggcctt tttaatttaa ttgaccccc gaggtggtct tttgttttaa    6900 acaggggca acagctggat ctccaagtac atatggattt tgtatatata ggagatttt    6960 agaaaaatca acaacctaac accagattca agtcacataa agtgttcca ataaaatgga    7020 tggatgtctt tttcctcccc attttgcttt atactgagta atgcactctt gcaagtgtat    7080
acaaaaacta aatagacttc tgccctccaa catctttta ttgcattact tcaaaatcct    7140
aattttgtct ctactgatat gtcttattaa catctgaaaa aatatatatt tttattgga    7200 aaattctaat ttgttaggcc ttgaaagttt tgtgacaatt attttgctgt gtttaaccac    7260
aatcattcac cttatggcat gctttgatta ctagacttca ggcagtctca ttcattgtat    7320
catacttaca cacaattagt aagttgtctc catgtgtgct atatgtctga ggtgtatgga    7380
gtttttattt aaaaagtgtg ccagtctgaa tataagcatt tgattttgta acattggact    7440
tttcttaaaa gtacagaggt tcaaagtata ggtatgtcca ttggcataag aatagagtgg    7500
gtgagggtct ggaccaggtt ccaggttggt ccagtcagat gccagaacaa agaagaacag    7560
tcaactaaac tggtctactt caaaaatagt gggcctgtgt gaagaatgag accacatgtg    7620
ggtgtgcaca cctcttgtcc ccaggtttcc ctcccttga gcttttcttt ccctccctaa    7680
cttctctggc ctattgtcat tgttgtttct ttaaacttaa ggagagaaaa acaaaaatga    7740
gattcctaca ctttgcctaa ttgagccact accaggtttt ctggcagctg tggccacatt    7800
atttgtgaga tgatttttt tctttatgtt cagagtgact tttgattctg attctttatg    7860
ttttgtatgg agcggcactt ttatctgtgt tttagcagaa ctgttcctct gtatccttta    7920
cggttttcct ttgtttttgt ttccttttta aattatgcat agagtttttt tgtgtgtatg    7980
aaattaaagc ctttattaac cttcaaaaaa aaaaa                              8015
```

<210> SEQ ID NO 23  
<211> LENGTH: 4450  
<212> TYPE: DNA  
<213> ORGANISM: Homo sapiens  
<220> FEATURE:  
<221> NAME/KEY: misc_feature  
<222> LOCATION: (1)...(4450)  
<223> OTHER INFORMATION: ubiquitin specific protease 37 (USP37),
      ubiquitin hydrolase, KIAA1594 protein partial CDS

<400> SEQUENCE: 23

```
caaggatatt tcagctaagt cataacatta aaaatgtggt gcttcgaccc agtggagcga        60
aacaaagccg cctaatgtta actctgcaag ataacagctt cttgtctatt gacaaagtac       120
caagtaagga tgcagaggaa atgaggttgt ttctagatgc agtccatcaa aacagacttc       180
ctgcagccat gaaaccgtct caggggtctg gtagttttgg agccattctg gcagcagga        240
cctcacagaa ggaaaccagc aggcagcttt cttactcaga caatcaggct tctgcaaaaa       300
gaggaagttt ggaaactaaa gatgatattc catttcgaaa agttcttggt aatccgggta       360
gaggatcgat taagactgta gcaggaagtg gaatagctcg gacgattcct tctttgacat       420
ctacttcaac acctcttaga tcagggttgc tagaaaatcg tactgaaaag aggaaaagaa       480
tgatatcaac tggctcagaa ttgaatgaag attaccctaa ggaaaatgat tcatcatcga       540
acaacaaggc catgacagat ccctccagaa agtatttaac cagcagtaga gaaaagcagc       600
tgagtttgaa acagtcagaa gagaatagga catcagggct tttacctttta cagtcatcat       660
cctttatgg tagcagagct ggatccaagg aacactcttc tggtggcact aacttagaca       720
ggactaatgt ttcaagccag actccctctg ccaaaagaag tttgggattt cttcctcagc       780
cagttcctct ttctgttaaa aaactgaggt gtaaccagga ttacactggc tggaataaac       840
caagagtgcc cctttcctct caccaacagc agcaactgca gggcttctcc aatttgggaa       900
atacctgcta tatgaatgct attctacaat ctctattttc actccagtca tttgcaaatg       960
acttgcttaa acaaggtatc ccatggaaga aaattccact caatgcactt atcagacgct      1020
ttgcacactt gcttgttaaa aaagatatct gtaattcaga gaccaaaaag gatttactca      1080
agaaggttaa aaatgccatt tcagctacag cagagagatt ctctggttat atgcagaatg      1140
atgctcatga atttttaagt cagtgtttgg accagctgaa agaagatatg gaaaaattaa      1200
ataaaacttg gaagactgaa cctgtttctg gagaagaaaa ttcaccagat atttcagcta      1260
ccagagcata cacttgccct gttattacta atttggagtt tgaggttcag cactccatca      1320
tttgtaaagc atgtgagag attatcccca aaagagaaca gtttaatgac ctctctattg      1380
accttcctcg taggaaaaaa ccactccctc ctcgttcaat tcaagattct cttgatcttt      1440
tctttagggc cgaagaactg gagtattctt gtgagaagtg tggtgggaag tgtgctcttg      1500
tcaggcacaa atttaacagg cttcctaggg tcctcattct ccatttgaaa cgatatagct      1560
tcaatgtggc tctctcgctt aacaataaga ttgggcagca agtcatcatt ccaagatacc      1620
tgaccctgtc atctcattgc actgaaaata caaaaccacc ttttacccctt ggttggagtg      1680
cacatatggc aatttctaga ccattgaaag cctctcaaat ggtgaattcc tgcatcacca      1740
gcccttctac accttcaaag aaattcaccct tcaaatccaa gagctccttg gctttatgcc      1800
ttgattcaga cagtgaggat gagctaaaac gttctgtggc cctcagccag agactttgtg      1860
aaatgttagg caacgaacag cagcaggaag acctggaaaa agattcaaaa ttatgcccaa      1920
tagagcctga caagtctgaa ttggaaaact caggatttga cagaatgagc gaagaagagc      1980
ttctagcagc tgtcttggag ataagtaaga gagatgcttc accatctctg agtcatgaag      2040
atgatgataa gccaactagc agcccagata ccggatttgc agaagatgat attcaagaaa      2100
tgccagaaaa tccagacact atggaaactg agaagcccaa aacaatcaca gagctggatc      2160
ctgccagttt tactgagata actaaagact gtgatgagaa taagaaaac aaaactccag      2220
aaggatctca gggagaagtt gattggctcc agcagtatga tatggagcgt gaaagggaag      2280
agcaagagct tcagcaggca ctggctcaga gccttcaaga gcaagaggct tgggaacaga      2340
```

```
aagaagatga tgacctcaaa agagctaccg agttaagtct tcaagagttt aacaactcct    2400
ttgtggatgc attgggttct gatgaggact ctggaaatga ggatgttttt gatatggagt    2460
acacagaagc tgaagctgag gaactgaaaa gaaatgctga gacaggaaat ctgcctcatt    2520
cgtaccggct catcagtgtt gtcagtcaca ttggtagcac ttcttcttca ggtcattaca    2580
ttagtgatgt atatgacatt aagaagcaag cgtggtttac ttacaatgac ctggaggtat    2640
caaaaatcca agaggctgcc gtgcagagtg atcgagatcg gagtggctac atcttctttt    2700
atatgcacaa ggagatcttt gatgagctgc tggaaacaga aaagaactct cagtcactta    2760
gcacggaagt ggggaagact acccgtcagg cctcgtgagg aacaaactcc tgggttggca    2820
gcatgcactg catatttgtt actgctgccc acctcacctt tcctctgctg aaggagaatt    2880
tggaattcta cttgatgcgg gagcaacaaa cagctcaggg ccaaaccaaa agacaaaaat    2940
tggagtaacg tagaatgctc catgctattt tatggaaact ttggtctcac atccgtagct    3000
gattatcctc tttttctcct atgagtggca cttcttttgt cttaggaata catgttgtaa    3060
atatatatct gtgtatgtgt gtatacacac acacagacac acacacacac acacgggatg    3120
aatggagcct taaagagtta ggatgagcca ccagaatatg cctgctcaaa attaatagca    3180
cagcagtttg gagaagaaat gaaggtgtca aagagtccat tcacctgaga aatgtgtgaa    3240
gacatactta tcagttggct tttagctttt atgttccttg agtagtttca ctcaagtctg    3300 taacctttg tgtttcctta ttagtaaaat tcactggaaa gccagctctt catgttacac    3360
taatgacagt ttgttctctt tgcaagagag gggcattact gtcacctgac ttgaggagct    3420
gttttgttgt tgttgttgtc tgcaaatttc atgaatttgt gatgtctttg ctgtttacat    3480
gcagtcccaa gaaatggatt gttggtgctt tggaatatgt tacagtccca catttgatat    3540
ttcttatata ctttgttttc tctaaggaga tttcttcaca cagtatgttc atcatatatc    3600
atcatcatta ttatggtggt aaagatagaa tctttttttct tttttgtcat tctgccatgg    3660
agcagcatta ccctaatgga ttgcaaccaa aactttaaac aagtagaaag ataatatttc    3720
tccaattggg actccccagc aggaatactt agggataagg aagaatgcta gcatctctgt    3780
ctctcaaaca tagggaggat aagaagagtg ttcttctggt aaagctaaaa ttctggacca    3840
ctgaagctaa aagcccctatt gcaagtatga aattaagtac ttgagctata ggacaaacct    3900
tgggcattta accatttact gtctggcttt gcccttaaaa taggggttgca attaaaatgt    3960 gattggctta ggtaatccca aaaactaaca aataacaaag gtgcataatt tatttatcta    4020 cttttaggt gctctgagtt gaggcaaagt agagcggcaa cattaagtgc tatgctagtc    4080
acttagctga cgtaaccagc ttggttaagc agcttatgaa accatataaa gaattctttt    4140
gaggatggaa ttctgtccac aaaataattt tgtgagccca gatatcatta ggatcacaca    4200
gagttaaata tagaaaaatg aaaccatcat tatattcttt cgtgtttttt cttttattat    4260
aaacaagggg attattcttt agttctcaga ggtagggaca aaaccacatc aggttttcag    4320
aaggaaaaaa catttaaaaa cccaccatca catgagagaa tcacttgaac ccaggaggca    4380
gaggttgcag tgagctgaga tcgcatcatt gcactgcagt ctgagtgaca gagtgagact    4440
ccatctcatt                                                          4450
```

<210> SEQ ID NO 24
<211> LENGTH: 7
<212> TYPE: PRT
<213> ORGANISM: Artificial Sequence
<220> FEATURE:

<223> OTHER INFORMATION: ubiquitin hydrolase Cys box conserved catalytic
       residues

<400> SEQUENCE: 24

Gly Asn Thr Cys Tyr Met Asn
 1               5

<210> SEQ ID NO 25
<211> LENGTH: 10
<212> TYPE: PRT
<213> ORGANISM: Artificial Sequence
<220> FEATURE:
<223> OTHER INFORMATION: ubiquitin hydrolase His box conserved catalytic
       residues

<400> SEQUENCE: 25

His Ile Gly Ser Thr Ser Ser Ser Asp His
 1               5                  10

<210> SEQ ID NO 26
<211> LENGTH: 4
<212> TYPE: PRT
<213> ORGANISM: Artificial Sequence
<220> FEATURE:
<223> OTHER INFORMATION: DDX5 RNA helicase DEAD box protein conserved
       motif

<400> SEQUENCE: 26

Asp Glu Ala Asp
 1

<210> SEQ ID NO 27
<211> LENGTH: 200
<212> TYPE: PRT
<213> ORGANISM: Artificial Sequence
<220> FEATURE:
<223> OTHER INFORMATION: synthetic poly Gly flexible linker
<220> FEATURE:
<221> NAME/KEY: MOD_RES
<222> LOCATION: (6)...(200)
<223> OTHER INFORMATION: Gly at positions 6-200 may be present or absent

<400> SEQUENCE: 27

Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

```
Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly
            180                 185                 190

Gly Gly Gly Gly Gly Gly Gly Gly
        195                 200
```

MODULATORS OF ANGIOGENESIS

CROSS-REFERENCES TO RELATED APPLICATIONS

The present application claims the benefit of U.S. Ser. No. 60/536,310, filed Jan. 13, 2004, herein incorporated by reference in its entirety.

STATEMENT AS TO RIGHTS TO INVENTIONS MADE UNDER FEDERALLY SPONSORED RESEARCH AND DEVELOPMENT

Not applicable.

Field of the Invention

The present invention relates to regulation of angiogenesis. The invention further relates to methods for identifying and using agents, including small organic molecules, antibodies, peptides, cyclic peptides, nucleic acids, antisense nucleic acids, RNAi, and ribozymes, that modulate angiogenesis; as well as to the use of expression profiles and compositions in diagnosis and therapy of angiogenesis and cancer.

BACKGROUND OF THE INVENTION

The migration of activated endothelial cells through a vitronectin-rich provisional matrix is critical to the formation of new blood vessels during angiogenesis and is dependent on adhesion receptors containing alphav integrins (such as alphavbeta3 which binds to vitronectin). Peptide and antibody inhibitors of alphavbeta3 integrin inhibit tumor growth in vivo.

Angiogenesis is typically limited in a normal adult to the placenta, ovary, endometrium and sites of wound healing. However, angiogenesis, or its absence, plays an important role in the maintenance of a variety of pathological states. Some of these states are characterized by neovascularization, e.g., cancer and tumorigenesis, e.g., endometriosis, diabetic retinopathy, glaucoma, glomerulonephritis, and age related macular degeneration. Others, e.g., stroke, infertility, heart disease, e.g., restenosis, ulcers, and scleroderma, are diseases of angiogenic insufficiency. Therefore, there is a need to identify nucleic acids encoding proteins involved in the regulation of angiogenesis, to identify, e.g., modulators of angiogenesis, as well as new therapeutic and diagnostic applications.

SUMMARY OF THE INVENTION

Novel targets for anti-angiogenic therapy have been identified using a functional genetic screen based on vascular endothelial growth factor receptor 2 (VEGFR2) ligand binding triggered receptor internalization. Inhibition or activation of these targets (by small molecule inhibitors; protein, antibody and peptide therapeutics; RNAi; antisense; gene therapy etc.) have therapeutic value in modulating angiogenesis, e.g., breast, lung, colon, ovarian, liver, thyroid, stomach, bladder, and prostate cancer, basal cell carcinoma, melanoma, lymphomas, leukemias, e.g., myeloid leukemia (CML and AML), endometriosis, diabetic retinopathy, glaucoma, glomerulonephritis, age related macular degeneration, as well as, e.g., stroke, infertility, heart disease, e.g., restenosis, ulcers, and scleroderma.

The present invention therefore provides nucleic acids encoding proteins involved in modulation of (VEGFR2) ligand binding triggered receptor internalization and modulation of angiogenesis. The invention therefore provides methods of screening for compounds, e.g., small organic molecules, antibodies, nucleic acids, peptides, cyclic peptides, nucleic acids, antisense molecules, RNAi, and ribozymes, that are capable of modulating angiogenesis, e.g., either activating or inhibiting angiogenesis. Therapeutic and diagnostic methods and reagents are also provided.

In one aspect, the present invention provides a method for identifying a compound that modulates angiogenesis, the method comprising the steps of: (i) contacting the compound with an angiogenesis modulating polypeptide or fragment thereof, the polypeptide encoded by a nucleic acid that hybridizes under stringent conditions to a reference nucleic acid encoding the polypeptide, the polypeptide selected from the group consisting of ubiquitin hydrolase (USP37; SEQ ID NOS:22 and 23), calcium/calmodulin-dependent protein kinase β (CAMKK2; SEQ ID NO:5), methionine adenosyltransferase II α (Mat2A; SEQ ID NO:1), carnitine palmitoyltransferase II (CPT-2; SEQ ID NOS:2 and 3), DDX5 RNA helicase (SEQ ID NO:4), acetyl-coenzyme A acyltransferase (ACAA1; SEQ ID NO:6), glucosamine-6-phosphate isomerase (GNPI: SEQ ID NO:7), 24-dehydrocholesterol reductase (DHCR24; SEQ ID NO:8), selenoprotein T (SELT SEQ ID NOS:9 and 10), protein tyrosine phosphatase, receptor type, B (PTPRB; SEQ ID NO:11), glucosidase β acid (GBA; SEQ ID NO:12), UDP-N-acetylglucosamine pyrophosphorylase 1 (UAP1; SEQ ID NO:13), mitochondrial ribosomal protein L30 (MRPL30; SEQ ID NOS:14 and 15), chaperonin containing TCP1, subunit 3 γ (CCT3; SEQ ID NOS:16 and 17), HSPA8 (SEQ ID NO:18), solute carrier family 16 (monocarboxylic acid transporters), and member 1 (SLC16A1; SEQ ID NO:19), SH2 of Abl (SEQ ID NOS:20 and 21); and (ii) determining the functional effect of the compound upon the polypeptide.

In one embodiment, the functional effect is determined in vitro. In another embodiment, the functional effect is a physical effect. In another embodiment, the functional effect is determined by measuring ligand binding to the polypeptide. In another embodiment, the functional effect is a chemical effect.

In one embodiment, the polypeptide is expressed in a eukaryotic host cell. In another embodiment, the functional effect is a physical effect. In another embodiment, the functional effect is determined by measuring ligand binding to the polypeptide. In another embodiment, the functional effect is a chemical or phenotypic effect. In another embodiment, the polypeptide is expressed in a eukaryotic host cell, e.g., an endothelial cell. In another embodiment, the functional effect is determined by measuring VEGF-R2 surface expression, αvβ3 expression, haptotaxis, or tumor growth in vivo.

In one embodiment, modulation is inhibition of angiogenesis.

In one embodiment, the polypeptide is recombinant.

In one embodiment, the compound is an antibody, a peptide, an antisense molecule, a RNAi molecule, or a small organic molecule.

In another aspect, the present invention provides a method for identifying a compound that modulates angiogenesis, the method comprising the steps of (i) contacting the compound with an angiogenesis modulating polypeptide or fragment or inactive variant thereof, the polypeptide selected from the group consisting of ubiquitin hydrolase (USP37), calcium/calmodulin-dependent protein kinase β (CAMKK2), methionine adenosyltransferase II α (Mat2A), carnitine palmitoyltransferase II (CPT-2), DDX5 RNA helicase, acetyl-coenzyme A acyltransferase (ACAA1), glucosamine- 6-phosphate isomerase (GNPI), 24-dehydrocholesterol reductase (DHCR24), selenoprotein T (SELT), protein tyrosine phosphatase, receptor type, B (PTPRB), glucosidase β acid (GBA), UDP-N-acteylglucosamine pyrophosphorylase 1 (UAP1), mitochondrial ribosomal protein L30 (MRPL30), chaperonin containing TCP1, subunit 3 γ (CCT3), HSPA8, solute carrier family 16 (monocarboxylic acid transporters), and member 1 (SLC16A1), SH2 of Abl; (ii) determining the physical effect of the compound upon the polypeptide or fragment thereof or inactive variant thereof; and (iii) determining the chemical or phenotypic effect of the compound upon a cell comprising the polypeptide or fragment thereof or inactive variant thereof, thereby identifying a compound that modulates or angiogenesis.

In another aspect, the present invention provides a method of modulating angiogenesis in a subject, the method comprising the step of administering to the subject a therapeutically effective amount of a compound identified using the methods described herein.

In one embodiment, the subject is a human.

In one embodiment, the compound is an antibody, an antisense molecule, a peptide, or an RNAi molecule, or a small organic molecule.

In one embodiment, the compound inhibits angiogenesis.

BRIEF DESCRIPTION OF THE DRAWINGS

FIG. 9 summarizes USP-37 data.

FIG. 14 shows a CaMKK2 inhibitor STO-609.

FIG. 16 shows a summary of CaMKK2 data.

FIG. 18 shows STO-609 data.

FIG. 19 shows STO-609 data.

FIG. 20 summarizes STO-609 data.

DETAILED DESCRIPTION OF THE INVENTION

I. Introduction

Figure 1:
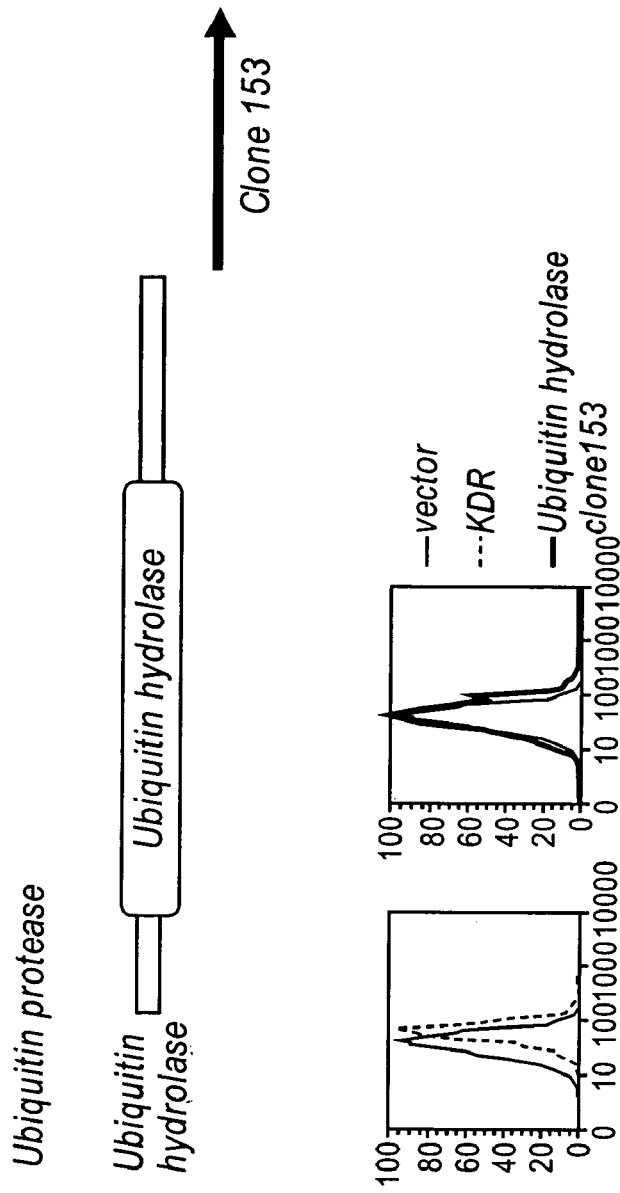
FIG. 1 shows a clone encoding USP-37 isolated in a VEGFR-2 upregulation assay.
Figure 2:
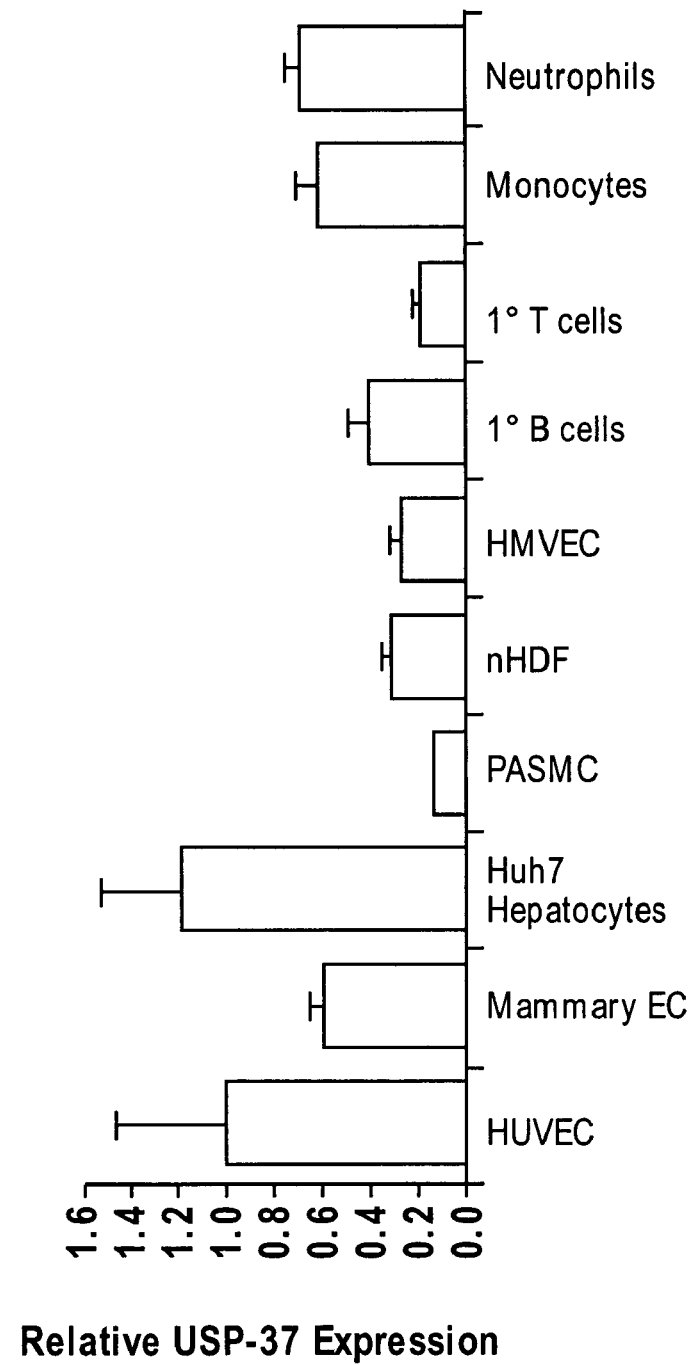
FIG. 2 shows USP37 RNA expression in cell lines.
Figure 3:
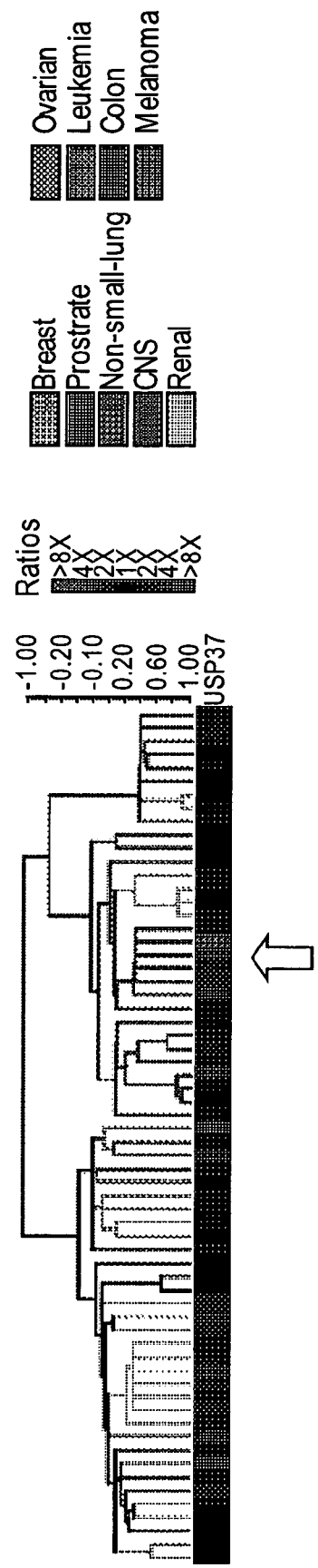
FIG. 3 shows that USP-37 is overexpressed in colon carcinomas.
Figure 4:
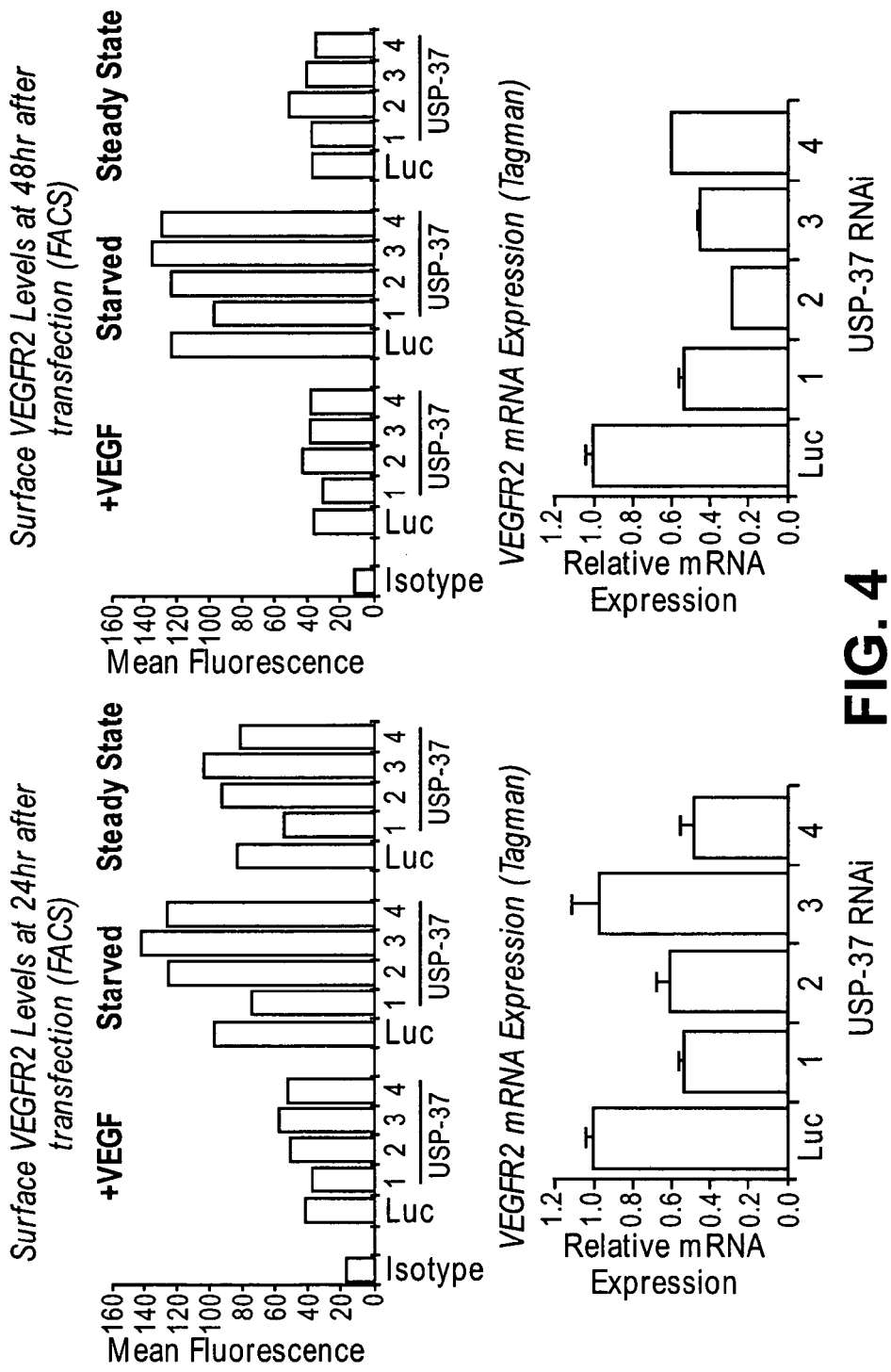
FIG. 4 shows USP-37 RNAi data.
Figure 5:
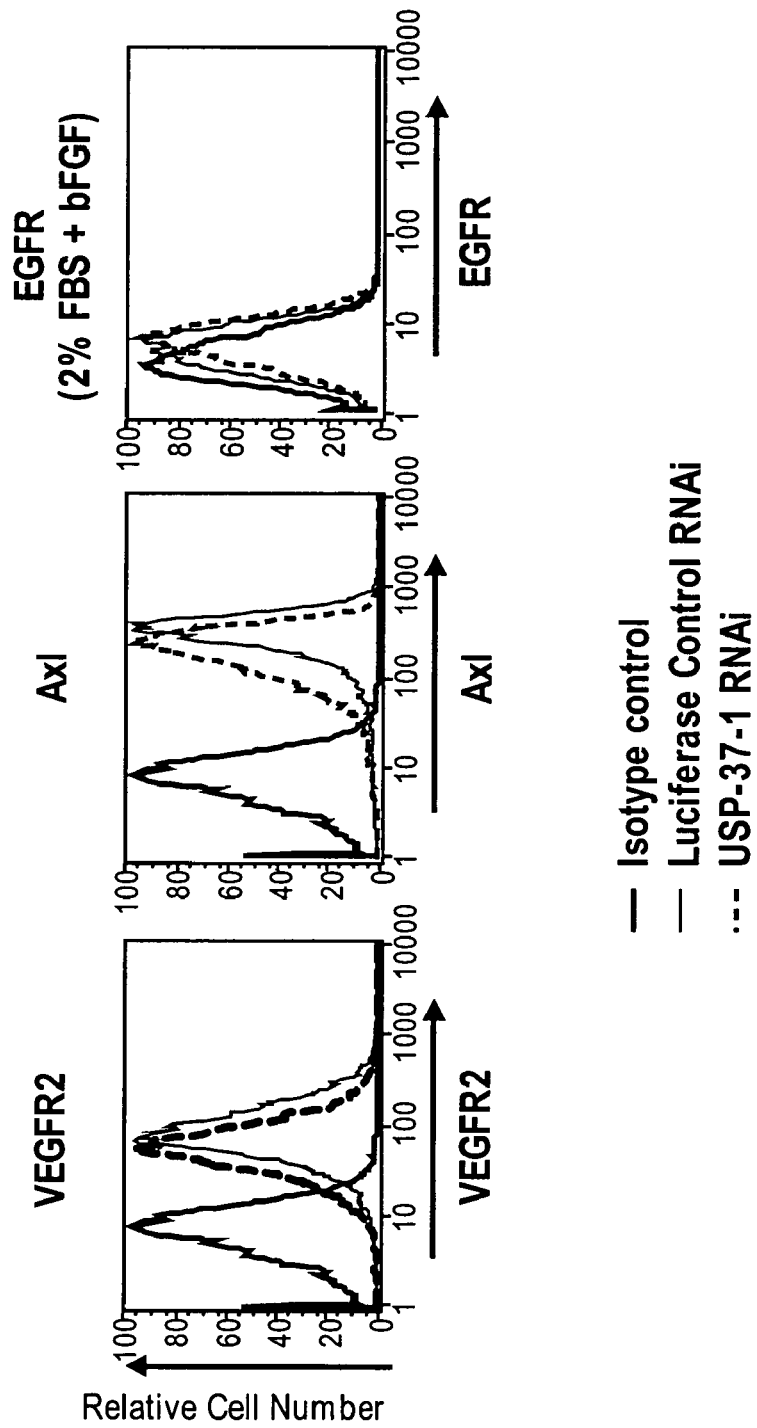
FIG. 5 shows USP-37 RNAi data.
Figure 6:
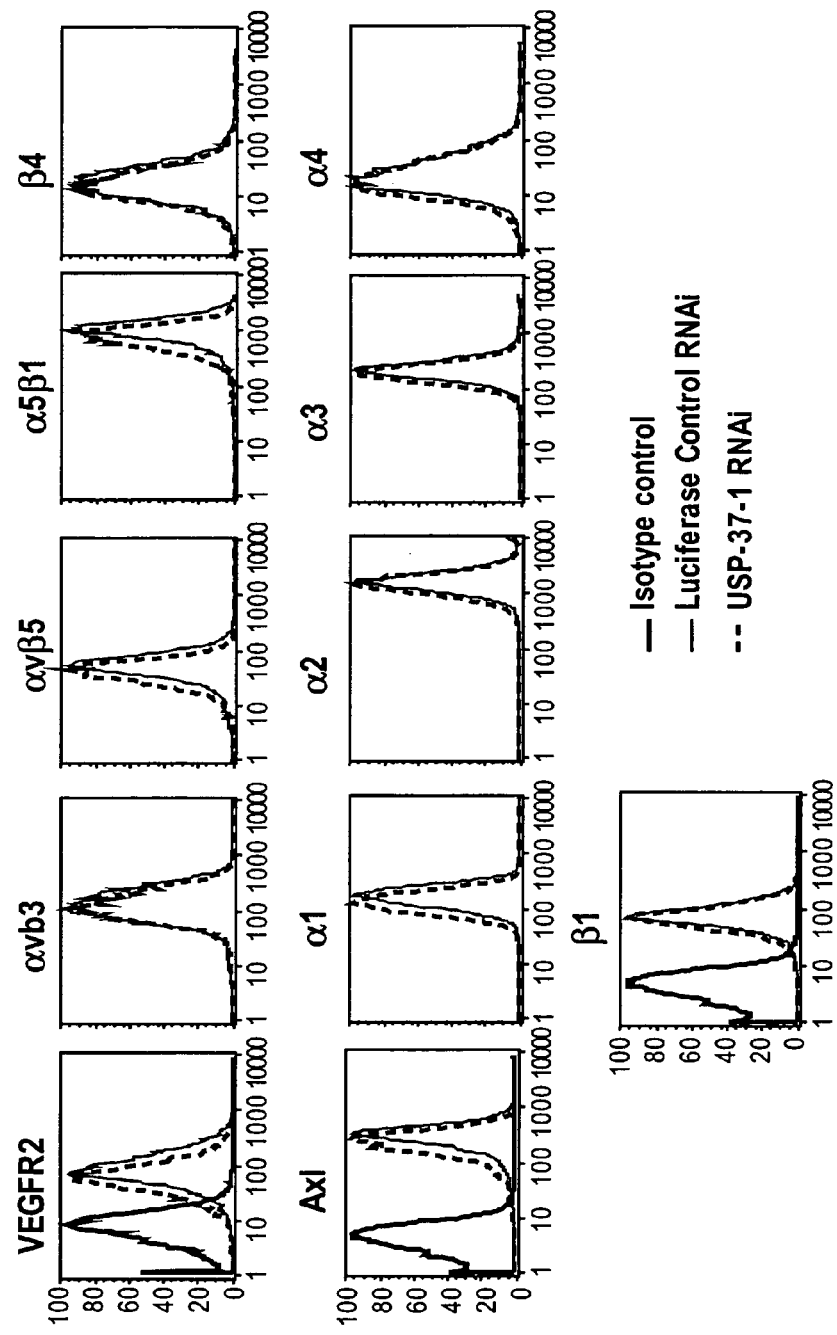
FIG. 6 shows USP-37 RNAi data.
Figure 7:
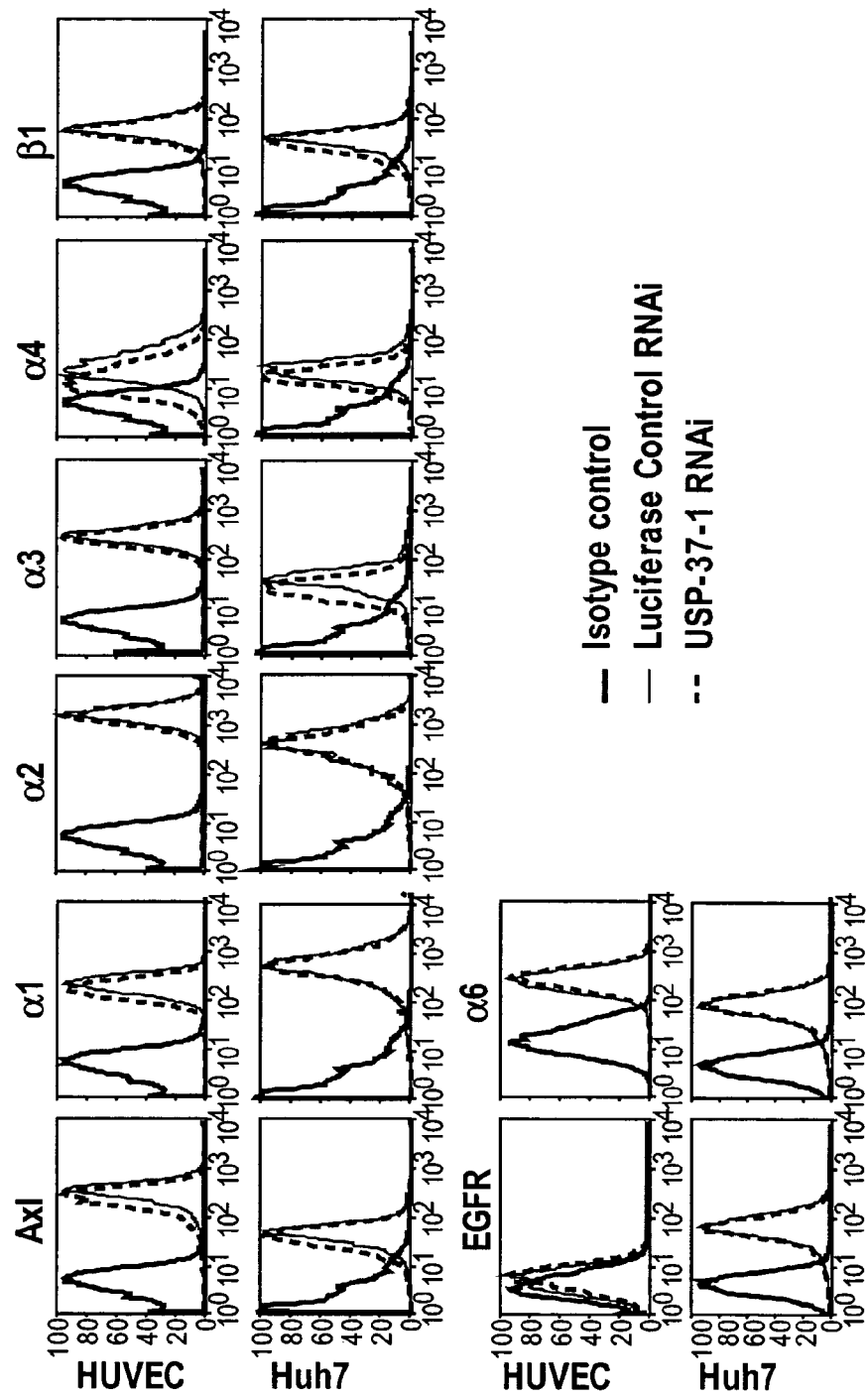
FIG. 7 shows USP-37 RNAi data.
Figure 8:
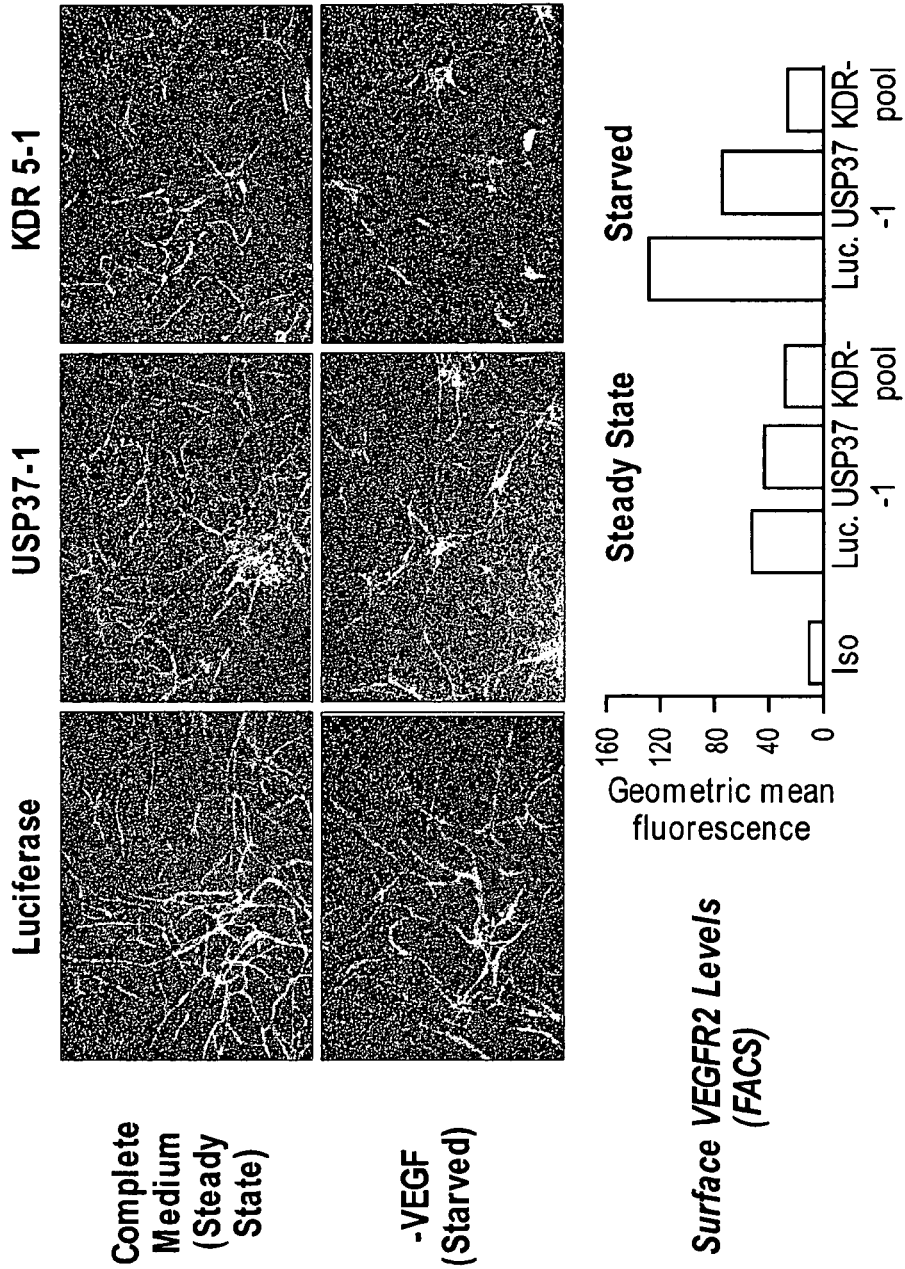
FIG. 8 shows USP-37 RNAi data.
Figure 10:
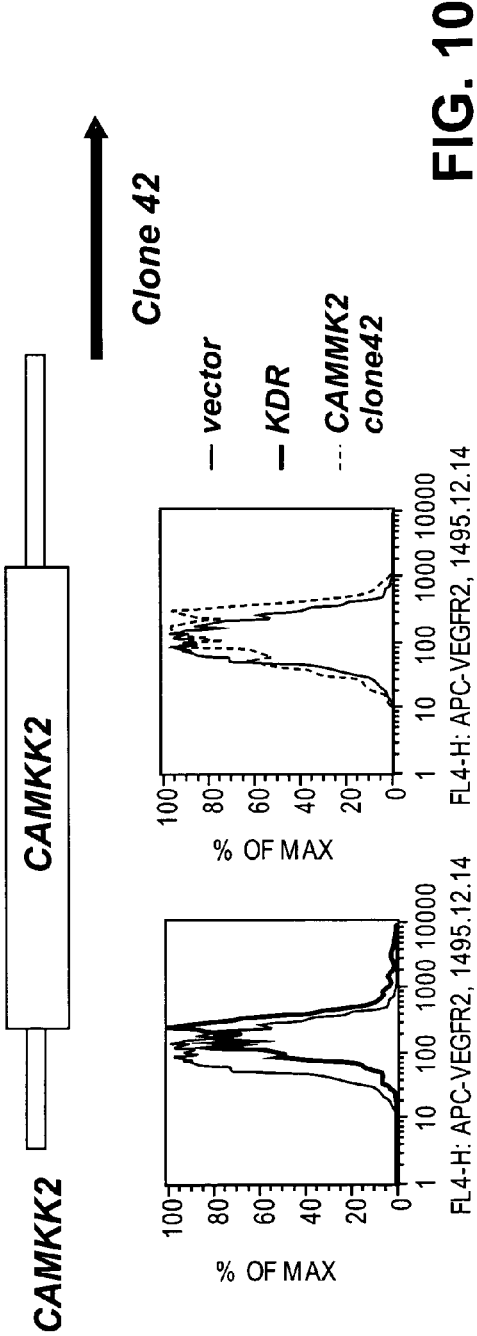
FIG. 10 shows a clone encoding CaMKK2 isolated in a VEGFR-2 upregulation assay.
Figure 11:
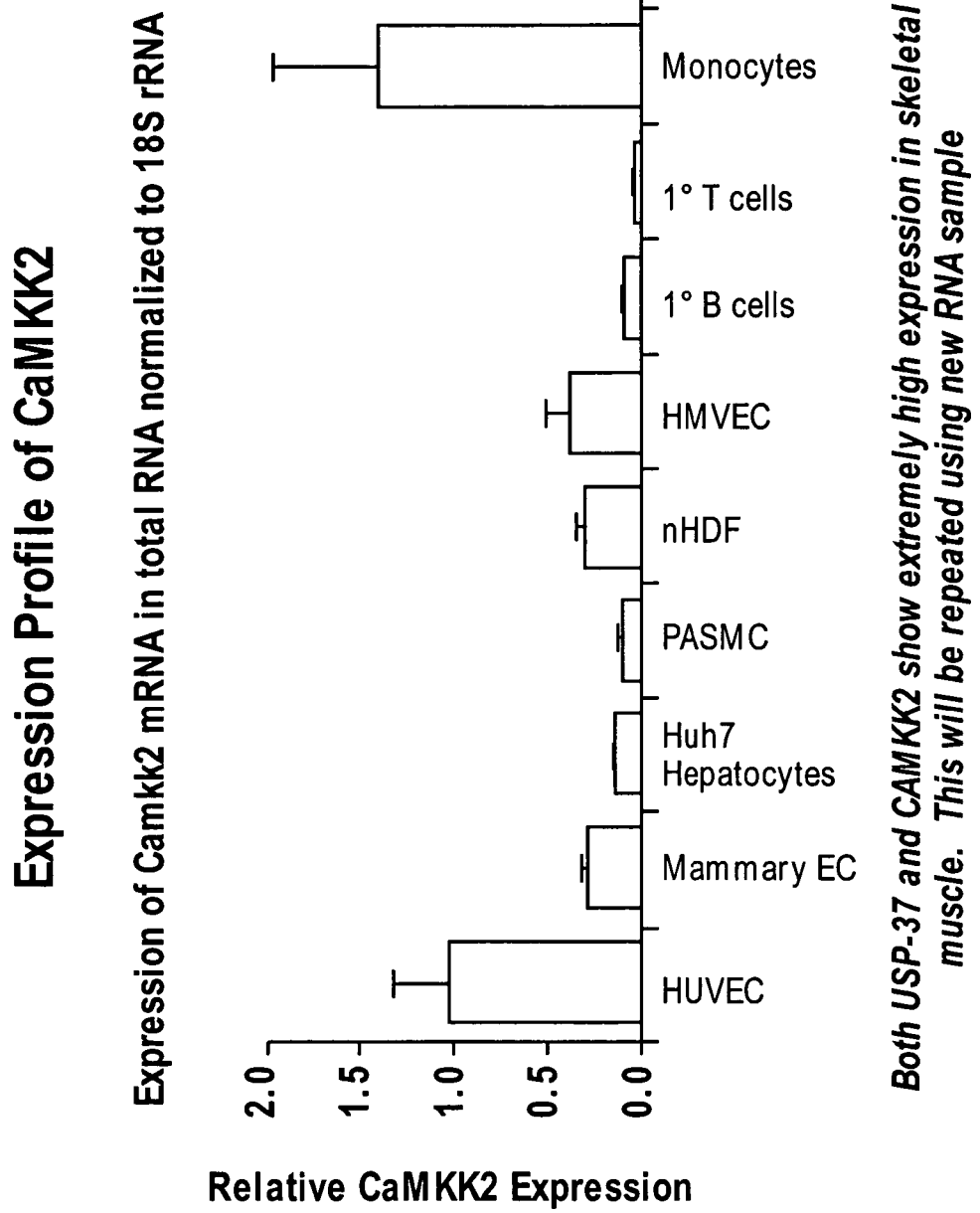
FIG. 11 shows the mRNA expression profile of CaMKK2.
Figure 12:
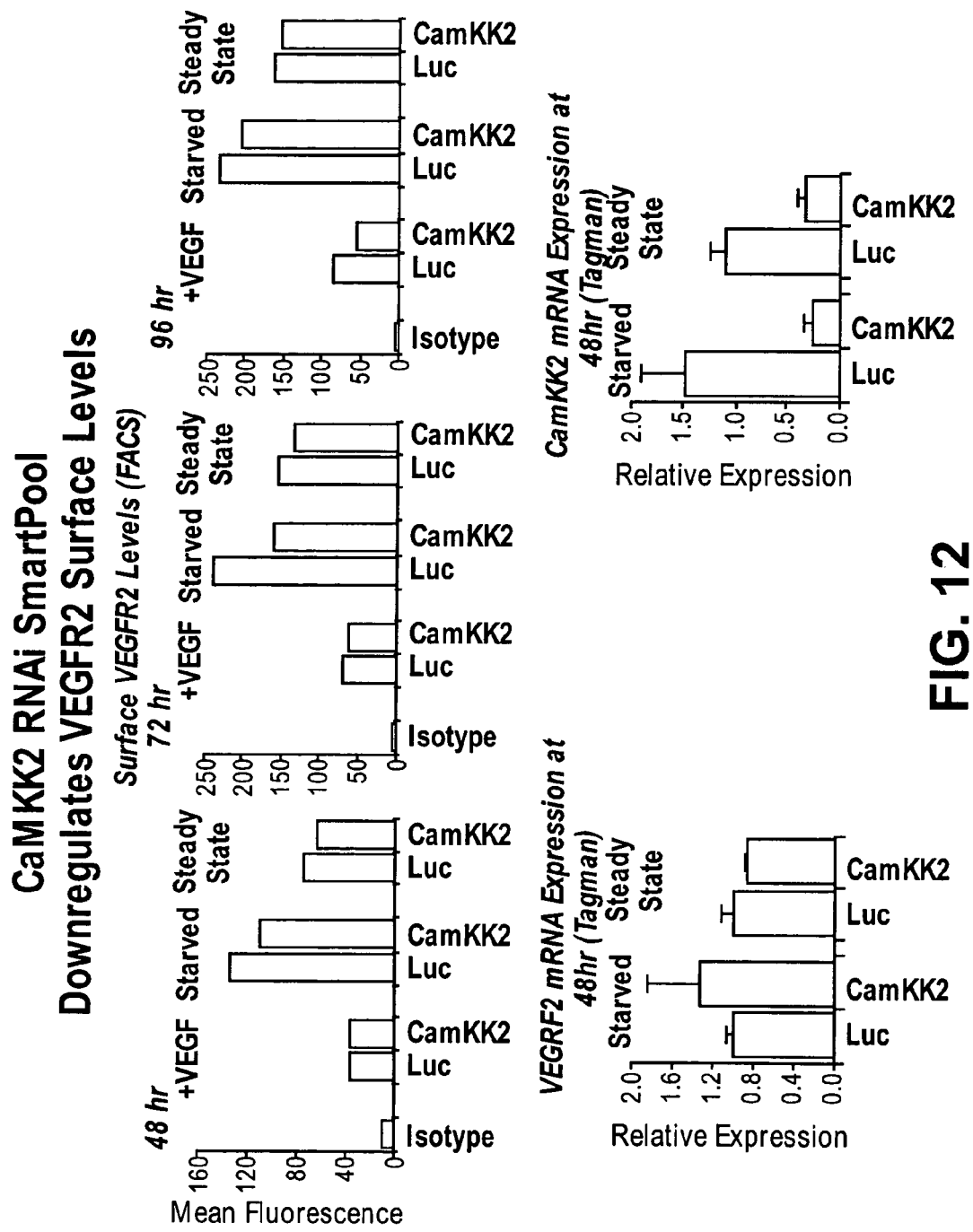
FIG. 12 shows CaMKK2 RNAi data.
Figure 13:
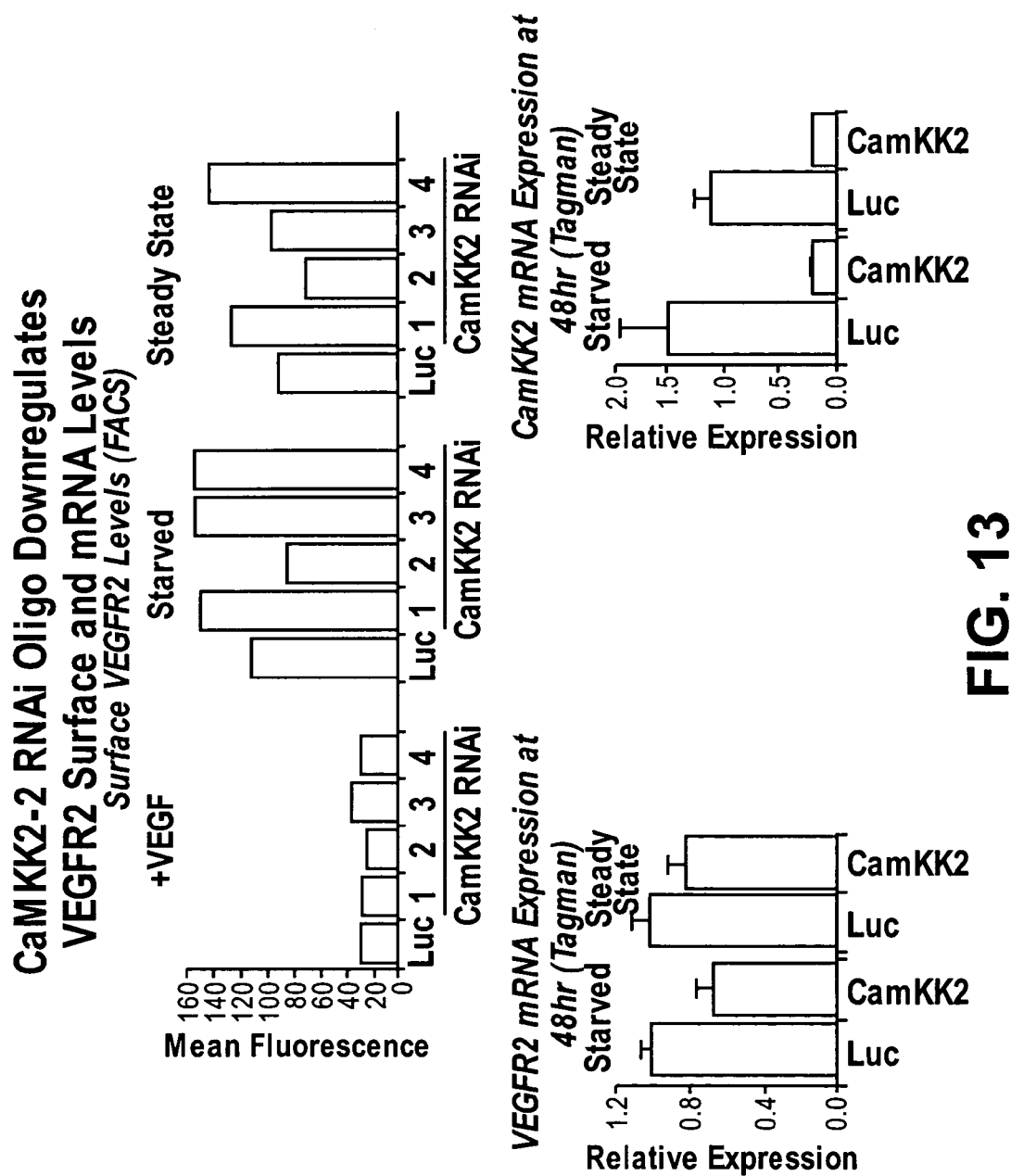
FIG. 13 shows CaMKK2 RNAi data.
Figure 15:
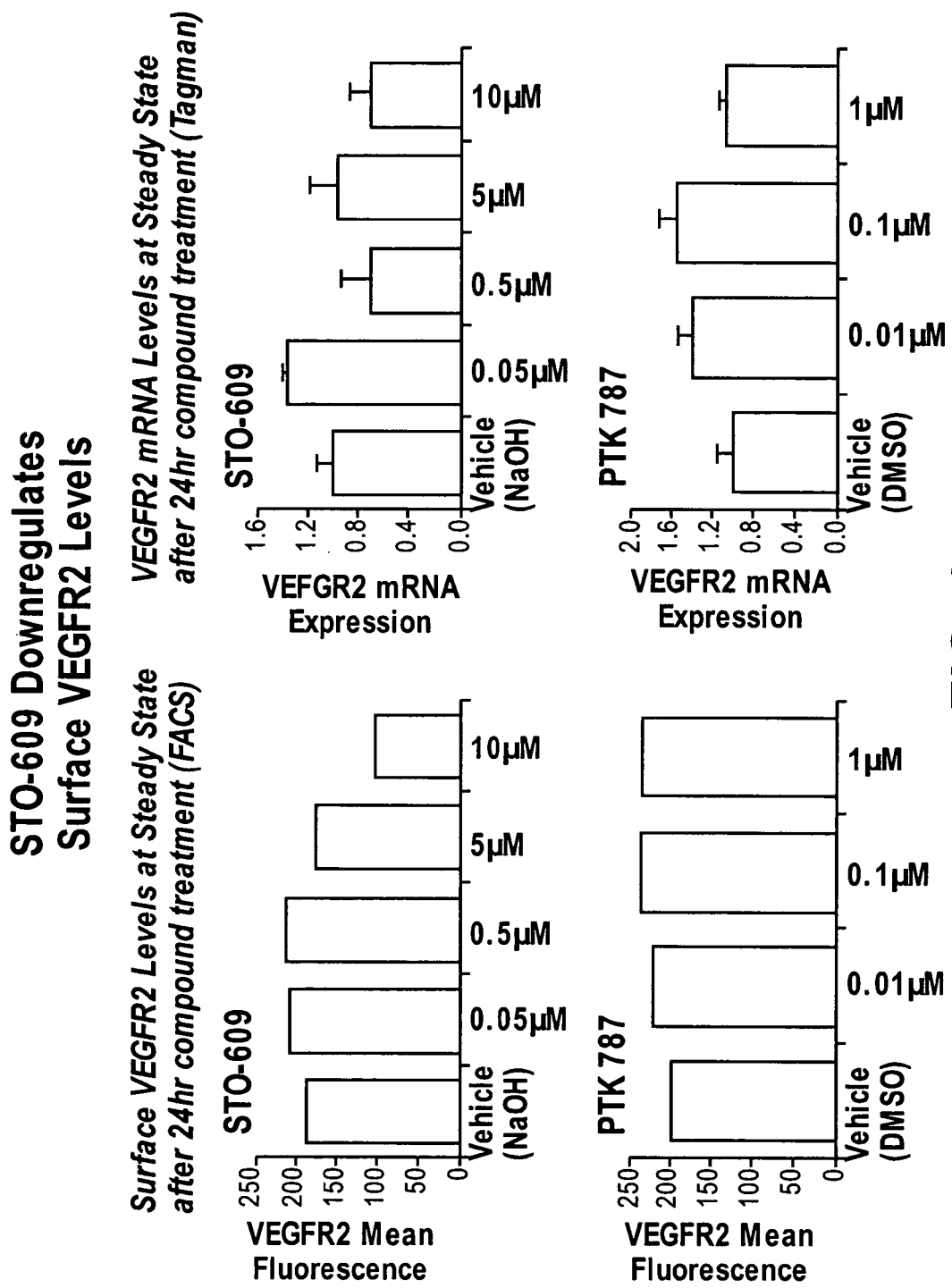
FIG. 15 shows that STO-609 downregulates VEGF2-R levels.
Figure 17:
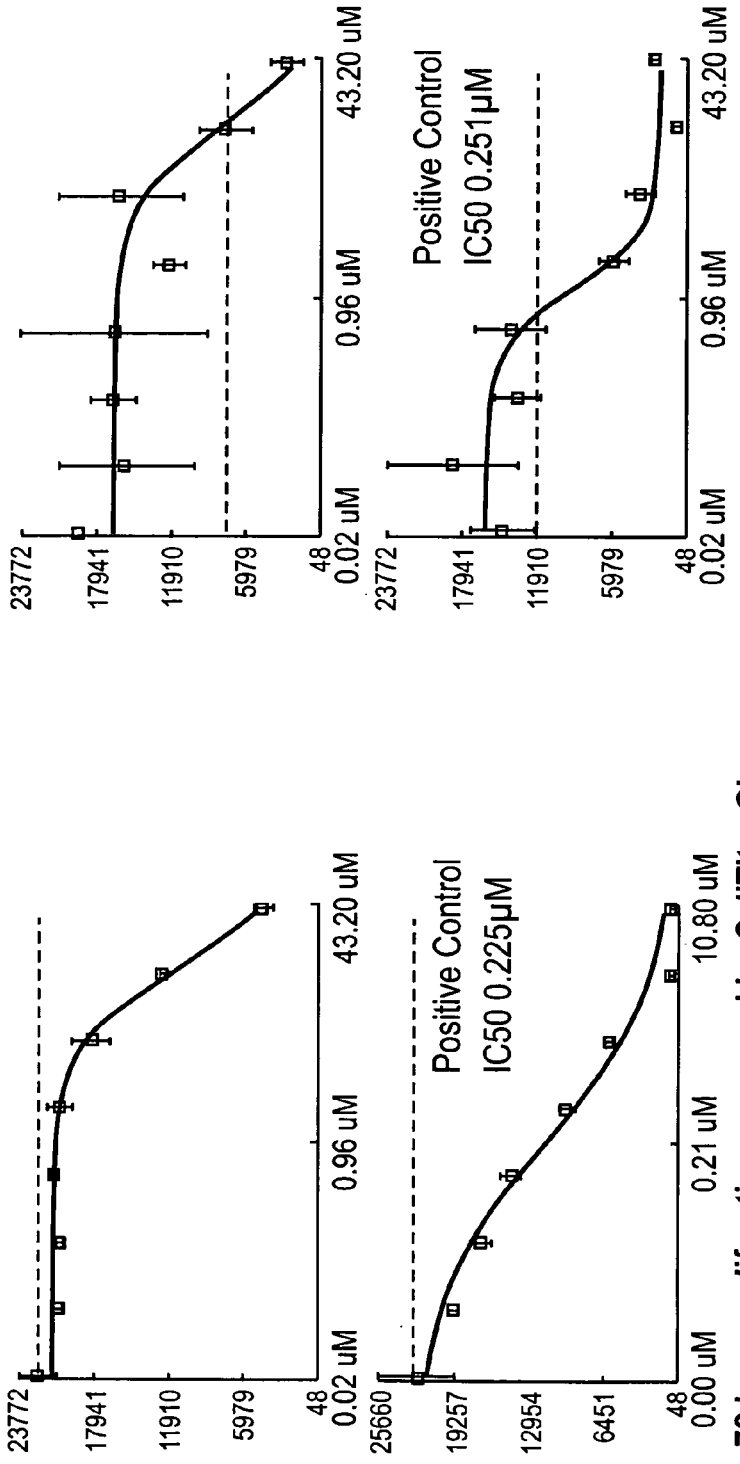
FIG. 17 shows STO-609 data.

We have used a VEGF receptor internalization screening strategy to identify proteins involved in regulating angiogenesis. Using a retroviral system, complex libraries of cDNAs were expressed in human primary endothelial cells (e.g., HUVECS, Clonetic CC-2519). HUVEC cells that switch to a differentiated angiostatic state can be identified using a VEGFR2 internalization assay. After infection with a retroviral cDNA library, cells are seeded in EGM-2 media (Clonetics EGM-2 bullet kit CC-3162) and grown to log phase. Cells are are cultured in starvation medium (EGMS with 0.1% FCS plus 1% BSA in place of VEGF and FCS) at 37° C. for 16 hours. The starved HUVECs are stimulated with VEGF stimulation medium at 37° C. for 1.5 hours, trypsinized, and stained with VEGFR2 antibody. Single cells exhibiting increased VEGF-R2 expression (i.e., blocked receptor internalization) were selected using FACS analysis. The cDNAs are isolated and sequenced to identify proteins involved in angiogenesis. The cDNAs can represent, e.g., full length transcripts, transcript fragments, 3' untranslated regions, or antisense molecules. In one embodiment, the cDNA acts as a dominant negative mutant.

A functional genetic screening strategy can also be used to identify proteins involved in regulating endothelial cell migration on specific matrix components, e.g. vitronectin. A retroviral-based system can be used to stably express complex libraries of various types of genetic elements (e.g. cDNAs and GFP-fusions) in human primary endothelial cells (e.g. HUVECs). Starting with early passage primary endothelial cells representing an "angiogenic state" (i.e., proliferative, highly motile), single cells that have switched to a more differentiated "angiostatic state" (i.e., quiescent, reduced motility) can be identified. To focus on the migration step of the angiogenic cycle, conditions can be established which allowed highly efficient migration of HUVEC cells along a haptotactic gradient of specific matrix proteins (e.g. vitronectin/fibronectin) in a Boyden chamber assay. Large populations of HUVEC cells are infected with a GFP-fused cDNA library and selected for impaired haptotaxis. Additional assays for proteins involved in angiogenesis include a HUVEC/smooth muscle cell co-culture assay for endothelial tube formation, and chemo-invasion assays. Finally, human/mouse tumor xenograft assays, mouse sponge angiogenesis and tumorigenesis assays (sponge with human ECs +/−human tumor cells in SCID mice), a collagen-antibody induced arthritis model for RA, and retinal neovascularization assays can be used to identify angiogenesis proteins in vivo and to assay for modulators of such proteins.

The angiogenesis proteins identified using the VEGFR2 internalization assay described herein, e.g., methionine adenosyltransferase II α (Mat2A) (hit: fragment), carnitine palmitoyltransferase II (CPT-2) (hit: fragment), DDX5 RNA helicase (hit: full-length), calcium/calmodulin-dependent protein kinase β (CAMKK2) (hit: fragment), acetyl-coenzyme A acyltransferase (ACAA1) (hit: fragment), glucosamine-6-phosphate isomerase (GNPI) (hit: full-length), 24-dehydrocholesterol reductase (DHCR24) (hit: fragment), selenoprotein T (SELT) (hit: fragment), protein tyrosine phosphatase, receptor type, B (PTPRB) (hit: full-length), glucosidase β acid (GBA) (hit: antisense), UDP-N-acteylglucosamine pyrophosphorylase 1 (UAP1) (hit: full-length), mitochondrial ribosomal protein L30 (MRPL30) (hit: fragment), chaperonin containing TCP1, subunit 3 γ (CCT3) (hit: fragment), HSPA8 (hit: full-length), solute carrier family 16 (monocarboxylic acid transporters), member 1 (SLC16A1) (hit: fragment), SH2 of Abl (hit: fragment), and ubiquitin hydrolase (USP37) (hit: 3' UTR), therefore represent targets for the development of angiogenic drugs, preferably anti-angiogenic drugs, e.g., anti-angiogenic drugs for treatment of neovascularization, e.g., cancer, diabetic retinopathy, endometriosis, glomerulonephritis, restenosis, glaucoma, rheumatoid arthritis, and age related macular degeneration, or angiogenic drugs for treatment of angiogenic insufficiency, e.g., stroke, infertility, heart disease, ulcers, and scleroderma. Modulators include small organic molecules, nucleic acids, peptides, cyclic peptides, antibodies, antisense molecules, RNAi molecules, and ribozymes. The nucleic acids and proteins of the invention are also useful for diagnostic applications, using, e.g., nucleic acid probes, oligonucleotides, and antibodies. These polypeptides are also involved in tumorigenesis and cellular proliferation, and are useful for the development of therapeutic molecules to treat diseases associated with angiogenesis, tumorigenesis, and cellular proliferation. Furthermore, the polypeptides described herein and the nucleic acids encoding them are useful for diagnostic assays for diseases associated with angiogenesis, tumorigenesis, and cellular proliferation.

In another embodiment, the protein ubiquitin hydrolase (USP37) is involved in angiogenesis. Ubiquitin hydrolase plays a role in the hydrolysis of esters formed between thiols and the C-terminal glycine residue of the polypeptide ubiquitin, and of AMP-ubiquitin. In vitro hydrolase assays with ubiquitin hydrolase can be used to assay for ubiquitin hydrolase modulators and thus for modulators of angiogenesis. The accession number for USP37 polypeptide is NP_065986 and the accession number for the nucleic acid is NM_020935. See also AB046814 and BAB13420. USP-37 is part of a novel family of ubiquitin hydrolases, most closely related to USP 26 and 29. Conserved catalytic residues include the Cys box (GNTCYmN) and the His box (HIGSTSSSDH).

In another embodiment, the protein CAMKK2 is involved in angiogenesis. CAMKK2 belongs to the Serine/Threonine protein kinase family, and to the Ca(2+)/calmodulin-dependent protein kinase subfamily. CAMKK2 plays a role in the calcium/calmodulin-dependent (CaM) kinase cascade by phosphorylating the downstream kinases CaMK1 and CaMK4. Seven transcript variants encoding six distinct isoforms have been identified for CAMKK2. Additional splice variants have been described but their full-length nature has not been determined. The identified isoforms exhibit a distinct ability to undergo autophosphorylation and to phosphorylate the downstream kinases. In vitro serine/threonine kinase assays with CAMKK2 can be used to assay for CAMKK2 modulators and thus for modulators of angiogenesis. Accession numbers for CAMKK2 nucleic acids are as follows: NM_006549 (variant 1), NM_153499 (variant 2), NM_172216 (variant 3), NM_153500 (variant 4), and NM_172226 (variant 7). Accession numbers for CAMKK2 polypeptides are as follows: NP_006540 (variant 1), NP_757380 (variant 2), NP_757365 (variant 3), NP_705720 (variant 4), and NP_757380 (variant 7).

In another embodiment, the protein Mat2A is involved in angiogenesis. Mat2A is an enzyme that catalyzes the formation of S-adenosylmethionine from methionine and ATP. In mammalian tissues, there are three distinct forms of a Mat2A designated as α, β, and γ. α and β are expressed only in adult liver, while γ is widely distributed in extrahepatic tissues. Mat2A is expressed in, e.g., invasive adenocarcinoma, bronchioalveolar carcinoma, CD34+, T negative chronic myelogenous leukemia, invasive carcinoma, early stage papillary serous carcinoma, serous adenocarcinoma, oligodendroglioma, metastatic melanoma, and normal gingival. In vitro enzyme assays with Mat2A can be used to assay for Mat2A modulators and thus for modulators of angiogenesis. The accession number for Mar2A polypeptide is NP005902 and the accession number for the nucleic acid is NM_005911.

In another embodiment, the protein CPT-2 is involved in angiogenesis. CPT2 is a nuclear protein which is transported to the mitochondrial inner membrane. CPT2 together with carnitine palmitoyltransferase I oxidizes long-chain fatty acids in the mitochondria. Defects in this gene are associated with mitochondrial long-chain fatty-acid (LCFA) oxidation disorders. Defects in CPT2 are the cause of carnitine palmitoyltransferase II deficiency (CPT-II deficiency), an autosomal recessive disorder characterized by recurrent myoglobinuria, episodes of muscle pain, stiffness, and rhabdomyolysis. these symptoms are triggered by prolonged exercise, fasting or viral infection and patients are usually young adults. in addition to this classical, late-onset, muscular type, a hepatic or hepatocardiomuscular form has been reported in infants. clinical pictures in these children or neonates include hypoketotic hypoglycemia, liver dysfunction, cardiomyopathy and sudden death. CPT2 is a component of the fatty acid β-oxidation cycle. CPT2 is expressed in pituitary adenomas, posterior rhombomeres, lens, mammary gland, and human placenta. The accession number for CPT-2 polypeptide is NP_000089 and the accession number for CPT-2 nucleic acid is NM_000098.

In another embodiment, the protein DDX5 is involved in angiogenesis. DDX5 RNA helicase is a DEAD (SEQ ID NO:26) box protein, characterized by the conserved motif Asp-Glu-Ala-Asp (DEAD; (SEQ ID NO:26)). DEAD (SEQ ID NO:26) box proteins are putative RNA helicases. They are implicated in a number of cellular processes involving alteration of RNA secondary structure such as translation initiation, nuclear and mitochondrial splicing, and ribosome and spliceosome assembly. Based on their distribution patterns, some members of this family are believed to be involved in embryogenesis, spermatogenesis, and cellular growth and division. DDX5 encodes a DEAD (SEQ ID NO:26) box protein, which is a RNA-dependent ATPase, and also a proliferation-associated nuclear antigen, highly specifically reacting with the simian virus 40 tumor antigen. DDX5 consists of 13 exons, and alternatively splicing transcripts containing several intron sequences have been detected, but no isoforms encoded by these transcripts are identified. DDX5 also has an RNA-dependent ATPase activity. the rate of ATP hydrolysis is highly stimulated by single-stranded RNA. DDX5 is expressed in bulk germ cell seminoma, follicular adenoma, bulk alveolar tumor, juvenile granulosa tumor, normal gingival, anterior rhombomeres, thymus, pituitary, and liver. In vitro helicase assays with DDX5 can be used to assay for DDX5 modulators and thus for modulators of angiogenesis. The accession number for DDX5 nucleic acid is NM_004396 and the accession number for the polypeptide is NP_004387.

In another embodiment, the protein ACAA1 is involved in angiogenesis. ACAA1 is a thiolase operative in the β-oxidation system of the peroxisomes. Deficiency of ACAA1 leads to pseudo-Zellweger syndrome. In vitro thiolase assays with ACAA1 can be used to assay for ACAA1 modulators and thus for modulators of angiogenesis. The accession number for the nucleic acid is NM_001607 and the accession number for the polypeptide is NP_001598.

In another embodiment, the protein GNPI is involved in angiogenesis. GNPI converts glucosamine-6-phosphate to fructose-6-phosphate. GNPI is expressed in invasive ductal carcinoma, meningioma, melanoma, melanotic melanoma, moderately-differentiated adenocarcinoma, adult brain, hypernephroma, pheochromocytoma, and lung tumors. The accession number for the nucleic acid is NM_005471 and the accession number for the protein is NP_005462.

In another embodiment, the protein DHCR24 is involved in angiogenesis. DHCR24 catalyzes the reduction of the δ-24 double bond of sterol intermediates during cholesterol biosynthesis. DHCR24 protects cells from oxidative stress by reducing caspase 3 activity during apoptosis induced by oxidative stress. DHCR24 also protects against amyloid-beta peptide-induced apoptosis. DHCR24 is highly expressed in brain and adrenal gland, with moderate expression in liver, lung, spleen, prostate and spinal cord. low expression in heart, uterus and prostate. The accession number for the nucleic acid is NM_014762 and the accession number for the polypeptide is NP_055577.

In another embodiment, the protein SELT is involved in angiogenesis. SELT plays a role in selenocysteine incorporation and is associated with endothelial cells, probably through heparin-binding properties. SELT prevents the damage of vascular endothelium caused by reactive oxygen species. SELT is expressed in melanotic melanoma, acute myelogenous leukemia, embryonal carcinoma, hypernephroma, and chronic myelogenous leukemia. The accession number for the nucleic acid is BC026350 and the accession number for the protein is AAH26350.

In another embodiment, the protein PTPRB is involved in angiogenesis. PTPRB is a signaling molecule that regulates a variety of cellular processes including cell growth, differentiation, mitotic cycle, and oncogenic transformation. PTPRB is specifically expressed in vascular Ecs throughout mouse development. PTPRB binds to VE-cadherin in COS cells, dephosphorylates VEGFR2 phosphorylated VE-cadherin, co-immunoprecipitates with TieII and dephosphorylates TieII. The accession number for the nucleic acid is NM_002837 and the accession number for the protein is NP_002828.

In another embodiment, the protein GBA is involved in angiogenesis. GBA is a β-glucocerebrosidase (glucosylceramidase, β-D-glucosyl-N-acylsphingosine glucohydrolase) that degrades sphingolipid glucocerebrosides. Defects in GBA are the cause of gaucher disease (gd), the most prevalent lysosomal storage disease. In vitro β-glucocerebrosidase assays with GBA can be used to assay for GBA modulators and thus for modulators of angiogenesis. The accession number for the nucleic acid is NM_000157 and the accession number for the polypeptide is NP_000148.

In another embodiment, the protein UAP1 is involved in angiogenesis. UAP1 is expressed in skin, carcinoma cell, normal gingival, colonic mucosa, normal endometrium, and Ewing's sarcoma. The accession number for the nucleic acid is NM_003115 and the accession number for the polypeptide is NP_003106.

In another embodiment, the protein MRPL30 is involved in angiogenesis. MRPL30 catalyzes the transfer of the lipoyl group from lipoyl-AMP to the specific lysine residue of the lipoate-dependent enzymes. The accession number for the nucleic acid is NM_145212 and the accession number for the polypeptide is NP_660213.

In another embodiment, the protein CCT3 is involved in angiogenesis. CCT3 is a molecular chaperone that assists protein folding upon ATP hydrolysis. CCT3 is known to play a role, in vitro, in the folding of actin and tubulin. CCT3 plays a role in the assembly of the Von Hippel-Lindau ubiquitylation complex. The accession number for the nucleic acid is AL833197 and the accession number for the polypeptide is NP_005989.

In another embodiment, the protein HSPA8 is involved in angiogenesis. HSPA8 belongs to the heat shock protein 70 family. HSPA8 binds to nascent polypeptides to facilitate correct folding. HSPA8 also functions as an ATPase in the disassembly of clathrin-coated vesicles during transport of membrane components through the cell. The accession number for the nucleic acid is NM_006597 and the accession number for the polypeptide is NP_006588.

In another embodiment, the protein SLC16A1 is involved in angiogenesis. SLC16A1 is a proton-linked monocarboxylate transporter. SLC16A1 catalyzes the rapid transport across the plasma membrane of many monocarboxylates such as lactate, pyruvate, branched-chain oxo acids derived from leucine, valine and isoleucine, and the ketone bodies acetoacetate, beta-hydroxybutyrate and acetate. Defects in SLC16A1 are the cause of symptomatic deficiency in lactate transport (SDLT), characterized by a subnormal erythrocyte lactate transport and signs of muscle injury during exercise and heat exposure. The accession number for the nucleic acid is NM_003051 and the accession number for the polypeptide is NP_003042.

In another embodiment, the protein SH2 of Abl is involved in angiogenesis. SH2 of Abl is a SH2 domain protein, similar to the tyrosine-protein kinase Abl. Arm and Abl proteins function cooperatively at adherens junctions in both the cns and epidermis. In vitro tyrosine kinase assays with SH2 of Abl can be used to assay for SH2 of Abl modulators and thus for modulators of angiogenesis. The accession number for the nucleic acid is AK074067 and the accession number for the protein is BAB84893.

II. Definitions

By "disorder associated with angiogenesis" or "disease associated with angiogenesis" herein is meant a disease state which is marked by either an excess or a deficit of vessel development. Angiogenesis disorders associated with increased angiogenesis include, but are not limited to, breast, lung, colon, ovarian, liver, stomach, bladder, thyroid, and prostate cancer, basal cell carcinoma, melanoma, lymphomas, leukemias, e.g., myeloid leukemia (AML, CML), endometriosis, diabetic retinopathy, glaucoma, glomerulonephritis, rheumatoid arthritis, and age related macular degeneration. Pathological states for which it may be desirable to increase angiogenesis include stroke, infertility, heart disease, e.g., restenosis, ulcers, and scleroderma. An increase in angiogenesis may also be desirable in transplantation or for artificial or in vitro growth of organs.

By "disorder associated with cellular proliferation or tumorigenesis" or "disease associated with cellular proliferation or tumorigenesis" herein is meant a disease state which is marked by either an excess or a deficit of cellular proliferation or apoptosis. Such disorders associated with increased cellular proliferation include, but are not limited to, cancer and non-cancerous pathological proliferation.

The term "angiogenesis polypeptide" or a nucleic acid encoding an "angiogenesis polypeptide" refer to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster;

cow, pig, horse, sheep, or any mammal. The nucleic acids and proteins of the invention include both naturally occurring or recombinant molecules.

The phrase "functional effects" in the context of assays for testing compounds that modulate activity of an angiogenesis protein includes the determination of a parameter that is indirectly or directly under the influence of an angiogenesis polypeptide, e.g., a chemical or phenotypic effect such as loss-of angiogenesis phenotype represented by a change in expression of a cell surface marker αvβ3 integrin, changes in cellular migration, e.g., haptotaxis, changes in endothelial tube formation, changes in VEGF receptor internalization, and changes in tumor growth; or enzymatic activity; or, e.g., a physical effect such as ligand binding or inhibition of ligand binding. A functional effect therefore includes ligand binding activity, the ability of cells to proliferate, expression in cells undergoing angiogenesis, and other characteristics of angiogenic cells. "Functional effects" include in vitro, in vivo, and ex vivo activities.

By "determining the functional effect" is meant assaying for a compound that increases or decreases a parameter that is indirectly or directly under the influence of an angiogenesis protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the angiogenesis protein; measuring changes in enzymatic activity; the ability to increase or decrease cellular proliferation, apoptosis, cell cycle arrest, measuring changes in cell surface markers, e.g., αvβ3 integrin. Determination of the functional effect of a compound on angiogenesis can also be performed using assays known to those of skill in the art such as endothelial cell tube formation assays; haptotaxis assays; the chick CAM assay; the mouse corneal assay; VEGF receptor assays, co-culture tube formation assays, and assays that assess vascularization of an implanted tumor. Tumorigenesis can be measured using in vivo mouse models such as a xenograft model. The functional effects can be evaluated by many means known to those skilled in the art, e.g., microscopy for quantitative or qualitative measures of alterations in morphological features, e.g., tube or blood vessel formation, measurement of changes in RNA or protein levels for angiogenesis-associated sequences, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of angiogenesis polynucleotide and polypeptide sequences are used to refer to activating, inhibitory, or modulating molecules identified using in vitro and in vivo assays of angiogenesis polynucleotide and polypeptide sequences. Inhibitors are compounds that, e.g., bind to, partially or totally block activity, decrease, prevent, delay activation, inactivate, desensitize, or down regulate the activity or expression of angiogenesis proteins, e.g., antagonists. "Activators" are compounds that increase, open, activate, facilitate, enhance activation, sensitize, agonize, or up regulate angiogenesis protein activity, agonists. Inhibitors, activators, or modulators also include genetically modified versions of angiogenesis proteins, e.g., versions with altered activity, as well as naturally occurring and synthetic ligands, antagonists, agonists, antibodies, peptides, cyclic peptides, nucleic acids, antisense molecules, ribozymes, RNAi molecules, small organic molecules and the like. Such assays for inhibitors and activators include, e.g., expressing angiogenesis protein in vitro, in cells, or cell extracts, applying putative modulator compounds, and then determining the functional effects on activity, as described above.

Samples or assays comprising angiogenesis proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of an angiogenesis protein is achieved when the activity value relative to the control is about 80%, preferably 50%, more preferably 25-0%. Activation of an angiogenesis protein is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate angiogenesis. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., SEQ ID NO:1 or 2), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., ligand binding domains, etc. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)).

Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies, polymorphic variants, alleles, orthologs, and conservatively modified variants, or splice variants, or portions thereof, can be selected to obtain only those polyclonal antibodies that are specifically immunoreactive with angiogenesis proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

III. Assays for Proteins that Modulate Angiogenesis

High throughput functional genomics assays can be used to identify modulators of angiogenesis. Such assays can monitor changes in cell surface marker expression, $\alpha v \beta 3$ integrin production, proliferation, and differentiation using either cell lines or primary cells. Typically, early passage or primary endothelial cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the endothelial cells is then monitored, using an assay such as cell surface marker expression (e.g., $\alpha v \beta 3$ integrin) or a phenotypic assay for angiogenesis such as migration towards an ECM (extracellular matrix) component (see, e.g., Klemke et al., *J. Cell Biol.* 4:961-972 (1998)) or endothelial cell tube formation assays, as well as other bioassays such as the chick CAM assay, the mouse corneal assay, haptotaxis assays, VEGF-R assays, co-culture tube formation assays, and assays measuring the effect of administering potential modulators on implanted tumors. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tags. In vivo assays for tumor growth, such as mouse xenograft models, can also be used.

Proteins interacting with the peptide or with the protein encoded by the cDNA can be isolated using a yeast two-hybrid system, mammalian two hybrid system, or phage display screen, etc. Targets so identified can be further used as bait in these assays to identify additional members of the angiogenesis pathway, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637, 463).

Suitable endothelial cell lines include human umbilical vein cells (see, e.g., Jaffe et al., *J. Clin. Invest.* 52:2745-2754 (1973)); human adult dermal capillary-derived cells (see, e.g., Davison et al., *In Vitro* 19:937-945 (1983)); human adipose capillary derived cells (see, e.g., Kern et al., *J. Clin Invest.* 71:1822-1829 (1983); bovine aorta (see, e.g., Booyse et al., *Thromb. Diathes. Ahemorrh.* 34:825-839 (1975); and rat brain capillary derived cells (see, e.g., Bowman et al., *In Vitro* 17:353-362 (1981)). For culture of endothelial cell lines, explants, and primary cells, see Freshney et al., *Culture of Animal Cells* (3$^{rd}$ ed. 1994). Suitable angiogenesis cell surface markers include alphavbeta3 integrin (see, e.g., Elicerir & Cheresh, *Cancer J. Sci. Am.* 6 Supp. 3:S245-249 (2000), Maeshima et al., *J. Biol. Chem.* (Jun. 8, 2001)).

Cell surface markers such as $\alpha v \beta 3$ can be assayed using fluorescently labeled antibodies and FACS. Cell proliferation can be measured using $^3$H-thymidine or dye inclusion. Angiogenesis phenotype is measured by loss of phenotype observation.

cDNA libraries are made from any suitable source, preferably from endothelial cells. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

In a preferred embodiment, target proteins that modulate angiogenesis are identified using a high throughput cell based assay (using a microtiter plate format) and FACS screening for αvβ3 cell surface expression. cDNA libraries are made which include, e.g., sense, antisense, full length, and truncated cDNAs. The cDNAs are cloned into a retroviral vector. Endothelial cells are infected with the library, cultured for a short effector phase and then the cells with reduced αvβ3 surface levels are enriched by antibody staining and magnetic cell sorting. The enriched cell population is then sorted into microtiter plates using fluorescent antibodies and FACS. Resultant cell colonies are analyzed by immunofluorescence for reduced αvβ3 surface levels. Selected colonies are infected with wild type MMLV virus to rescue the proviral vector. The infectious supernatant is used to infect endothelial cells, which are subsequently analyzed for αvβ3 levels by FACS. The cDNA is isolated and sequenced to determined if it represents a wild type or mutated cDNA, e.g., whether the cDNA represents a negative transdominant mutant. Optionally, a marker such as GFP can be used to select for retrovirally infected cells.

Isolation of Nucleic Acids

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Nucleic acids, polymorphic variants, orthologs, and alleles can be isolated using nucleic acid probes and oligonucleotides under stringent hybridization conditions, by screening libraries. Alternatively, expression libraries can be used to clone angiogenesis proteins, polymorphic variants, orthologs, and alleles by detecting expressed homologs immunologically with antisera or purified antibodies made against human angiogenesis proteins or portions thereof.

To make a cDNA library, one should choose a source that is rich in the desired RNA, e.g., endothelial cells. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating nucleic acids and orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of angiogenesis protein encoding mRNA in physiological samples, for nucleic acid sequencing, or for other purposes. Genes amplified by the PCR reaction can be purified from agarose gels and cloned into an appropriate vector.

Gene expression can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids can be used with high density oligonucleotide array technology (e.g., GeneChip™) to identify angiogenesis protein, orthologs, alleles, conservatively modified variants, and polymorphic variants in this invention. In the case where the homologs being identified are linked to a known disease state, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding an angiogenesis protein, one typically subclones the desired nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

In one embodiment, the vectors of the invention have a regulatable promoter, e.g., tet-regulated systems and the RU-486 system (see, e.g., Gossen & Bujard, *Proc. Nat'l Acad. Sci. USA* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the protein of choice, which is recovered from the culture using standard techniques identified below.

Purification of Polypeptides

Either naturally occurring or recombinant protein can be purified for use in functional assays. Naturally occurring protein can be purified, e.g., from human tissue. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand, angiogenesis protein can be selectively adsorbed to a purification column and then freed from the column in a relatively pure form. The fused protein is then removed by enzymatic activity. Finally, protein could be purified using immunoaffinity columns.

A. Purification of Protein from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of Angiogenesis Proteins

A. Assays

Modulation of an angiogenesis protein, and corresponding modulation of angiogenesis, can be assessed using a variety of in vitro and in vivo assays, including high throughput ligand binding and cell based assays, as described herein. Such assays can be used to test for inhibitors and activators of the angiogenesis protein, and, consequently, inhibitors and activators of angiogenesis. Such modulators of the angiogenesis protein are useful for treating angiogenesis disorders. Modulators of the angiogenesis protein are tested using either recombinant or naturally occurring protein, preferably human protein.

Measurement of an angiogenic or loss-of-angiogenesis phenotype on the protein or cell expressing the protein, either recombinant or naturally occurring, can be performed using a variety of assays, in vitro, in vivo, and ex vivo. For example, recombinant or naturally occurring protein can be used in vitro, in a ligand binding or enzymatic function assay. Protein present in a cellular extract can also be used in in vitro assays. Cell- and animal-based in vivo assays can also be used to assay for angiogenesis modulators. Any suitable physical, chemical, or phenotypic change that affects activity or binding can be used to assess the influence of a test compound on the polypeptide of this invention. When the functional effects are determined using intact cells or animals, one can also measure a variety of effects such as, in the case of angiogenesis associated with tumors, tumor growth, neovascularization, endothelial tube formation, cell surface markers such as $\alpha v\beta 3$, hormone release, transcriptional changes to both known and uncharacterized genetic markers (e.g., northern blots), changes in cell metabolism such as cell growth or pH changes, and changes in intracellular second messengers such as cGMP. In one embodiment, measurement of $\alpha v\beta 3$ integrin cell surface expression and FACS sorting is used to identify modulators of angiogenesis.

In Vitro Assays

Assays to identify compounds with angiogenesis modulating activity, e.g., anti-angiogenic activity, can be performed in vitro, e.g., binding assays. Purified recombinant or naturally occurring protein can be used in the in vitro methods of the invention. In addition to purified protein, the recombinant or naturally occurring protein can be part of a cellular lysate. As described below, the assay can be either solid state or soluble.

Preferably, the protein is bound to a solid support, either covalently or non-covalently. Often, the in vitro assays of the invention are ligand binding or ligand affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the protein or chimera comprising a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, and antibodies. A wide variety of assays can be used to identify angiogenesis-modulator binding, including labeled protein-protein binding assays, electrophoretic mobility shifts, immunoassays, and the like. In some cases, the binding of the candidate modulator is determined through the use of competitive binding assays, where interference with binding of a known ligand is measured in the presence of a potential modulator. Often, either the potential modulator or the known ligand is labeled.

Cell-Based In Vivo Assays

In another embodiment, the protein is expressed in a cell, and functional, e.g., physical and chemical or phenotypic, changes are assayed to identify angiogenesis modulators, preferably anti-angiogenesis compounds. Cells expressing angiogenesis proteins can also be used in binding assays or enzymatic assays. Any suitable functional effect can be measured, as described herein. For example, ligand binding, cell surface marker expression, cellular proliferation, VEGF-R assays, co-culture assays for tube formation, and cell migration assays are all suitable assays to identify potential modulators using a cell based system. Suitable cells for such cell based assays include both primary endothelial cells and cell lines, as described herein. The protein can be naturally occurring or recombinant.

As described above, in one embodiment, loss-of angiogenesis phenotype is measured by contacting endothelial cells comprising an angiogenesis target with a potential modulator. Modulation of angiogenesis is identified by screening for cell surface marker expression, e.g., $\alpha v\beta 3$ integrin expression levels, using fluorescent antibodies and FACS sorting.

In another embodiment, cellular proliferation can be measured using $^3$H-thymidine incorporation or dye inclusion.

In another embodiment, cellular polypeptide levels are determined by measuring the level of protein or mRNA. The level of protein or proteins are measured using immunoassays such as western blotting, ELISA and the like with an antibody that selectively binds to the polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, protein expression can be measured using a reporter gene system. Such a system can be devised using an angiogenesis protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

A variety of phenotypic angiogenesis assays are known to those of skill in the art. Various models have been employed to evaluate angiogenesis (e.g., Croix et al., *Science* 289:1197-1202 (2000) and Kahn et al., *Amer. J. Pathol.* 156:1887-1900). Assessment of angiogenesis in the presence of a potential modulator can be performed using cell-culture-based assays, e.g., endothelial cell tube formation assays and haptotaxis assays, as well as other animal based bioassays such as the chick CAM assay, the mouse corneal assay, and assays measuring the effect of administering potential modulators on implanted tumors.

For determination of cellular proliferation, any suitable functional effect can be measured, as described herein. For example, cellular morphology (e.g., cell volume, nuclear volume, cell perimeter, and nuclear perimeter), ligand binding, kinase activity, apoptosis, cell surface marker expression, cellular proliferation, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoescht dye with FACS analysis), $G_0/G_1$ cell cycle arrest, are all suitable assays to identify potential modulators using a cell based system. Suitable cells for such cell based assays include both primary cancer or tumor cells and cell lines, as described herein, e.g., A549 (lung), MCF7 (breast, p53 wild-type), H1299 (lung, p53 null), Hela (cervical), PC3 (prostate, p53 mutant), MDA-MB-231 (breast, p53 wild-type). Cancer cell lines can be p53 mutant, p53 null, or express wild type p53.

Animal Models

A number of animal based assays for angiogenesis phenotypes are known to those of skill in the art and can be used to assay for modulators of angiogenesis. For example, the chick CAM assay is described by O'Reilly, et al. Cell 79: 315-328 (1994). Briefly, 3 day old chicken embryos with intact yolks are separated from the egg and placed in a petri dish. After 3 days of incubation, a methylcellulose disc containing the protein to be tested is applied to the CAM of individual embryos. After about 48 hours of incubation, the embryos and CAMs are observed to determine whether endothelial growth has been inhibited.

The mouse corneal assay involves implanting a growth factor-containing pellet, along with another pellet containing the suspected endothelial growth inhibitor, in the cornea of a mouse and observing the pattern of capillaries that are elaborated in the cornea.

Angiogenesis can also be measured by determining the extent of neovascularization of a tumor. For example, carcinoma cells can be subcutaneously inoculated into athymic or nude mice or SCID mice and tumor growth then monitored. Immunoassays using endothelial cell-specific antibodies are typically used to stain for vascularization of tumor and the number of vessels in the tumor.

As described above, animal models of angiogenesis find use in screening for modulators of angiogenesis. Similarly, transgenic animal technology including gene knockout technology, for example as a result of homologous recombination with an appropriate gene targeting vector, or gene overexpression, will result in the absence or increased expression of the protein. The same technology can also be applied to make knock-out cells. When desired, tissue-specific expression or knockout of the protein may be necessary. Transgenic animals generated by such methods find use as animal models of angiogenesis and are additionally useful in screening for modulators of angiogenesis.

Knock-out cells and transgenic mice can be made by insertion of a marker gene or other heterologous gene into the endogenous gene site in the mouse genome via homologous recombination. Such mice can also be made by substituting the endogenous gene with a mutated version of the gene, or by mutating the endogenous gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators

The compounds tested as modulators of the angiogenesis protein can be any small organic molecule, or a biological entity, such as a protein, e.g., an antibody or peptide, a sugar, a nucleic acid, e.g., an antisense oligonucleotide, RNAi molecule, or a ribozyme, or a lipid. Alternatively, modulators can be genetically altered versions of an angiogenesis protein. Typically, test compounds will be small organic molecules, peptides, lipids, and lipid analogs.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using an angiogenesis protein, or a cell or tissue expressing an angiogenesis protein, either naturally occurring or recombinant. In another embodiment, the invention provides solid phase based in vitro assays in a high throughput format, where the angiogenesis protein is attached to a solid phase substrate. Any one of the assays described herein can be adapted for high throughput screening, e.g., ligand binding, cellular proliferation, cell surface marker flux, e.g., $\alpha v \beta 3$ integrin, etc. In one preferred embodiment, the cell-based system using $\alpha v \beta 3$ integrin modulation and FACS assays is used in a high throughput format for identifying modulators of angiogenesis proteins, and therefore modulators of T cell angiogenesis.

In the high throughput assays of the invention, either soluble or solid state, it is possible to screen up to several thousand different modulators or ligands in a single day. This methodology can be used for angiogenesis proteins in vitro, or for cell-based assays comprising an angiogenesis protein.

In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids. (SEQ ID NO:27). Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Antibodies to Angiogenesis Polypeptides

In addition to the detection of gene and gene expression using nucleic acid hybridization technology, one can also use immunoassays to detect proteins of the invention. Such assays are useful for screening for modulators of angiogenesis, as well as for therapeutic and diagnostic applications. Immunoassays can be used to qualitatively or quantitatively analyze angiogenesis protein. A general overview of the applicable technology can be found in Harlow & Lane, *Antibodies: A Laboratory Manual* (1988).

A. Production of Antibodies

Methods of producing polyclonal and monoclonal antibodies that react specifically with the angiogenesis proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of an angiogenesis protein may be used to produce antibodies specifically reactive with protein. For example, recombinant protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-angiogenesis proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular ortholog, such as a human ortholog, can also be made, by subtracting out other cross-reacting orthologs from a species such as a non-human mammal. In this manner, antibodies that bind only to a desired protein may be obtained.

Once the specific antibodies against the protein are available, the protein can be detected by a variety of immunoassay methods. In addition, the antibody can be used therapeutically as modulators. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

Protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology: Antibodies in Cell Biology, volume 37 (Asai, ed. 1993); Basic and Clinical Immunology (Stites & Terr, eds., 7th ed. 1991). Immunological binding assays (or immunoassays) typically use an antibody that specifically binds to a protein or antigen of choice (in this case the protein or antigenic subsequence thereof). The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled protein or a labeled antibody. Alternatively, the labeling agent may be a third moiety, such a secondary antibody, that specifically binds to the antibody/protein complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting protein in samples may be either competitive or noncompetitive. Noncompetitive immunoassays are assays in which the amount of antigen is directly measured. In one preferred "sandwich" assay, for example, the antibodies can be bound directly to a solid substrate on which they are immobilized. These immobilized antibodies then capture protein present in the test sample. Proteins thus immobilized are then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of protein present in the sample is measured indirectly by measuring the amount of a known, added (exogenous) protein displaced (competed away) from an antibody by the unknown protein present in a sample. In one competitive assay, a known amount of protein is added to a sample and the sample is then contacted with an antibody that specifically binds to protein. The amount of exogenous protein bound to the antibody is inversely proportional to the concentration of protein present in the sample. In a particularly preferred embodiment, the antibody is immobilized on a solid substrate. The amount of protein bound to the antibody may be determined either by measuring the amount of protein present in protein/antibody complex, or alternatively by measuring the amount of remaining uncomplexed protein. The amount of protein may be detected by providing a labeled molecule.

A hapten inhibition assay is another preferred competitive assay. In this assay the known protein is immobilized on a solid substrate. A known amount of antibody is added to the sample, and the sample is then contacted with the immobilized protein. The amount of antibody bound to the known immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein can be immobilized to a solid support. Proteins are added to the assay that compete for binding of the antisera to the immobilized antigen. The ability of the added proteins to compete for binding of the antisera to the immobilized protein is compared to the ability of the protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding inimunoassay as described above to compare a second protein, thought to be perhaps an allele or polymorphic variant of a protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein that is required to inhibit 50% of binding, then the second protein is said to specifically bind to the polyclonal antibodies generated to the immunogen.

Other Assay Formats

Western blot (immunoblot) analysis is used to detect and quantify the presence of protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the protein. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the protein, or secondary antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Gene Therapy

The present invention provides the nucleic acids of angiogenesis associated protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a protein of the present invention, thereby mitigating the effects of absent, partial inactivation, or abnormal expression of the angiogenesis gene, particularly as it relates to angiogenesis. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

The nucleic acids of the invention can also be used to make transgenic animals, such as transgenic mice, either by knockout or overexpression. Such animals are useful, e.g., for testing modulators of angiogenesis.

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the angiogenesis protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of Genes Involved in Modulation of Angiogenesis In Vitro

Using a retroviral system, complex libraries of cDNAs have been expressed in human primary endothelial cells (e.g., HUVECS, Cloneitc CC-2519). HUVEC cells that switch to a differentiated angiostatic state can be identified using a VEGFR2 internalization assay. After infection with a retroviral cDNA library, cells are seeded in EGM-2 media (Clonetics EGM-2 bullet kit CC-3162) and grown to log phase. Cells are cultured in starvation medium (EGMS with 0.1% FCS plus 1% BSA in place of VEGF and FCS) at 37° C. for 16 hours. The starved HUVECs are stimulated with VEGF stimulation medium at 37° C. for 1.5 hours, trypsinized, and stained with VEGFR2 antibody. Single cells exhibiting increased VEGF-R2 expression (i.e., blocked or inhibited receptor internalization) were selected using FACS analysis.

Co-culture of HUVECs on smooth muscle cells was used to confirm that genes identified via VEGR2 internalization are genes that encode angiogenesis proteins. Smooth muscle cells (Clonetics Pulmonary Artery SMCs CC-2581) are plated at 40,000 cells per well of a collagen coated 24 well tissue culture plate and grown to confluency. HUVECs are plated onto the smooth muscle cells at 22,000 cells per well. The phenotype of vascular bed formation is determined as follows: photographs are taken and formation of tubular morphology of the HUVECs is determined empirically. The co-culture assay is typically used to confirm an anti-angiogenic phenotype.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying a compound that inhibits angiogenesis, the method comprising the steps of:
   (i) contacting human ubiquitin hydrolase specific protease 37 (USP37) polypeptide with the compound,
   (ii) measuring USP37 polypeptide for ubiquitin hydrolase activity in the presence of the compound, wherein the USP37 polypeptide has ubiquitin hydrolase activity in the absence of the compound,
   (iii) contacting an endothelial cell with said compound identified in step (ii),
   (iv) measuring a change in angiogenesis phenotype in the endothelial cell by measuring VEGF-R2 surface expression, $\alpha v \beta 5$ integrin expression, endothelial cell tube formation or haptotaxis in the presence of said compound
   wherein inhibition of ubiquitin hydrolase activity in the presence of said compound as compared with activity in the absence of said compound, and reduction in VEGF-R2 surface expression, $\alpha v \beta 5$ integrin expression, endothelial cell tube formation or haptotaxis, identifies said compound as a compound that inhibits angiogenesis.

2. The method of claim 1, wherein the angiogenesis phenotype is determined in vitro.

3. The method of claim 1, wherein the USP37 polypeptide is recombinant.

4. The method of claim 1, wherein the compound is an antibody.

5. The method of claim 1, wherein the compound is an antisense molecule.

6. The method of claim 1, wherein the compound is an RNAi molecule.

7. The method of claim 1, wherein the compound is a small organic molecule.

8. A method for identifying a compound that inhibits angiogenesis, the method comprising:
   contacting the compound with an endothelial cell comprising a recombinant human ubiquitin hydrolase specific protease 37 (USP37) polypeptide, wherein the recombinant human USP37 polypeptide has ubiquitin hydrolase activity; and
   measuring a change in angiogenesis phenotype in the endothelial cell by measuring VEGF-R2 surface expression, $\alpha v \beta 5$ integrin expression, endothelial cell tube formation or haptotaxis in the presence of said compound,
   wherein reduction in VEGF-R2 surface expression, $\alpha v \beta 5$ integrin expression, endothelial cell tube formation or haptotaxis in the presence of said compound as compared with VEGF-R2 surface expression, $\alpha v \beta 5$ integrin expression, endothelial cell tube formation or haptotaxis in the absence of said compound, identifies said compound as a compound that inhibits angiogenesis.

9. The method of claim 8, wherein the compound is an antibody.

10. The method of claim 8, wherein the compound is an antisense molecule.

11. The method of claim 8, wherein the compound is an RNAi molecule.

12. The method of claim 8, wherein the compound is a small organic molecule.

13. The method of claim 8, further comprising measuring the USP37 polypeptide ubiquitin hydrolase activity in vitro in the presence of said compound.

14. The method of claim 1, wherein the USP37 polypeptide is encoded by the nucleotide sequence of SEQ ID NO:22.

15. The method of claim 8, wherein the USP37 polypeptide is encoded by the nucleotide sequence of SEQ ID NO:22.

16. The method of claim 1, wherein the angiogenesis phenotype is determined by measuring VEGF-R2 surface expression.

17. The method of claim 8, wherein the angiogenesis phenotype is determined by measuring VEGF-R2 surface expression.

18. The method of claim 1, wherein the angiogenesis phenotype is determined by measuring $\alpha v \beta 5$ integrin expression.

19. The method of claim 1, wherein the angiogenesis phenotype is determined by measuring endothelial cell tube formation.

20. The method of claim 1, wherein the angiogenesis phenotype is determined by measuring haptotaxis.

21. The method of claim 8, wherein the angiogenesis phenotype is determined by measuring $\alpha v \beta 5$ integrin expression.

22. The method of claim 8, wherein the angiogenesis phenotype is determined by measuring endothelial cell tube formation.

23. The method of claim 8, wherein the angiogenesis phenotype is determined by measuring haptotaxis.

* * * * *